United States Patent
Beesley

(10) Patent No.: US 12,173,036 B2
(45) Date of Patent: Dec. 24, 2024

(54) EXPRESSION IN MAMMALIAN CELLS WITH GAUSSIA LUCIFERASE SIGNAL PEPTIDE

(71) Applicant: DAPCEL, Inc., Cleveland, OH (US)

(72) Inventor: Jennet Orazmuradovna Beesley, Manchester (GB)

(73) Assignee: DAPCEL, INC., Cleveland, OH (US)

( * ) Notice: Subject to any disclaimer, the term of this patent is extended or adjusted under 35 U.S.C. 154(b) by 878 days.

(21) Appl. No.: 15/769,180

(22) PCT Filed: Oct. 21, 2016

(86) PCT No.: PCT/EP2016/075415
§ 371 (c)(1),
(2) Date: Apr. 18, 2018

(87) PCT Pub. No.: WO2017/068142
PCT Pub. Date: Apr. 27, 2017

(65) Prior Publication Data
US 2018/0319854 A1    Nov. 8, 2018

(30) Foreign Application Priority Data
Oct. 23, 2015   (GB) ..................................... 1518792

(51) Int. Cl.
| C07K 14/435 | (2006.01) |
| C12N 15/62 | (2006.01) |
| C12N 15/85 | (2006.01) |
| C12P 21/02 | (2006.01) |
| C12Q 1/66 | (2006.01) |

(52) U.S. Cl.
CPC ...... *C07K 14/43509* (2013.01); *C12N 15/625* (2013.01); *C12N 15/85* (2013.01); *C12Q 1/66* (2013.01); *C07K 2319/02* (2013.01); *C12P 21/02* (2013.01)

(58) Field of Classification Search
CPC .............................. C12N 15/85; C12N 15/625
See application file for complete search history.

(56) References Cited

U.S. PATENT DOCUMENTS

| 2007/0207545 A1* | 9/2007 | Asada ....................... C12N 9/78 |
| | | 435/455 |
| 2011/0097798 A1* | 4/2011 | Li .......................... C12N 15/85 |
| | | 435/375 |
| 2014/0242638 A1* | 8/2014 | Fontayne ........... C07K 16/2896 |
| | | 435/69.6 |
| 2017/0029826 A1* | 2/2017 | van der Heijden ... C12P 21/005 |

FOREIGN PATENT DOCUMENTS

| WO | WO 1991014780 A1 * | 10/1991 |
| WO | WO 2005/001099 A2 | 1/2005 |
| WO | WO 2010/038145 A2 | 4/2010 |
| WO | WO 2011/018766 A1 | 2/2011 |
| WO | WO2013151665 A2 | 10/2013 |

OTHER PUBLICATIONS

Williams et al. (2009) Plasmid DNA vaccine vector design: Impact on efficacy, safety and upstream production. Biotechnology Advances, 27:353-370 (Year: 2009).*
PcDNA4/HisMax plasmid vector (pcDNA™ 4/HisMax A, B, and C product manual by Invitrogen, published Nov. 8, 2011) (Year: 2011).*
Stern et al. (2007) Improving mammalian cell factories: The selection of signal peptide has a major impact on recombinant protein synthesis and secretion in mammalian cells. Trends in Cell and Molecular Biology, 17 pages (Year: 2007).*
Peroutka et al. (2008) Enhanced protein expression in mammalian cells using engineered SUMO fusions: Secreted phospholipase A2. Protein Science, 17:1586-1595. (Year: 2008).*
PShooter™ Vector (pCMV/myc vectors), Invitrogen by Life Technologies (Year: 2012).*
Clonetech (pEGFP-C2 Vector Information; published Oct. 3, 2002), (Year: 2002).*
GenBank Accession #: U57606, pEGFP-C2 https://www.ncbi.nlm.nih.gov/nuccore/U57606 [retrieved Jul. 4, 2022]. (Year: 2013).*
Montgomery (Montgomery and Prather Design of Plasmid DNA Constructs for Vaccines. DNA Vaccines, Methods and Protocols (2006), Humana Press, pp. 11-22). (Year: 2006).*
ZeoCassette™ Vectors Manual, https://tools.thermofisher.com/content/sfs/manuals/zeocassette_man.pdf, [retrieved Jul. 8, 2022], published 2016) (Year: 2016).*
Kendell Morgan, Plasmids 101: The Promoter Region—Let's Go!, Blog post https://blog.addgene.org/plasmids-101-the-promoter-region, [retrieved Jul. 8, 2022]; published Apr. 3, 2014 (Year: 2014).*
Loew et al, Improved Tet-responsive promoters with minimized background expression. BMC Biotechnology (2010), 10(81): 1-13 (Year: 2010).*
Life Technologies, pSecTag2 A, B, and C Manuel, published Jan. 19, 2012 (Year: 2012).*
Life Technologies, T-Rex system and pcDNA4/TO/myc-His map, published Nov. 8, 2011 (Year: 2011).*
Expresso® CMV system: effortless mammalian expression cloning, Lucigen Corporation, published Mar. 2012 (Year: 2012).*
Plasmids 101: Origin of Replication, Addgene blog post from Feb. 6, 2014, https://web.archive.org/web/20140412114138/http://blog.addgene.org/plasmid-101-origin-of-replication (Year: 2014).*

(Continued)

*Primary Examiner* — Celine X Qian
*Assistant Examiner* — Catherine Konopka
(74) *Attorney, Agent, or Firm* — Lippes Mathias LLP

(57) ABSTRACT

The present invention relates to in vitro expression of proteins and particularly, although not exclusively, to expression of proteins in mammalian cell lines. In particular, the present invention relates to the provision of a novel vector for protein expression, and methods of using such vector in the expression of proteins in mammalian cell lines.

21 Claims, 54 Drawing Sheets

Specification includes a Sequence Listing.

(56) References Cited

OTHER PUBLICATIONS

Genbank AY894991.1, https://www.ncbi.nlm.nih.gov/nuccore/AY894991.1 [retrieved Mar. 4, 2024] (Year: 2006).*

Jager et al., Chapter 2: Transient Recombinant Protein Expression in Mammalian Cells, Animal Cell Culture, Cell Engineering 9, (2015) (Year: 2015).*

Maucksch et al., Chapter 5: Plasmid DNA Concatemers: Influence of Plasmid Structure on Transfection Efficiency, Minicircle and Miniplasmid DNA Vectors: The Future of Nonviral and Viral Gene Transfer, 1st ed., (2013) (Year: 2013).*

Addgene vector #80901, mycBioID-pBABE-puro, https://www.addgene.org/80901/, [retrieved Mar. 4, 2024] (Year: 2012).*

PcDNA4/HisMax sequence, https://www.addgene.org/vector-database/2121/ [retrieved Mar. 1, 2024] (Year: 2011).*

Stern et al., "Improving Mammalian cell factories: The selection of signal peptide has a major impact on recombinant protein synthesis and secretion in mammalian cells", Trends in Cell & Molecular Biology, Research Trends, IN., vol. 2, 2007, pp. 1-17, XP002603748, ISSN: 0972-8449.

Knappskog et al., "The level of synthesis and secretion of Gaussia princeps luciferase in transfected CHO cells is heavily dependent on the choice of signal peptide", Journal of Biotechnology, Elsevier Science Publishers, Amsterdam, NL, vol. 128, No. 4, Mar. 6, 2007, pp. 705-715.

Trosse Christiane et al., "Vectors encoding seven seven oikosin signal peptides transfected into CHO cells differ greatly in mediating Gaussia luciferase and human endostatin production although mRNA levels are largely unaffected", Gene Regulation and Systems Biology, Libertas Academica Ltd, NZ, vol. 1, Dec. 11, 2007 (Dec. 11, 2007), pp. 303-312, XP002603749.

"pTRE2hyg Vector Information: Map and Multiple Cloning Site (MCS) of pTRE2hyg Vector", clontech May 7, 2007 (May 7, 2007), XP002765550, Retrieved from the Internet: URL:Clontechwww.clontech.com/xxclt_ibcGetAttachment.jsp?cltemId=17951.

"pTRE2hyg Sequence and Map—SnapGene", Snapgene, 2016, XP002765551, Retrieved from the Internet: URL:http://www.snapgene.com/resources/plasmid_files/mammalian_expression_vectors/pTRE2hyg/.

"Plasmid map of pcDNA4_His-Max_A", BVTech 2005, XP002765552, Retrieved from the Internet: URL:http://www.biovisualtech.com/bvplasmid/pcDNA4His-Max_A.htm.

Gossen M. et al: "Tight control of gene expression in mammalian cells by tetracycline-responsive promoters", Proceedings of the National Academy of Sciences, National Academy of Sciences, US, vol. 89, No. 12, Jun. 15, 1992 (Jun. 15, 1992), pp. 5547-5551, XP002202393, ISSN: 0027-8424.

Lars Kober et al: "Optimized signal peptides for the development of high expressing CHO cell lines", Biotechnology and Bioengineering, vol. 110, No. 4, Apr. 17, 2013 (Apr. 17, 2013), pp. 1164-1173, XP055074908, ISSN: 0006-3592.

B. Wen et al: "Signal peptide replacements enhance expression and secretion of hepatitis C virus envelope glycoproteins", Acta Biochimica Et Biophysica Sinica, vol. 43, No. 2, Dec. 31, 2010 (Dec. 31, 2010), pp. 96-102, XP055328372, US ISSN: 1672-9145.

Mark J. Pearson et al: "Albumin 3'untranslated region facilitates increased recombinant protein production from Chinese hamster ovary cells", Biotechnology Journal, vol. 7, No. 11, Nov. 1, 2012 (Nov. 1, 2012), pp. 1405-1411, XP055328368, DE ISSN: 1860-6768.

International Search Report for PCT Application No. PCT/EP2016/075415 dated Apr. 27, 2017.

Makino, Shigeru, et al. "Illegitimate translation causes unexpected gene expression from on-target out-of-frame alleles created by CRISPR-Cas9" Scientific Reports, Dec. 21, 2016, 6, 39608; doi: 10.1038/srep39608 (2016).

Nair, Ayyappan, R., et al. "Effect of different UCOE-prompter combinations in creation of engineered cell lines for the production of Factor VIII" BMC Research Notes, 2011, 4:178; doi: 10.1186/1756-0500-4-178.

Xia, Wei, et al. "High levels of protein expression using different mammalian CMV promoters in several cell lines" Protein Expression & Purification, 2006, 45, 115-124, doi: 10.1016/j.pep.2005.07.008.

Cook et al., "Genetic tools for reliable gene expression and recombineering in Pseudomonas putida", J. Ind. Microbiol. Biotechnol. Jul. 2018; vol. 45(7): pp. 517-527; doi: 10.1007/s10295-017-2001-5.

* cited by examiner

GCTGGGTACCGAAATTA*ATACGACTCACTATAGGG*AGACCCAAGCTGGCT*T*GCGTTTAAACTTAAG
CTTAGCGCAGAGGCTTGGGGCAGCCGAGCGGCAGCCAGGCCCCGGCCCGGGCCTCGGTTCCAGAAG
GGAGAGGAGCCCGCCAAGGCGCGCAAGAGAGCGGGCTGCCTCGCAGTCCGAGCCGGAGAGGGAGCG
CGAGCCGCGCCGGCCCCGGACGGCCTCCGAAACC*ATG*agggcctggatcttctttctcctttgcct
ggccgggagggctctggcagccccgctagccgag

FIG. 3A

GCTGGGTACCGAAATTA*ATACGACTCACTATAGGG*AGACCCAAGCTGGCT*T*GCGTTTAAACTTAAG
CTTAGCGCAGAGGCTTGGGGCAGCCGAGCGGCAGCCAGGCCCCGGCCCGGGCCTCGGTTCCAGAAG
GGAGAGGAGCCCGCCAAGGCGCGCAAGAGAGCGGGCTGCCTCGCAGTCCGAGCCGGAGAGGGAGCG
CGAGCCGCGCCGGCCCCGGACGGCCTCCGAAACC*ATG*ggagtcaaagttctgtttgccctgatctg
catcgctgtggccgaggccaagcccacgctagccgag

FIG. 3B

GCTGGGTACCGAAATTA*ATACGACTCACTATAGGG*AACCAGCCACC*ATG*ggagtcaaagttctgt
ttgccctgatctgcatcgctgtggccgaggccaagcccacgctagccgag

FIG. 3C

GCGCCCTGTAGCGGCGCATTAAGCGCGGCGGGTGTGGTGGTTACGCGCAGCGTGACCGCTACACT
TGCCAGCGCCCTAGCGCCCGCTCCTTTCGCTTTCTTCCCTTCCTTTCTCGCCACGTTCGCCGGCT
TTCCCCGTCAAGCTCTAAATCGGGGGCTCCCTTTAGGGTTCCGATTTAGTGCTTTACGGCACCTC
GACCCCAAAAAACTTGATTAGGGTGATGGTTCACGTAGTGGGCCATCGCCCTGATAGACGGTTTT
TCGCCCTTTGACGTTGGAGTCCACGTTCTTTAATAGTGGACTCTTGTTCCAAACTGGAACAACAC
TCAACCCTATCTCGGTCTATTCTTTTGATTTATAAGGGATTTTGCCGATTTCGGCCTATTGGTTA
AAAAATGAGCTGATTTAACAAAAATTTAACGCGAATTA

FIG. 3D cagCACGTGTTGACAATTAATCATCGGCATAGTATATCGGCATAGTATAATACGACAAGGTGAGGA
ACTAAATC

FIG. 3E

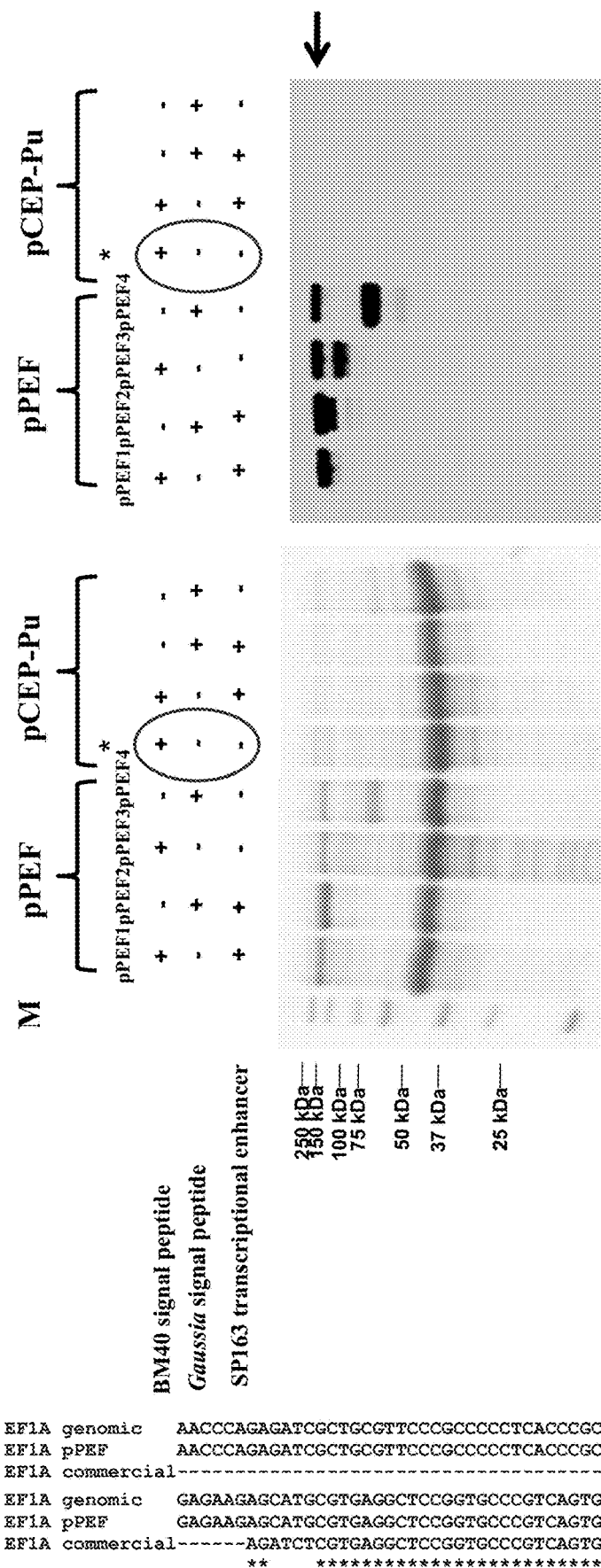

```
EF1A genomic     AACCCAGAGATCGCTGCGTTCCCGCCCCCTCACCCGCCCGCTCTCGTCATCACTGAGGTG  60
EF1A pPEF        AACCCAGAGATCGCTGCGTTCCCGCCCCCTCACCCGCCCGCTCTCGTCATCACTGAGGTG  60
EF1A commercial  ------------------------------------------------------------

EF1A genomic     GAGAAGAGCATGCGTGAGGCTCCGGTGCCCGTCAGTGGGCAGAGCGCACATCGCCCACAG  120
EF1A pPEF        GAGAAGAGCATGCGTGAGGCTCCGGTGCCCGTCAGTGGGCAGAGCGCACATCGCCCACAG  120
EF1A commercial  ------AGATCTCGTGAGGCTCCGGTGCCCGTCAGTGGGCAGAGCGCACATCGCCCACAG  54
                       **  ****************************************************
```

```
EF1A genomic      TCCCCGAGAAGTTGGGGGGAGGGGTCGGCAATTGAACCGGTGCCTAGAGAAGGTGGCGCG 180
EF1A pPEF         TCCCCGAGAAGTTGGGGGGAGGGGTCGGCAATTGAACCGGTGCCTAGAGAAGGTGGCGCG 180
EF1A commercial   TCCCCGAGAAGTTGGGGGGAGGGGTCGGCAATTGAACCGGTGCCTAGAGAAGGTGGCGCG 114
                  ************************************************************

EF1A genomic      GGGTAAACTGGGAAAGTGATGTCGTGTACTGGCTCCGCCTTTTCCCGAGGGTGGGGGAG 240
EF1A pPEF         GGGTAAACTGGGAAAGTGATGTCGTGTACTGGCTCCGCCTTTTCCCGAGGGTGGGGGAG 240
EF1A commercial   GGGTAAACTGGGAAAGTGATGTCGTGTACTGGCTCCGCCTTTTCCCGAGGGTGGGGGAG 174
                  ************************************************************

EF1A genomic      AACCGTATATAAGTGCAGTAGTCGCCGTGAACGTTCTTTTTCGCAACGGGTTTGCCGCCA 300
EF1A pPEF         AACCGTATATAAGTGCAGTAGTCGCCGTGAACGTTCTTTTTCGCAACGGGTTTGCCGCCA 300
EF1A commercial   AACCGTATATAAGTGCACTAGTCGCCGTGAACGTTCTTTTTCGCAACGGGTTTGCCGCCA 234
                  ***************** ******************************************

EF1A genomic      GAACACAGGTAAGTGCCGTGTGTGGTTCCCGCGGGCCTGGCCTCTTTACGGGTTATGGCC 360
EF1A pPEF         GAACACAGGT-------------------------------------------------- 310
EF1A commercial   GAACACAGGTAAGTGCCGTGTGTGGTTCCCGCGGGCCTGGCCTCTTTACGGGTTATGGCC 294
                  **********

EF1A genomic      CTTGCGTGCCTTGAATTACTTCCACGCCCCTGGCTGCAGTACGTGATTCTTGATCCCGAG 420
EF1A pPEF         ------------------------------------------------------------
EF1A commercial   CTTGCGTGCCTTGAATTACTTCCAC------CTGGCTGCAGTACGTGATTCTTGATCCCGAG 350

EF1A genomic      CTTCGGGTTGGAAGTGGGTGGGAGAGTTCGAGGCCTTGCGCTTAAGGAGCCCCTTCGCCT 480
EF1A pPEF         ------------------------------------------------------------
EF1A commercial   CTTCGGGTTGGAAGTGGGTGGGAGAGTTCGTGGCCTTGCGCTTAAGGAGCCCCTTCGCCT 410

EF1A genomic      CGTGCTTGAGTTGAGGCCTGGCCTGGGCGCTGGGGCCGCCGCGTGCGAATCGGTGGCAC 540
EF1A pPEF         ------------------------------------------------------------
EF1A commercial   CGTGCTTGAGTTGTGGCCTGGCCTGGGCGCTGGGGCCGCCGCGTGCGAATCGGTGGCAC 470

EF1A genomic      CTTCGCGCCTGTCTCGCTGCTTTCGATAAGTCTCTAGCCATTTAAAATTTTTGATGACCT 600
EF1A pPEF         ------------------------------------------------------------
EF1A commercial   CTTCGCGCCTGTCTCGCTGCTTTCGATAAGTCTCTAGCCATTTAAAATTTTTGATGACCT 530

EF1A genomic      GCTGCGACGCTTTTTTTCTGGCAAGATAGTCTTGTAAATGCGGGCCAAGATCTGCACACT 660
EF1A pPEF         ------------------------------------------------------------
EF1A commercial   GCTGCGACGCTTTTTTTCTGGCAAGATAGTCTTGTAAATGCGGGCCAAGATCAGCACACT 590

EF1A genomic      GGTATTTCGGTTTTTGGGGCCGCGGGCGGCGACGGGGCCCGTGCGTCCCAGCGCACATGT 720
EF1A pPEF         ------------------------------------------------------------
EF1A commercial   GGTATTTCGGTTTTTGGGGCCGCGGGCGGCGACGGGGCCCGTGCGTCCCAGCGCACATGT 650

EF1A genomic      TCGGCGAGGCGGGGCCTGCGAGCGCGGCCACCGAGAATCGGACGGGGGTAGTCTCAAGCT 780
EF1A pPEF         ------------------------------------------------------------
EF1A commercial   TCGGCGAGGCGGGGCCTGCGAGCGCGGCCACCGAGAATCGGACGGGGGTAGTCTCAAGCT 710

EF1A genomic      GGCCGGCCTGCTCTGGTGCCTGGCCTCGCGCCGCCGTGTATCGCCCCGCCCTGGGCGGCA 840
EF1A pPEF         ------------------------------------------------------------
EF1A commercial   GCCCGGCCTGCTCTGGTGCCTGGCCTCGCGCCGCCGTGTATCGCCCCGCCCTGGGCGGCA 770

EF1A genomic      AGGCTGGCCCGGTCGGCACCAGTTGCGTGAGCGGAAAGATGGCCGCTTCCCGGCCCTGCT 900
EF1A pPEF         ------------------------------------------------------------
EF1A commercial   AGGCTGGCCCGGTCGGCACCAGTTGCGTGAGCGGAAAGATGGCCGCTTCCCGGCCCTGCT 830
```

FIG. 6A

```
EF1A genomic     GCAGGGAGCTCAAAATGGAGGAGACGCGGGCTCGGGGAGAGCGGGCGGGTGAGTCACCCACA  960
EF1A pPEF        ------------------------------------------------------------
EF1A commercial  GCAGGGAGCACAAAATGGAGGAGACGCGGGCTCGGGGAGAGCGGGCGGGTGAGTCACCCACA 890

EF1A genomic     CAAAGGAAAAGGGCCCTTTCCGTCCTCAGCCGTCGCTTCATGTGACTCCACGGAGTACCGG 1020
EF1A pPEF        ------------------------------------------------------------
EF1A commercial  CAAAGGAAAAGGGCCCTTTCCGTCCTCAGCCGTCGCTTCATGTGACTCCACGGAGTACCGG  950

EF1A genomic     GCGCCGTCCAGGCACCTCGATTAGTTCTCGAGCTTTTGGAGTACGTCGTCTTTAGGTTGG 1080
EF1A pPEF        ------------------------------------------------------------
EF1A commercial  GCGCCGTCCAGGCACCTCGATTAGTTCTCCAGCTTTTGGAGTACGTCGTCTTTAGGTTGG 1010

EF1A genomic     GGGGAGGGGTTTTATGCGATGGAGTTTCCCCACACTGAGTGGGTGGAGACTGAAGTTAGG 1140
EF1A pPEF        ------------------------------------------------------------
EF1A commercial  GGGGAGGGGTTTTATGCGATGGAGTTTCCCCACACTGAGTGGGTGGAGACTGAAGTTAGG 1070

EF1A genomic     CCAGCTTGGCACTTGATGTAATTCTCCTTGGAATTTGCCCTTTTTGAGTTTGGATCTTGG 1200
EF1A pPEF        ------------------------------------------------------------
EF1A commercial  CCAGCTTGGCACTTGATGTAATTCTCCTTGGAATTTGCCCTTTTTGAGTTTGGATCTTGG 1130

EF1A genomic     TTCATTCTCAAGCCCTCAGACAGTGGTTCAAAGTTTTTTTCTTCCATTTCAGGTGTCGTGA 1260
EF1A pPEF        -----------------------------------------------GTCGTGA  317
EF1A commercial  TTCATTCTCAAGCCCTCAGACAGTGGTTCAAAGTTTTTTTCTTCCATTTCAGGTGTCGTGA 1190
                                                                ******

EF1A genomic     AAACTACCCCTAAAAGCCAAAATGGGAAAG 1290
EF1A pPEF        AAACTACCCCTAAAAGCCAAAATGG----  342
EF1A commercial  AAACTACCCCTAAAAGCCAAAAGATCT--- 1217
                 *********************
```

FIG. 6B gctagccgaggttaactgttgtcctggctgttgcggttccggacaccatcatcaccacca
tcaccatcaccattgaggatccagtgtggtggaattctgcagatatccagcacagtggcg
gccgctcgagtctagagggcccgtttaaacccgctgatcagcctcgactgtgccttctag
ttgccagccatctgttgtttgccctccccgtgccttccttgacctggaaggtgccac
tcccactgtcctttcctaataaaatgaggaaattgcatcgcattgtctgagtaggtgtca
ttctattctgggggtgggtggggcaggacagcaaggggaggattgggaagacaatag
caggcatgctggggatgcggtggctctatggcttctgaggcggaagaaccagctgggg
ctctagggggtatccccacgcgccctgtagcggcgcattaagcgcggcgggtgtggtggt
tacgcaacccagagatcgctgcgttcccgcccctcacccgcccgctctcgtcatcactg
aggtggagaagagcatgcgtgaggctccggtgcccgtcagtgggcagagcgcacatcgcc
cacagtccccgagaagttgggggagggtcggcaattgaaccggtgcctagagaaggtg
gcgcggggtaaactgggaaagtgatgtcgtgtactggctccgccttttcccgagggtgg
gggagaaccgtatataagtgcagtagtcgccgtgaacgttcttttcgcaacgggtttgc
cgccagaacacaggtgtcgtgaaaactaccctaaaagcttcaaaatggccaagttgaccag
tgccgttccggtgctcaccgcgcgcgacgtcgccggagcggtcgagttctggaccgaccg
gctcgggttctcccgggacttcgtggaggacgacttcgccggtgtggtccgggacgacgt
gaccctgttcatcagcgcggtccaggaccaggtggtgccggacaacaccctggcctgggt
gtgggtgcgcggcctggacgagctgtacgccgagtggtcggaggtcgtgtccacgaactt
ccgggacgcctccggccggccatgaccgagatcggcgagcagccgtggggcgggagtt
cgccctgcgcgacccggccggcaactgcgtgcacttcgtggccgaggagcaggactgaca
cgtg

FIG. 6C gctagccgaggttaactgttgtcctggctgttgcggttccggacaccatcatcaccacca
tcaccatcaccattgaggatccagtgtggtggaattctgcagatatccagcacagtggcg
gccgctcgagtctagagggcccgtttaaacccgctgatcagcctcgactgtgccttctag
ttgccagccatctgttgtttgccctccccgtgccttccttgacctggaaggtgccac
tcccactgtcctttcctaataaaatgaggaaattgcatcgcattgtctgagtaggtgtca
ttctattctgggggtgggtggggcaggacagcaaggggaggattgggaagacaatag
caggcatgctggggatgcggtggctctatggcttctgaggcggaagaaccagctgggg
ctctagggggtatccccacgcgccctgtagcggcgcattaagcgcggcgggtgtggtggt
tacgcctgtggaatgtgtgtcagttagggtgtggaaagtccccaggctccccagcaggca
gaagtatgcaaagcatgcatctcaattagtcagcaaccaggtgtggaaagtccccaggct
ccccagcaggcagaagtatgcaaagcatgcatctcaattagtcagcaaccatagtcccgc
ccctaactccgcccatcccgcccctaactccgcccagttccgcccattctccgcccatg
gctgactaattttttttatttatgcagaggccgaggccgcctctgcctctgagctattcc
agaagtagtgaggaggctttttggaggcctaggcttttgcaaaaagcttaaaatggccaa
gttgaccagtgccgttccggtgctcaccgcgcgcgacgtcgccggagcggtcgagttctg
gaccgaccggctcgggttctcccgggacttcgtggaggacgacttcgccggtgtggtccg
ggacgacgtgaccctgttcatcagcgcggtccaggaccaggtggtgccggacaacaccct
ggcctgggtgtgggtgcgcggcctggacgagctgtacgccgagtggtcggaggtcgtgtc
cacgaacttccgggacgcctccggccggccatgaccgagatcggcgagcagccgtgggg
gcgggagttcgccctgcgcgacccggccggcaactgcgtgcacttcgtggccgaggagca
ggactgacacgtg

FIG. 6D

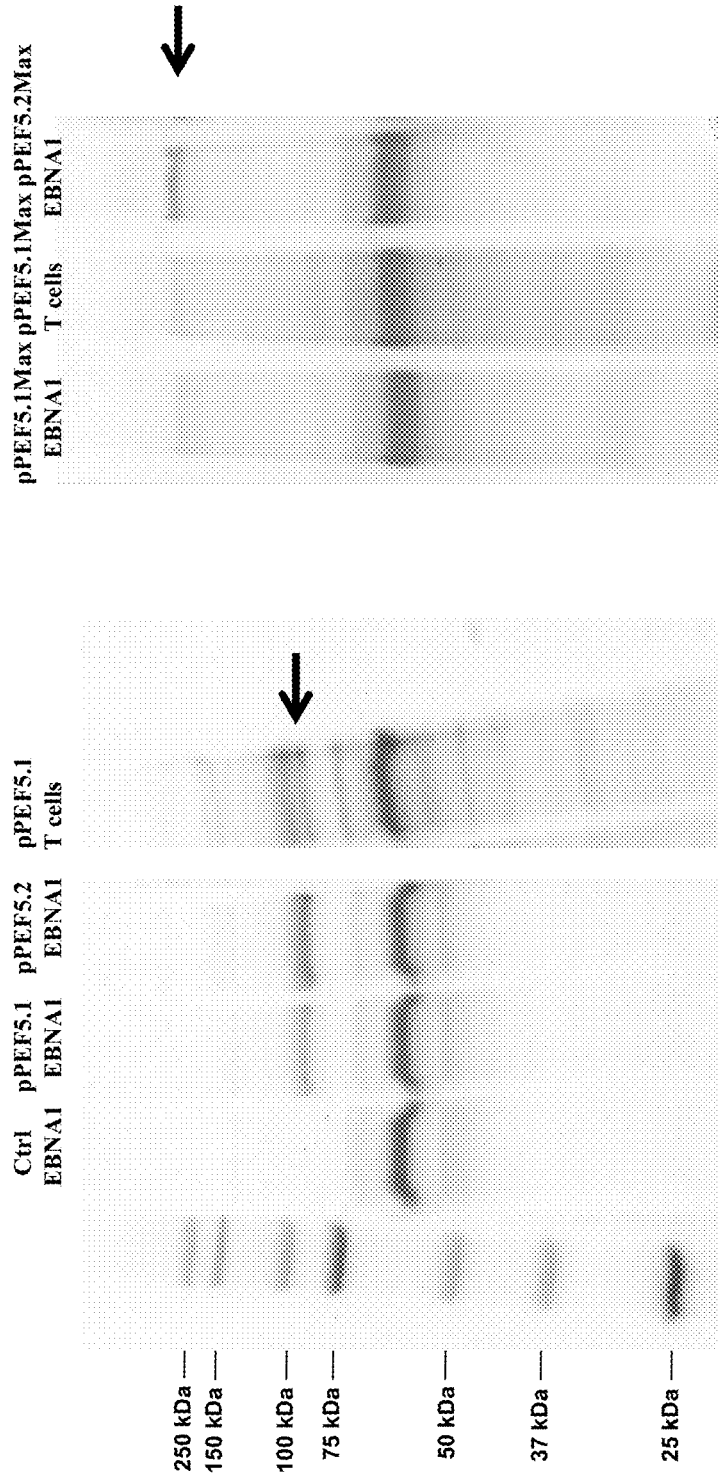

Coomassie staining

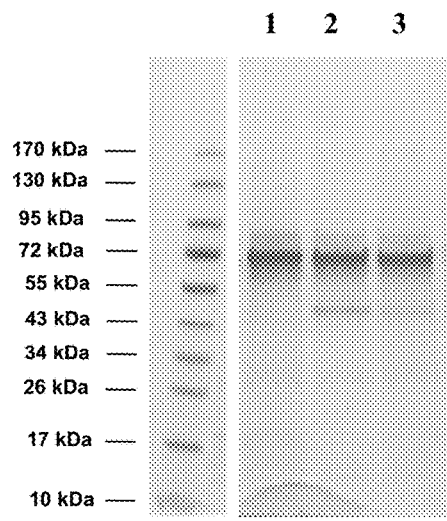

FIG. 9A

Western analysis

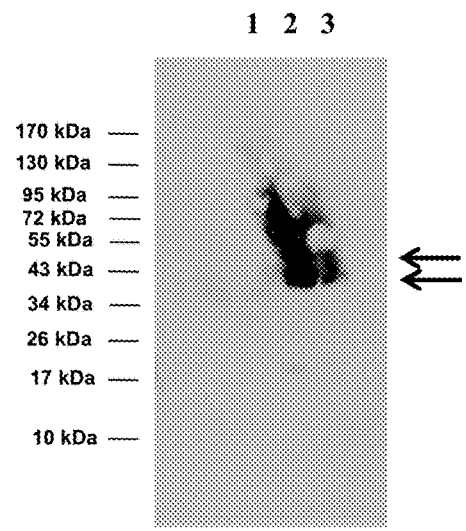

FIG. 9B

HHHHHHHHHHGSLQDSEVNQEAKPEVKPEVKPETHINLKVSDGSSEIFFKIKKTTPLRRLMEAFAK
RQGKEMDSLTFLYDGIEIQADQTPEDLDMEDNDIIEAHREQIGGQHYLHIRPAPSDNLPLVDLIEH
PDPIFDPKEKDLNETLLRSLLGGHYDPGFMATSPPEDRPGGGGGPAGGAEDLAELDQLLRQRPSGA
MPSEIKGLEFSEGLAQGKKQRLSKKLRRKLQMWLWSQTFCPVLYAWNDLGSRFWPRYVKVGSCFSK
RSCSVPEGMVCKPSKSVHLTVLRWRCQRRGGQRCGW
IPIQYPIISECKCSC

FIG. 9C

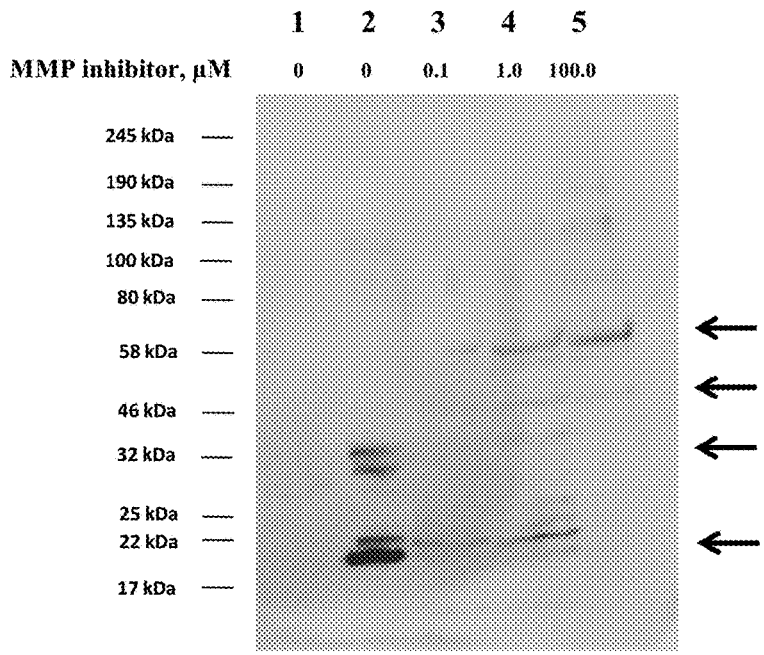

FIG. 13

LAEGVAAALTPERLLEWQDKGIFVIQSESLKKCIQAGKSVLTLENCKQANKHMLWKWVSNHGLFNIGGSG
CLGLNFSAPEQPLSLYECDSTLVSLRWRCNRKMITGPLQYSVQVAHDNTVVASRKYIHKWISYGSGGGDIC
EYLHKDLHTIKGNTGSGHHHHHHHHHHRRKRGSG<u>ATNFSLLKQAGDVEENPGPQEGWERHGGFCYKID</u>
<u>TVLRSFDQASSGYYCPPALVTITNRFEQAFITSLISSVVKMKDSYFWIALQDQNDTGEYTWKPVGQKPEPV</u>
<u>QYTHWNTHQPRYSGGCVAMRGRHPLGRWEVKHCRHFKAMSLCKQPVENQEKAEYEERWP</u>GSHHH
HHHHHH

FIG. 14

| Name | Min/Max | Length | Direction | Type |
|---|---|---|---|---|
| CMV enhancer | 235..614 | 380 | == | enhancer |
| CMV promoter | 615..818 | 204 | => | promoter |
| pCEP Forward primer | 810..832 | 23 | => | primer_bind |
| T7 promoter | 862..880 | 19 | => | primer_bind |
| GLuc Signal Peptide | 894..948 | 55 | => | sig_peptide |
| MCS | 952..1046 | 95 | == | polylinker |
| BGH Reverse pimer | 1058..1075 | 18 | <= | primer_bind |
| bGH poly(A) signal | 1064..1288 | 225 | == | polyA_signal |
| SV40 promoter | 1391..1720 | 330 | => | promoter |
| BleoR/Zeocin | 1730..2104 | 375 | => | CDS |
| SV40 poly(A) signal | 2234..2355 | 122 | == | polyA_signal |
| ori | 2806..3394 | 589 | <= | rep_origin |
| AmpR | 3565..4425 | 861 | <= | CDS |
| AmpR promoter | 4426..4530 | 105 | <= | promoter |

FIG. 18 pPEF5.2 sequence:

```
GACGGATCGG GAGATCTCCC GATCCCCTAT GGTCGACTCT CAGTACAATC TGCTCTGATG    60
CCGCATAGTT AAGCCAGTAT CTGCTCCCTG CTTGTGTGTT GGAGGTCGCT GAGTAGTGCG   120
CGAGCAAAAT TAAGCTACA  ACAAGGCAAG GCTTGACCGA CAATTGCATG AAGAATCTGC   180
TTAGGGTTAG GCGTTTTGCG CTGCTTCGCG ATGTACGGGC CAGATATACG CGTTGACATT   240
GATTATTGAC TAGTTATTAA TAGTAATCAA TTACGGGGTC ATTAGTTCAT AGCCCATATA   300
TGGAGTTCCG CGTTACATAA CTTACGGTAA ATGGCCCGCC TGGCTGACCG CCCAACGACC   360
CCCGCCCATT GACGTCAATA ATGACGTATG TTCCCATAGT AACGCCAATA GGGACTTTCC   420
ATTGACGTCA ATGGGTGGAC TATTTACGGT AAACTGCCCA CTTGGCAGTA CATCAAGTGT   480
ATCATATGCC AAGTCCGCCC CCTATTGACG TCAATGACGG TAAATGGCCC GCCTGGCATT   540
ATGCCCAGTA CATGACCTTA CGGGACTTTC CTACTTGGCA GTACATCTAC GTATTAGTCA   600
TCGCTATTAC CATGGTGATG CGGTTTTGGC AGTACACCAA TGGGCGTGGA TAGCGGTTTG   660
ACTCACGGGG ATTTCCAAGT CTCCACCCCA TTGACGTCAA TGGGAGTTTG TTTTGGCACC   720
AAAATCAACG GGACTTTCCA AAATGTCGTA ATAACCCCGC CCGTTGACG  CAAATGGGCG   780
GTAGGCGTGT ACGGTGGGAG GTCTATATAA GCAGAGCTCG TTTAGTGAAC CGTCAGATCT   840
CTAGAAGCTG GGTACCGAAA TTAATACGAC TCACTATAGG GAACCAGCC  ACCATGGGAG   900
TCAAAGTTCT GTTTGCCCTG ATCTGCATCG CTGTGGCCGA GGCCAAGCCC ACGCTAGCCG   960
AGGTTGCTTT GAGGATCCAG TGTGGTGGAA TTCTGCAGAT ATCCAGCACA GTGGCGGCCG  1020
CTCGAGTCTA GAGGGCCCGT TTAAACCCGC TGATCAGCCT CGACTGTGCC TTCTAGTTGC  1080
CAGCCATCTG TTGTTTGCCC CTCCCCCGTG CCTTCCTTGA CCCTGGAAGG TGCCACTCCC  1140
ACTGTCCTTT CCTAATAAAA TGAGGAAATT GCATCGCATT GTCTGAGTAG GTGTCATTCT  1200
ATTCTGGGGG GTGGGGTGGG GCAGGACAGC AAGGGGGAGG ATTGGGAAGA CAATAGCAGG  1260
CATGCTGGGG ATGCGGTGGG CTCTATGGCT TCTGAGGCGG AAAGAACCAG CTGGGGCTCT  1320
AGGGGGTATC CCCACGCGCC CTGTAGCGGC GCATTAAGCG CGGCGGGTGT GGTGGTTACG  1380
CCTGTGGAAT GTGTGTCAGT TAGGGTGTGG AAAGTCCCCA GGCTCCCCAG CAGGCAGAAG  1440
TATGCAAAGC ATGCATCTCA ATTAGTCAGC AACCAGGTGT GGAAAGTCCC CAGGCTCCCC  1500
AGCAGGCAGA AGTATGCAAA GCATGCATCT CAATTAGTCA GCAACCATAG TCCCGCCCCT  1560
AACTCCGCCC ATCCCGCCCC TAACTCCGCC CAGTTCCGCC CATTCTCCGC CCCATGGCTG  1620
ACTAATTTTT TTTATTTATG CAGAGGCCGA GGCCGCCTCT GCCTCTGAGC TATTCCAGAA  1680
GTAGTGAGGA GGCTTTTTTG GAGGCCTAGG CTTTTGCAAA AAGCTTAAAA TGGCCAAGTT  1740
GACCAGTGCC GTTCCGGTGC TCACCGCGCG CGACGTCGCC GGAGCGGTCG AGTTCTGGAC  1800
CGACCGGCTC GGGTTCTCCC GGGACTTCGT GGAGGACGAC TTCGCCGGTG TGGTCCGGGA  1860
CGACGTGACC CTGTTCATCA GCGCGGTCCA GGACCAGGTG GTGCCGGACA ACACCCTGGC  1920
CTGGGTGTGG GTGCGCGGCC TGGACGAGCT GTACGCCGAG TGGTCGGAGG TCGTGTCCAC  1980
GAACTTCCGG GACGCCTCCG GCCGGCCAT  GACCGAGATC GGCGAGCAGC CGTGGGGGCG  2040
GGAGTTCGCC CTGCGCGACC CGGCCGGCAA CTGCGTGCAC TTCGTGGCCG AGGAGCAGGA  2100
CTGACACGTG CTACGAGATT TCGATTCCAC CGCCGCCTTC TATGAAAGGT TGGGCTTCGG  2160
AATCGTTTTC CGGGACGCCG GCTGGATGAT CCTCCAGCGC GGGATCTCA  TGCTGGAGTT  2220
CTTCGCCCAC CCCAACTTGT TTATTGCAGC TTATAATGGT TACAAATAAA GCAATAGCAT  2280
CACAAATTTC ACAAATAAAG CATTTTTTTC ACTGCATTCT AGTTGTGGTT TGTCCAAACT  2340
CATCAATGTA TCTTATCATG TCTGTATACC GTCGACCTCT AGCTAGAGCT TGGCGTAATC  2400
ATGGTCATAG CTGTTTCCTG TGTGAAATTG TTATCCGCTC ACAATTCCAC ACAACATACG  2460
AGCCGGAAGC ATAAAGTGTA AAGCCTGGGG TGCCTAATGA GTGAGCTAAC TCACATTAAT  2520
TGCGTTGCGC TCACTGCCCG CTTTCCAGTC GGGAAACCTG TCGTGCCAGC TGCATTAATG  2580
AATCGGCCAA CGCGCGGGA  GAGGCGGTTT GCGTATTGGG CGCTCTTCCG CTTCCTCGCT  2640
CACTGACTCG CTGCGCTCGG TCGTTCGGCT GCGGCGAGCG GTATCAGCTC ACTCAAAGGC  2700
GGTAATACGG TTATCCACAG AATCAGGGGA TAACGCAGGA AGAACATGT  GAGCAAAAGG  2760
```

FIG. 19A

```
CCAGCAAAAG GCCAGGAACC GTAAAAAGGC CGCGTTGCTG GCGTTTTTCC ATAGGCTCCG  2820
CCCCCCTGAC GAGCATCACA AAAATCGACG CTCAAGTCAG AGGTGGCGAA ACCCGACAGG  2880
ACTATAAAGA TACCAGGCGT TTCCCCCTGG AAGCTCCCTC GTGCGCTCTC CTGTTCCGAC  2940
CCTGCCGCTT ACCGGATACC TGTCCGCCTT CTCCCTTCG GGAAGCGTGG CGCTTTCTCA  3000
ATGCTCACGC TGTAGGTATC TCAGTTCGGT GTAGGTCGTT CGCTCCAAGC TGGGCTGTGT  3060
GCACGAACCC CCCGTTCAGC CCGACCGCTG CGCCTTATCC GGTAACTATC GTCTTGAGTC  3120
CAACCCGGTA AGACACGACT TATCGCCACT GGCAGCAGCC ACTGGTAACA GGATTAGCAG  3180
AGCGAGGTAT GTAGGCGGTG CTACAGAGTT CTTGAAGTGG TGGCCTAACT ACGGCTACAC  3240
TAGAAGGACA GTATTTGGTA TCTGCGCTCT GCTGAAGCCA GTTACCTTCG GAAAAGAGT  3300
TGGTAGCTCT TGATCCGGCA ACAAACCAC CGCTGGTAGC GGTGGTTTTT TTGTTTGCAA  3360
GCAGCAGATT ACGCGCAGAA AAAAAGGATC TCAAGAAGAT CCTTTGATCT TTTCTACGGG  3420
GTCTGACGCT CAGTGGAACG AAAACTCACG TTAAGGGATT TTGGTCATGA GATTATCAAA  3480
AAGGATCTTC ACCTAGATCC TTTTAAATTA AAAATGAAGT TTTAAATCAA TCTAAAGTAT  3540
ATATGAGTAA ACTTGGTCTG ACAGTTACCA ATGCTTAATC AGTGAGGCAC CTATCTCAGC  3600
GATCTGTCTA TTTCGTTCAT CCATAGTTGC CTGACTCCCC GTCGTGTAGA TAACTACGAT  3660
ACGGGAGGGC TTACCATCTG GCCCCAGTGC TGCAATGATA CCGCGAGACC CACGCTCACC  3720
GGCTCCAGAT TTATCAGCAA TAAACCAGCC AGCCGGAAGG GCCGAGCGCA GAAGTGGTCC  3780
TGCAACTTTA TCCGCCTCCA TCCAGTCTAT TAATTGTTGC CGGGAAGCTA GAGTAAGTAG  3840
TTCGCCAGTT AATAGTTTGC GCAACGTTGT TGCCATTGCT ACAGGCATCG TGGTGTCACG  3900
CTCGTCGTTT GGTATGGCTT CATTCAGCTC CGGTTCCCAA CGATCAAGGC GAGTTACATG  3960
ATCCCCCATG TTGTGCAAAA AAGCGGTTAG CTCCTTCGGT CCTCCGATCG TTGTCAGAAG  4020
TAAGTTGGCC GCAGTGTTAT CACTCATGGT TATGGCAGCA CTGCATAATT CTCTTACTGT  4080
CATGCCATCC GTAAGATGCT TTTCTGTGAC TGGTGAGTAC TCAACCAAGT CATTCTGAGA  4140
ATAGTGTATG CGGCGACCGA GTTGCTCTTG CCCGGCGTCA ATACGGGATA ATACCGCGCC  4200
ACATAGCAGA ACTTTAAAAG TGCTCATCAT GGAAAACGT TCTTCGGGGC GAAAACTCTC  4260
AAGGATCTTA CCGCTGTTGA GATCCAGTTC GATGTAACCC ACTCGTGCAC CCAACTGATC  4320
TTCAGCATCT TTTACTTTCA CCAGCGTTTC TGGGTGAGCA AAAACAGGAA GGCAAAATGC  4380
CGCAAAAAAG GGAATAAGGG CGACACGGAA ATGTTGAATA CTCATACTCT TCCTTTTTCA  4440
ATATTATTGA AGCATTTATC AGGGTTATTG TCTCATGAGC GGATACATAT TTGAATGTAT  4500
TTAGAAAAAT AAACAAATAG GGGTTCCGCG CACATTTCCC CGAAAAGTGC CACCTGACGT  4560
C                                                                  4561
```

FIG. 19B pPEF5.2 Max

```
GACGGATCGG GAGATCTCCC GATCCCCTAT GGTCGACTCT CAGTACAATC TGCTCTGATG    60
CCGCATAGTT AAGCCAGTAT CTGCTCCCTG CTTGTGTGTT GGAGGTCGCT GAGTAGTGCG   120
CGAGCAAAAT TTAAGCTACA ACAAGGCAAG GCTTGACCGA CAATTGCATG AAGAATCTGC   180
TTAGGGTTAG GCGTTTTGCG CTGCTTCGCG ATGTACGGGC CAGATATACG CGTTGACATT   240
GATTATTGAC TAGTTATTAA TAGTAATCAA TTACGGGGTC ATTAGTTCAT AGCCCATATA   300
TGGAGTTCCG CGTTACATAA CTTACGGTAA ATGGCCCGCC TGGCTGACCG CCCAACGACC   360
CCCGCCCATT GACGTCAATA ATGACGTATG TTCCCATAGT AACGCCAATA GGGACTTTCC   420
ATTGACGTCA ATGGGTGGAC TATTTACGGT AAACTGCCCA CTTGGCAGTA CATCAAGTGT   480
ATCATATGCC AAGTCCGCCC CCTATTGACG TCAATGACGG TAAATGGCCC GCCTGGCATT   540
ATGCCCAGTA CATGACCTTA CGGGACTTTC CTACTTGGCA GTACATCTAC GTATTAGTCA   600
TCGCTATTAC CATGGTGATG CGGTTTTGGC AGTACACCAA TGGGCGTGGA TAGCGGTTTG   660
ACTCACGGGG ATTTCCAAGT CTCCACCCCA TTGACGTCAA TGGGAGTTTG TTTTGGCACC   720
AAAATCAACG GGACTTTCCA AAATGTCGTA ATAACCCCGC CCCGTTGACG CAAATGGGCG   780
GTAGGCGTGT ACGGTGGGAG GTCTATATAA GCAGAGCTCG TTTAGTGAAC CGTCAGATCT   840
CTAGAAGCTG GGTACCGAAA TTAATACGAC TCACTATAGG GAGACCCAAG CTGGCTTGCG   900
TTTAAACTTA AGCTTAGCGC AGAGGCTTGG GGCAGCCGAG CGGCAGCCAG GCCCCGGCCC   960
GGGCCTCGGT TCCAGAAGGG AGAGGAGCCC GCCAAGGCGC GCAAGAGAGC GGGCTGCCTC  1020
GCAGTCCGAG CCGGAGAGGG AGCGCGAGCC GCGCCGGCCC CGGACGGCCT CCGAAACCAT  1080
GGGAGTCAAA GTTCTGTTTG CCCTGATCTG CATCGCTGTG GCCGAGGCCA AGCCCACGCT  1140
AGCCGAGGTT GCTTTGAGGA TCCAGTGTGG TGGAATTCTG CAGATATCCA GCACAGTGGC  1200
GGCCGCTCGA GTCTAGAGGG CCCGTTTAAA CCCGCTGATC AGCCTCGACT GTGCCTTCTA  1260
GTTGCCAGCC ATCTGTTGTT TGCCCCTCCC CCGTGCCTTC CTTGACCCTG GAAGGTGCCA  1320
CTCCCACTGT CCTTTCCTAA TAAAATGAGG AAATTGCATC GCATTGTCTG AGTAGGTGTC  1380
ATTCTATTCT GGGGGGTGGG GTGGGGCAGG ACAGCAAGGG GGAGGATTGG GAAGACAATA  1440
GCAGGCATGC TGGGGATGCG GTGGGCTCTA TGGCTTCTGA GGCGGAAAGA ACCAGCTGGG  1500
GCTCTAGGGG GTATCCCCAC GCGCCCTGTA GCGGCGCATT AAGCGCGGCG GGTGTGGTGG  1560
TTACGCCTGT GGAATGTGTG TCAGTTAGGG TGTGGAAAGT CCCCAGGCTC CCCAGCAGGC  1620
AGAAGTATGC AAAGCATGCA TCTCAATTAG TCAGCAACCA GGTGTGGAAA GTCCCCAGGC  1680
TCCCCAGCAG GCAGAAGTAT GCAAAGCATG CATCTCAATT AGTCAGCAAC CATAGTCCCG  1740
CCCCTAACTC CGCCCATCCC GCCCCTAACT CCGCCCAGTT CCGCCCATTC TCCGCCCCAT  1800
GGCTGACTAA TTTTTTTTAT TTATGCAGAG GCCGAGGCCG CCTCTGCCTC TGAGCTATTC  1860
CAGAAGTAGT GAGGAGGCTT TTTTGGAGGC CTAGGCTTTT GCAAAAAGCT TAAAATGGCC  1920
AAGTTGACCA GTGCCGTTCC GGTGCTCACC GCGCGCGACG TCGCCGGAGC GGTCGAGTTC  1980
TGGACCGACC GGCTCGGGTT CTCCCGGGAC TTCGTGGAGG ACGACTTCGC CGGTGTGGTC  2040
CGGGACGACG TGACCCTGTT CATCAGCGCG GTCCAGGACC AGGTGGTGCC GGACAACACC  2100
CTGGCCTGGG TGTGGGTGCG CGGCCTGGAC GAGCTGTACG CCGAGTGGTC GGAGGTCGTG  2160
TCCACGAACT TCCGGGACGC CTCCGGGCCG GCCATGACCG AGATCGGCGA GCAGCCGTGG  2220
GGGCGGGAGT TCGCCCTGCG CGACCCGGCC GGCAACTGCG TGCACTTCGT GGCCGAGGAG  2280
CAGGACTGAC ACGTGCTACG AGATTTCGAT TCCACCGCCG CCTTCTATGA AAGGTTGGGC  2340
TTCGGAATCG TTTTCCGGGA CGCCGGCTGG ATGATCCTCC AGCGCGGGGA TCTCATGCTG  2400
GAGTTCTTCG CCCACCCCAA CTTGTTTATT GCAGCTTATA ATGGTTACAA ATAAAGCAAT  2460
AGCATCACAA ATTTCACAAA TAAAGCATTT TTTTCACTGC ATTCTAGTTG TGGTTTGTCC  2520
AAACTCATCA ATGTATCTTA TCATGTCTGT ATACCGTCGA CCTCTAGCTA GAGCTTGGCG  2580
TAATCATGGT CATAGCTGTT TCCTGTGTGA AATTGTTATC CGCTCACAAT TCCACACAAC  2640
ATACGAGCCG GAAGCATAAA GTGTAAAGCC TGGGGTGCCT AATGAGTGAG CTAACTCACA  2700
TTAATTGCGT TGCGCTCACT GCCCGCTTTC CAGTCGGGAA ACCTGTCGTG CCAGCTGCAT  2760
TAATGAATCG GCCAACGCGC GGGGAGAGGC GGTTTGCGTA TTGGGCGCTC TTCCGCTTCC  2820
```

FIG. 20A

```
TCGCTCACTG ACTCGCTGCG CTCGGTCGTT CGGCTGCGGC GAGCGGTATC AGCTCACTCA  2880
AAGGCGGTAA TACGGTTATC CACAGAATCA GGGGATAACG CAGGAAAGAA CATGTGAGCA  2940
AAAGGCCAGC AAAAGGCCAG GAACCGTAAA AAGGCCGCGT TGCTGGCGTT TTTCCATAGG  3000
CTCCGCCCCC CTGACGAGCA TCACAAAAAT CGACGCTCAA GTCAGAGGTG GCGAAACCCG  3060
ACAGGACTAT AAAGATACCA GGCGTTTCCC CCTGGAAGCT CCCTCGTGCG CTCTCCTGTT  3120
CCGACCCTGC CGCTTACCGG ATACCTGTCC GCCTTTCTCC CTTCGGGAAG CGTGGCGCTT  3180
TCTCAATGCT CACGCTGTAG GTATCTCAGT TCGGTGTAGG TCGTTCGCTC CAAGCTGGGC  3240
TGTGTGCACG AACCCCCCGT TCAGCCCGAC CGCTGCGCCT TATCCGGTAA CTATCGTCTT  3300
GAGTCCAACC CGGTAAGACA CGACTTATCG CCACTGGCAG CAGCCACTGG TAACAGGATT  3360
AGCAGAGCGA GGTATGTAGG CGGTGCTACA GAGTTCTTGA AGTGGTGGCC TAACTACGGC  3420
TACACTAGAA GGACAGTATT TGGTATCTGC GCTCTGCTGA AGCCAGTTAC CTTCGGAAAA  3480
AGAGTTGGTA GCTCTTGATC CGGCAAACAA ACCACCGCTG GTAGCGGTGG TTTTTTTGTT  3540
TGCAAGCAGC AGATTACGCG CAGAAAAAAA GGATCTCAAG AAGATCCTTT GATCTTTTCT  3600
ACGGGGTCTG ACGCTCAGTG GAACGAAAAC TCACGTTAAG GGATTTTGGT CATGAGATTA  3660
TCAAAAGGA TCTTCACCTA GATCCTTTTA AATTAAAAAT GAAGTTTTAA ATCAATCTAA  3720
AGTATATATG AGTAAACTTG GTCTGACAGT TACCAATGCT TAATCAGTGA GGCACCTATC  3780
TCAGCGATCT GTCTATTTCG TTCATCCATA GTTGCCTGAC TCCCCGTCGT GTAGATAACT  3840
ACGATACGGG AGGGCTTACC ATCTGGCCCC AGTGCTGCAA TGATACCGCG AGACCCACGC  3900
TCACCGGCTC CAGATTTATC AGCAATAAAC CAGCCAGCCG GAAGGGCCGA GCGCAGAAGT  3960
GGTCCTGCAA CTTTATCCGC CTCCATCCAG TCTATTAATT GTTGCCGGGA AGCTAGAGTA  4020
AGTAGTTCGC CAGTTAATAG TTTGCGCAAC GTTGTTGCCA TTGCTACAGG CATCGTGGTG  4080
TCACGCTCGT CGTTTGGTAT GGCTTCATTC AGCTCCGGTT CCCAACGATC AAGGCGAGTT  4140
ACATGATCCC CCATGTTGTG CAAAAAAGCG GTTAGCTCCT TCGGTCCTCC GATCGTTGTC  4200
AGAAGTAAGT TGGCCGCAGT GTTATCACTC ATGGTTATGG CAGCACTGCA TAATTCTCTT  4260
ACTGTCATGC CATCCGTAAG ATGCTTTTCT GTGACTGGTG AGTACTCAAC CAAGTCATTC  4320
TGAGAATAGT GTATGCGGCG ACCGAGTTGC TCTTGCCCGG CGTCAATACG GATAATACC  4380
GCGCCACATA GCAGAACTTT AAAAGTGCTC ATCATTGGAA AACGTTCTTC GGGGCGAAAA  4440
CTCTCAAGGA TCTTACCGCT GTTGAGATCC AGTTCGATGT AACCCACTCG TGCACCCAAC  4500
TGATCTTCAG CATCTTTTAC TTTCACCAGC GTTTCTGGGT GAGCAAAAAC AGGAAGGCAA  4560
AATGCCGCAA AAAAGGGAAT AAGGGCGACA CGGAAATGTT GAATACTCAT ACTCTTCCTT  4620
TTTCAATATT ATTGAAGCAT TTATCAGGGT TATTGTCTCA TGAGCGGATA CATATTTGAA  4680
TGTATTTAGA AAAATAAACA AATAGGGGTT CCGCGCACAT TTCCCCGAAA AGTGCCACCT  4740
GACGTC                                                             4746
```

FIG. 20B pPEF1

```
GACGGATCGG GAGATCTCCC GATCCCCTAT GGTCGACTCT CAGTACAATC TGCTCTGATG    60
CCGCATAGTT AAGCCAGTAT CTGCTCCCTG CTTGTGTGTT GGAGGTCGCT GAGTAGTGCG   120
CGAGCAAAAT TTAAGCTACA ACAAGGCAAG GCTTGACCGA CAATTGCATG AAGAATCTGC   180
TTAGGGTTAG GCGTTTTGCG CTGCTTCGCG ATGTACGGGC CAGATATACG CGTTGACATT   240
GATTATTGAC TAGTTATTAA TAGTAATCAA TTACGGGGTC ATTAGTTCAT AGCCCATATA   300
TGGAGTTCCG CGTTACATAA CTTACGGTAA ATGGCCCGCC TGGCTGACCG CCCAACGACC   360
CCCGCCCATT GACGTCAATA ATGACGTATG TTCCCATAGT AACGCCAATA GGGACTTTCC   420
ATTGACGTCA ATGGGTGGAC TATTTACGGT AAACTGCCCA CTTGGCAGTA CATCAAGTGT   480
ATCATATGCC AAGTCCGCCC CCTATTGACG TCAATGACGG TAAATGGCCC GCCTGGCATT   540
ATGCCCAGTA CATGACCTTA CGGGACTTTC CTACTTGGCA GTACATCTAC GTATTAGTCA   600
TCGCTATTAC CATGGTGATG CGGTTTTGGC AGTACACCAA TGGGCGTGGA TAGCGGTTTG   660
ACTCACGGGG ATTTCCAAGT CTCCACCCCA TTGACGTCAA TGGGAGTTTG TTTTGGCACC   720
AAAATCAACG GGACTTTCCA AAATGTCGTA ATAACCCCGC CCCGTTGACG CAAATGGGCG   780
GTAGGCGTGT ACGGTGGGAG GTCTATATAA GCAGAGCTCG TTTAGTGAAC CGTCAGATCT   840
CTAGAAGCTG GGTACCGAAA TTAATACGAC TCACTATAGG GAGACCCAAG CTGGCTTGCG   900
TTTAAACTTA AGCTTAGCGC AGAGGCTTGG GGCAGCCGAG CGGCAGCCAG GCCCCGGCCC   960
GGGCCTCGGT TCCAGAAGGG AGAGGAGCCC GCCAAGGCGC GCAAGAGAGC GGGCTGCCTC  1020
GCAGTCCGAG CCGGAGAGGG AGCGCGAGCC GCGCCGGCCC CGGACGGCCT CCGAAACCAT  1080
GAGGGCCTGG ATCTTCTTTC TCCTTTGCCT GGCCGGGAGG GCTCTGGCAG CCCCGCTAGC  1140
CGAGGGATCC AGTGTGGTGG AATTCTGCAG ATATCCAGCA CAGTGGCGGC CGCTCGAGTC  1200
TAGAGGGCCC GTTTAAACCC GCTGATCAGC CTCGACTGTG CCTTCTAGTT GCCAGCCATC  1260
TGTTGTTTGC CCCTCCCCCG TGCCTTCCTT GACCCTGGAA GGTGCCACTC CCACTGTCCT  1320
TTCCTAATAA AATGAGGAAA TTGCATCGCA TTGTCTGAGT AGGTGTCATT CTATTCTGGG  1380
GGGTGGGGTG GGCAGGACA GCAAGGGGGA GGATTGGGAA GACAATAGCA GGCATGCTGG  1440
GGATGCGGTG GGCTCTATGG CTTCTGAGGC GGAAAGAACC AGCTGGGGCT CTAGGGGGTA  1500
TCCCCACGCG CCCTGTAGCG GCGCATTAAG CGCGGCGGGT GTGGTGGTTA CGCGCAGCGT  1560
GACCGCTACA CTTGCCAGCG CCCTAGCGCC CGCTCCTTTC GCTTTCTTCC CTTCCTTTCT  1620
CGCCACGTTC GCCGGCTTTC CCCGTCAAGC TCTAAATCGG GGCATCCCTT TAGGGTTCCG  1680
ATTTAGTGCT TTACGGCACC TCGACCCCAA AAAACTTGAT TAGGGTGATG GTTCACGTAG  1740
TGGGCCATCG CCCTGATAGA CGGTTTTTCG CCCTTTGACG TTGGAGTCCA CGTTCTTTAA  1800
TAGTGGACTC TTGTTCCAAA CTGGAACAAC ACTCAACCCT ATCTCGGTCT ATTCTTTTGA  1860
TTTATAAGGG ATTTTGGGGA TTTCGGCCTA TTGGTTAAAA AATGAGCTGA TTTAACAAAA  1920
ATTTAACGCG AATTAATTCT GTGGAATGTG TGTCAGTTAG GGTGTGGAAA GTCCCCAGGC  1980
TCCCCAGGCA GGCAGAAGTA TGCAAAGCAT GCATCTCAAT TAGTCAGCAA CCAGGTGTGG  2040
AAAGTCCCCA GGCTCCCCAG CAGGCAGAAG TATGCAAAGC ATGCATCTCA ATTAGTCAGC  2100
AACCATAGTC CCGCCCCTAA CTCCGCCCAT CCCGCCCCTA ACTCCGCCCA GTTCCGCCCA  2160
TTCTCCGCCC CATGGCTGAC TAATTTTTTT TATTTATGCA GAGGCCGAGG CCGCCTCTGC  2220
CTCTGAGCTA TTCCAGAAGT AGTGAGGAGG CTTTTTTGGA GGCCTAGGCT TTTGCAAAAA  2280
GCTCCCGGGA GCTTGTATAT CCATTTTCGG ATCTGATCAG CACGTGTTGA CAATTAATCA  2340
TCGGCATAGT ATATCGGCAT AGTATAATAC GACAAGGTGA GGAACTAAAC CATGGCCAAG  2400
TTGACCAGTG CCGTTCCGGT GCTCACCGCG CGCGACGTCG CCGGAGCGGT CGAGTTCTGG  2460
ACCGACCGGC TCGGGTTCTC CCGGGACTTC GTGGAGGACG ACTTCGCCGG TGTGGTCCGG  2520
GACGACGTGA CCCTGTTCAT CAGCGCGGTC CAGGACCAGG TGGTGCCGGA CAACACCCTG  2580
GCCTGGGTGT GGGTGCGCGG CCTGGACGAG CTGTACGCCG AGTGGTCGGA GGTCGTGTCC  2640
ACGAACTTCC GGGACGCCTC CGGGCCGGCC ATGACCGAGA TCGGCGAGCA GCCGTGGGGG  2700
CGGGAGTTCG CCCTGCGCGA CCCGGCCGGC AACTGCGTGC ACTTCGTGGC CGAGGAGCAG  2760
GACTGACACG TGCTACGAGA TTTCGATTCC ACCGCCGCCT TCTATGAAAG GTTGGGCTTC  2820
GGAATCGTTT TCCGGGACGC CGGCTGGATG ATCCTCCAGC GCGGGGATCT CATGCTGGAG  2880
TTCTTCGCCC ACCCCAACTT GTTTATTGCA GCTTATAATG GTTACAAATA AAGCAATAGC  2940
```

FIG. 21A

```
ATCACAAATT TCACAAATAA AGCATTTTTT TCACTGCATT CTAGTTGTGG TTTGTCCAAA 3000
CTCATCAATG TATCTTATCA TGTCTGTATA CCGTCGACCT CTAGCTAGAG CTTGGCGTAA 3060
TCATGGTCAT AGCTGTTTCC TGTGTGAAAT TGTTATCCGC TCACAATTCC ACACAACATA 3120
CGAGCCGGAA GCATAAAGTG TAAAGCCTGG GGTGCCTAAT GAGTGAGCTA ACTCACATTA 3180
ATTGCGTTGC GCTCACTGCC CGCTTTCCAG TCGGGAAACC TGTCGTGCCA GCTGCATTAA 3240
TGAATCGGCC AACGCGCGGG GAGAGGCGGT TTGCGTATTG GGCGCTCTTC CGCTTCCTCG 3300
CTCACTGACT CGCTGCGCTC GGTCGTTCGG CTGCGGCGAG CGGTATCAGC TCACTCAAAG 3360
GCGGTAATAC GGTTATCCAC AGAATCAGGG GATAACGCAG GAAAGAACAT GTGAGCAAAA 3420
GGCCAGCAAA AGGCCAGGAA CCGTAAAAAG GCCGCGTTGC TGGCGTTTTT CCATAGGCTC 3480
CGCCCCCCTG ACGAGCATCA CAAAAATCGA CGCTCAAGTC AGAGGTGGCG AAACCCGACA 3540
GGACTATAAA GATACCAGGC GTTTCCCCCT GGAAGCTCCC TCGTGCGCTC TCCTGTTCCG 3600
ACCCTGCCGC TTACCGGATA CCTGTCCGCC TTTCTCCCTT CGGGAAGCGT GGCGCTTTCT 3660
CAATGCTCAC GCTGTAGGTA TCTCAGTTCG GTGTAGGTCG TTCGCTCCAA GCTGGGCTGT 3720
GTGCACGAAC CCCCCGTTCA GCCCGACCGC TGCGCCTTAT CCGGTAACTA TCGTCTTGAG 3780
TCCAACCCGG TAAGACACGA CTTATCGCCA CTGGCAGCAG CCACTGGTAA CAGGATTAGC 3840
AGAGCGAGGT ATGTAGGCGG TGCTACAGAG TTCTTGAAGT GGTGGCCTAA CTACGGCTAC 3900
ACTAGAAGGA CAGTATTTGG TATCTGCGCT CTGCTGAAGC CAGTTACCTT CGGAAAAAGA 3960
GTTGGTAGCT CTTGATCCGG CAAACAAACC ACCGCTGGTA GCGGTGGTTT TTTTGTTTGC 4020
AAGCAGCAGA TTACGCGCAG AAAAAAAGGA TCTCAAGAAG ATCCTTTGAT CTTTTCTACG 4080
GGGTCTGACG CTCAGTGGAA CGAAAACTCA CGTTAAGGGA TTTTGGTCAT GAGATTATCA 4140
AAAAGGATCT TCACCTAGAT CCTTTTAAAT TAAAAATGAA GTTTTAAATC AATCTAAAGT 4200
ATATATGAGT AAACTTGGTC TGACAGTTAC CAATGCTTAA TCAGTGAGGC ACCTATCTCA 4260
GCGATCTGTC TATTTCGTTC ATCCATAGTT GCCTGACTCC CCGTCGTGTA GATAACTACG 4320
ATACGGGAGG GCTTACCATC TGGCCCCAGT GCTGCAATGA TACCGCGAGA CCCACGCTCA 4380
CCGGCTCCAG ATTTATCAGC AATAAACCAG CCAGCCGGAA GGGCCGAGCG CAGAAGTGGT 4440
CCTGCAACTT TATCCGCCTC CATCCAGTCT ATTAATTGTT GCCGGGAAGC TAGAGTAAGT 4500
AGTTCGCCAG TTAATAGTTT GCGCAACGTT GTTGCCATTG CTACAGGCAT CGTGGTGTCA 4560
CGCTCGTCGT TTGGTATGGC TTCATTCAGC TCCGGTTCCC AACGATCAAG GCGAGTTACA 4620
TGATCCCCCA TGTTGTGCAA AAAAGCGGTT AGCTCCTTCG GTCCTCCGAT CGTTGTCAGA 4680
AGTAAGTTGG CCGCAGTGTT ATCACTCATG GTTATGGCAG CACTGCATAA TTCTCTTACT 4740
GTCATGCCAT CCGTAAGATG CTTTTCTGTG ACTGGTGAGT ACTCAACCAA GTCATTCTGA 4800
GAATAGTGTA TGCGGCGACC GAGTTGCTCT TGCCCGGCGT CAATACGGGA TAATACCGCG 4860
CCACATAGCA GAACTTTAAA AGTGCTCATC ATTGGAAAAC GTTCTTCGGG GCGAAAACTC 4920
TCAAGGATCT TACCGCTGTT GAGATCCAGT TCGATGTAAC CCACTCGTGC ACCCAACTGA 4980
TCTTCAGCAT CTTTTACTTT CACCAGCGTT TCTGGGTGAG CAAAAACAGG AAGGCAAAAT 5040
GCCGCAAAAA AGGGAATAAG GGCGACACGG AAATGTTGAA TACTCATACT CTTCCTTTTT 5100
CAATATTATT GAAGCATTTA TCAGGGTTAT TGTCTCATGA GCGGATACAT ATTTGAATGT 5160
ATTTAGAAAA ATAAACAAAT AGGGGTTCCG CGCACATTTC CCCGAAAAGT GCCACCTGAC 5220
GTC                                                               5223
```

FIG. 21B pPEF2

| | | | | | |
|---|---|---|---|---|---|
| GACGGATCGG | GAGATCTCCC | GATCCCCTAT | GGTCGACTCT | CAGTACAATC | TGCTCTGATG | 60
| CCGCATAGTT | AAGCCAGTAT | CTGCTCCCTG | CTTGTGTGTT | GGAGGTCGCT | GAGTAGTGCG | 120
| CGAGCAAAAT | TTAAGCTACA | ACAAGGCAAG | GCTTGACCGA | CAATTGCATG | AAGAATCTGC | 180
| TTAGGGTTAG | GCGTTTTGCG | CTGCTTCGCG | ATGTACGGGC | CAGATATACG | CGTTGACATT | 240
| GATTATTGAC | TAGTTATTAA | TAGTAATCAA | TTACGGGGTC | ATTAGTTCAT | AGCCCATATA | 300
| TGGAGTTCCG | CGTTACATAA | CTTACGGTAA | ATGGCCCGCC | TGGCTGACCG | CCCAACGACC | 360
| CCCGCCCATT | GACGTCAATA | ATGACGTATG | TTCCCATAGT | AACGCCAATA | GGGACTTTCC | 420
| ATTGACGTCA | ATGGGTGGAC | TATTTACGGT | AAACTGCCCA | CTTGGCAGTA | CATCAAGTGT | 480
| ATCATATGCC | AAGTCCGCCC | CCTATTGACG | TCAATGACGG | TAAATGGCCC | GCCTGGCATT | 540
| ATGCCCAGTA | CATGACCTTA | CGGGACTTTC | CTACTTGGCA | GTACATCTAC | GTATTAGTCA | 600
| TCGCTATTAC | CATGGTGATG | CGGTTTTGGC | AGTACACCAA | TGGGCGTGGA | TAGCGGTTTG | 660
| ACTCACGGGG | ATTTCCAAGT | CTCCACCCCA | TTGACGTCAA | TGGGAGTTTG | TTTTGGCACC | 720
| AAAATCAACG | GGACTTTCCA | AAATGTCGTA | ATAACCCCGC | CCCGTTGACG | CAAATGGGCG | 780
| GTAGGCGTGT | ACGGTGGGAG | GTCTATATAA | GCAGAGCTCG | TTTAGTGAAC | CGTCAGATCT | 840
| CTAGAAGCTG | GGTACCGAAA | TTAATACGAC | TCACTATAGG | GAGACCCAAG | CTGGCTTGCG | 900
| TTTAAACTTA | AGCTTAGCGC | AGAGGCTTGG | GGCAGCCGAG | CGGCAGCCAG | GCCCCGGCCC | 960
| GGGCCTCGGT | TCCAGAAGGG | AGAGGAGCCC | GCCAAGGCGC | GCAAGAGAGC | GGGCTGCCTC | 1020
| GCAGTCCGAG | CCGGAGAGGG | AGCGCGAGCC | GCGCCGGCCC | CGGACGGCCT | CCGAAACCAT | 1080
| GGGAGTCAAA | GTTCTGTTTG | CCCTGATCTG | CATCGCTGTG | GCCGAGGCCA | AGCCCACGCT | 1140
| AGCCGAGGGA | TCCAGTGTGG | TGGAATTCTG | CAGATATCCA | GCACAGTGGC | GGCCGCTCGA | 1200
| GTCTAGAGGG | CCCGTTTAAA | CCCGCTGATC | AGCCTCGACT | GTGCCTTCTA | GTTGCCAGCC | 1260
| ATCTGTTGTT | TGCCCCTCCC | CCGTGCCTTC | CTTGACCCTG | GAAGGTGCCA | CTCCCACTGT | 1320
| CCTTTCCTAA | TAAAATGAGG | AAATTGCATC | GCATTGTCTG | AGTAGGTGTC | ATTCTATTCT | 1380
| GGGGGGTGGG | GTGGGGCAGG | ACAGCAAGGG | GGAGGATTGG | GAAGACAATA | GCAGGCATGC | 1440
| TGGGGATGCG | GTGGGCTCTA | TGGCTTCTGA | GGCGGAAAGA | ACCAGCTGGG | GCTCTAGGGG | 1500
| GTATCCCCAC | GCGCCCTGTA | GCGGCGCATT | AAGCGCGGCG | GGTGTGGTGG | TTACGCGCAG | 1560
| CGTGACCGCT | ACACTTGCCA | GCGCCCTAGC | GCCCGCTCCT | TTCGCTTTCT | TCCCTTCCTT | 1620
| TCTCGCCACG | TTCGCCGGCT | TTCCCCGTCA | AGCTCTAAAT | CGGGGCATCC | CTTTAGGGTT | 1680
| CCGATTTAGT | GCTTTACGGC | ACCTCGACCC | CAAAAAACTT | GATTAGGGTG | ATGGTTCACG | 1740
| TAGTGGGCCA | TCGCCCTGAT | AGACGGTTTT | TCGCCCTTTG | ACGTTGGAGT | CCACGTTCTT | 1800
| TAATAGTGGA | CTCTTGTTCC | AAACTGGAAC | AACACTCAAC | CCTATCTCGG | TCTATTCTTT | 1860
| TGATTTATAA | GGGATTTTGG | GGATTTCGGC | CTATTGGTTA | AAAAATGAGC | TGATTTAACA | 1920
| AAAATTTAAC | GCGAATTAAT | TCTGTGGAAT | GTGTGTCAGT | TAGGGTGTGG | AAAGTCCCCA | 1980
| GGCTCCCCAG | GCAGGCAGAA | GTATGCAAAG | CATGCATCTC | AATTAGTCAG | CAACCAGGTG | 2040
| TGGAAAGTCC | CCAGGCTCCC | CAGCAGGCAG | AAGTATGCAA | AGCATGCATC | TCAATTAGTC | 2100
| AGCAACCATA | GTCCCGCCCC | TAACTCCGCC | CATCCCGCCC | CTAACTCCGC | CCAGTTCCGC | 2160
| CCATTCTCCG | CCCCATGGCT | GACTAATTTT | TTTTATTTAT | GCAGAGGCCG | AGGCCGCCTC | 2220
| TGCCTCTGAG | CTATTCCAGA | AGTAGTGAGG | AGGCTTTTTT | GGAGGCCTAG | GCTTTTGCAA | 2280
| AAAGCTCCCG | GGAGCTTGTA | TATCCATTTT | CGGATCTGAT | CAGCACGTGT | TGACAATTAA | 2340
| TCATCGGCAT | AGTATATCGG | CATAGTATAA | TACGACAAGG | TGAGGAACTA | AACCATGGCC | 2400
| AAGTTGACCA | GTGCCGTTCC | GGTGCTCACC | GCGCGCGACG | TCGCCGGAGC | GGTCGAGTTC | 2460
| TGGACCGACC | GGCTCGGGTT | CTCCCGGGAC | TTCGTGGAGG | ACGACTTCGC | CGGTGTGGTC | 2520
| CGGGACGACG | TGACCCTGTT | CATCAGCGCG | GTCCAGGACC | AGGTGGTGCC | GGACAACACC | 2580
| CTGGCCTGGG | TGTGGGTGCG | CGGCCTGGAC | GAGCTGTACG | CCGAGTGGTC | GGAGGTCGTG | 2640
| TCCACGAACT | TCCGGGACGC | CTCCGGGCCG | GCCATGACCG | AGATCGGCGA | GCAGCCGTGG | 2700
| GGGCGGGAGT | TCGCCCTGCG | CGACCCGGCC | GGCAACTGCG | TGCACTTCGT | GGCCGAGGAG | 2760
| CAGGACTGAC | ACGTGCTACG | AGATTTCGAT | TCCACCGCCG | CCTTCTATGA | AAGGTTGGGC | 2820
| TTCGGAATCG | TTTTCCGGGA | CGCCGGCTGG | ATGATCCTCC | AGCGCGGGGA | TCTCATGCTG | 2880
| GAGTTCTTCG | CCCACCCCAA | CTTGTTTATT | GCAGCTTATA | ATGGTTACAA | ATAAAGCAAT | 2940
| AGCATCACAA | ATTTCACAAA | TAAAGCATTT | TTTTCACTGC | ATTCTAGTTG | TGGTTTGTCC | 3000
| AAACTCATCA | ATGTATCTTA | TCATGTCTGT | ATACCGTCGA | CCTCTAGCTA | GAGCTTGGCG | 3060

FIG. 22A

```
TAATCATGGT CATAGCTGTT TCCTGTGTGA AATTGTTATC CGCTCACAAT TCCACACAAC    3120
ATACGAGCCG GAAGCATAAA GTGTAAAGCC TGGGGTGCCT AATGAGTGAG CTAACTCACA    3180
TTAATTGCGT TGCGCTCACT GCCCGCTTTC CAGTCGGGAA ACCTGTCGTG CCAGCTGCAT    3240
TAATGAATCG GCCAACGCGC GGGGAGAGGC GGTTTGCGTA TTGGGCGCTC TTCCGCTTCC    3300
TCGCTCACTG ACTCGCTGCG CTCGGTCGTT CGGCTGCGGC GAGCGGTATC AGCTCACTCA    3360
AAGGCGGTAA TACGGTTATC CACAGAATCA GGGGATAACG CAGGAAAGAA CATGTGAGCA    3420
AAAGGCCAGC AAAAGGCCAG GAACCGTAAA AAGGCCGCGT TGCTGGCGTT TTTCCATAGG    3480
CTCCGCCCCC CTGACGAGCA TCACAAAAAT CGACGCTCAA GTCAGAGGTG GCGAAACCCG    3540
ACAGGACTAT AAAGATACCA GGCGTTTCCC CCTGGAAGCT CCCTCGTGCG CTCTCCTGTT    3600
CCGACCCTGC CGCTTACCGG ATACCTGTCC GCCTTTCTCC CTTCGGAAG CGTGGCGCTT     3660
TCTCAATGCT CACGCTGTAG GTATCTCAGT TCGGTGTAGG TCGTTCGCTC CAAGCTGGGC    3720
TGTGTGCACG AACCCCCCGT TCAGCCCGAC CGCTGCGCCT TATCCGGTAA CTATCGTCTT    3780
GAGTCCAACC CGGTAAGACA CGACTTATCG CCACTGGCAG CAGCCACTGG TAACAGGATT    3840
AGCAGAGCGA GGTATGTAGG CGGTGCTACA GAGTTCTTGA AGTGGTGGCC TAACTACGGC    3900
TACACTAGAA GGACAGTATT TGGTATCTGC GCTCTGCTGA AGCCAGTTAC CTTCGGAAAA    3960
AGAGTTGGTA GCTCTTGATC CGGCAAACAA ACCACCGCTG GTAGCGGTGG TTTTTTTGTT    4020
TGCAAGCAGC AGATTACGCG CAGAAAAAAA GGATCTCAAG AAGATCCTTT GATCTTTTCT    4080
ACGGGGTCTG ACGCTCAGTG GAACGAAAAC TCACGTTAAG GGATTTTGGT CATGAGATTA    4140
TCAAAAGGA TCTTCACCTA GATCCTTTTA AATTAAAAAT GAAGTTTTAA ATCAATCTAA     4200
AGTATATATG AGTAAACTTG GTCTGACAGT TACCAATGCT TAATCAGTGA GGCACCTATC    4260
TCAGCGATCT GTCTATTTCG TTCATCCATA GTTGCCTGAC TCCCCGTCGT GTAGATAACT    4320
ACGATACGGG AGGGCTTACC ATCTGGCCCC AGTGCTGCAA TGATACCGCG AGACCCACGC    4380
TCACCGGCTC CAGATTTATC AGCAATAAAC CAGCCAGCCG GAAGGGCCGA GCGCAGAAGT    4440
GGTCCTGCAA CTTTATCCGC CTCCATCCAG TCTATTAATT GTTGCCGGGA AGCTAGAGTA    4500
AGTAGTTCGC CAGTTAATAG TTTGCGCAAC GTTGTTGCCA TTGCTACAGG CATCGTGGTG    4560
TCACGCTCGT CGTTTGGTAT GGCTTCATTC AGCTCCGGTT CCCAACGATC AAGGCGAGTT    4620
ACATGATCCC CCATGTTGTG CAAAAAAGCG GTTAGCTCCT TCGGTCCTCC GATCGTTGTC    4680
AGAAGTAAGT TGGCCGCAGT GTTATCACTC ATGGTTATGG CAGCACTGCA TAATTCTCTT    4740
ACTGTCATGC CATCCGTAAG ATGCTTTTCT GTGACTGGTG AGTACTCAAC CAAGTCATTC    4800
TGAGAATAGT GTATGCGGCG ACCGAGTTGC TCTTGCCCGG CGTCAATACG GGATAATACC    4860
GCGCCACATA GCAGAACTTT AAAAGTGCTC ATCATTGGAA AACGTTCTTC GGGGCGAAAA    4920
CTCTCAAGGA TCTTACCGCT GTTGAGATCC AGTTCGATGT AACCCACTCG TGCACCCAAC    4980
TGATCTTCAG CATCTTTTAC TTTCACCAGC GTTTCTGGGT GAGCAAAAAC AGGAAGGCAA    5040
AATGCCGCAA AAAAGGGAAT AAGGGCGACA CGGAAATGTT GAATACTCAT ACTCTTCCTT    5100
TTTCAATATT ATTGAAGCAT TTATCAGGGT TATTGTCTCA TGAGCGGATA CATATTTGAA    5160
TGTATTTAGA AAAATAAACA AATAGGGGTT CCGCGCACAT TTCCCCGAAA AGTGCCACCT    5220
GACGTC                                                              5226
```

FIG. 22B pPEF3

| | | | | | | |
|---|---|---|---|---|---|---|
|GACGGATCGG|GAGATCTCCC|GATCCCCTAT|GGTCGACTCT|CAGTACAATC|TGCTCTGATG|60|
|CCGCATAGTT|AAGCCAGTAT|CTGCTCCCTG|CTTGTGTGTT|GGAGGTCGCT|GAGTAGTGCG|120|
|CGAGCAAAAT|TTAAGCTACA|ACAAGGCAAG|GCTTGACCGA|CAATTGCATG|AAGAATCTGC|180|
|TTAGGGTTAG|GCGTTTTGCG|CTGCTTCGCG|ATGTACGGGC|CAGATATACG|CGTTGACATT|240|
|GATTATTGAC|TAGTTATTAA|TAGTAATCAA|TTACGGGTC|ATTAGTTCAT|AGCCCATATA|300|
|TGGAGTTCCG|CGTTACATAA|CTTACGGTAA|ATGGCCCGCC|TGGCTGACCG|CCCAACGACC|360|
|CCCGCCCATT|GACGTCAATA|ATGACGTATG|TTCCCATAGT|AACGCCAATA|GGGACTTTCC|420|
|ATTGACGTCA|ATGGGTGGAC|TATTTACGGT|AAACTGCCCA|CTTGGCAGTA|CATCAAGTGT|480|
|ATCATATGCC|AAGTCCGCCC|CCTATTGACG|TCAATGACGG|TAAATGGCCC|GCCTGGCATT|540|
|ATGCCCAGTA|CATGACCTTA|CGGGACTTTC|CTACTTGGCA|GTACATCTAC|GTATTAGTCA|600|
|TCGCTATTAC|CATGGTGATG|CGGTTTTGGC|AGTACACCAA|TGGGCGTGGA|TAGCGGTTTG|660|
|ACTCACGGGG|ATTTCCAAGT|CTCCACCCCA|TTGACGTCAA|TGGGAGTTTG|TTTTGGCACC|720|
|AAAATCAACG|GGACTTTCCA|AAATGTCGTA|ATAACCCCGC|CCCGTTGACG|CAAATGGGCG|780|
|GTAGGCGTGT|ACGGTGGGAG|GTCTATATAA|GCAGAGCTCG|TTTAGTGAAC|CGTCAGATCT|840|
|CTAGAAGCTG|GGTACCTTAA|GGCGCCAGCT|GATCAAGCTT|CTGCCTGCCG|CCTGCCTGCC|900|
|TGCCACTGAG|GGTTCCAGC|ACCATGAGGG|CCTGGATCTT|CTTTCTCCTT|TGCCTGGCCG|960|
|GGAGGGCTCT|GGCAGCCCCG|CTAGCCGAGG|GATCCAGTGT|GGTGGAATTC|TGCAGATATC|1020|
|CAGCACAGTG|GCGGCCGCTC|GAGTCTAGAG|GGCCCGTTTA|AACCCGCTGA|TCAGCCTCGA|1080|
|CTGTGCCTTC|TAGTTGCCAG|CCATCTGTTG|TTTGCCCCTC|CCCCGTGCCT|TCCTTGACCC|1140|
|TGGAAGGTGC|CACTCCCACT|GTCCTTTCCT|AATAAAATGA|GGAAATTGCA|TCGCATTGTC|1200|
|TGAGTAGGTG|TCATTCTATT|CTGGGGGGTG|GGGTGGGCA|GGACAGCAAG|GGGGAGGATT|1260|
|GGGAAGACAA|TAGCAGGCAT|GCTGGGGATG|CGGTGGGCTC|TATGGCTTCT|GAGGCGGAAA|1320|
|GAACCAGCTG|GGGCTCTAGG|GGGTATCCCC|ACGCGCCCTG|TAGCGGCGCA|TTAAGCGCGG|1380|
|CGGGTGTGGT|GGTTACGCGC|AGCGTGACCG|CTACACTTGC|CAGCGCCCTA|GCGCCCGCTC|1440|
|CTTTCGCTTT|CTTCCCTTCC|TTTCTCGCCA|CGTTCGCCGG|CTTTCCCCGT|CAAGCTCTAA|1500|
|ATCGGGGCAT|CCCTTTAGGG|TTCCGATTTA|GTGCTTTACG|GCACCTCGAC|CCCAAAAAAC|1560|
|TTGATTAGGG|TGATGGTTCA|CGTAGTGGGC|CATCGCCCTG|ATAGACGGTT|TTTCGCCCTT|1620|
|TGACGTTGGA|GTCCACGTTC|TTTAATAGTG|GACTCTTGTT|CCAAACTGGA|ACAACACTCA|1680|
|ACCCTATCTC|GGTCTATTCT|TTTGATTTAT|AAGGGATTTT|GGGGATTTCG|GCCTATTGGT|1740|
|TAAAAAATGA|GCTGATTTAA|CAAAAATTTA|ACGCGAATTA|ATTCTGTGGA|ATGTGTGTCA|1800|
|GTTAGGGTGT|GGAAAGTCCC|CAGGCTCCCC|AGCAGGCAG|AAGTATGCAA|AGCATGCATC|1860|
|TCAATTAGTC|AGCAACCAGG|TGTGGAAAGT|CCCCAGGCTC|CCCAGCAGGC|AGAAGTATGC|1920|
|AAAGCATGCA|TCTCAATTAG|TCAGCAACCA|TAGTCCCGCC|CCTAACTCCG|CCCATCCCGC|1980|
|CCCTAACTCC|GCCCAGTTCC|GCCCATTCTC|CGCCCCATGG|CTGACTAATT|TTTTTTATTT|2040|
|ATGCAGAGGC|CGAGGCCGCC|TCTGCCTCTG|AGCTATTCCA|GAAGTAGTGA|GGAGGCTTTT|2100|
|TTGGAGGCCT|AGGCTTTTGC|AAAAAGCTCC|CGGGAGCTTG|TATATCCATT|TTCGGATCTG|2160|
|ATCAGCACGT|GTTGACAATT|AATCATCGGC|ATAGTATATC|GGCATAGTAT|AATACGACAA|2220|
|GGTGAGGAAC|TAAACCATGG|CCAAGTTGAC|CAGTGCCGTT|CCGGTGCTCA|CCGCGCGCGA|2280|
|CGTCGCCGGA|GCGGTCGAGT|TCTGGACCGA|CCGGCTCGGG|TTCTCCCGGG|ACTTCGTGGA|2340|
|GGACGACTTC|GCCGGTGTGG|TCCGGGACGA|CGTGACCCTG|TTCATCAGCG|CGGTCCAGGA|2400|
|CCAGGTGGTG|CCGGACAACA|CCCTGGCCTG|GGTGTGGGTG|CGCGGCCTGG|ACGAGCTGTA|2460|
|CGCCGAGTGG|TCGGAGGTCG|TGTCCACGAA|CTTCCGGGAC|GCCTCGGGC|CGGCCATGAC|2520|
|CGAGATCGGC|GAGCAGCCGT|GGGGGCGGGA|GTTCGCCCTG|CGCGACCCGG|CCGGCAACTG|2580|
|CGTGCACTTC|GTGGCCGAGG|AGCAGGACTG|ACACGTGCTA|CGAGATTTCG|ATTCCACCGC|2640|
|CGCCTTCTAT|GAAAGGTTGG|GCTTCGGAAT|CGTTTTCCGG|GACGCCGGCT|GGATGATCCT|2700|
|CCAGCGCGGG|GATCTCATGC|TGGAGTTCTT|CGCCCACCCC|AACTTGTTTA|TTGCAGCTTA|2760|
|TAATGGTTAC|AAATAAAGCA|ATAGCATCAC|AAATTTCACA|AATAAAGCAT|TTTTTTCACT|2820|
|GCATTCTAGT|TGTGGTTTGT|CCAAACTCAT|CAATGTATCT|TATCATGTCT|GTATACCGTC|2880|
|GACCTCTAGC|TAGAGCTTGG|CGTAATCATG|GTCATAGCTG|TTTCCTGTGT|GAAATTGTTA|2940|

FIG. 23A

```
TCCGCTCACA ATTCCACACA ACATACGAGC CGGAAGCATA AAGTGTAAAG CCTGGGGTGC   3000
CTAATGAGTG AGCTAACTCA CATTAATTGC GTTGCGCTCA CTGCCCGCTT TCCAGTCGGG   3060
AAACCTGTCG TGCCAGCTGC ATTAATGAAT CGGCCAACGC GCGGGGAGAG GCGGTTTGCG   3120
TATTGGGCGC TCTTCCGCTT CCTCGCTCAC TGACTCGCTG CGCTCGGTCG TTCGGCTGCG   3180
GCGAGCGGTA TCAGCTCACT CAAAGGCGGT AATACGGTTA TCCACAGAAT CAGGGGATAA   3240
CGCAGGAAAG AACATGTGAG CAAAAGGCCA GCAAAAGGCC AGGAACCGTA AAAAGGCCGC   3300
GTTGCTGGCG TTTTTCCATA GGCTCCGCCC CCTGACGAG CATCACAAAA ATCGACGCTC   3360
AAGTCAGAGG TGGCGAAACC CGACAGGACT ATAAAGATAC CAGGCGTTTC CCCCTGGAAG   3420
CTCCCTCGTG CGCTCTCCTG TTCCGACCCT GCCGCTTACC GGATACCTGT CCGCCTTTCT   3480
CCCTTCGGGA AGCGTGGCGC TTTCTCAATG CTCACGCTGT AGGTATCTCA GTTCGGTGTA   3540
GGTCGTTCGC TCCAAGCTGG GCTGTGTGCA CGAACCCCCC GTTCAGCCCG ACCGCTGCGC   3600
CTTATCCGGT AACTATCGTC TTGAGTCCAA CCCGGTAAGA CACGACTTAT CGCCACTGGC   3660
AGCAGCCACT GGTAACAGGA TTAGCAGAGC GAGGTATGTA GGCGGTGCTA CAGAGTTCTT   3720
GAAGTGGTGG CCTAACTACG GCTACACTAG AAGGACAGTA TTTGGTATCT GCGCTCTGCT   3780
GAAGCCAGTT ACCTTCGGAA AAAGAGTTGG TAGCTCTTGA TCCGGCAAAC AAACCACCGC   3840
TGGTAGCGGT GGTTTTTTTG TTTGCAAGCA GCAGATTACG CGCAGAAAAA AAGGATCTCA   3900
AGAAGATCCT TTGATCTTTT CTACGGGGTC TGACGCTCAG TGGAACGAAA ACTCACGTTA   3960
AGGGATTTTG GTCATGAGAT TATCAAAAAG GATCTTCACC TAGATCCTTT TAAATTAAAA   4020
ATGAAGTTTT AAATCAATCT AAAGTATATA TGAGTAAACT TGGTCTGACA GTTACCAATG   4080
CTTAATCAGT GAGGCACCTA TCTCAGCGAT CTGTCTATTT CGTTCATCCA TAGTTGCCTG   4140
ACTCCCCGTC GTGTAGATAA CTACGATACG GGAGGGCTTA CCATCTGGCC CCAGTGCTGC   4200
AATGATACCG CGAGACCCAC GCTCACCGGC TCCAGATTTA TCAGCAATAA ACCAGCCAGC   4260
CGGAAGGGCC GAGCGCAGAA GTGGTCCTGC AACTTTATCC GCCTCCATCC AGTCTATTAA   4320
TTGTTGCCGG GAAGCTAGAG TAAGTAGTTC GCCAGTTAAT AGTTTGCGCA ACGTTGTTGC   4380
CATTGCTACA GGCATCGTGG TGTCACGCTC GTCGTTTGGT ATGGCTTCAT TCAGCTCCGG   4440
TTCCCAACGA TCAAGGCGAG TTACATGATC CCCATGTTG TGCAAAAAAG CGGTTAGCTC   4500
CTTCGGTCCT CCGATCGTTG TCAGAAGTAA GTTGGCCGCA GTGTTATCAC TCATGGTTAT   4560
GGCAGCACTG CATAATTCTC TTACTGTCAT GCCATCCGTA AGATGCTTTT CTGTGACTGG   4620
TGAGTACTCA ACCAAGTCAT TCTGAGAATA GTGTATGCGG CGACCGAGTT GCTCTTGCCC   4680
GGCGTCAATA CGGGATAATA CCGCGCCACA TAGCAGAACT TTAAAAGTGC TCATCATTGG   4740
AAAACGTTCT TCGGGGCGAA AACTCTCAAG GATCTTACCG CTGTTGAGAT CCAGTTCGAT   4800
GTAACCCACT CGTGCACCCA ACTGATCTTC AGCATCTTTT ACTTTCACCA GCGTTTCTGG   4860
GTGAGCAAAA ACAGGAAGGC AAAATGCCGC AAAAAAGGGA ATAAGGGCGA CACGGAAATG   4920
TTGAATACTC ATACTCTTCC TTTTTCAATA TTATTGAAGC ATTTATCAGG GTTATTGTCT   4980
CATGAGCGGA TACATATTTG AATGTATTTA GAAAAATAAA CAAATAGGGG TTCCGCGCAC   5040
ATTTCCCCGA AAAGTGCCAC CTGACGTC                                      5068
```

FIG. 23B pPEF4

```
GACGGATCGG GAGATCTCCC GATCCCCTAT GGTCGACTCT CAGTACAATC TGCTCTGATG    60
CCGCATAGTT AAGCCAGTAT CTGCTCCCTG CTTGTGTGTT GGAGGTCGCT GAGTAGTGCG   120
CGAGCAAAAT TTAAGCTACA ACAAGGCAAG GCTTGACCGA CAATTGCATG AAGAATCTGC   180
TTAGGGTTAG GCGTTTTGCG CTGCTTCGCG ATGTACGGGC CAGATATACG CGTTGACATT   240
GATTATTGAC TAGTTATTAA TAGTAATCAA TTACGGGGTC ATTAGTTCAT AGCCCATATA   300
TGGAGTTCCG CGTTACATAA CTTACGGTAA ATGGCCCGCC TGGCTGACCG CCCAACGACC   360
CCCGCCCATT GACGTCAATA ATGACGTATG TTCCCATAGT AACGCCAATA GGGACTTTCC   420
ATTGACGTCA ATGGGTGGAC TATTTACGGT AAACTGCCCA CTTGGCAGTA CATCAAGTGT   480
ATCATATGCC AAGTCCGCCC CCTATTGACG TCAATGACGG TAAATGGCCC GCCTGGCATT   540
ATGCCCAGTA CATGACCTTA CGGGACTTTC CTACTTGGCA GTACATCTAC GTATTAGTCA   600
TCGCTATTAC CATGGTGATG CGGTTTTGGC AGTACACCAA TGGGCGTGGA TAGCGGTTTG   660
ACTCACGGGG ATTTCCAAGT CTCCACCCCA TTGACGTCAA TGGGAGTTTG TTTTGGCACC   720
AAAATCAACG GGACTTTCCA AAATGTCGTA ATAACCCCGC CCGTTGACG CAAATGGGCG   780
GTAGGCGTGT ACGGTGGGAG GTCTATATAA GCAGAGCTCG TTTAGTGAAC CGTCAGATCT   840
CTAGAAGCTG GGTACCGAAA TTAATACGAC TCACTATAGG GAACCAGCC ACCATGGGAG   900
TCAAAGTTCT GTTTGCCCTG ATCTGCATCG CTGTGGCCGA GGCCAAGCCC ACGCTAGCCG   960
AGGGATCCAG TGTGGTGGAA TTCTGCAGAT ATCCAGCACA GTGGCGGCCG CTCGAGTCTA  1020
GAGGGCCCGT TTAAACCCGC TGATCAGCCT CGACTGTGCC TTCTAGTTGC CAGCCATCTG  1080
TTGTTTGCCC CTCCCCCGTG CCTTCCTTGA CCCTGGAAGG TGCCACTCCC ACTGTCCTTT  1140
CCTAATAAAA TGAGGAAATT GCATCGCATT GTCTGAGTAG GTGTCATTCT ATTCTGGGGG  1200
GTGGGGTGGG GCAGGACAGC AAGGGGGAGG ATTGGGAAGA CAATAGCAGG CATGCTGGGG  1260
ATGCGGTGGG CTCTATGGCT TCTGAGGCGG AAAGAACCAG CTGGGGCTCT AGGGGGTATC  1320
CCCACGCGCC CTGTAGCGGC GCATTAAGCG CGGCGGGTGT GGTGGTTACG CGCAGCGTGA  1380
CCGCTACACT TGCCAGCGCC CTAGCGCCCG CTCCTTTCGC TTTCTTCCCT TCCTTTCTCG  1440
CCACGTTCGC CGGCTTTCCC CGTCAAGCTC TAAATCGGGG CATCCCTTTA GGGTTCCGAT  1500
TTAGTGCTTT ACGGCACCTC GACCCCAAAA AACTTGATTA GGGTGATGGT TCACGTAGTG  1560
GGCCATCGCC CTGATAGACG GTTTTTCGCC CTTTGACGTT GGAGTCCACG TTCTTTAATA  1620
GTGGACTCTT GTTCCAAACT GGAACAACAC TCAACCCTAT CTCGGTCTAT TCTTTTGATT  1680
TATAAGGGAT TTTGGGGATT TCGGCCTATT GGTTAAAAAA TGAGCTGATT TAACAAAAAT  1740
TTAACGCGAA TTAATTCTGT GGAATGTGTG TCAGTTAGGG TGTGGAAAGT CCCCAGGCTC  1800
CCCAGGCAGG CAGAAGTATG CAAAGCATGC ATCTCAATTA GTCAGCAACC AGGTGTGGAA  1860
AGTCCCCAGG CTCCCCAGCA GGCAGAAGTA TGCAAAGCAT GCATCTCAAT TAGTCAGCAA  1920
CCATAGTCCC GCCCCTAACT CCGCCCATCC CGCCCTAAC TCCGCCCAGT TCCGCCCATT  1980
CTCCGCCCCA TGGCTGACTA ATTTTTTTTA TTTATGCAGA GGCCGAGGCC GCCTCTGCCT  2040
CTGAGCTATT CCAGAAGTAG TGAGGAGGCT TTTTTGGAGG CCTAGGCTTT TGCAAAAAGC  2100
TCCCGGGAGC TTGTATATCC ATTTTCGGAT CTGATCAGCA CGTGTTGACA ATTAATCATC  2160
GGCATAGTAT ATCGGCATAG TATAATACGA CAAGGTGAGG AACTAAACCA TGGCCAAGTT  2220
GACCAGTGCC GTTCCGGTGC TCACCGCGCG CGACGTCGCC GGAGCGGTCG AGTTCTGGAC  2280
CGACCGGCTC GGGTTCTCCC GGGACTTCGT GGAGGACGAC TTCGCCGGTG TGGTCCGGGA  2340
CGACGTGACC CTGTTCATCA GCGCGGTCCA GGACCAGGTG GTGCCGGACA ACACCCTGGC  2400
CTGGGTGTGG GTGCGCGGCC TGGACGAGCT GTACGCCGAG TGGTCGGAGG TCGTGTCCAC  2460
GAACTTCCGG GACGCCTCCG GCCGGCCAT GACCGAGATC GGCGAGCAGC GTGGGGGCG  2520
GGAGTTCGCC CTGCGCGACC CGGCCGGCAA CTGCGTGCAC TTCGTGGCCG AGGAGCAGGA  2580
CTGACACGTG CTACGAGATT TCGATTCCAC CGCCGCCTTC TATGAAAGGT TGGGCTTCGG  2640
AATCGTTTTC CGGGACGCCG GCTGGATGAT CCTCCAGCGC GGGGATCTCA TGCTGGAGTT  2700
CTTCGCCCAC CCCAACTTGT TTATTGCAGC TTATAATGGT TACAAATAAA GCAATAGCAT  2760
CACAAATTTC ACAAATAAAG CATTTTTTC ACTGCATTCT AGTTGTGGTT TGTCCAAACT  2820
CATCAATGTA TCTTATCATG TCTGTATACC GTCGACCTCT AGCTAGAGCT TGGCGTAATC  2880
ATGGTCATAG CTGTTTCCTG TGTGAAATTG TTATCCGCTC ACAATTCCAC ACAACATACG  2940
AGCCGGAAGC ATAAAGTGTA AAGCCTGGGG TGCCTAATGA GTGAGCTAAC TCACATTAAT  3000
TGCGTTGCGC TCACTGCCCG CTTTCCAGTC GGGAAACCTG TCGTGCCAGC TGCATTAATG  3060
```

FIG. 24A

```
AATCGGCCAA CGCGCGGGGA GAGGCGGTTT GCGTATTGGG CGCTCTTCCG CTTCCTCGCT  3120
CACTGACTCG CTGCGCTCGG TCGTTCGGCT GCGGCGAGCG GTATCAGCTC ACTCAAAGGC  3180
GGTAATACGG TTATCCACAG AATCAGGGGA TAACGCAGGA AAGAACATGT GAGCAAAAGG  3240
CCAGCAAAAG GCCAGGAACC GTAAAAAGGC CGCGTTGCTG GCGTTTTCC  ATAGGCTCCG  3300
CCCCCCTGAC GAGCATCACA AAAATCGACG CTCAAGTCAG AGGTGGCGAA ACCCGACAGG  3360
ACTATAAAGA TACCAGGCGT TTCCCCCTGG AAGCTCCCTC GTGCGCTCTC CTGTTCCGAC  3420
CCTGCCGCTT ACCGGATACC TGTCCGCCTT TCTCCCTTCG GAAGCGTGG  CGCTTTCTCA  3480
ATGCTCACGC TGTAGGTATC TCAGTTCGGT GTAGGTCGTT CGCTCCAAGC TGGGCTGTGT  3540
GCACGAACCC CCCGTTCAGC CCGACCGCTG CGCCTTATCC GGTAACTATC GTCTTGAGTC  3600
CAACCCGGTA AGACACGACT TATCGCCACT GGCAGCAGCC ACTGGTAACA GGATTAGCAG  3660
AGCGAGGTAT GTAGGCGGTG CTACAGAGTT CTTGAAGTGG TGGCCTAACT ACGGCTACAC  3720
TAGAAGGACA GTATTTGGTA TCTGCGCTCT GCTGAAGCCA GTTACCTTCG GAAAAGAGT   3780
TGGTAGCTCT TGATCCGGCA AACAAACCAC CGCTGGTAGC GGTGGTTTTT TGTTTGCAA   3840
GCAGCAGATT ACGCGCAGAA AAAAGGATC  TCAAGAAGAT CCTTTGATCT TTTCTACGGG  3900
GTCTGACGCT CAGTGGAACG AAAACTCACG TTAAGGGATT TTGGTCATGA GATTATCAAA  3960
AAGGATCTTC ACCTAGATCC TTTTAAATTA AAAATGAAGT TTTAAATCAA TCTAAAGTAT  4020
ATATGAGTAA ACTTGGTCTG ACAGTTACCA ATGCTTAATC AGTGAGGCAC CTATCTCAGC  4080
GATCTGTCTA TTTCGTTCAT CCATAGTTGC CTGACTCCCC GTCGTGTAGA TAACTACGAT  4140
ACGGGAGGGC TTACCATCTG GCCCCAGTGC TGCAATGATA CCGCGAGACC CACGCTCACC  4200
GGCTCCAGAT TTATCAGCAA TAAACCAGCC AGCCGGAAGG GCCGAGCGCA GAAGTGGTCC  4260
TGCAACTTTA TCCGCCTCCA TCCAGTCTAT TAATTGTTGC CGGGAAGCTA GAGTAAGTAG  4320
TTCGCCAGTT AATAGTTTGC GCAACGTTGT TGCCATTGCT ACAGGCATCG TGGTGTCACG  4380
CTCGTCGTTT GGTATGGCTT CATTCAGCTC CGGTTCCCAA CGATCAAGGC GAGTTACATG  4440
ATCCCCCATG TTGTGCAAAA AAGCGGTTAG CTCCTTCGGT CCTCCGATCG TTGTCAGAAG  4500
TAAGTTGGCC GCAGTGTTAT CACTCATGGT TATGGCAGCA CTGCATAATT CTCTTACTGT  4560
CATGCCATCC GTAAGATGCT TTTCTGTGAC TGGTGAGTAC TCAACCAAGT CATTCTGAGA  4620
ATAGTGTATG CGGCGACCGA GTTGCTCTTG CCCGGCGTCA ATACGGGATA ATACCGCGCC  4680
ACATAGCAGA ACTTTAAAAG TGCTCATCAT TGGAAAACGT TCTTCGGGGC GAAAACTCTC  4740
AAGGATCTTA CCGCTGTTGA GATCCAGTTC GATGTAACCC ACTCGTGCAC CCAACTGATC  4800
TTCAGCATCT TTTACTTTCA CCAGCGTTTC TGGGTGAGCA AAAACAGGAA GGCAAAATGC  4860
CGCAAAAAAG GGAATAAGGG CGACACGGAA ATGTTGAATA CTCATACTCT TCCTTTTTCA  4920
ATATTATTGA AGCATTTATC AGGGTTATTG TCTCATGAGC GGATACATAT TTGAATGTAT  4980
TTAGAAAAAT AAACAAATAG GGGTTCCGCG CACATTTCCC CGAAAAGTGC CACCTGACGT  5040
C                                                         5041
```

FIG. 24B pPEF5.1

```
GACGGATCGG GAGATCTCCC GATCCCCTAT GGTCGACTCT CAGTACAATC TGCTCTGATG      60
CCGCATAGTT AAGCCAGTAT CTGCTCCCTG CTTGTGTGTT GGAGGTCGCT GAGTAGTGCG     120
CGAGCAAAAT TTAAGCTACA ACAAGGCAAG GCTTGACCGA CAATTGCATG AAGAATCTGC     180
TTAGGGTTAG GCGTTTTGCG CTGCTTCGCG ATGTACGGGC CAGATATACG CGTTGACATT     240
GATTATTGAC TAGTTATTAA TAGTAATCAA TTACGGGGTC ATTAGTTCAT AGCCCATATA     300
TGGAGTTCCG CGTTACATAA CTTACGGTAA ATGGCCCGCC TGGCTGACCG CCCAACGACC     360
CCCGCCCATT GACGTCAATA ATGACGTATG TTCCCATAGT AACGCCAATA GGGACTTTCC     420
ATTGACGTCA ATGGGTGGAC TATTTACGGT AAACTGCCCA CTTGGCAGTA CATCAAGTGT     480
ATCATATGCC AAGTCCGCCC CCTATTGACG TCAATGACGG TAAATGGCCC GCCTGGCATT     540
ATGCCCAGTA CATGACCTTA CGGGACTTTC CTACTTGGCA GTACATCTAC GTATTAGTCA     600
TCGCTATTAC CATGGTGATG CGGTTTTGGC AGTACACCAA TGGGCGTGGA TAGCGGTTTG     660
ACTCACGGGG ATTTCCAAGT CTCCACCCCA TTGACGTCAA TGGGAGTTTG TTTTGGCACC     720
AAAATCAACG GGACTTTCCA AAATGTCGTA ATAACCCCGC CCCGTTGACG CAAATGGGCG     780
GTAGGCGTGT ACGGTGGGAG GTCTATATAA GCAGAGCTCG TTTAGTGAAC CGTCAGATCT     840
CTAGAAGCTG GGTACCGAAA TTAATACGAC TCACTATAGG GAACCAGCC ACCATGGGAG      900
TCAAAGTTCT GTTTGCCCTG ATCTGCATCG CTGTGGCCGA GGCCAAGCCC ACGCTAGCCG     960
AGGTTGCTTT GAGGATCCAG TGTGGTGGAA TTCTGCAGAT ATCCAGCACA GTGGCGGCCG    1020
CTCGAGTCTA GAGGGCCCGT TTAAACCCGC TGATCAGCCT CGACTGTGCC TTCTAGTTGC    1080
CAGCCATCTG TTGTTTGCCC CTCCCCCGTG CCTTCCTTGA CCCTGGAAGG TGCCACTCCC    1140
ACTGTCCTTT CCTAATAAAA TGAGGAAATT GCATCGCATT GTCTGAGTAG TGTCATTCT     1200
ATTCTGGGGG GTGGGGTGGG GCAGGACAGC AAGGGGGAGG ATTGGGAAGA CAATAGCAGG    1260
CATGCTGGGG ATGCGGTGGG CTCTATGGCT TCTGAGGCGG AAAGAACCAG CTGGGGCTCT    1320
AGGGGGTATC CCCACGCGCC CTGTAGCGGC GCATTAAGCG CGGCGGGTGT GGTGGTTACG    1380
CAACCCAGAG ATCGCTGCGT TCCCGCCCCC TCACCCGCCC GCTCTCGTCA TCACTGAGGT    1440
GGAGAAGAGC ATGCGTGAGG CTCCGGTGCC CGTCAGTGGG CAGAGCGCAC ATCGCCCACA    1500
GTCCCCGAGA AGTTGGGGGG AGGGGTCGGC AATTGAACCG GTGCCTAGAG AAGGTGGCGC    1560
GGGGTAAACT GGGAAAGTGA TGTCGTGTAC TGGCTCCGCC TTTTTCCCGA GGGTGGGGGA    1620
GAACCGTATA TAAGTGCAGT AGTCGCCGTG AACGTTCTTT TTCGCAACGG GTTTGCCGCC    1680
AGAACACAGG TGTCGTGAAA ACTACCCCTA AAAGCTTCAA AATGGCCAAG TTGACCAGTG    1740
CCGTTCCGGT GCTCACCGCG CGCGACGTCG CCGGAGCGGT CGAGTTCTGG ACCGACCGGC    1800
TCGGGTTCTC CCGGGACTTC GTGGAGGACG ACTTCGCCGG TGTGGTCCGG GACGACGTGA    1860
CCCTGTTCAT CAGCGCGGTC CAGGACCAGG TGGTGCCGGA CAACACCCTG GCCTGGGTGT    1920
GGGTGCGCGG CCTGGACGAG CTGTACGCCG AGTGGTCGGA GGTCGTGTCC ACGAACTTCC    1980
GGGACGCCTC CGGGCCGGCC ATGACCGAGA TCGGCGAGCA GCCGTGGGGG CGGGAGTTCG    2040
CCCTGCGCGA CCCGGCCGGC AACTGCGTGC ACTTCGTGGC CGAGGAGCAG GACTGACACG    2100
TGCTACGAGA TTTCGATTCC ACCGCCGCCT TCTATGAAAG GTTGGGCTTC GGAATCGTTT    2160
TCCGGGACGC CGGCTGGATG ATCCTCCAGC GCGGGGATCT CATGCTGGAG TTCTTCGCCC    2220
ACCCCAACTT GTTTATTGCA GCTTATAATG GTTACAAATA AAGCAATAGC ATCACAAATT    2280
TCACAAATAA AGCATTTTTT TCACTGCATT CTAGTTGTGG TTTGTCCAAA CTCATCAATG    2340
TATCTTATCA TGTCTGTATA CCGTCGACCT CTAGCTAGAG CTTGGCGTAA TCATGGTCAT    2400
AGCTGTTTCC TGTGTGAAAT TGTTATCCGC TCACAATTCC ACACAACATA CGAGCCGGAA    2460
GCATAAAGTG TAAAGCCTGG GGTGCCTAAT GAGTGAGCTA ACTCACATTA ATTGCGTTGC    2520
GCTCACTGCC CGCTTTCCAG TCGGGAAACC TGTCGTGCCA GCTGCATTAA TGAATCGGCC    2580
AACGCGCGGG GAGAGGCGGT TTGCGTATTG GGCGCTCTTC CGCTTCCTCG CTCACTGACT    2640
CGCTGCGCTC GGTCGTTCGG CTGCGGCGAG CGGTATCAGC TCACTCAAAG GCGGTAATAC    2700
GGTTATCCAC AGAATCAGGG GATAACGCAG GAAAGAACAT GTGAGCAAAA GGCCAGCAAA    2760
AGGCCAGGAA CCGTAAAAAG GCCGCGTTGC TGGCGTTTTT CCATAGGCTC CGCCCCCCTG    2820
ACGAGCATCA CAAAAATCGA CGCTCAAGTC AGAGGTGGCG AAACCCGACA GGACTATAAA    2880
GATACCAGGC GTTTCCCCCT GGAAGCTCCC TCGTGCGCTC TCCTGTTCCG ACCCTGCCGC    2940
TTACCGGATA CCTGTCCGCC TTTCTCCCTT CGGGAAGCGT GGCGCTTTCT CAATGCTCAC    3000
GCTGTAGGTA TCTCAGTTCG GTGTAGGTCG TTCGCTCCAA GCTGGGCTGT GTGCACGAAC    3060
```

FIG. 25A

```
CCCCCGTTCA GCCCGACCGC TGCGCCTTAT CCGGTAACTA TCGTCTTGAG TCCAACCCGG  3120
TAAGACACGA CTTATCGCCA CTGGCAGCAG CCACTGGTAA CAGGATTAGC AGAGCGAGGT  3180
ATGTAGGCGG TGCTACAGAG TTCTTGAAGT GGTGGCCTAA CTACGGCTAC ACTAGAAGGA  3240
CAGTATTTGG TATCTGCGCT CTGCTGAAGC CAGTTACCTT CGGAAAAAGA GTTGGTAGCT  3300
CTTGATCCGG CAAACAAACC ACCGCTGGTA GCGGTGGTTT TTTTGTTTGC AAGCAGCAGA  3360
TTACGCGCAG AAAAAAAGGA TCTCAAGAAG ATCCTTTGAT CTTTTCTACG GGTCTGACG   3420
CTCAGTGGAA CGAAAACTCA CGTTAAGGGA TTTTGGTCAT GAGATTATCA AAAAGGATCT  3480
TCACCTAGAT CCTTTTAAAT TAAAAATGAA GTTTTAAATC AATCTAAAGT ATATATGAGT  3540
AAACTTGGTC TGACAGTTAC CAATGCTTAA TCAGTGAGGC ACCTATCTCA GCGATCTGTC  3600
TATTTCGTTC ATCCATAGTT GCCTGACTCC CCGTCGTGTA GATAACTACG ATACGGGAGG  3660
GCTTACCATC TGGCCCCAGT GCTGCAATGA TACCGCGAGA CCCACGCTCA CCGGCTCCAG  3720
ATTTATCAGC AATAAACCAG CCAGCCGGAA GGGCCGAGCG CAGAAGTGGT CCTGCAACTT  3780
TATCCGCCTC CATCCAGTCT ATTAATTGTT GCCGGGAAGC TAGAGTAAGT AGTTCGCCAG  3840
TTAATAGTTT GCGCAACGTT GTTGCCATTG CTACAGGCAT CGTGGTGTCA CGCTCGTCGT  3900
TTGGTATGGC TTCATTCAGC TCCGGTTCCC AACGATCAAG GCGAGTTACA TGATCCCCCA  3960
TGTTGTGCAA AAAAGCGGTT AGCTCCTTCG GTCCTCCGAT CGTTGTCAGA AGTAAGTTGG  4020
CCGCAGTGTT ATCACTCATG GTTATGGCAG CACTGCATAA TTCTCTTACT GTCATGCCAT  4080
CCGTAAGATG CTTTTCTGTG ACTGGTGAGT ACTCAACCAA GTCATTCTGA GAATAGTGTA  4140
TGCGGCGACC GAGTTGCTCT TGCCCGGCGT CAATACGGGA TAATACCGCG CCACATAGCA  4200
GAACTTTAAA AGTGCTCATC ATTGGAAAAC GTTCTTCGGG GCGAAAACTC TCAAGGATCT  4260
TACCGCTGTT GAGATCCAGT TCGATGTAAC CCACTCGTGC ACCCAACTGA TCTTCAGCAT  4320
CTTTTACTTT CACCAGCGTT TCTGGGTGAG CAAAAACAGG AAGGCAAAAT GCCGCAAAAA  4380
AGGGAATAAG GGCGACACGG AAATGTTGAA TACTCATACT CTTCCTTTTT CAATATTATT  4440
GAAGCATTTA TCAGGGTTAT TGTCTCATGA GCGGATACAT ATTTGAATGT ATTTAGAAAA  4500
ATAAACAAAT AGGGGTTCCG CGCACATTTC CCCGAAAAGT GCCACCTGAC GTC         4553
```

FIG. 25B pPEF5.1Max

```
GACGGATCGG GAGATCTCCC GATCCCCTAT GGTCGACTCT CAGTACAATC TGCTCTGATG    60
CCGCATAGTT AAGCCAGTAT CTGCTCCCTG CTTGTGTGTT GGAGGTCGCT GAGTAGTGCG   120
CGAGCAAAAT TAAGCTACA ACAAGGCAAG GCTTGACCGA CAATTGCATG AAGAATCTGC   180
TTAGGGTTAG GCGTTTTGCG CTGCTTCGCG ATGTACGGGC CAGATATACG CGTTGACATT   240
GATTATTGAC TAGTTATTAA TAGTAATCAA TTACGGGGTC ATTAGTTCAT AGCCCATATA   300
TGGAGTTCCG CGTTACATAA CTTACGGTAA ATGGCCCGCC TGGCTGACCG CCCAACGACC   360
CCCGCCCATT GACGTCAATA ATGACGTATG TTCCCATAGT AACGCCAATA GGGACTTTCC   420
ATTGACGTCA ATGGGTGGAC TATTTACGGT AAACTGCCCA CTTGGCAGTA CATCAAGTGT   480
ATCATATGCC AAGTCCGCCC CCTATTGACG TCAATGACGG TAAATGGCCC GCCTGGCATT   540
ATGCCCAGTA CATGACCTTA CGGGACTTTC CTACTTGGCA GTACATCTAC GTATTAGTCA   600
TCGCTATTAC CATGGTGATG CGGTTTTGGC AGTACACCAA TGGGCGTGGA TAGCGGTTTG   660
ACTCACGGGG ATTTCCAAGT CTCCACCCCA TTGACGTCAA TGGGAGTTTG TTTTGGCACC   720
AAAATCAACG GGACTTTCCA AAATGTCGTA ATAACCCCGC CCGTTGACG CAAATGGGCG   780
GTAGGCGTGT ACGGTGGGAG GTCTATATAA GCAGAGCTCG TTTAGTGAAC CGTCAGATCT   840
CTAGAAGCTG GGTACCGAAA TTAATACGAC TCACTATAGG GAGACCCAAG CTGGCTTGCG   900
TTTAAACTTA AGCTTAGCGC AGAGGCTTGG GGCAGCCGAG CGGCAGCCAG GCCCCGGCCC   960
GGGCCTCGGT TCCAGAAGGG AGAGGAGCCC GCCAAGGCGC GCAAGAGAGC GGGCTGCCTC  1020
GCAGTCCGAG CCGGAGAGGG AGCGCGAGCC GCGCCGGCCC CGGACGGCCT CCGAAACCAT  1080
GGGAGTCAAA GTTCTGTTTG CCCTGATCTG CATCGCTGTG GCCGAGGCCA AGCCCACGCT  1140
AGCCGAGGTT GCTTTGAGGA TCCAGTGTGG TGGAATTCTG CAGATATCCA GCACAGTGGC  1200
GGCCGCTCGA GTCTAGAGGG CCCGTTTAAA CCCGCTGATC AGCCTCGACT GTGCCTTCTA  1260
GTTGCCAGCC ATCTGTTGTT TGCCCCTCCC CCGTGCCTTC CTTGACCCTG GAAGGTGCCA  1320
CTCCCACTGT CCTTTCCTAA TAAAATGAGG AAATTGCATC GCATTGTCTG AGTAGGTGTC  1380
ATTCTATTCT GGGGGGTGGG GTGGGGCAGG ACAGCAAGGG GGAGGATTGG GAAGACAATA  1440
GCAGGCATGC TGGGGATGCG GTGGGCTCTA TGGCTTCTGA GGCGGAAAGA ACCAGCTGGG  1500
GCTCTAGGGG GTATCCCCAC GCGCCCTGTA GCGGCGCATT AAGCGCGGCG GGTGTGGTGG  1560
TTACGCAACC CAGAGATCGC TGCGTTCCCG CCCCCTCACC CGCCCGCTCT CGTCATCACT  1620
GAGGTGGAGA AGAGCATGCG TGAGGCTCCG GTGCCCGTCA GTGGGCAGAG CGCACATCGC  1680
CCACAGTCCC CGAGAAGTTG GGGGGAGGGG TCGGCAATTG AACCGGTGCC TAGAGAAGGT  1740
GGCGCGGGGT AAACTGGGAA AGTGATGTCG TGTACTGGCT CCGCCTTTTT CCCGAGGGTG  1800
GGGGAGAACC GTATATAAGT GCAGTAGTCG CCGTGAACGT TCTTTTTCGC AACGGGTTTG  1860
CCGCCAGAAC ACAGGTGTCG TGAAAACTAC CCCTAAAAGC TTCAAAATGG CCAAGTTGAC  1920
CAGTGCCGTT CCGGTGCTCA CCGCGCGCGA CGTCGCCGGA GCGGTCGAGT CTGGACCGA  1980
CCGGCTCGGG TTCTCCCGGG ACTTCGTGGA GGACGACTTC GCCGGTGTGG TCCGGGACGA  2040
CGTGACCCTG TTCATCAGCG CGGTCCAGGA CCAGGTGGTG CCGGACAACA CCCTGGCCTG  2100
GGTGTGGGTG CGCGGCCTGG ACGAGCTGTA CGCCGAGTGG TCGGAGGTCG TGTCCACGAA  2160
CTTCCGGGAC GCCTCCGGGC CGGCCATGAC CGAGATCGGC GAGCAGCCGT GGGGGCGGGA  2220
GTTCGCCCTG CGCGACCCGG CCGGCAACTG CGTGCACTTC GTGGCCGAGG AGCAGGACTG  2280
ACACGTGCTA CGAGATTTCG ATTCCACCGC CGCCTTCTAT GAAAGGTTGG GCTTCGGAAT  2340
CGTTTTCCGG GACGCCGGCT GGATGATCCT CCAGCGCGGG GATCTCATGC TGGAGTTCTT  2400
CGCCCACCCC AACTTGTTTA TTGCAGCTTA TAATGGTTAC AAATAAAGCA ATAGCATCAC  2460
AAATTTCACA AATAAAGCAT TTTTTCACT GCATTCTAGT TGTGGTTTGT CCAAACTCAT  2520
CAATGTATCT TATCATGTCT GTATACCGTC GACCTCTAGC TAGAGCTTGG CGTAATCATG  2580
GTCATAGCTG TTTCCTGTGT GAAATTGTTA TCCGCTCACA ATTCCACACA ACATACGAGC  2640
CGGAAGCATA AAGTGTAAAG CCTGGGGTGC CTAATGAGTG AGCTAACTCA CATTAATTGC  2700
GTTGCGCTCA CTGCCCGCTT TCCAGTCGGG AAACCTGTCG TGCCAGCTGC ATTAATGAAT  2760
CGGCCAACGC GCGGGGAGAG GCGGTTTGCG TATTGGGCGC TCTTCCGCTT CCTCGCTCAC  2820
TGACTCGCTG CGCTCGGTCG TTCGGCTGCG GCGAGCGGTA TCAGCTCACT CAAAGGCGGT  2880
AATACGGTTA TCCACAGAAT CAGGGGATAA CGCAGGAAAG AACATGTGAG CAAAAGGCCA  2940
GCAAAAGGCC AGGAACCGTA AAAAGGCCGC GTTGCTGGCG TTTTTCCATA GGCTCCGCCC  3000
CCCTGACGAG CATCACAAAA ATCGACGCTC AAGTCAGAGG TGGCGAAACC CGACAGGACT  3060
```

FIG. 26A

```
ATAAAGATAC CAGGCGTTTC CCCCTGGAAG CTCCCTCGTG CGCTCTCCTG TTCCGACCCT 3120
GCCGCTTACC GGATACCTGT CCGCCTTTCT CCCTTCGGGA AGCGTGGCGC TTTCTCAATG 3180
CTCACGCTGT AGGTATCTCA GTTCGGTGTA GGTCGTTCGC TCCAAGCTGG GCTGTGTGCA 3240
CGAACCCCCC GTTCAGCCCG ACCGCTGCGC CTTATCCGGT AACTATCGTC TTGAGTCCAA 3300
CCCGGTAAGA CACGACTTAT CGCCACTGGC AGCAGCCACT GGTAACAGGA TTAGCAGAGC 3360
GAGGTATGTA GGCGGTGCTA CAGAGTTCTT GAAGTGGTGG CCTAACTACG GCTACACTAG 3420
AAGGACAGTA TTTGGTATCT GCGCTCTGCT GAAGCCAGTT ACCTTCGGAA AAAGAGTTGG 3480
TAGCTCTTGA TCCGGCAAAC AAACCACCGC TGGTAGCGGT GGTTTTTTTG TTTGCAAGCA 3540
GCAGATTACG CGCAGAAAAA AAGGATCTCA AGAAGATCCT TTGATCTTTT CTACGGGGTC 3600
TGACGCTCAG TGGAACGAAA ACTCACGTTA AGGGATTTTG GTCATGAGAT TATCAAAAAG 3660
GATCTTCACC TAGATCCTTT TAAATTAAAA ATGAAGTTTT AAATCAATCT AAAGTATATA 3720
TGAGTAAACT TGGTCTGACA GTTACCAATG CTTAATCAGT GAGGCACCTA TCTCAGCGAT 3780
CTGTCTATTT CGTTCATCCA TAGTTGCCTG ACTCCCCGTC GTGTAGATAA CTACGATACG 3840
GGAGGGCTTA CCATCTGGCC CCAGTGCTGC AATGATACCG CGAGACCCAC GCTCACCGGC 3900
TCCAGATTTA TCAGCAATAA ACCAGCCAGC CGGAAGGGCC GAGCGCAGAA GTGGTCCTGC 3960
AACTTTATCC GCCTCCATCC AGTCTATTAA TTGTTGCCGG GAAGCTAGAG TAAGTAGTTC 4020
GCCAGTTAAT AGTTTGCGCA ACGTTGTTGC CATTGCTACA GGCATCGTGG TGTCACGCTC 4080
GTCGTTTGGT ATGGCTTCAT TCAGCTCCGG TTCCCAACGA TCAAGGCGAG TTACATGATC 4140
CCCCATGTTG TGCAAAAAAG CGGTTAGCTC CTTCGGTCCT CCGATCGTTG TCAGAAGTAA 4200
GTTGGCCGCA GTGTTATCAC TCATGGTTAT GGCAGCACTG CATAATTCTC TTACTGTCAT 4260
GCCATCCGTA AGATGCTTTT CTGTGACTGG TGAGTACTCA ACCAAGTCAT TCTGAGAATA 4320
GTGTATGCGG CGACCGAGTT GCTCTTGCCC GGCGTCAATA CGGGATAATA CCGCGCCACA 4380
TAGCAGAACT TTAAAAGTGC TCATCATTGG AAAACGTTCT TCGGGGCGAA AACTCTCAAG 4440
GATCTTACCG CTGTTGAGAT CCAGTTCGAT GTAACCCACT CGTGCACCCA ACTGATCTTC 4500
AGCATCTTTT ACTTTCACCA GCGTTTCTGG GTGAGCAAAA ACAGGAAGGC AAAATGCCGC 4560
AAAAAAGGGA ATAAGGGCGA CACGGAAATG TTGAATACTC ATACTCTTCC TTTTTCAATA 4620
TTATTGAAGC ATTTATCAGG GTTATTGTCT CATGAGCGGA TACATATTTG AATGTATTTA 4680
GAAAAATAAA CAAATAGGGG TTCCGCGCAC ATTTCCCCGA AAAGTGCCAC CTGACGTC   4738
```

FIG. 26B pCEP-Pu/AC7

| | | | | | | |
|---|---|---|---|---|---|---|
| GCCCCGCCGC | CGGACGAACT | AAACCTGACT | ACGGCATCTC | TGCCCCTTCT | TCGCTGGTAC | 60 |
| GAGGAGCGCT | TTTGTTTTGT | ATTCGGGGCA | GTGCATGTAA | TCCCTTCAGT | TGGTTGGTAC | 120 |
| AACTTGCCAA | CTGGGCCCTG | TTCCACATGT | GACACGGGGG | GGGACCAAAC | ACAAAGGGGT | 180 |
| TCTCTGACTG | TAGTTGACAT | CCTTATAAAT | GGATGTGCAC | ATTTGCCAAC | ACTGAGTGGC | 240 |
| TTTCATCCTG | GAGCAGACTT | TGCATGCTGT | GGACTGCAAC | ACAACATTGC | CTTTATGTGT | 300 |
| AACTCTTGGC | TGAAGCTCTT | ACACCAATGC | TGGGGGACAT | GTACCTCCCA | GGGGCCCAGG | 360 |
| AAGACTACGG | GAGGCTACAC | CAACGTCAAT | CAGAGGGGCC | TGTGTAGCTA | CCGATAAGCG | 420 |
| GACCCTCAAG | AGGGCATTAG | CAATAGTGTT | TATAAGGCCC | CCTTGTTAAC | CCTAAACGGG | 480 |
| TAGCATATGC | TTCCGGGTA | GTAGTATATA | CTATCCAGAC | TAACCCTAAT | TCAATAGCAT | 540 |
| ATGTTACCCA | ACGGGAAGCA | TATGCTATCG | AATTAGGGTT | AGTAAAAGGG | TCCTAAGGAA | 600 |
| CAGCGATATC | TCCCACCCCA | TGAGCTGTCA | CGGTTTTATT | TACATGGGGT | CAGGATTCCA | 660 |
| CGAGGGTAGT | GAACCATTTT | AGTCACAAGG | GCAGTGGCTG | AAGATCAAGG | AGCGGGCAGT | 720 |
| GAACTCTCCT | GAATCTTCGC | CTGCTTCTTC | ATTCTCCTTC | GTTAGCTAA | TAGAATAACT | 780 |
| GCTGAGTTGT | GAACAGTAAG | GTGTATGTGA | GGTGCTCGAA | ACAAGGTTT | CAGGTGACGC | 840 |
| CCCCAGAATA | AAATTTGGAC | GGGGGGTTCA | GTGGTGGCAT | TGTGCTATGA | CACCAATATA | 900 |
| ACCCTCACAA | ACCCCTTGGG | CAATAAATAC | TAGTGTAGGA | ATGAAACATT | CTGAATATCT | 960 |
| TTAACAATAG | AAATCCATGG | GGTGGGGACA | AGCCGTAAAG | ACTGGATGTC | CATCTCACAC | 1020 |
| GAATTTATGG | CTATGGGCAA | CACATAATCC | TAGTGCAATA | TGATACTGGG | GTTATTAAGA | 1080 |
| TGTGTCCCAG | GCAGGGACCA | AGACAGGTGA | ACCATGTTGT | TACACTCTAT | TTGTAACAAG | 1140 |
| GGGAAAGAGA | GTGGACGCCG | ACAGCAGCGG | ACTCCACTGG | TTGTCTCTAA | CACCCCGAA | 1200 |
| AATTAAACGG | GGCTCCACGC | CAATGGGGCC | CATAAACAAA | GACAAGTGGC | CACTCTTTTT | 1260 |
| TTTGAAATTG | TGGAGTGGGG | GCACGCGTCA | GCCCCACAC | GCCGCCCTGC | GGTTTTGGAC | 1320 |
| TGTAAAATAA | GGGTGTAATA | ACTTGGCTGA | TTGTAACCCC | GCTAACCACT | GCGGTCAAAC | 1380 |
| CACTTGCCCA | CAAAACCACT | AATGGCACCC | CGGGGAATAC | CTGCATAAGT | AGGTGGGCGG | 1440 |
| GCCAAGATAG | GGGCGCGATT | GCTGCGATCT | GGAGGACAAA | TTACACACAC | TTGCGCCTGA | 1500 |
| GCGCCAAGCA | CAGGGTTGTT | GGTCCTCATA | TTCACGAGGT | CGCTGAGAGC | ACGGTGGGCT | 1560 |
| AATGTTGCCA | TGGGTAGCAT | ATACTACCCA | AATATCTGGA | TAGCATATGC | TATCCTAATC | 1620 |
| TATATCTGGG | TAGCATAGGC | TATCCTAATC | TATATCTGGG | TAGCATATGC | TATCCTAATC | 1680 |
| TATATCTGGG | TAGTATATGC | TATCCTAATT | TATATCTGGG | TAGCATAGGC | TATCCTAATC | 1740 |
| TATATCTGGG | TAGCATATGC | TATCCTAATC | TATATCTGGG | TAGTATATGC | TATCCTAATC | 1800 |
| TGTATCCGGG | TAGCATATGC | TATCCTAATA | GAGATTAGGG | TAGTATATGC | TATCCTAATT | 1860 |
| TATATCTGGG | TAGCATATAC | TACCCAAATA | TCTGGATAGC | ATATGCTATC | CTAATCTATA | 1920 |
| TCTGGGTAGC | ATATGCTATC | CTAATCTATA | TCTGGGTAGC | ATAGGCTATC | CTAATCTATA | 1980 |
| TCTGGGTAGC | ATATGCTATC | CTAATCTATA | TCTGGGTAGT | ATATGCTATC | CTAATTTATA | 2040 |
| TCTGGGTAGC | ATAGGCTATC | CTAATCTATA | TCTGGGTAGC | ATATGCTATC | CTAATCTATA | 2100 |
| TCTGGGTAGT | ATATGCTATC | CTAATCTGTA | TCCGGGTAGC | ATATGCTATC | CTCATGCATA | 2160 |
| TACAGTCAGC | ATATGATACC | CAGTAGTAGA | GTGGGAGTGC | TATCCTTTGC | ATATGCCGCC | 2220 |
| ACCTCCCAAG | GGGGCGTGAA | TTTTCGCTGC | TTGTCCTTTT | CCTGCATGCT | GGTTGCTCCC | 2280 |
| ATTCTTAGGT | GAATTTAAGG | AGGCCAGGCT | AAAGCCGTCG | CATGTCTGAT | TGCTCACCAG | 2340 |
| GTAAATGTCG | CTAATGTTTT | CCAACGCGAG | AAGGTGTTGA | GCGCGGAGCT | GAGTGACGTG | 2400 |
| ACAACATGGG | TATGCCCAAT | TGCCCCATGT | TGGGAGGACG | AAAATGGTGA | CAAGACAGAT | 2460 |
| GGCCAGAAAT | ACACCAACAG | CACGCATGAT | GTCTACTGGG | GATTATTCT | TTAGTGCGGG | 2520 |
| GGAATACACG | GCTTTAATA | CGATTGAGGG | CGTCTCCTAA | CAAGTTACAT | CACTCCTGCC | 2580 |
| CTTCCTCACC | CTCATCTCCA | TCACCTCCTT | CATCTCCGTC | ATCTCCGTCA | TCACCCTCCG | 2640 |
| CGGCAGCCCC | TTCCACCATA | GGTGGAAACC | AGGGAGGCAA | ATCTACTCCA | TCGTCAAAGC | 2700 |
| TGCACACAGT | CACCCTGATA | TTGCAGGTAG | GAGCGGGCTT | TGTCATAACA | AGGTCCTTAA | 2760 |
| TCGCATCCTT | CAAAACCTCA | GCAAATATAT | GAGTTTGTAA | AAAGACCATG | AAATAACAGA | 2820 |
| CAATGGACTC | CCTTAGCGGG | CCAGGTTGTG | GGCCGGGTCC | AGGGGCCATT | CCAAGGGGA | 2880 |
| GACGACTCAA | TGGTGTAAGA | CGACATTGTG | GAATAGCAAG | GGCAGTTCCT | CGCCTTAGGT | 2940 |
| TGTAAAGGGA | GGTCTTACTA | CCTCCATATA | CGAACACACC | GGCGACCCAA | GTTCCTTCGT | 3000 |
| CGGTAGTCCT | TTCTACGTGA | CTCCTAGCCA | GGAGAGCTCT | TAAACCTTCT | GCAATGTTCT | 3060 |
| CAAATTTCGG | GTTGGAACCT | CCTTGACCAC | GATGCTTTCC | AAACCACCCT | CCTTTTTTGC | 3120 |
| GCCTGCCTCC | ATCACCCTGA | CCCCGGGGTC | CAGTGCTTGG | GCCTTCTCCT | GGGTCATCTG | 3180 |

FIG. 27A

```
CGGGGCCCTG CTCTATCGCT CCCGGGGGCA CGTCAGGCTC ACCATCTGGG CCACCTTCTT 3240
GGTGGTATTC AAAATAATCG GCTTCCCCTA CAGGGTGGAA AAATGGCCTT CTACCTGGAG 3300
GGGGCCTGCG CGGTGGAGAC CCGGATGATG ATGACTGACT ACTGGGACTC CTGGGCCTCT 3360
TTTCTCCACG TCCACGACCT CTCCCCCTGG CTCTTTCACG ACTTCCCCCC CTGGCTCTTT 3420
CACGTCCTCT ACCCCGGCGG CCTCCACTAC CTCCTCGACC CCGGCCTCCA CTACCTCCTC 3480
GACCCCGGCC TCCACTGCCT CCTCGACCCC GGCCTCCACC TCCTGCTCCT GCCCCTCCTG 3540
CTCCTGCCCC TCCTCCTGCT CCTGCCCCTC CTGCCCCTCC TGCTCCTGCC CCTCCTGCCC 3600
CTCCTGCTCC TGCCCCTCCT GCCCCTCCTG CTCCTGCCCC TCCTGCCCCT CCTCCTGCTC 3660
CTGCCCCTCC TGCCCCTCCT CCTGCTCCTG CCCTCCTGC CCTCCTGCT CCTGCCCCTC 3720
CTGCCCCTCC TGCTCCTGCC CCTCCTGCCC CTCCTGCTCC TGCCCCTCCT GCTCCTGCCC 3780
CTCCTGCTCC TGCCCCTCCT GCTCCTGCCC CTCCTGCCCC TCCTGCCCCT CCTCCTGCTC 3840
CTGCCCCTCC TGCTCCTGCC CCTCCTGCCC CTCCTGCCCC TCCTGCTCCT GCCCCTCCTC 3900
CTGCTCCTGC CCTCCTGCC CCTCCTGCCC CTCCTCCTGC TCCTGCCCCT CCTGCCCCTC 3960
CTCCTGCTCC TGCCCCTCCT CCTGCTCCTG CCCTCCTGC CCTCCTGCC CCTCCTCCTG 4020
CTCCTGCCCC TCCTGCCCCT CCTCCTGCTC CTGCCCCTCC TCCTGCTCCT GCCCCTCCTG 4080
CCCCTCCTGC CCCTCCTCCT GCTCCTGCCC CTCCTCCTGC TCCTGCCCCT CCTGCCCCTC 4140
CTGCCCCTCC TGCCCCTCCT GCTCCTGCTG CCCCTCCTCC TGCTCCTGCC CCTCCTGCTC 4200
CTGCCCCTCC CGCTCCTGCT CCTGCTCCTG TTCCACCGTG GGTCCCTTTG CAGCCAATGC 4260
AACTTGGACG TTTTTGGGGT CTCCGGACAC CATCTCTATG TCTTGGCCCT GATCCTGAGC 4320
CGCCCGGGGC TCCTGGTCTT CCGCCTCCTC GTCCTCGTCC TCTTCCCCGT CCTCGTCCAT 4380
GGTTATCACC CCTCTTCTT TGAGGTCCAC TGCCGCCGGA GCCTTCTGGT CCAGATGTGT 4440
CTCCCTTCTC TCCTAGGCCA TTTCCAGGTC CTGTACCTGG CCCTCGTCA GACATGATTC 4500
ACACTAAAAG AGATCAATAG ACATCTTTAT TAGACGACGC TCAGTGAATA CAGGGAGTGC 4560
AGACTCCTGC CCCCTCCAAC AGCCCCCCCA CCCTCATCCC CTTCATGGTC GCTGTCAGAC 4620
AGATCCAGGT CTGAAAATTC CCCATCCTCC GAACCATCCT CGTCCTCATC ACCAATTACT 4680
CGCAGCCCGG AAAACTCCCG CTGAACATCC TCAAGATTTG CGTCCTGAGC CTCAAGCCAG 4740
GCCTCAAATT CCTCGTCCCC CTTTTTGCTG GACGGTAGGG ATGGGGATTC TCGGGACCCC 4800
TCCTCTTCCT CTTCAAGGTC ACCAGACAGA GATGCTACTG GGGCAACGGA AGAAAAGCTG 4860
GGTGCGGCCT GTGAGGATCA GCTTATCGAT GATAAGCTGT CAAACATGAG AATTCTTGAA 4920
GACGAAAGGG CCTCGTGATA CGCCTATTTT TATAGGTTAA TGTCATGATA ATAATGGTTT 4980
CTTAGACGTC AGGTGGCACT TTTCGGGGAA ATGTGCGCGG AACCCCTATT TGTTTATTTT 5040
TCTAAATACA TTCAAATATG TATCCGCTCA TGAGACAATA ACCCTGATAA ATGCTTCAAT 5100
AATATTGAAA AAGGAAGAGT ATGAGTATTC AACATTTCCG TGTCGCCCTT ATTCCCTTTT 5160
TTGCGGCATT TTGCCTTCCT GTTTTTGCTC ACCCAGAAAC GCTGGTGAAA GTAAAAGATG 5220
CTGAAGATCA GTTGGGTGCA CGAGTGGGTT ACATCGAACT GGATCTCAAC AGCGGTAAGA 5280
TCCTTGAGAG TTTTCGCCCC GAAGAACGTT TTCCAATGAT GAGCACTTTT AAAGTTCTGC 5340
TATGTGGCGC GGTATTATCC CGTGTTGACG CCGGGCAAGA GCAACTCGGT CGCCGCATAC 5400
ACTATTCTCA GAATGACTTG GTTGAGTACT CACCAGTCAC AGAAAAGCAT CTTACGGATG 5460
GCATGACAGT AAGAGAATTA TGCAGTGCTG CCATAACCAT GAGTGATAAC ACTGCGGCCA 5520
ACTTACTTCT GACAACGATC GGAGGACCGA AGGAGCTAAC CGCTTTTTTG CACAACATGG 5580
GGGATCATGT AACTCGCCTT GATCGTTGGG AACCGGAGCT GAATGAAGCC ATACCAAACG 5640
ACGAGCGTGA CACCACGATG CCTGCAGCAA TGGCAACAAC GTTGCGCAAA CTATTAACTG 5700
GCGAACTACT TACTCTAGCT TCCCGGCAAC AATTAATAGA CTGGATGGAG GCGGATAAAG 5760
TTGCAGGACC ACTTCTGCGC TCGGCCCTTC CGGCTGGCTG GTTTATTGCT GATAAATCTG 5820
GAGCCGGTGA GCGTGGGTCT CGCGGTATCA TTGCAGCACT GGGGCCAGAT GGTAAGCCCT 5880
CCCGTATCGT AGTTATCTAC ACGACGGGGA GTCAGGCAAC TATGGATGAA CGAAATAGAC 5940
AGATCGCTGA GATAGGTGCC TCACTGATTA AGCATTGGTA ACTGTCAGAC CAAGTTTACT 6000
CATATATACT TTAGATTGAT TTAAAACTTC ATTTTAATT TAAAAGGATC TAGGTGAAGA 6060
TCCTTTTTGA TAATCTCATG ACCAAAATCC CTTAACGTGA GTTTCGTTC CACTGAGCGT 6120
CAGACCCCGT AGAAAAGATC AAAGGATCTT CTTGAGATCC TTTTTTTCTG CGCGTAATCT 6180
GCTGCTTGCA AACAAAAAAA CCACCGCTAC CAGCGGTGGT TTGTTTGCCG GATCAAGAGC 6240
TACCAACTCT TTTTCCGAAG GTAACTGGCT TCAGCAGAGC GCAGATACCA AATACTGTCC 6300
TTCTAGTGTA GCCGTAGTTA GGCCACCACT TCAAGAACTC TGTAGCACCG CCTACATACC 6360
TCGCTCTGCT AATCCTGTTA CCAGTGGCTG CTGCCAGTGG CGATAAGTCG TGTCTTACCG 6420
GGTTGGACTC AAGACGATAG TTACCGGATA AGGCGCAGCG GTCGGGCTGA ACGGGGGGTT 6480
CGTGCACACA GCCCAGCTTG GAGCGAACGA CCTACACCGA ACTGAGATAC CTACAGCGTG 6540
```

FIG. 27B

```
AGCTATGAGA AAGCGCCACG CTTCCCGAAG GGAGAAAGGC GGACAGGTAT CCGGTAAGCG 6600
GCAGGGTCGG AACAGGAGAG CGCACGAGGG AGCTTCCAGG GGGAAACGCC TGGTATCTTT 6660
ATAGTCCTGT CGGGTTTCGC CACCTCTGAC TTGAGCGTCG ATTTTTGTGA TGCTCGTCAG 6720
GGGGGCGGAG CCTATGGAAA AACGCCAGCA ACGCGGCCTT TTTACGGTTC CTGGCCTTTT 6780
GCTGCGCCGC GTGCGGCTGC TGGAGATGGC GGACGCGATG GATATGTTCT GCCAAGGGTT 6840
GGTTTGCGCA TTCACAGTTC TCCGCAAGAA TTGATTGGCT CCAATTCTTG GAGTGGTGAA 6900
TCCGTTAGCG AGGCCATCCA GCCTCGCGTC GAACTAGATG ATCCGCTGTG GAATGTGTGT 6960
CAGTTAGGGT GTGGAAAGTC CCCAGGCTCC CCAGCAGGCA GAAGTATGCA AAGCATGCAT 7020
CTCAATTAGT CAGCAACCAG GTGTGGAAAG TCCCCAGGCT CCCCAGCAGG CAGAAGTATG 7080
CAAAGCATGC ATCTCAATTA GTCAGCAACC ATAGTCCCGC CCCTAACTCC GCCCATCCCG 7140
CCCCTAACTC CGCCCAGTTC CGCCCATTCT CCGCCCCATG GCTGACTAAT TTTTTTTATT 7200
TATGCAGAGG CCGAGGCCGC CTCGGCCTCT GAGCTATTCC AGAAGTAGTG AGGAGGCTTT 7260
TTTGGAGGGT GACCGCCACG ACCGGTGCCG CCACCATCCC CTGACCCACG CCCCTGACCC 7320
CTCACAAGGA GACGACCTTC CATGACCGAG TACAAGCCCA CGGTGCGCCT CGCCACCCGC 7380
GACGACGTCC CCCGGGCCGT ACGCACCCTC GCCGCCGCGT TCGCCGACTA CCCCGCCACG 7440
CGCCACACCG TCGACCCCGA CCGCCACATC GAACGCGTCA CCGAGCTGCA AGAACTCTTC 7500
CTCACGCGCG TCGGGCTCGA CATCGGCAAG GTGTGGGTCG CGGACGACGG CGCCGCGGTG 7560
GCGGTCTGGA CCACGCCGGA GAGCGTCGAA GCGGGGGCGG TGTTCGCCGA GATCGGCCCG 7620
CGCATGGCCG AGTTGAGCGG TTCCCGGCTG GCCGCGCAGC AACAGATGGA AGGCCTCCTG 7680
GCGCCGCACC GGCCCAAGGA GCCCGCGTGG TTCCTGGCCA CCGTCGGCGT CTCGCCCGAC 7740
CACCAGGGCA AGGGTCTGGG CAGCGCCGTC GTGCTCCCCG GAGTGGAGGC GGCCGAGCGC 7800
GCCGGGGTGC CCGCCTTCCT GGAGACCTCC GCGCCCCGCA ACCTCCCCTT CTACGAGCGG 7860
CTCGGCTTCA CCGTCACCGC CGACGTCGAG TGCCCGAAGG ACCGCGCGAC CTGGTGCATG 7920
ACCCGCAAGC CCGGTGCCTG ACGCCCGCCC CACGACCCGC AGCGCCCGAC CGAAAGGAGC 7980
GCACGACCCG GTCCGACGGC GGCCCACGGG TCCCAGGGGG GTCGACCTCG AAACTTGTTT 8040
ATTGCAGCTT ATAATGGTTA CAAATAAAGC AATAGCATCA CAAATTTCAC AAATAAAGCA 8100
TTTTTTTCAC TGCATTCTAG TTGTGGTTTG TCCAAACTCA TCAATGTATC TTATCATGTC 8160
TGGATCGATC CGAACCCCTT CCTCGACCAA TTCTCATGTT TGACAGCTTA TCATCGCAGA 8220
TCCGGGCAAC GTTGTTGCAT TGCTGCAGGC GCAGAACTGG TAGGTATGGA AGATCTATAC 8280
ATTGAATCAA TATTGGCAAT TAGCCATATT AGTCATTGGT TATATAGCAT AAATCAATAT 8340
TGGCTATTGG CCATTGCATA CGTTGTATCT ATATCATAAT ATGTACATTT ATATTGGCTC 8400
ATGTCCAATA TGACCGCCAT GTTGACATTG ATTATTGACT AGTTATTAAT AGTAATCAAT 8460
TACGGGGTCA TTAGTTCATA GCCCATATAT GGAGTTCCGC GTTACATAAC TTACGGTAAA 8520
TGGCCCGCCT GGCTGACCGC CCAACGACCC CCGCCCATTG ACGTCAATAA TGACGTATGT 8580
TCCCATAGTA ACGCCAATAG GGACTTTCCA TTGACGTCAA TGGGTGGAGT ATTTACGGTA 8640
AACTGCCCAC TTGGCAGTAC ATCAAGTGTA TCATATGCCA AGTCCGCCCC CTATTGACGT 8700
CAATGACGGT AAATGGCCCG CCTGGCATTA TGCCCAGTAC ATGACCTTAC GGACTTTCC 8760
TACTTGGCAG TACATCTACG TATTAGTCAT CGCTATTACC ATGGTGATGC GGTTTTGGCA 8820
GTACACCAAT GGGCGTGGAT AGCGGTTTGA CTCACGGGGA TTTCCAAGTC TCCACCCCAT 8880
TGACGTCAAT GGGAGTTTGT TTTGGCACCA AAATCAACGG GACTTTCCAA AATGTCGTAA 8940
TAACCCCGCC CCGTTGACGC AAATGGGCGG TAGGCGTGTA CGGTGGGAGG TCTATATAAG 9000
CAGAGCTCGT TTAGTGAACC GTCAGATCTC TAGAAGCTGG GTACCTTAAG GCCCAGCTG 9060
ATCAAGCTTC TGCCTGCCGC CTGCCTGCCT GCCACTGAGG GTTCCCAGCA CCATGAGGGC 9120
CTGGATCTTC TTTCTCCTTT GCCTGGCCGG GAGGGCTCTG GCAGCCCCGC TAGCTCTCAC 9180
TGAAACAGAT ATATGCAAGT TGCCGAAAGA CGAAGGAACT TGCAGGGATT TCATATTAAA 9240
ATGGTACTAT GATCCAAACA CCAAAAGCTG TGCAAGATTC TGGTATGGAG TTGTGGTGG 9300
AAACGAAAAC AAATTTGGAT CACAGAAAGA ATGTGAAAAG GTTTGCGCTC CTGTGCTCGC 9360
CAAACCCGGA GTCATCAGTG TGATGGGAAC CTAAGCGTGG GTGGCCAACA TCATATACCT 9420
CTTGAAGAAG AAGGAGTCAG CCATCGCCAA CTTGTCTCGA GGTCCGCGGC CGCTCGAGGC 9480
CGGCAAGGCC GGATCCAGAC ATGATAAGAT ACATTGATGA GTTTGGACAA ACCACAACTA 9540
GAATGCAGTG AAAAAAATGC TTTATTTGTG AAATTTGTGA TGCTATTGCT TTATTTGTAA 9600
CCATTATAAG CTGCAATAAA CAAGTTAACA ACAACAATTG CATTCATTTT ATGTTTCAGG 9660
TTCAGGGGGA GGTGGGGAGG TTTTTTAAAG CAAGTAAAAC CTCTACAAAT GTGGTATGGC 9720
TGATTATGAT CCGGCTGCCT CGCGCGTTTC GGTGATGACG GTGAAAACCT CTGACACATG 9780
CAGCTCCCGG AGACGGTCAC AGCTTGTCTG TAAGCGGATG CCGGGAGCAG ACAAGCCCGT 9840
CAGGGCGCGT CAGCGGGTGT TGGCGGGTGT CGGGGCGCAG CCATGACCGG TCGACTCTAG 9900
A                9901
```

FIG. 27C

AGCGCAGAGGCTTGGGGCAGCCGAGCGGCAGCCAGGCCCCGGCCCGGGCCTCGGTTCC
AGAAGGGAGAGGAGCCCGCCAAGGCGCGCAAGAGAGCGGGCTGCCTCGCAGTCCGAG
CCGGAGAGGGAGCGCGAGCCGCGCCGGCCCCGGACGGCCTCCGAAACC

FIG. 28A

*NheI*       *HpaI*
AC<u>GCTAGC</u>CGAG<u>GTTAAC</u>TGTTGTCCTGGCTGTTGCGGTTCCGGACACCATCATCACCA
CCATCACCATCACC

*BamHI*       *EcoRI*  *PstI*  *EcoRV*       *NotI*
*XhoI*    *ApaI*
ATTGA<u>GGATCC</u>AGTGTGGTG<u>GAATTCTGCAGATATC</u>CAGCACAGTG<u>GCGGCCGCTCGAG</u>
TCTAGA<u>GGGCCC</u>GTTTAA

FIG. 28B

*NheI*            *BamHI*       *EcoRI*  *PstI*  *EcoRV*
*NotI*
AC<u>GCTAGC</u>CGAGGTTGCTTTGA<u>GGATCC</u>AGTGTGGTG<u>GAATTCTGCAGATATC</u>CAGCAC
AGTG<u>GCGGCCGCTC</u>

*XhoI*        *ApaI*
<u>GAG</u>TCTAGA<u>GGGCCC</u>GTTTAA

FIG. 28C

MPSSVSWGILLLAGLCCLVPVSLA

FIG. 28D

```
CTGTGGAATG TGTGTCAGTT AGGGTGTGGA AAGTCCCCAG GCTCCCCAGC AGGCAGAAGT    60
ATGCAAAGCA TGCATCTCAA TTAGTCAGCA ACCAGGTGTG GAAAGTCCCC AGGCTCCCCA   120
GCAGGCAGAA GTATGCAAAG CATGCATCTC AATTAGTCAG CAACCATAGT CCCGCCCCTA   180
ACTCCGCCCA TCCCGCCCCT AACTCCGCCC AGTTCCGCCC ATTCTCCGCC CCATGGCTGA   240
CTAATTTTTT TTATTTATGC AGAGGCCGAG GCCGCCTCTG CCTCTGAGCT ATTCCAGAAG   300
TAGTGAGGAG GCTTTTTTGG AGGCCTAGGC TTTTGCAAAA AGCT                    344
```

FIG. 28E

```
ACATTGATTA TTGACTAGTT ATTAATAGTA ATCAATTACG GGGTCATTAG TTCATAGCCC    60
ATATATGGAG TTCCGCGTTA CATAACTTAC GGTAAATGGC CCGCCTGGCT GACCGCCCAA   120
CGACCCCCGC CCATTGACGT CAATAATGAC GTATGTTCCC ATAGTAACGC CAATAGGGAC   180
TTTCCATTGA CGTCAATGGG TGGACTATTT ACGGTAAACT GCCCACTTGG CAGTACATCA   240
AGTGTATCAT ATGCCAAGTC CGCCCCCTAT TGACGTCAAT GACGGTAAAT GGCCCGCCTG   300
GCATTATGCC CAGTACATGA CCTTACGGGA CTTTCCTACT TGGCAGTACA TCTACGTATT   360
AGTCATCGCT ATTACCATGG TGATGCGGTT TTGGCAGTAC ACCAATGGGC GTGGATAGCG   420
GTTTGACTCA CGGGGATTTC CAAGTCTCCA CCCCATTGAC GTCAATGGGA GTTTGTTTTG   480
GCACCAAAAT CAACGGGACT TTCCAAAATG TCGTAATAAC CCCGCCCCGT TGACGCAAAT   540
GGGCGGTAGG CGTGTACGGT GGGAGGTCTA TATAAGC                            577
```

FIG. 28F

```
AACCCAGAGA TCGCTGCGTT CCCGCCCCCT CACCCGCCCG CTCTCGTCAT CACTGAGGTG    60
GAGAAGAGCA TGCGTGAGGC TCCGGTGCCC GTCAGTGGGC AGAGCGCACA TCGCCCACAG   120
TCCCCGAGAA GTTGGGGGGA GGGGTCGGCA ATTGAACCGG TGCCTAGAGA AGGTGGCGCG   180
GGGTAAACTG GGAAAGTGAT GTCGTGTACT GGCTCCGCCT TTTTCCCGAG GGTGGGGGAG   240
AACCGTATAT AAGTGCAGTA GTCGCCGTGA ACGTTCTTTT TCGCAACGGG TTTGCCGCCA   300
GAACACAGGT GTCGTGAAAA CTACCCCTAA AAGCCAAAAT GG                      342
```

FIG. 28G

```
AACCCAGAGA TCGCTGCGTT CCCGCCCCCT CACCCGCCCG CTCTCGTCAT CACTGAGGTG   60
GAGAAGAGCA TGCGTGAGGC TCCGGTGCCC GTCAGTGGGC AGAGCGCACA TCGCCCACAG  120
TCCCCGAGAA GTTGGGGGGA GGGGTCGGCA ATTGAACCGG TGCCTAGAGA AGGTGGCGCG  180
GGGTAAACTG GAAAGTGAT GTCGTGTACT GGCTCCGCCT TTTTCCCGAG GGTGGGGGAG  240
AACCGTATAT AAGTGCAGTA GTCGCCGTGA ACGTTCTTTT TCGCAACGGG TTTGCCGCCA  300
GAACACAGGT AAGTGCCGTG TGTGGTTCCC GCGGGCCTGG CCTCTTTACG GGTTATGGCC  360
CTTGCGTGCC TTGAATTACT TCCACGCCCC TGGCTGCAGT ACGTGATTCT TGATCCCGAG  420
CTTCGGGTTG AAGTGGGTG GGAGAGTTCG AGGCCTTGCG CTTAAGGAGC CCCTTCGCCT  480
CGTGCTTGAG TTGAGGCCTG GCCTGGGCGC TGGGGCCGCC GCGTGCGAAT CTGGTGGCAC  540
CTTCGCGCCT GTCTCGCTGC TTTCGATAAG TCTCTAGCCA TTTAAAATTT TTGATGACCT  600
GCTGCGACGC TTTTTTTCTG GCAAGATAGT CTTGTAAATG CGGGCCAAGA TCTGCACACT  660
GGTATTTCGG TTTTTGGGGC CGCGGGCGGC GACGGGGCCC GTGCGTCCCA GCGCACATGT  720
TCGGCGAGGC GGGGCCTGCG AGCGCGGCCA CCGAGAATCG GACGGGGGTA GTCTCAAGCT  780
GGCCGGCCTG CTCTGGTGCC TGGCCTCGCG CCGCCGTGTA TCGCCCCGCC CTGGGCGGCA  840
AGGCTGGCCC GGTCGGCACC AGTTGCGTGA GCGGAAAGAT GGCCGCTTCC CGGCCCTGCT  900
GCAGGGAGCT CAAAATGGAG GACGCGGCGC TCGGGAGAGC GGGCGGGTGA GTCACCCACA  960
CAAAGGAAAA GGGCCTTTCC GTCCTCAGCC GTCGCTTCAT GTGACTCCAC GGAGTACCGG 1020
GCGCCGTCCA GGCACCTCGA TTAGTTCTCG AGCTTTTGGA GTACGTCGTC TTTAGGTTGG 1080
GGGGAGGGGT TTTATGCGAT GGAGTTTCCC CACACTGAGT GGGTGGAGAC TGAAGTTAGG 1140
CCAGCTTGGC ACTTGATGTA ATTCTCCTTG GAATTTGCCC TTTTTGAGTT TGGATCTTGG 1200
TTCATTCTCA AGCCTCAGAC AGTGGTTCAA AGTTTTTTTC TTCCATTTCA GGTGTCGTGA 1260
AAACTACCCC TAAAAGCCAA AATGG                                      1285
```

FIG. 28H

```
AGATCTCGTG AGGCTCCGGT GCCCGTCAGT GGGCAGAGCG CACATCGCCC ACAGTCCCCG   60
AGAAGTTGGG GGGAGGGGTC GGCAATTGAA CCGGTGCCTA GAGAAGGTGG CGCGGGGTAA  120
ACTGGGAAAG TGATGTCGTG TACTGGCTCC GCCTTTTTCC CGAGGGTGGG GGAGAACCGT  180
ATATAAGTGC ACTAGTCGCC GTGAACGTTC TTTTCGCAA CGGGTTTGCC GCCAGAACAC  240
AGGTAAGTGC CGTGTGTGGT TCCCGCGGGC CTGGCCTCTT TACGGGTTAT GGCCCTTGCG  300
TGCCTTGAAT TACTTCCACC TGGCTGCAGT ACGTGATTCT TGATCCCGAG CTTCGGGTTG  360
GAAGTGGGTG GGAGAGTTCG TGGCCTTGCG CTTAAGGAGC CCCTTCGCCT CGTGCTTGAG  420
TTGTGGCCTG GCCTGGGCGC TGGGGCCGCC GCGTGCGAAT CTGGTGGCAC CTTCGCGCCT  480
GTCTCGCTGC TTTCGATAAG TCTCTAGCCA TTTAAAATTT TTGATGACCT GCTGCGACGC  540
TTTTTTTCTG GCAAGATAGT CTTGTAAATG CGGGCCAAGA TCAGCACACT GGTATTTCGG  600
TTTTTGGGGC CGCGGGCGGC GACGGGGCCC GTGCGTCCCA GCGCACATGT TCGGCGAGGC  660
GGGGCCTGCG AGCGCGGCCA CCGAGAATCG GACGGGGGTA GTCTCAAGCT GCCCGGCCTG  720
CTCTGGTGCC TGGCCTCGCG CCGCCGTGTA TCGCCCCGCC CTGGGCGGCA AGGCTGGCCC  780
GGTCGGCACC AGTTGCGTGA GCGGAAAGAT GGCCGCTTCC CGGCCCTGCT GCAGGGAGCA  840
CAAAATGGAG GACGCGGCGC TCGGGAGAGC GGGCGGGTGA GTCACCCACA CAAAGGAAAA  900
GGGCCTTTCC GTCCTCAGCC GTCGCTTCAT GTGACTCCAC GGAGTACCGG GCGCCGTCCA  960
GGCACCTCGA TTAGTTCTCC AGCTTTTGGA GTACGTCGTC TTTAGGTTGG GGGAGGGGT 1020
TTTATGCGAT GGAGTTTCCC CACACTGAGT GGGTGGAGAC TGAAGTTAGG CCAGCTTGGC 1080
ACTTGATGTA ATTCTCCTTG GAATTTGCCC TTTTTGAGTT TGGATCTTGG TTCATTCTCA 1140
AGCCTCAGAC AGTGGTTCAA AGTTTTTTTC TTCCATTTCA GGTGTCGTGA AAACTACCCC 1200
TAAAAGCCAA AAGATCT                                               1217
```

FIG. 28I

```
                                              HpaI        Lumio tag
CGCTGTGGCCGAGGCCAAGCCCACGCTAGCCGAGGTTAACTGTTGTCCTGGCTGTTGCGGTTCCGGACACCAT
                                              ← Reverse primer
  10xHis tag                    BamHI
CATCACCACCATCACCATCACCATTGAGGATCCAGTGTGGTGGAATTCT
                              Forward primer →
``` pPEF5.2 Reverse primer: CAACAGCCAGGACAACAGTTA pPEF5.2 Forward primer introducing AfeI: GGTGAGCGCTTTGAGGATCCAGTGTGGTGG

FIG. 29

```
CAAAGCATGCATCTCAATTAGTCAGCAACCAGGTGTGGAAAGTCCCCAGGCTCCCCAGCAGGCA
GAAGTATGCAAAGCATGCATCTCAATTAGTCAGCAACCATAGTCCCGCCCCTAACTCCGCCCAT
CCCGCCCCTAACTCCGCCCAGTTCCGCCCATTCTCCGCCCCATGGCTGACTAATTTTTTTATT
TATGCAGAGGCCGAGGCCGCCTCTGCCTCTGAGCTATTCCAGAAGTAGTGAGGAGGCTTTTTG
GAGGCCTAGGCTTTTGCAAAAAGCTTGAGGAACTAAACCATGACCGAGTACAAGCCCACGGTGC
GCCTCGCCACCCGCGACGACGTCCCCAGGGCCGTACGCACCCTCGCCGCCGCGTTCGCCGACTA
CCCCGCCACGCGCCACACCGTCGATCCGGACCGCCACATCGAGCGGGTCACCGAGCTGCAAGAA
CTCTTCCTCACGCGCGTCGGGCTCGACATCGGCAAGGTGTGGGTCGCGGACGACGGCGCCGCGG
TGGCGGTCTGGACCACGCCGGAGAGCGTCGAAGCGGGGCGGTGTTCGCCGAGATCGGCCCGCG
CATGGCCGAGTTGAGCGGTTCCCGGCTGGCCGCGCAGCAACAGATGGAAGGCCTCCTGGCGCCG
CACCGGCCCAAGGAGCCCGCGTGGTTCCTGGCCACCGTCGGCGTCTCGCCCGACCACCAGGGCA
AGGGTCTGGGCAGCGCCGTCGTGCTCCCCGGAGTGGAGGCGGCCGAGCGCGCCGGGGTGCCCGC
CTTCCTGGAGACATCCGCGCCCCGCAACCTCCCCTTCTACGAGCGGCTCGGCTTCACCGTCACC
GCCGACGTCGAGGTGCCCGAAGGACCGCGCACCTGGTGCATGACCCGCAAGCCCGGTGCCTGAC
ACGTG
```

FIG. 30

DNA sequence of pPEF5PuroR

```
GACGGATCGGGAGATCTCCCGATCCCCTATGGTCGACTCTCAGTACAATCTGCTCTGATG   60
CCGCATAGTTAAGCCAGTATCTGCTCCCTGCTTGTGTGTTGGAGGTCGCTGAGTAGTGCG  120
CGAGCAAAATTTAAGCTACAACAAGGCAAGGCTTGACCGACAATTGCATGAAGAATCTGC  180
TTAGGGTTAGGCGTTTTGCGCTGCTTCGCGATGTACGGGCCAGATATACGCGTTGACATT  240
GATTATTGACTAGTTATTAATAGTAATCAATTACGGGGTCATTAGTTCATAGCCCATATA  300
TGGAGTTCCGCGTTACATAACTTACGGTAAATGGCCCGCCTGGCTGACCGCCCAACGACC  360
CCCGCCCATTGACGTCAATAATGACGTATGTTCCCATAGTAACGCCAATAGGGACTTTCC  420
ATTGACGTCAATGGGTGGACTATTTACGGTAAACTGCCCACTTGGCAGTACATCAAGTGT  480
ATCATATGCCAAGTCCGCCCCCTATTGACGTCAATGACGGTAAATGGCCCGCCTGGCATT  540
ATGCCCAGTACATGACCTTACGGGACTTTCCTACTTGGCAGTACATCTACGTATTAGTCA  600
TCGCTATTACCATGGTGATGCGGTTTTGGCAGTACACCAATGGGCGTGGATAGCGGTTTG  660
ACTCACGGGGATTTCCAAGTCTCCACCCCATTGACGTCAATGGGAGTTTGTTTTGGCACC  720
AAAATCAACGGGACTTTCCAAAATGTCGTAATAACCCCGCCCGTTGACGCAAATGGGCG  780
GTAGGCGTGTACGGTGGGAGGTCTATATAAGCAGAGCTCGTTTAGTGAACCGTCAGATCT  840
CTAGAAGCTGGGTACCGAAATTAATACGACTCACTATAGGGGAACCAGCCACCATGGGAG  900
TCAAAGTTCTGTTTGCCCTGATCTGCATCGCTGTGGCCGAGGCCAAGCCCACGCTAGCCG  960
AGGTTGCTTTGAGGATCCAGTGTGGTGGAATTCTGCAGATATCCAGCACAGTGGCGGCCG 1020
CTCGAGTCTAGAGGGCCCGTTTAAACCCGCTGATCAGCCTCGACTGTGCCTTCTAGTTGC 1080
CAGCCATCTGTTGTTTGCCCCTCCCCGTGCCTTCCTTGACCCTGGAAGGTGCCACTCCC 1140
ACTGTCCTTTCCTAATAAAATGAGGAAATTGCATCGCATTGTCTGAGTAGGTGTCATTCT 1200
ATTCTGGGGGGTGGGGTGGGGCAGGACAGCAAGGGGGAGGATTGGGAAGACAATAGCAGG 1260
CATGCTGGGGATGCGGTGGGCTCTATGGCTTCTGAGGCGGAAAGAACCAGCTGGGGCTCT 1320
AGGGGGTATCCCCACGCGCCCTGTAGCGGCGCATTAAGCGCGGCGGGTGTGGTGGTTACG 1380
CCTGTGGAATGTGTGTCAGTTAGGGTGTGGAAAGTCCCCAGGCTCCCCAGCAGGCAGAAG 1440
TATGCAAAGCATGCATCTCAATTAGTCAGCAACCAGGTGTGGAAAGTCCCCAGGCTCCCC 1500
AGCAGGCAGAAGTATGCAAAGCATGCATCTCAATTAGTCAGCAACCATAGTCCGCCCCT 1560
AACTCCGCCCATCCCGCCCCTAACTCCGCCCAGTTCCGCCCATTCTCCGCCCCATGGCTG 1620
ACTAATTTTTTTATTTATGCAGAGGCCGAGGCCGCCTCTGCCTCTGAGCTATTCCAGAA 1680
GTAGTGAGGAGGCTTTTTTGGAGGCCTAGGCTTTTGCAAAAAGCTTGAGGAACTAAACCA 1740
TGACCGAGTACAAGCCCACGGTGCGCCTCGCCACCCGCGACGACGTCCCCAGGGCCGTAC 1800
GCACCCTCGCCGCCGCGTTCGCCGACTACCCCGCCACGCGCCACACCGTCGATCCGGACC 1860
GCCACATCGAGCGGGTCACCGAGCTGCAAGAACTCTTCCTCACGCGCGTCGGGCTCGACA 1920
TCGGCAAGGTGTGGGTCGCGGACGACGGCGCCGCGGTGGCGGTCTGGACCACGCCGGAGA 1980
GCGTCGAAGCGGGGCGGTGTTCGCCGAGATCGGCCCGCGCATGGCCGAGTTGAGCGGTT 2040
CCCGGCTGGCCGCGCAGCAACAGATGGAAGGCCTCCTGGCGCCGCACCGGCCCAAGGAGC 2100
CCGCGTGGTTCCTGGCCACCGTCGGCGTCTCGCCCGACCACCAGGGCAAGGGTCTGGGCA 2160
GCGCCGTCGTGCTCCCCGGAGTGGAGGCGGCCGAGCGCGCCGGGGTGCCCGCCTTCCTGG 2220
AGACATCCGCGCCCGCAACCTCCCCTTCTACGAGCGGCTCGGCTTCACCGTCACCGCCG 2280
ACGTCGAGGTGCCCGAAGGACCGCGCACCTGGTGCATGACCCGCAAGCCCGGTGCCTGAC 2340
ACGTGAAAGTGCTACGAGATTTCGATTCCACCGCCGCCTTCTATGAAAGGTTGGGCTTCG 2400
GAATCGTTTTCCGGGACGCCGGCTGGATGATCCTCCAGCGCGGGGATCTCATGCTGGAGT 2460
```

FIG. 31A

```
TCTTCGCCCACCCCAACTTGTTTATTGCAGCTTATAATGGTTACAAATAAAGCAATAGCA 2520
TCACAAATTTCACAAATAAAGCATTTTTTTCACTGCATTCTAGTTGTGGTTTGTCCAAAC 2580
TCATCAATGTATCTTATCATGTCTGTATACCGTCGACCTCTAGCTAGAGCTTGGCGTAAT 2640
CATGGTCATAGCTGTTTCCTGTGTGAATTGTTATCCGCTCACAATTCCACACAACATAC 2700
GAGCCGGAAGCATAAAGTGTAAAGCCTGGGGTGCCTAATGAGTGAGCTAACTCACATTAA 2760
TTGCGTTGCGCTCACTGCCCGCTTTCCAGTCGGGAAACCTGTCGTGCCAGCTGCATTAAT 2820
GAATCGGCCAACGCGCGGGAGAGGCGGTTTGCGTATTGGGCGCTCTTCCGCTTCCTCGC 2880
TCACTGACTCGCTGCGCTCGGTCGTTCGGCTGCGGCGAGCGGTATCAGCTCACTCAAAGG 2940
CGGTAATACGGTTATCCACAGAATCAGGGGATAACGCAGGAAAGAACATGTGAGCAAAAG 3000
GCCAGCAAAAGGCCAGGAACCGTAAAAAGGCCGCGTTGCTGGCGTTTTTCCATAGGCTCC 3060
GCCCCCCTGACGAGCATCACAAAAATCGACGCTCAAGTCAGAGGTGGCGAAACCCGACAG 3120
GACTATAAAGATACCAGGCGTTTCCCCCTGGAAGCTCCCTCGTGCGCTCTCCTGTTCCGA 3180
CCCTGCCGCTTACCGGATACCTGTCCGCCTTTCTCCCTTCGGGAAGCGTGGCGCTTTCTC 3240
AATGCTCACGCTGTAGGTATCTCAGTTCGGTGTAGGTCGTTCGCTCCAAGCTGGGCTGTG 3300
TGCACGAACCCCCCGTTCAGCCCGACCGCTGCGCCTTATCCGGTAACTATCGTCTTGAGT 3360
CCAACCCGGTAAGACACGACTTATCGCCACTGGCAGCAGCCACTGGTAACAGGATTAGCA 3420
GAGCGAGGTATGTAGGCGGTGCTACAGAGTTCTTGAAGTGGTGGCCTAACTACGGCTACA 3480
CTAGAAGGACAGTATTTGGTATCTGCGCTCTGCTGAAGCCAGTTACCTTCGGAAAAGAG 3540
TTGGTAGCTCTTGATCCGGCAAACAAACCACCGCTGGTAGCGGTGGTTTTTTTGTTTGCA 3600
AGCAGCAGATTACGCGCAGAAAAAAAGGATCTCAAGAAGATCCTTTGATCTTTTCTACGG 3660
GGTCTGACGCTCAGTGGAACGAAAACTCACGTTAAGGGATTTTGGTCATGAGATTATCAA 3720
AAAGGATCTTCACCTAGATCCTTTTAAATTAAAAATGAAGTTTTAAATCAATCTAAAGTA 3780
TATATGAGTAAACTTGGTCTGACAGTTACCAATGCTTAATCAGTGAGGCACCTATCTCAG 3840
CGATCTGTCTATTTCGTTCATCCATAGTTGCCTGACTCCCCGTCGTGTAGATAACTACGA 3900
TACGGGAGGGCTTACCATCTGGCCCCAGTGCTGCAATGATACCGCGAGACCCACGCTCAC 3960
CGGCTCCAGATTTATCAGCAATAAACCAGCCAGCCGGAAGGGCCGAGCGCAGAAGTGGTC 4020
CTGCAACTTTATCCGCCTCCATCCAGTCTATTAATTGTTGCCGGGAAGCTAGAGTAAGTA 4080
GTTCGCCAGTTAATAGTTTGCGCAACGTTGTTGCCATTGCTACAGGCATCGTGGTGTCAC 4140
GCTCGTCGTTTGGTATGGCTTCATTCAGCTCCGGTTCCCAACGATCAAGGCGAGTTACAT 4200
GATCCCCCATGTTGTGCAAAAAAGCGGTTAGCTCCTTCGGTCCTCCGATCGTTGTCAGAA 4260
GTAAGTTGGCCGCAGTGTTATCACTCATGGTTATGGCAGCACTGCATAATTCTCTTACTG 4320
TCATGCCATCCGTAAGATGCTTTTCTGTGACTGGTGAGTACTCAACCAAGTCATTCTGAG 4380
AATAGTGTATGCGGCGACCGAGTTGCTCTTGCCCGGCGTCAATACGGGATAATACCGCGC 4440
CACATAGCAGAACTTTAAAAGTGCTCATCATTGGAAAACGTTCTTCGGGGCGAAAACTCT 4500
CAAGGATCTTACCGCTGTTGAGATCCAGTTCGATGTAACCCACTCGTGCACCCAACTGAT 4560
CTTCAGCATCTTTTACTTTCACCAGCGTTTCTGGGTGAGCAAAAACAGGAAGGCAAAATG 4620
CCGCAAAAAAGGGAATAAGGGCGACACGGAAATGTTGAATACTCATACTCTTCCTTTTTC 4680
AATATTATTGAAGCATTTATCAGGGTTATTGTCTCATGAGCGGATACATATTTGAATGTA 4740
TTTAGAAAAATAAACAAATAGGGGTTCCGCGCACATTTCCCCGAAAAGTGCCACCTGACG 4800
TC
```

FIG. 31A Cont...

| Name | Min/Max | Length | Direction | Type |
|---|---|---|---|---|
| CMV enhancer | 235..614 | 380 | == | enhancer |
| CMV promoter | 615..818 | 204 | => | promoter |
| pCEP Forward primer | 810..832 | 23 | => | primer_bind |
| T7 promoter | 862..880 | 19 | => | primer_bind |
| GLuc Signal Peptide | 894..948 | 55 | => | sig_peptide |
| MCS | 952..1046 | 95 | == | polylinker |
| BGH Reverse pimer | 1058..1075 | 18 | <= | primer_bind |
| bGH poly(A) signal | 1064..1288 | 225 | == | polyA_signal |
| SV40 promoter | 1391..1720 | 330 | => | promoter |
| PuroR | 1740..2339 | 600 | => | CDS |
| SV40 poly(A) signal | 2475..2596 | 122 | == | polyA_signal |
| ori | 3047..3635 | 589 | <= | rep_origin |
| AmpR | 3806..4666 | 861 | <= | CDS |

M – Colour Pre-stained Protein Ladder (NEB)
C – control, conditioned SFM from untransfected HEK 293 EBNA1 cells after 7 days of sub-culturing, 20 µl
T – conditioned SFM from HEK 293 EBNA1 cells stably expressing Trastuzumab after 7 days of sub-culturing, 20 µl

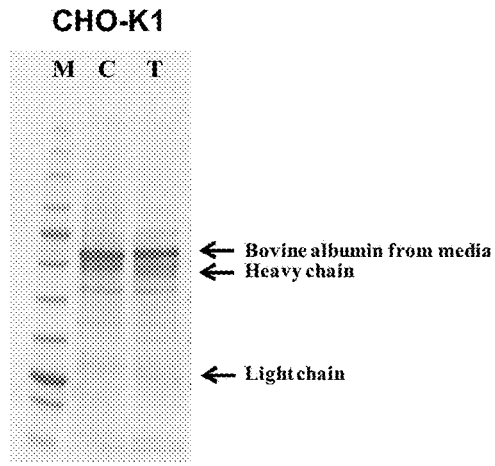

M – Colour Pre-stained Protein Ladder (NEB)
C – control, conditioned SFM from untransfected after 7 days of sub-culturing, 20 µl
T – conditioned SFM from cells stably expressing Trastuzumab after 7 days of sub-culturing, 20 µl

FIG. 35

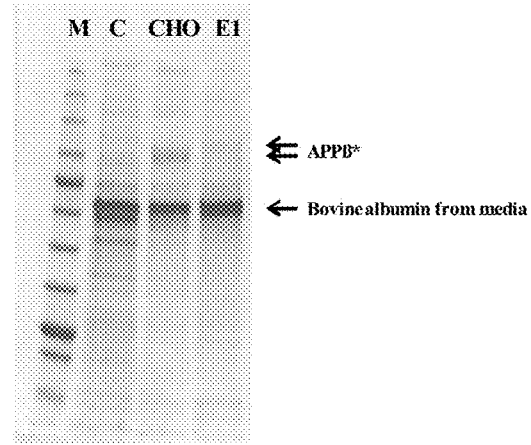

M – Colour Pre-stained Protein Ladder (NEB)
C – control, conditioned SFM from untransfected CHO-K1 after 7 days of sub-culturing, 20 µl
CHO – conditioned SFM from CHO-K1 cells stably expressing APPβ after 7 days of sub-culturing, 20 µl
E1 – conditioned SFM from HEK293 EBNA1 cells stably expressing APPβ after 7 days of sub-culturing, 20 µl

* The difference in APPβ size between HEK293EBNA1 and CHO-K1 is due to variability in glycosylation pattern between the two species.

FIG. 36

Our original version of EF1A, 330bp

Minimal version of EF1A1, 290bp

Minimal version of EF1A2, 156bp

Minimal version of EF1A3, 157bp

FIG. 37A

DNA sequence of the minimal EF1A1, 290 bp:

CCTCACCCGCCCGCTCTCGTCATCACTGAGGTGGAGAAGAGCATGCGTGAGGCTCCGGTGCCCGTCAGTGGGCAGAGCGCACATCGCCC
ACAGTCCCCGAGAAGTTGGGGGAGGGGTCGGCAATTGAACCGGTGCCTAGAGAAGTGGCGCGGGTAAACTGGAAGTGATGTCGT
GTACTGGCTCCGCCTTTTCCGAGGGTGGGGGAGAACCGTATATAAGTGCAGTAGTCGCCGTGAACGTTCTTTTTCGCAACGGGTTG
CCGCCAGAACACAGGTGTCGTGA

DNA sequence of the minimal EF1A2, 156 bp:

GCCTAGAGAAGTGGCGCGGGTAAACTGGAAAGTGATGTCGTGTACTGGCTCCGCCTTTTTCCCGAGGGTGGGGGAGAACCGTATAT
AAGTGCAGTAGTCGCCGTGAACGTTCTTTTTTCGCAACGGGTTTGCCGCCAGAACACAGGTGTCGTGA

DNA sequence of the minimal EF1A3, 157 bp:

AACCCAGAGATCGCTGCGTTCCCGCCCCTCACCCGCCCGCTCTCGTCATCACTGAGCCTTTTCCCGAGGGTGGGGGAGAACCGTATA
TAAGTGCAGTAGTCGCCGTGAACGTTCTTTTTCGCAACGGGTTTGCCGCCAGAACACAGGTGTCGTGA

FIG. 37B

Forward primer EF_Forward1: TTTAGGCCTCACCCGCCCGCTCTCGT

Forward primer EF_Forward2: TTTAGGCCTAGAGAAGGTGGCG

Reverse primer EF_Reverse1&2: TTTAGGCCTGCGTAACCACCACACCCGCCG

Forward primer EF_Forward3: TTTAGGCCTTTTTCCCGAGGGTGG

Reverse primer EF_Reverse3: TTTAGGCCTCAGTGATGACGAGAGCGG

FIG. 37C

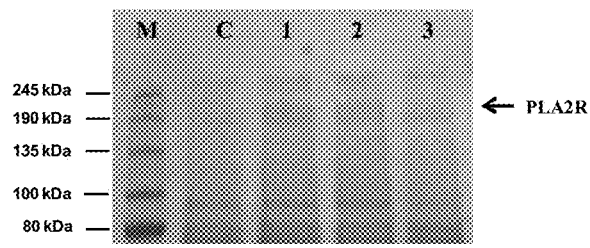

M – Colour Pre-stained Protein Ladder (NEB)
C – control, conditioned SFM from untransfected HEK293T cells after 7 days of sub-culturing
1 – conditioned SFM from HEK293T cells stably expressing pPEF5.11:PLA2R after 7 days of sub-culturing
2 – conditioned SFM from HEK293T cells stably expressing pPEF5.12:PLA2R after 7 days of sub-culturing
3 – conditioned SFM from HEK293T cells stably expressing pPEF5.13:PLA2R after 7 days of sub-culturing

FIG. 38

EXPRESSION IN MAMMALIAN CELLS WITH GAUSSIA LUCIFERASE SIGNAL PEPTIDE

CROSS-REFERENCE TO RELATED APPLICATIONS

This is a 371 of PCT Patent Application Serial No. PCT/EP2016/075415 filed Oct. 21, 2016, which claims priority to Great Britain Patent Application Serial No. 1518792.5 filed Oct. 23, 2015, the entire contents of which are incorporated herein by reference.

FIELD OF THE INVENTION

The present invention relates to in vitro expression of proteins and particularly, although not exclusively, to expression of proteins in mammalian cell lines. In particular, the present invention relates to the provision of a novel vector for protein expression, and methods of using such vector in the expression of proteins in mammalian cell lines.

BACKGROUND TO THE INVENTION

According to MarketResearch.com, a supplier of the latest in independent medical market research in diagnostics, biotech, pharmaceuticals, medical devices and healthcare, the biopharmaceutical and vaccine production market was estimated to reach $41 billion in 2014. Despite the recent economic crisis, the demand for biologics production is on the increase, as it has been for the last almost 3 decades. Mammalian cell culture occupies a central role in supplying biotech drug products and vaccines targeting various diseases.

Proteins produced in the mammalian cells are very important not only as therapeutics with least side effects due to their identical chemical and physical properties to their natural prototypes, but also for the production of drug targets. While the microbial expression platform is more economical in terms of overall yield, only the mammalian system can deliver the best qualities of the expected product: proper glycosylation, protein folding and, as a result, full function.

Protein expression and purification is not a routine process and still remains somewhat of an art, predicated on valuable skillsets of technicians. It can also be very restrictive and its success is strongly dictated by the quality of the personnel, their relevant practical experiences and availability of advanced instrumentation.

The progress achieved in terms of driving up mammalian recombinant yields is astonishing: from a few micrograms to a few grams per litre. This has been achieved by extensive research and development work aimed at the several bottlenecks in the production process. They have included creation of genetically engineered fine-tuned cell lines, improved media formulation and design of very efficient expression vectors. However, this research and development work remains costly and sustainable by big companies only.

Academic set up occupies the other end of the scale for recombinant protein production. While it does not require industrial amounts of proteins, it often deals with difficult targets which need to be produced on a limited budget. Also, even at a smaller scale, protein production faces one of the main challenges when compared with *E. coli* expression— low yield.

SUMMARY OF THE INVENTION

The present invention provides a nucleic acid expression vector for expressing a peptide in a mammalian cell, the vector comprising an expression cassette;
the expression cassette comprising:
    a promoter;
    nucleic acid encoding signal peptide from *Gaussia* luciferase;
    a multiple cloning site, for inserting nucleic acid encoding the peptide in-frame with the signal peptide; and
    a 3' UTR sequence.

Preferably, the nucleic acid expression vector consists of 6000 or fewer nucleic acid base pairs, or more preferably 5000 or fewer nucleic acid base pairs.

At it's most general, the invention provides a nucleic acid expression vector having fewer than 5000 base pairs, and comprising a *Gaussia* signal peptide sequence. The nucleic acid expression vector may additionally comprise a selectable marker, expressed under the control of a weak promoter.

In some cases, the vector also comprises a selectable marker. The selectable marker may be arranged downstream of a weak promoter. The nucleic acid encoding the signal peptide from *Gaussia* luciferase (GLUC) may encode a peptide having at least 90% sequence identity to SEQ ID NO: 1. The expression cassette may further comprise nucleic acid encoding the peptide of interest, such as a mammalian protein.

Expression of the gene of interest is under the control of a promoter. The promotor may be a promoter for constitutive expression, such as a CMV promoter. The promoter may be a promoter for inducible expression, such as a doxycycline inducible promoter or a riboswitch.

The expression cassette may additionally comprise a translational enhancer, such as SP163. The expression cassette may further comprise nucleic acid encoding a tag, such as a SUMO-tag.

In some cases, the vector is smaller than 5.5 Kb, preferably smaller than 5 kb.

In another aspect, the invention provides a host cell comprising a nucleic acid expression vector. The host cell may be a mammalian cell, such as a HEK293 cell, a CHO cell, a COS cell, a HeLa cell, a Vero cell, a NSO cell, a Jurkat cell, a BHK cell, an MCF cell, or an L cell mouse fibroblast (such as the cell line deposited as ATCC CRL-2648).

In a further aspect, the invention provides a nucleic acid expression vector comprising an expression cassette, the expression cassette comprising:
    a promoter;
    nucleic acid encoding *Gaussia* luciferase signal peptide;
    a multiple cloning site, for inserting nucleic acid encoding a polypeptide of interest in-frame with the *Gaussia* luciferase signal peptide; and
    a polyadenylation sequence;
    the nucleic acid expression vector further comprising nucleic acid encoding a selectable marker downstream of an SV40 promoter, or a promoter that has weaker expression induction than an SV40 promoter.

Also provided are kits, such as kit for gene expression comprising a vector according to any one of claims, a mammalian cell, and a reagent.

In a further aspect, the invention provides methods. Methods include methods of making a nucleic acid expression vector, comprising introducing a *Gaussia* signal peptide into a vector, such as a pPEF vector. Such methods result in a nucleic acid expression vector that is smaller than 5000 base pairs in length.

Certain aspects disclosed herein provide methods for producing a protein. Some methods disclosed herein comprise inserting nucleic acid encoding the gene of interest into a nucleic acid expression vector according to the invention, transfecting the nucleic acid expression vector comprising the gene of interest into a mammalian cell; and culturing the transfected cell. Methods disclosed herein may also involve a step of purifying the protein encoded by the gene of interest.

In an aspect of the invention, there is provided a vector having the sequence set out in any one of FIG. 19, 20, 21, 22, 23, 24, 25 or 26. Preferably, the vector has a sequence as shown in any one of FIGS. 19, 20, 25, 26. In some cases, the vector has a sequence of at least 80% sequence identity to the nucleic acid sequence set out in one of FIG. 19, 20, 21, 22, 23, 24, 25 or 26. More preferably, the sequence is about 85%, 90%, 95%, 97%, 98%, 99% or 100% identical to the nucleic acid sequence set out in one of FIG. 19, 20, 21, 22, 23, 24, 25 or 26.

The vector may comprise a degree of sequence identity to a sequence set out in on of FIG. 19, 20, 21, 22, 23, 24, 25 or 26, and additionally include one or more elements selected from an expression cassette, promotor, signal peptide, multiple cloning site, 3'UTR, and selectable marker under the control of a weak promoter. In addition to having the stated degree of sequence identity, the vector may be smaller than 5.5 kb, smaller than 5. kb, or smaller than 4.5 kb.

In certain aspects disclosed herein, the vector does not comprise a sequence encoding F1ori, or a sequence having at least 80%, 85%, 90%, 95% or 100% sequence identity to a sequence encoding F1ori, or does not comprise a sequence encoding EM7, or a sequence having at least 80%, 85%, 90%, 95% or 100% sequence identity to a sequence encoding EM7.

An alternative embodiment of the present invention provides a nucleic acid expression vector for expressing a peptide in a mammalian cell, the vector comprising an expression cassette;
the expression cassette comprising:
a promoter;
nucleic acid encoding signal peptide from PDX-Furin;
a multiple cloning site, for inserting nucleic acid encoding the peptide in-frame with the signal peptide; and
a 3' UTR sequence;
Preferably, the nucleic acid expression vector consists of 6000 or fewer nucleic acid base pairs.

Also provided herein is a modified EF1A promotor. The modified EF1A promotor may be used in the vectors described herein to drive expression of the selectable marker. Modified EF1A promoter may have the sequence of "minimal version of EF1A1" or "minimal version of EF1A2" as set out in FIG. 37, or a sequence having at least 90%, 91%, 92%, 93%, 94%, 95%, 96%, 97% 98%, or 99% sequence identity to the sequence set out in FIG. 37. The modified EF1A promoter described herein has a reduced size as compared to native EF1A promoter. In some aspects, the modified EF1A promoter described herein contains fewer than 350 bp, 330 bp, 310 bp, 300 bp, 290 bp, 280 bp, 270 bp, 260 bp, 250 bp, 240 bp, 230 bp, 220 bp, 210 bp, 200 bp, 190 bp, 180 bp, 170 bp, 160 bp, 150 bp, or 140 bp. Preferably, the modified EF1A promoter described herein contains fewer than 200 bp. The modified EF1A promoter preferably has attenuated activity as compared to the native EF1A sequence.

In some aspects, the invention is vector pPEF5PuroR, having a sequence as set out in FIG. 31A, or having 80%, 85%, 90%, 95% or 98% sequence identity to the sequence set out in FIG. 31A.

In one preferred arrangement, the vector is pPEF5PuroR deposited by University of Manchester on 18 Oct. 2016 at PHE Culture Collections (Public Health England, Porton Down, Salisbury, SP4 OJG, UK) under Provisional accession number 16101801 in accordance with the provisions of the Budapest Treaty. This is the European Collection of Authenticated Cell Culture (ECACC).

BRIEF DESCRIPTION OF THE FIGURES

Embodiments and experiments illustrating the principles of the invention will now be discussed with reference to the accompanying figures in which:

FIG. 3. Synthetic DNA fragments. A. Fragment 1 (SEQ ID NO:4) with SP163 enhancer (capitalised, underlined), T7 promoter/priming site (capitalised, italics), BM40 signal peptide, Kpnl at the 5'end (capitalised, bold), NheI at the 3' end (lower case, bold) and silenced internal NheI site (enlarged, capitalised, italicised)—298 bp; B. Fragment 2 (SEQ ID NO:5) with SP163 enhancer (capitalised, underlined), T7 promoter/priming site (capitalised, italics), *Gaussia* signal peptide, Kpnl at the 5' end (capitalised, bold), NheI at the 3' end (lower case, bold) and silenced internal NheI site (enlarged, capitalised, italicised)—301 bp; C. Fragment 3 (SEQ ID NO:6) with T7 promoter/priming site (capitalised, italics), *Gaussia* signal peptide, Kpnl at the 5'end (capitalised, bold), NheI at the 3' end and (lower case, bold) silenced internal BamHI site (enlarged and italicised)—116 bp D. F1ori sequence (SEQ ID NO: 7); E. EM7 sequence (SEQ ID NO:8)

FIG. 5. Differential expression of PLA2R1 in the modified vectors. A: Coomassie Staining; B: Western blot; Yield in pCEP-Pu—20-200 µg/ml; Yield in pPEF2—6 mg/L.

*indicates a combination which has been routinely tested in the laboratory and was used here as a control.

FIG. 6. A. Clustal alignment of our minimal (pPEF)(SEQ ID NO:10), commercial (based on the DNA sequence provided by Oxford Genetics) (SEQ ID NO:11) and published chromosomal sequence of EF1A promoter (GenBank: J04617.1) (SEQ ID NO:9) Part 1; B. Clustal alignment part 2. C. Synthetic fragment I with the minimal EF1A (1206 bp) SEQ ID NO:12); D. Synthetic fragment II with the SV40 promoter (1214 bp) (SEQ ID NO:13).

Figure 8:
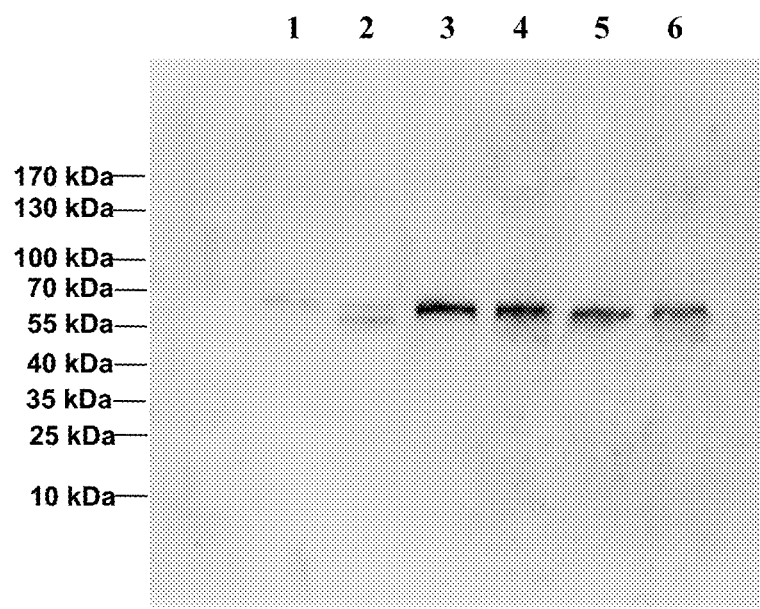

FIG. 7. Comparison of human EF1A promoter with SV40 for A. sVAP expression in pPEF5.1 vector and B. PLA2R expression in pPEF5.1Max vector. pPEF5.1 vector contains antibiotic resistance gene under minimal EF1-alpha promoter (4× smaller than the commercial version); pPEF5.2 and pPEF5.2Max contain antibiotic resistance gene under SV40 promoter/origin of replication;

FIG. 8. Expression of HPSE2 1. Conditioned serum-free medium from HEK293 cells stably expressing pcDNA™3.1: HPSE2_FL vector; 2. Cell lysate of HEK293 cells stably expressing pcDNA™3.1:HPSE2_FL vector; 3. Conditioned serum-free medium from HEK293 EBNA1 cells stably expressing pPEF4:HPSE2_Δ41; 4. Cell lysate of HEK293EBNA1 cells stably expressing pPEF4: HPSE2_Δ41; 5. Conditioned serum-free medium from HEK293EBNA1 cells stably expressing pPEF4:HPSE2_FL; 6. Cell lysate of HEK293EBNA1 cells stably expressing pPEF4:HPSE2_FL. No published yield to compare to. pPEF4 and pcDNA™3.1 vectors share high identity in terms of vector backbone sequence similarity.

FIG. 9. Expression of Sumo-Noggin in pPEF5.2 and pPEF5.2Max A. Coomassie staining and B. western blot analysis of conditioned serum free medium from 1. Non-transfected HEK293EBNA1 cells (negative control); 2. pPEF5.2 Sumo-Noggin cells, 5 day harvest; and 3. pPEF5.2/Max Sumo-Noggin cells, 5-day harvest; C. Fusion protein made up of 10×His tag, N-terminal SUMOstar secretory tag (LifeSensors) and the mature form of Noggin aa 28-232 (underlined) (SEQ ID NO:14).

Figure 10:
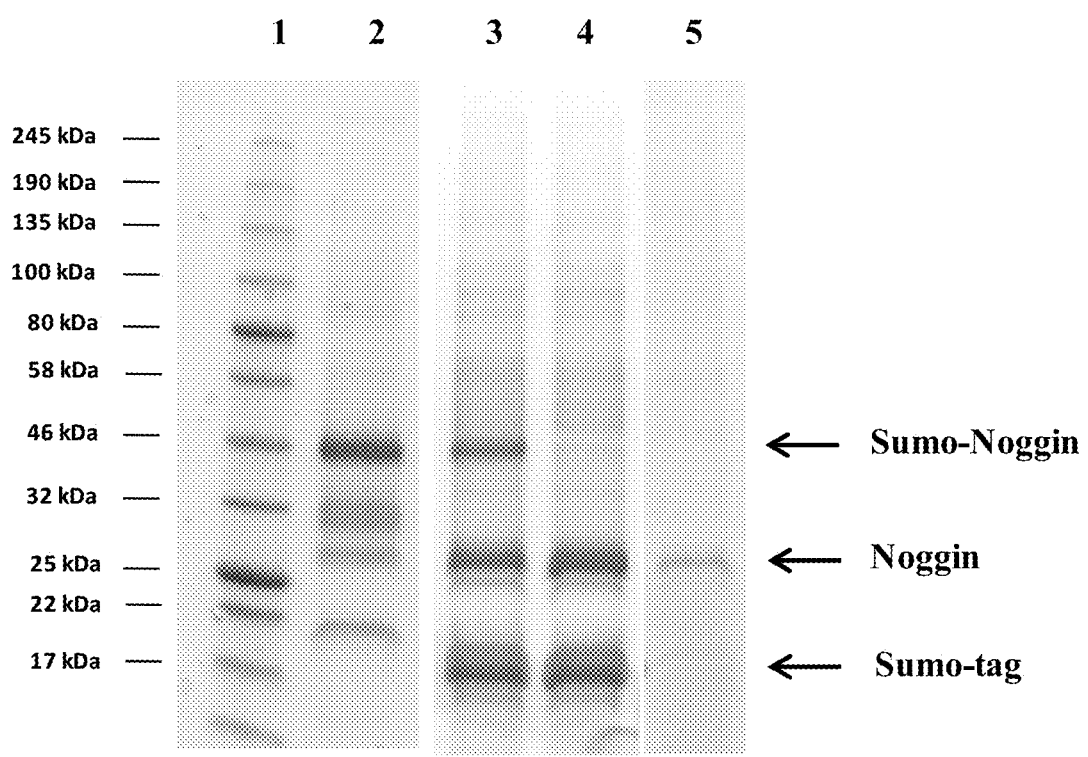

FIG. 10. Sumo-Noggin digest and recovery of Noggin. 1. Protein size marker; 2. Initial input (pooled eluted fractions of Ni-purified Sumo-Noggin); 3. SUMOstar digest at 30° C. for 1 hour (recommended by manufacturer); 4. SUMOstar digest at 40° C. for ⅓ hour (optimal conditions); 5. Noggin recovery after digest.

Figure 11A:
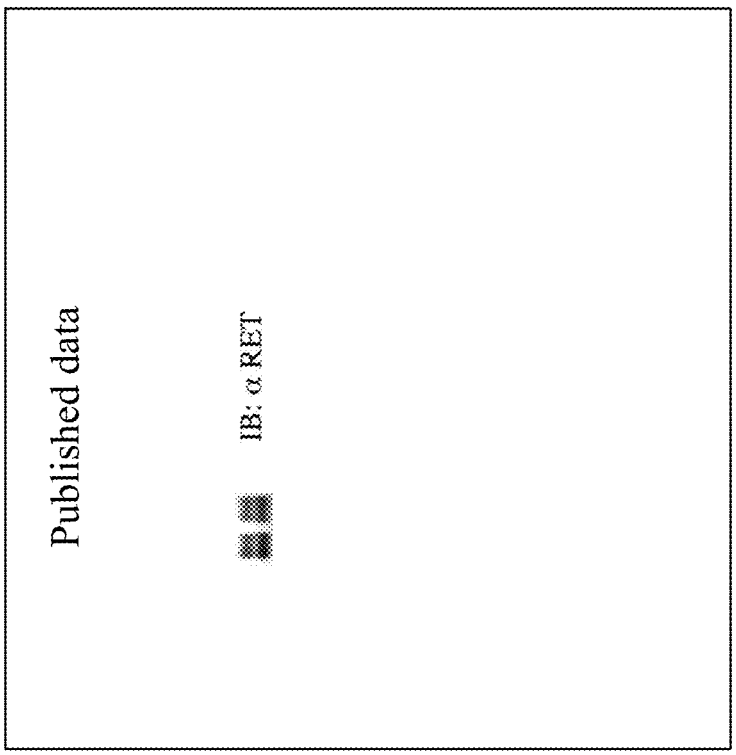
Figure 11B:
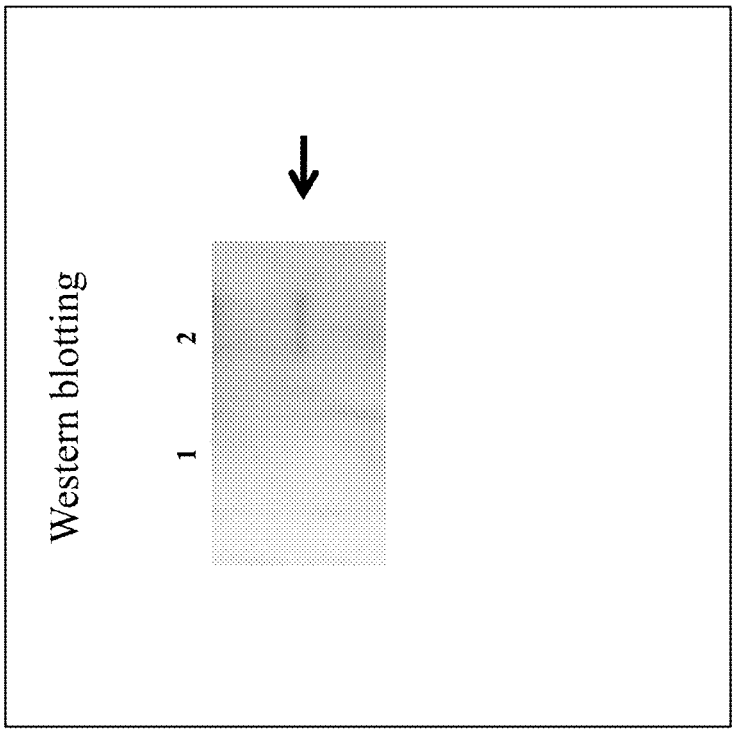

FIG. 11. Expression of RET (a transmembrane domain containing protein). A. Published data of Myers S M and Mulligan L M (Cancer Res. 2004: 64:4453-4463. RET expression in HEK293EBNA1 cells stably expressing RET in pCEP derivative vector. RET protein was immunoprecipitated from lysed cells with isoform specific antisera and immunoblotted with the same antisera; and B. Western blotting of pPEF5.1 Max; lane 1: cell lysate of Non-transfected HEK 293 EBNA cells; Lane 2 cell lysate of HEK293 EBNA 1 cells stably expressing RET in pPEF5.1Max.

Figures 12A, 12B:
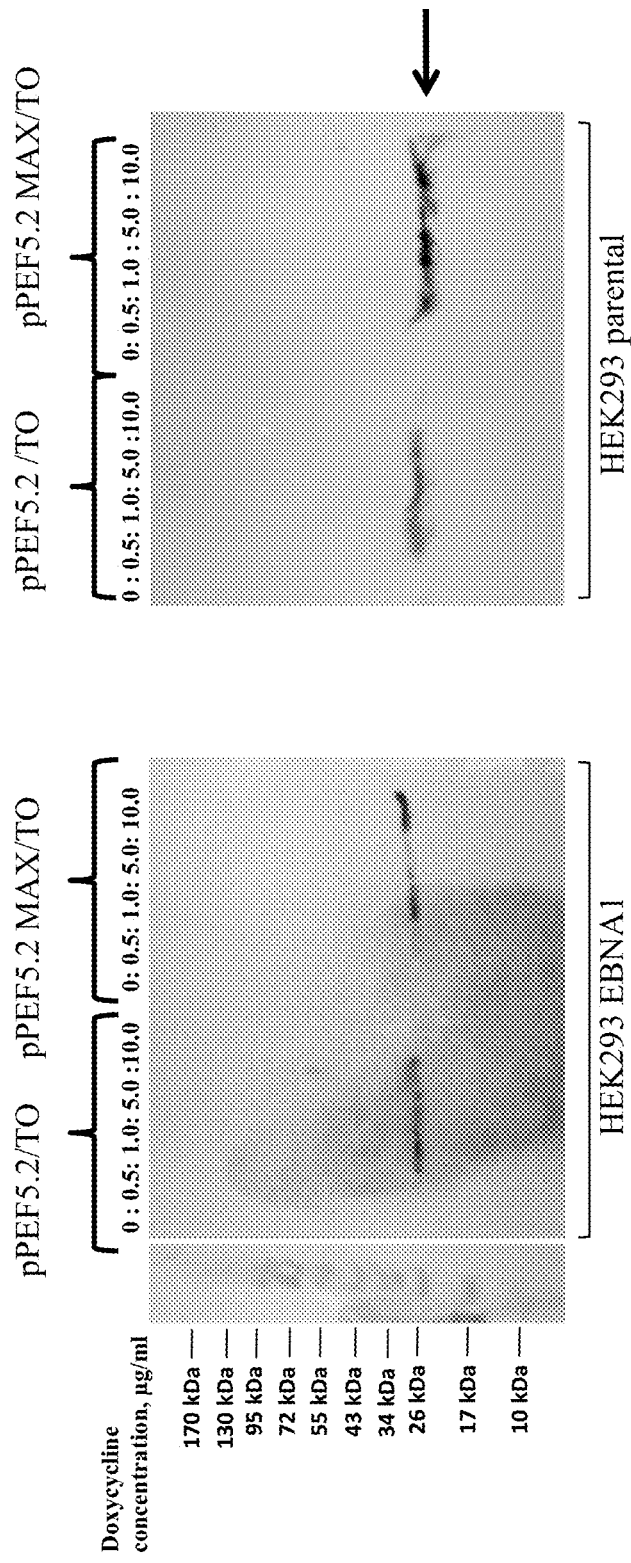

FIG. 12. The induction of Δ105 MMP-12 expression in HEK293 parental and HEK293 EBNA1 cell lines. Western blotting with anti-MMP12 (hemopexin domain). A. HEK293EBNA1 cells; B: HEK293 parental cells.

FIG. 13. Expression of MMP-12 proprotein and the effect of MMP inhibitor. Western blotting with anti-MMP12 (catalytic domain); 1. Conditioned medium from nontransfected parental HEK293EBNA1 cells (negative control); 2. Conditioned medium harvested from MMP12 pro-form HEK293 EBNA1 cells (positive control); 3-5 conditioned media from the inhibitor-treated MMP12 pro-form HEK293 EBBA1 cells.

FIG. 14. Cloning of Ricin-C3 P2A of PLA2R1 (SEQ ID NO:15). Ricin (aa 20-173) C3 (aa 516-660) domains with P2A bicistronic motif (underlined) and engineered Furin cleavage site (enlarged, bold, italicised).

Figure 15:
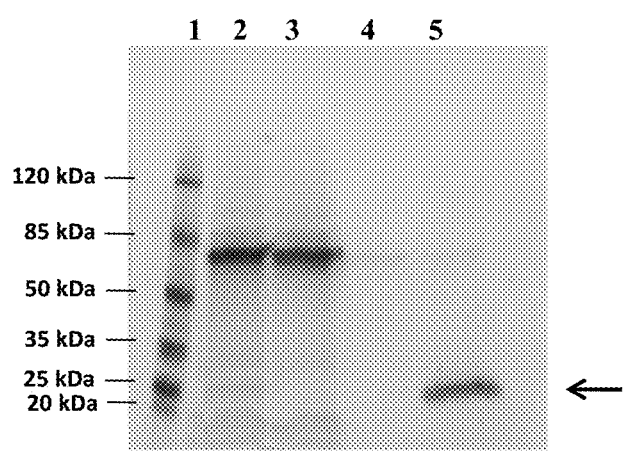
Figure 16A:
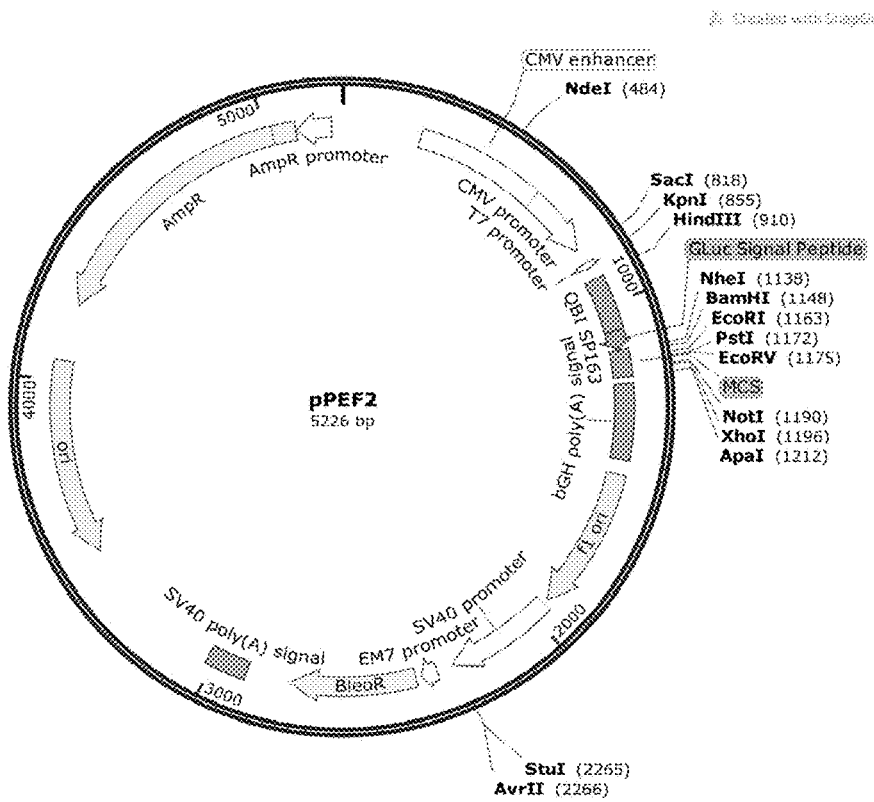
Figure 16B:
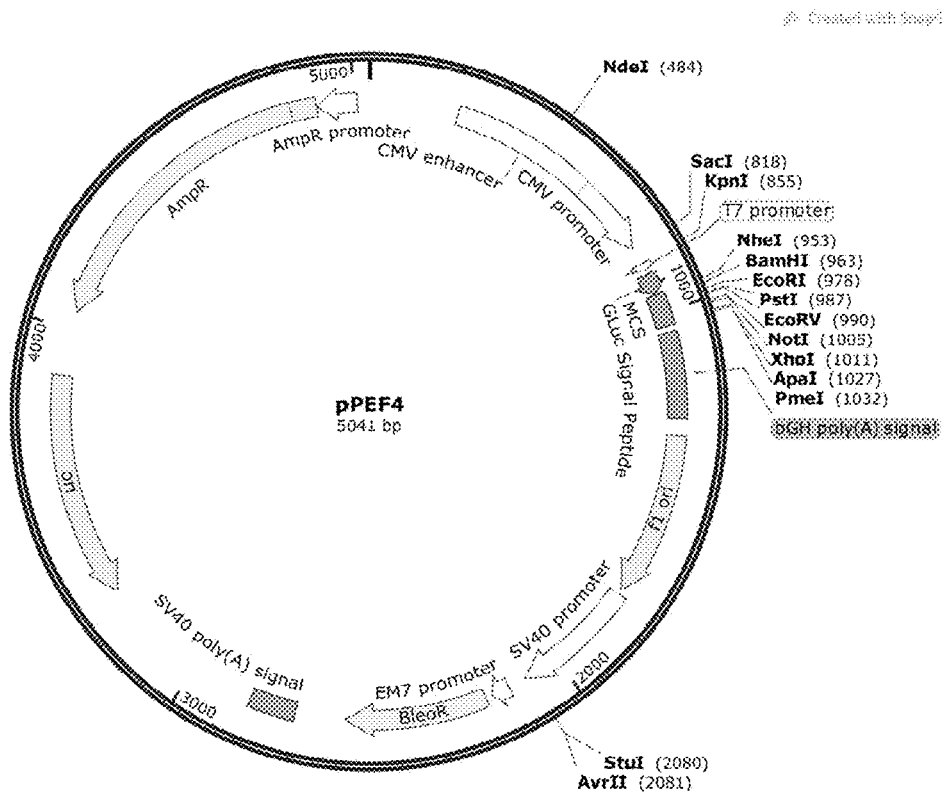
Figure 16C:
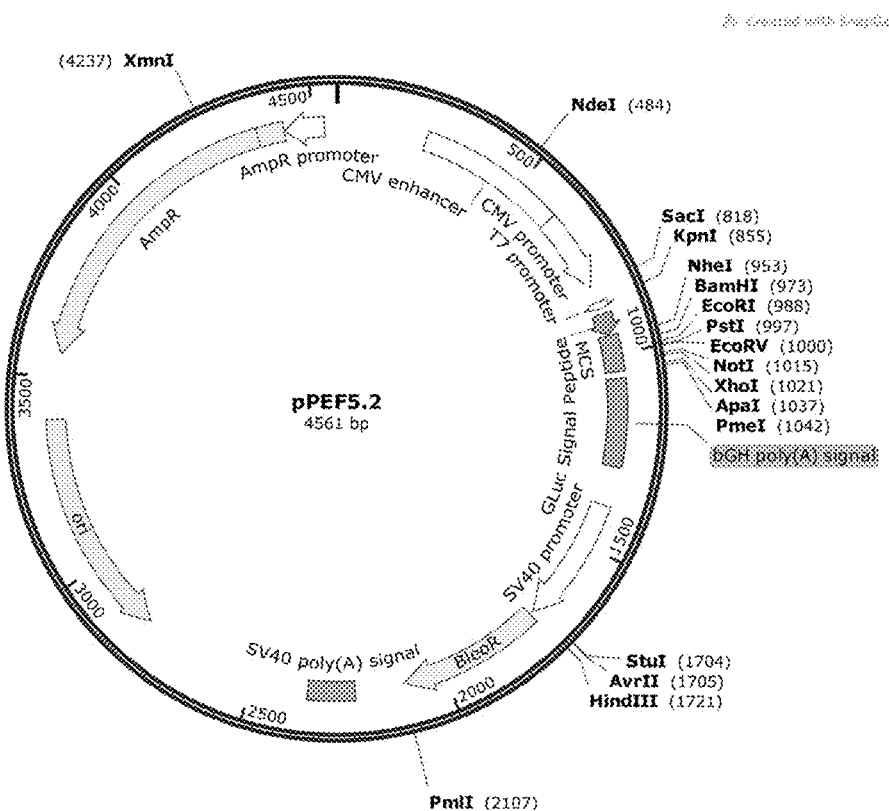
Figure 16D:
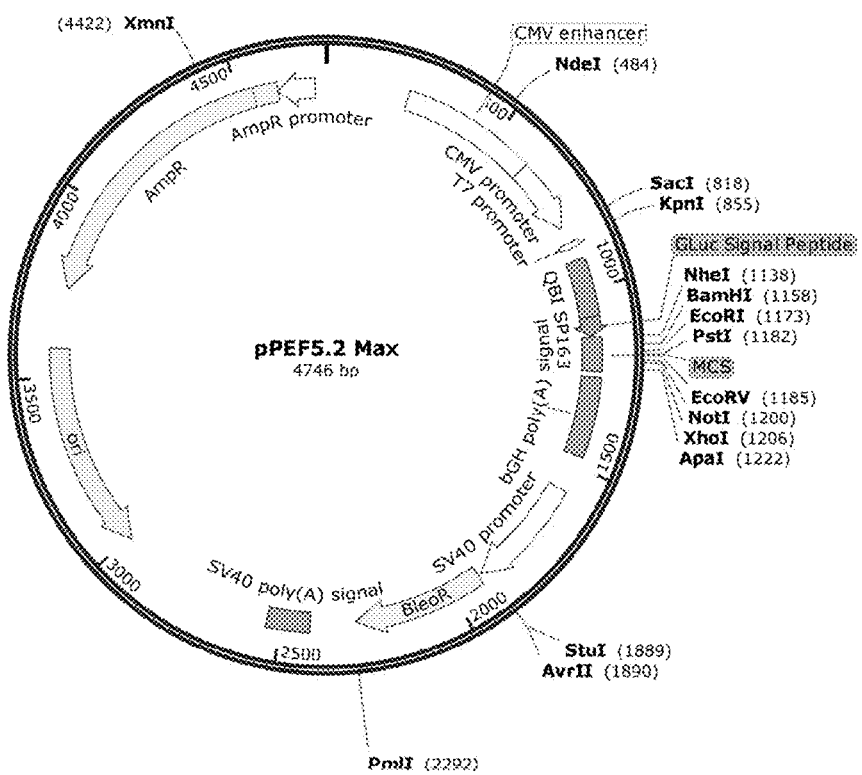
Figure 16E:
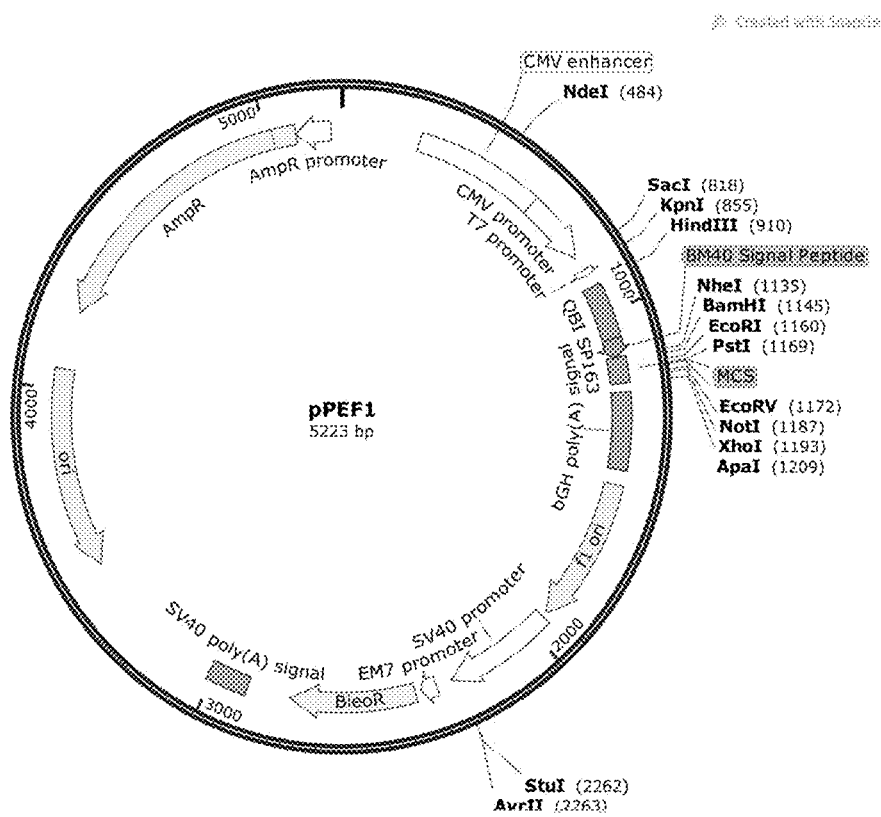
Figure 16F:
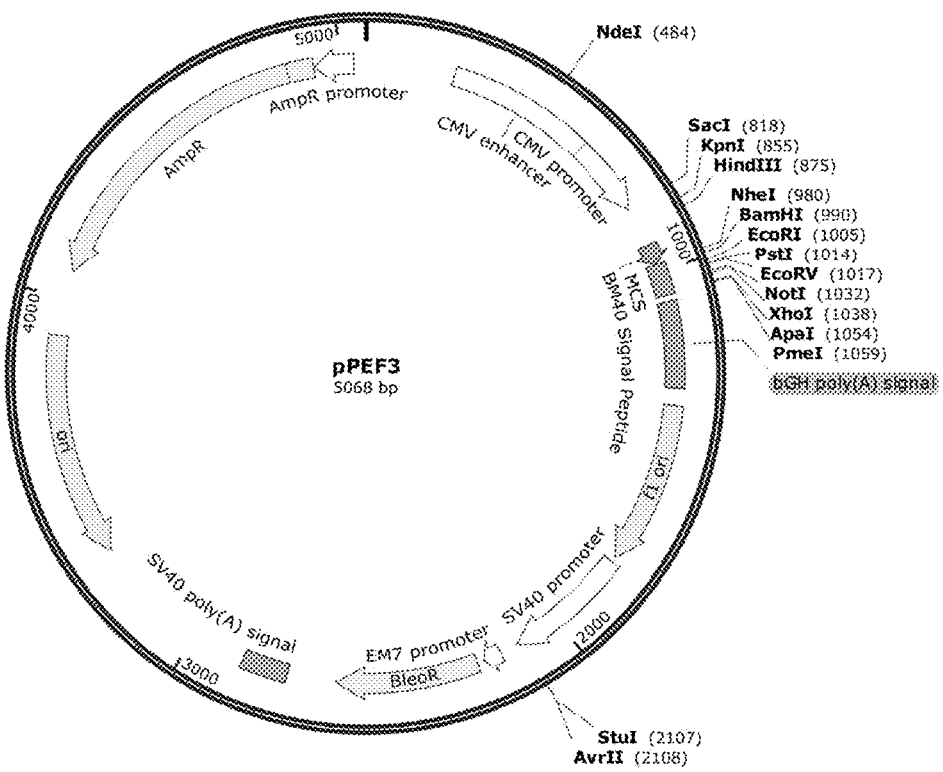
Figure 16G:
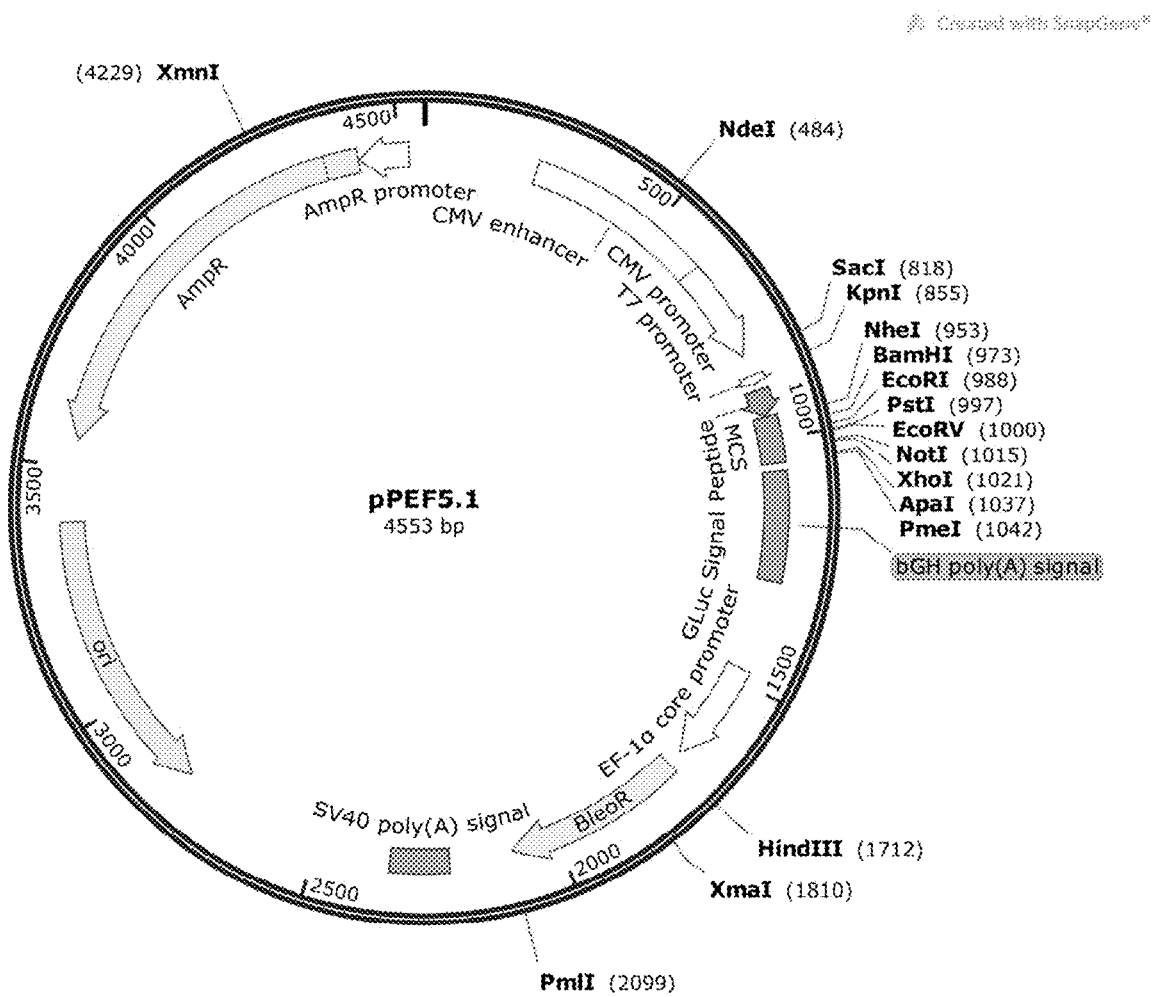

FIG. 15. Purification of Ricin domain of PLA2R1. 1. Protein size marker; 2. Conditioned serum-free medium from Ricin C3P2A cells, 7 day harvest input; 3. Unbound flow-through; 4. Wash; 5. Eluate.

FIG. 16. A. pPEF2 vector carrying elements of pCEP-Pu/AC7 and pcDNA™4/HisMax vector; B. pPEF4 vector corresponding to pPEF2 vector but lacking SP16 Transcriptional enhancer; C. pPEF5.2 vector corresponding to the pPEF4 vector but lacking f1 origin and EM-7 promoter. D. pPEF5.2Max vector as pPEF2 but without f1 origin and EM1 promoter; E. pPEF1 vector; F. pPEF3 vector; G. pPEF5.1 vector.

Figure 17:
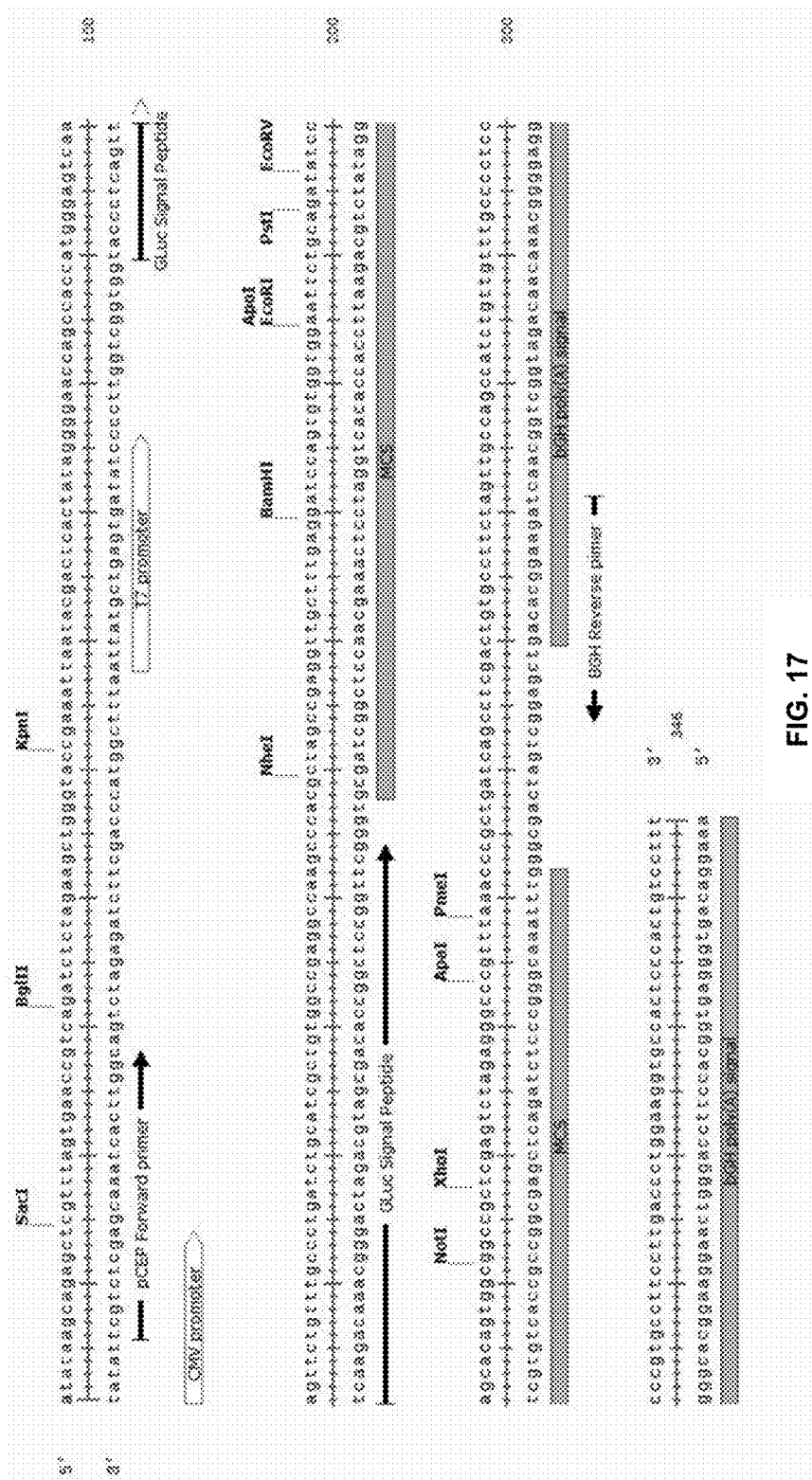

FIG. 17. pPEF5.2 (SEQ ID NO:16) Multiple cloning site

FIG. 18. pPEF5.2 annotations table

FIG. 19. pPEF5.2 sequence (SEQ ID NO:17), A. nucleic acids 1 to 2750; B. nucleic acids 2751 to 4561.

FIG. 20. Ppef5.2Max sequence (SEQ ID NO:18)A. nucleic acids 1 to 2820; B nucleic acids 2821 to 4746.

FIG. 21. pPEF1 sequence (SEQ ID NO:19)A. nucleic acids 1 to 2940; B: nucleic acids 2941 to 5223.

FIG. 22. pPEF2 sequence (SEQ ID NO:20) A. nucleic acids 1 to 3060; B: nucleic acids 3061 to 5226.

FIG. 23. pPEF3 sequence SEQ ID NO:21) A. nucleic acids 1 to 3060; B: nucleic acids 3061 to 5068.

FIG. 24. pPEF4 sequence (SEQ ID NO:22) A. nucleic acids 1 to 3060; B: nucleic acids 3061 to 5041.

FIG. 25. pPEF5.1 sequence (SEQ ID NO:23) A. nucleic acids 1 to 3060; B: nucleic acids 3061 to 4553.

FIG. 26. pPEF5.1Max sequence (SEQ ID NO:24) A. nucleic acids 1 to 3060; B: nucleic acids 3061 to 4738.

FIG. 27. pCEP-Pu/AC7 sequence (SEQ ID NO:25) A. nucleic acids 1 to 3180; B: nucleic acids 3181 to 6540; C: nucleic acids 6541 to 9901.

FIG. 28. Sequences of vector elements. A: QBI SP163 translational enhancer (SEQ ID NO:26). B. Polylinker/MCS with Lumio and 10×His tags embedded (SEQ ID NO:27) (SEQ ID NO:28); C: Polylinker/MCS without Lumio and 10×His tag (SEQ ID NO:29) (SEQ ID NO:30); D: a1-PDX Furin inhibitor Signal Peptide (SEQ ID NO:2): E: SV40 promoter (SEQ ID NO:31); F: CMV immediate early promoter (SEQ ID NO:32); G: EF1 alpha promoter minimal (Ppef) (SEQ ID NO:33); H: EF1 alpha promoter genomic (SEQ ID NO:34); I: EF1 alpha promoter commercial (Oxford Genetics Ltd)(SEQ ID NO:35).

FIG. 29. Primers designed in order to delete a fragment of the MCS containing Lumio and 10×His tags (SEQ ID NO:36) (SEQ ID NO:37) (SEQ ID NO:38).

FIG. 30. Synthetic PuroR DNA sequence (SEQ ID NO:39) with internal HindIII and PmlI restriction sites.

Figure 31B:
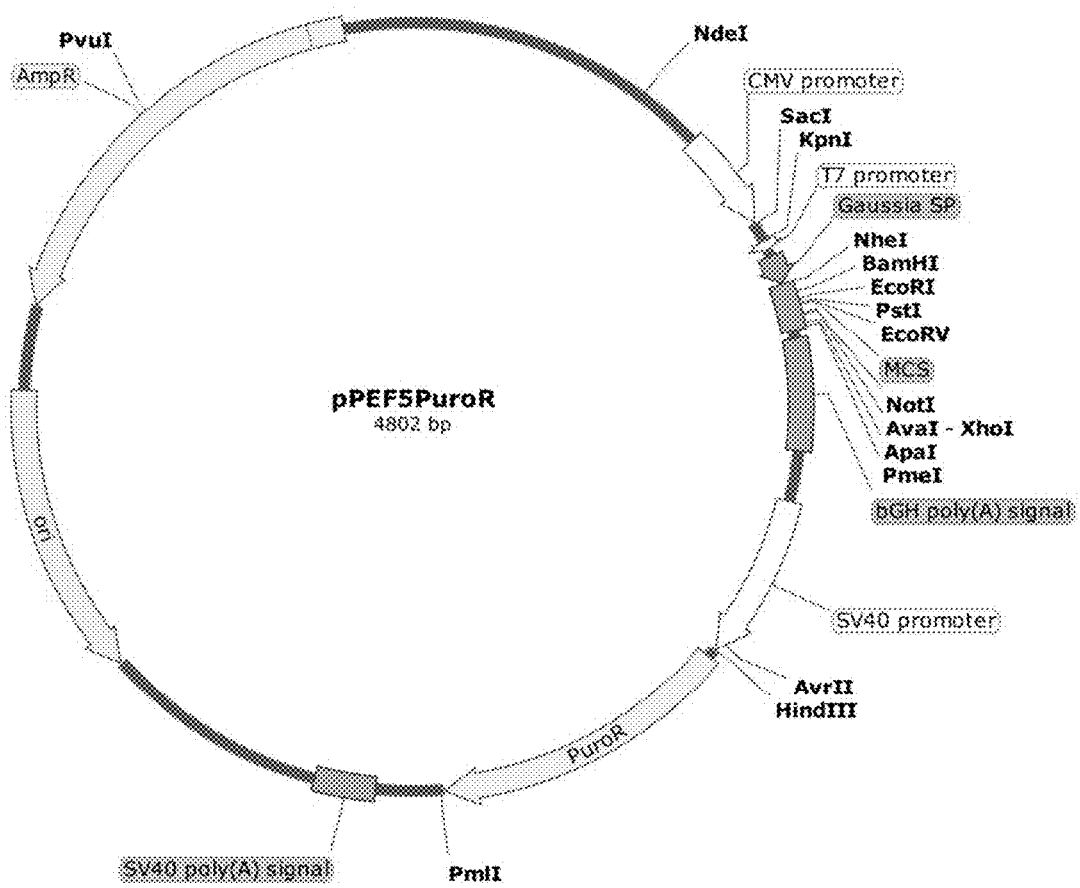

FIG. 31. A. DNA sequence of pPEF5PuroR (SEQ ID NO:40). B. Plasmid map for pPEFPuroR; C Feature map from pPEF5PuroR.

Figures 31C, 32:
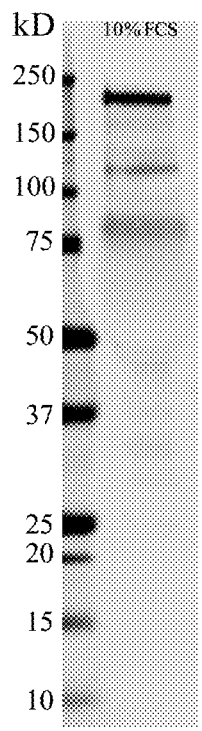

FIG. 32. Western Blot analysis of the complete conditioned media demonstrating THSD7A expression.

Figure 33A:
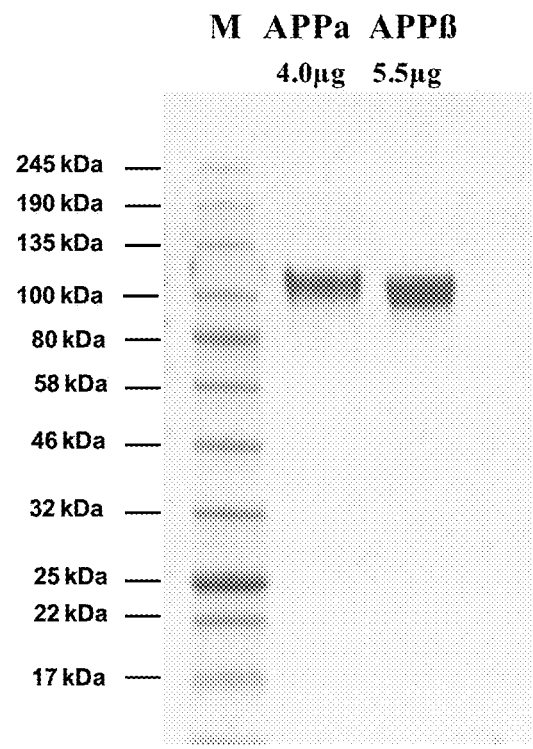
Figure 33B:
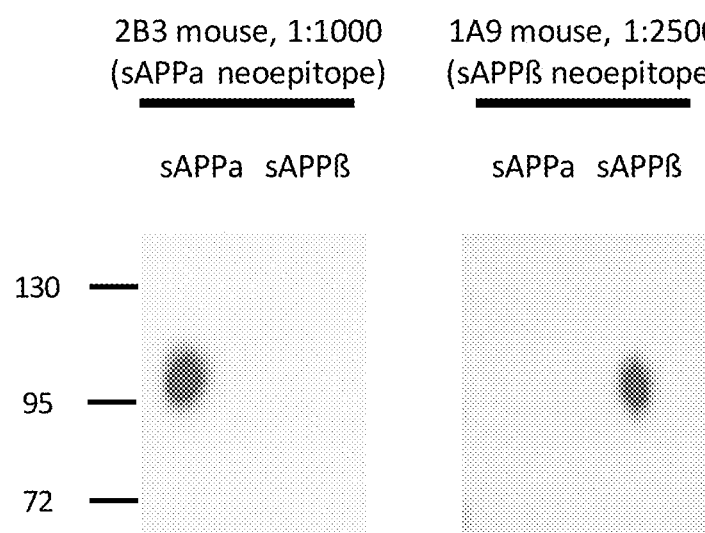

FIG. 33. A Coomassie staining for protein integrity and purity for stable cell lines expressing Amyloid Precursor Protein (APP) α and β forms. B. analysis with isoform-specific neopepitope antibodies. C. comparison of the purified proteins with their commercial analogues.

Figure 34:
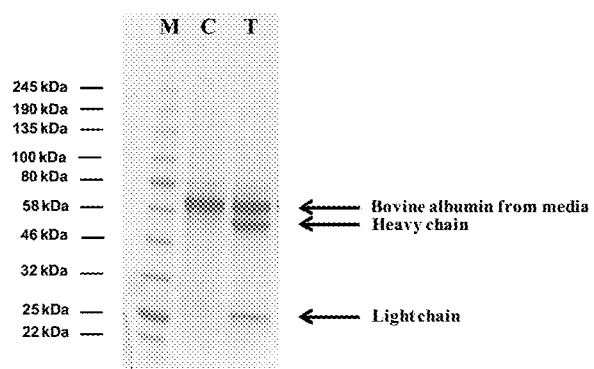

FIG. 34. Coomassie staining of conditioned serum free medium showing high expression levels of Trastuzumab.

FIG. 35. Coomassie staining of conditioned serum free media revealing perceptible Trastuzumab expression in CHO-K1 cells.

FIG. 36. Coomassie staining revealing a higher expression level of Amyloid Precursor Protein beta form in CHO-K1 cells.

FIG. 37. A. representation of EF1a constructs tested. B. DNA sequences of minimal EF1A1 proteins (SEQ ID NO:41); C. Primers (SEQ ID NO:42) (SEQ ID NO:43) designed to delete regions from the 5' end of the EF1a promoter in pPEF5.1 vector.

FIG. 38. Coomassie staining analysis of the conditioned media from all 3 stable cell line demonstrating a comparable expression level of PLA2R for pPEF5.11 and pPEF5.12 and no detectable expression for pPEF5.13 (SEQ ID NO:44) (SEQ ID NO:45) (SEQ ID NO:46) (SEQ ID NO:47) (SEQ ID NO:48).

DETAILED DESCRIPTION

The present invention relates to in vitro expression of proteins and particularly, although not exclusively, to expression of proteins in mammalian cell lines. The present inventors have developed an expression vector which is useful for the expression of a wide range of proteins, including proteins that have historically proved challenging to express with adequate yield, or to express at all.

In one aspect, the present invention provides a nucleic acid expression vector that comprises a *Gaussia* signal peptide. The *Gaussia* signal peptide may be present as part of an expression cassette. The expression cassette may allow for insertion of nucleic acid encoding a gene of interest into the expression vector.

In some aspects, vectors utilise *Gaussia* signal peptide. *Gaussia* signal peptide has been used for a number of years to improve protein yield. However, the inventor has appreciated that inclusion of the signal peptide alone is not sufficient to ensure efficient recombination, but rather the context in which that signal peptide is present is also important. The inventor realised that other aspects of the vector must also be optimized in order to enhance the expression of the target protein, in addition to the presence of *Gaussia* signal peptide. The size of the vector and the stringency of selection are important aspects, particularly for vectors optimized for the expression of proteins and peptides that are normally considered to be challenging to produce using recombination expression. The inventor has determined that optimum protein yield may be obtained by using a vector comprising a *Gaussia* signal peptide and which is smaller than 5000 kb.

Vectors

Vectors are autonomously replicating nucleic acid molecules that can be used to carry foreign nucleic acid fragments. Nucleic acid of interest is first cloned into an appropriate vector. The vector containing the nucleic acid of interest is then transfected into a host cell for expression. Expression of a nucleic acid of interest in mammalian cells usually utilizes vectors derived from mammalian viruses, or which include elements derived from human viruses, such as Simian Viruses 40 (SV40), polyomavirus, herpesvirus and papovirus. In order to construct vector the requirement is to select an efficient promoter and also the selection marker.

One type of vector is a plasmid. Plasmids are genetic structures that can replicate in a cell, independently of the chromosomes. Plasmids are typically small circular DNA strands in the cytoplasm. Particularly preferred plasmids herein are expression plasmids. Expression plasmids are plasmids designed for protein expression in cells. The plasmids are used to deliver nucleic acid encoding a protein of interest into cells, but are further able to interact with the cell to synthesize that protein, for example by utilizing the cell's protein synthesis machinery.

Operably Linked

In this specification the term "operably linked" means that the promoter is in the correct location and orientation in relation to a nucleic acid that is to be transcribed to control the initiation of transcription by RNA polymerase.

In some cases, this may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Preferably, the nucleic acid expression vector of the present invention consists of fewer than 6000 base pairs of DNA. When the nucleic acid of interest, or gene of interest, is inserted into the vector, the size may be increased. However, preferably, the vector backbone (i.e. the elements of the vector which do not include the nucleic acid of interest or gene of interest) consists of fewer than 6000 base pairs. More preferably, the backbone consists of fewer than 5800 base pairs, more preferably fewer than 5600 base pairs, more preferably fewer than, more preferably fewer than 5400 base pairs, more preferably fewer than 5200 base pairs, more preferably fewer than 5000 base pairs, more preferably fewer than 4900 base pairs, more preferably fewer than 4800 base pairs, more preferably fewer than 4700 base pairs, more preferably fewer than 4600 base pairs, more preferably fewer than 4500 base pairs, more preferably fewer than 4400 base pairs, more preferably fewer than 4300 base pairs, more preferably fewer than 4200 base pairs, more preferably fewer than 4100 base pairs, more preferably fewer than 4000 base pairs, more preferably fewer than 3900 base pairs, more preferably fewer than 3800 base pairs, more preferably fewer than 3700 base pairs, more preferably fewer than 3600 base pairs, more preferably fewer than 3500 base pairs, more preferably fewer than 3400 base pairs, more preferably fewer than 3300 base pairs more preferably fewer than 3200 base pairs, more preferably fewer than 3100 base pairs, more preferably fewer than 3000 base pairs, more preferably fewer than 2900 base pairs, more preferably fewer than 2800 base pairs, more preferably fewer than 2700 base pairs, more preferably fewer than 2600 base pairs, more preferably fewer than 2500 base pairs. In some cases, the size of the backbone is minimised by removing elements that are not essential for transfection. For example, in some cases, the backbone does not contain a selectable marker, such as an antibiotic resistance gene.

In some cases, the vector backbone includes nucleic acid sequences encoding Ubiquitous Chromatin Opening Elements (UCOEs). UCOEs can give rise to populations of cells that express transgenes at highly reproducible and stable levels, to ensure sufficient expression of a protein of interest in one or more cell types. More than one UCOE sequence may be included in the vector. A UCOE sequence may be used to link two sequences of interest together, such as where antibody $V_H$ and $V_L$ sequences are expressed in the same vector. For example, the $V_H$ sequence may be expressed under the control of a promoter, and the $V_L$ sequence may be expressed under the control of a second promoter, with a UCOE separating the sequences.

Expression Cassette

An expression cassette is part of a nucleic acid expression vector that directs a host cell's machinery to make RNA and protein from the vector. An expression cassette normally comprises nucleic acid encoding a promoter and a 3' untranslated region, such as a polyadenylation sequence. The expression cassette preferably includes a multiple cloning site (MCS) for inserting nucleic acid of interest. The expression cassette may comprise the nucleic acid of interest. The expression cassette may include an open reading frame in which the nucleic acid of interest may be inserted. Alternatively, the expression cassette may be adapted for insertion of an open reading frame containing the nucleic acid of interest. An open reading frame preferably includes an upstream start codon, and may include a downstream stop codon. The gene of interest, or the open reading frame, may be in frame with the promoter.

Promoter

The vectors described herein use a promoter. A promoter is a region of nucleic acid that initiates transcription of a particular gene or downstream nucleic acid. Promoters may be located near the transcription start site of genes. In bacterial cells, promoters may be recognised by RNA polymerase in the cell, and an associated sigma factor, to initiate transcription. In Eukaryotic cells the process is more complicated, with at least seven different factors facilitating the binding of RNA polymerase I to the promoter. Promoters are critical elements of expression vectors, and may work in conjunction with other regulatory elements, such as enhancers, silencers and insulators to direct the level of transcription of a given gene. As such, different promoters may direct different levels of transcription.

In certain aspects of the present disclosure, the promoters that drive expression of the selectable marker are weak promoters. That is, they direct lower levels of transcription of a selectable marker gene than other promoters. In particularly preferred aspects, the promoter is weaker than the EF1A promoter. That is to say that the promoter directs lower levels of expression of the selectable marker than the EF1A promoter. The relative weakness of the promoter may be determined by methods known in the art, such as by methods disclosed in Qin et al., 2010 (PLoS ONE 5(5): e10611; 1-4), the entire contents of which are incorporated herein by reference. The promoter may be weaker than EF1A when used in an identical vector context (i.e. all other elements of the vector are identical), and when expressed in the same cell type and under the same conditions. In this context, any suitable measure for promoter strength may be used, for example transcript number, or amount of protein produced.

Promoters useful for driving expression of the selectable marker in the nucleic acid vectors disclosed herein include SV40, UBC, PGK, TRE, CAGG or EF1A promoters. Particularly preferred promoters are SV40, UBC and PGK. In particularly preferred vectors, the promoter is SV40.

Nucleic acid vectors according to the invention also comprise a promoter to drive expression of the gene of interest. Preferably, this promoter is a strong promoter. In some cases, the promoter is a constitutive promoter. In other cases, the promoter is an inducible promoter, and only directs expression of the gene of interest in response to a particular stimulus.

Suitable constitutive promoters for driving expression of the gene of interest are known in the art, and include CMV.

Suitable inducible promoters are also known in the art, and are particularly useful in the expression of a gene of interest which is harmful to the cell in which it is to be expressed, such as a gene of interest encoding a toxic protein. By using intermittent expression of the toxic protein, negative effects on the growth and proliferation of host cells by the toxic protein may be minimised or avoided. Inducible promoters are those which initiate gene transcription in response to a stimulus, such as the presence of an inducing agent such as doxycycline (i.e. a doxycycline inducible promoter). An alternative strategy for expression of toxic proteins is to use riboswitches. A riboswitch is a regulator segment of a messenger RNA (mRNA) molecule that is able to bind a small molecule, resulting in a change in production of protein encoded by the mRNA. Thus, addition of the small molecule to the cell may stimulate production of the toxic protein from the mRNA, whereas the absence of the small molecule may allow the cells to grow and proliferate.

As used herein, "upstream" and "downstream" refer to a relative position in the nucleic acid sequence. Nucleic acid sequence has a 5' end and a 3' end. The 5' end is the upstream end, and the 3' is the downstream end. Transcription begins at the 5' end and moves along the nucleic acid sequence towards the 3' end. Where the nucleic acid is double stranded, such as with dsDNA, the terms are used in the context of the strand that encodes the gene of interest, or the "coding strand".

The vector may comprise an untranslated region (UTR), such as a polyadenylation sequence (polyA tail), downstream of the MCS or nucleic acid of interest. This downstream sequence, or 3' UTR is positioned immediately downstream of the stop codon of the open reading frame. The 3' UTR may comprise regulatory regions that influence polyadenylaton, translation efficiency, localisation and stability of mRNA translated from the expression vector. The 3' UTR may encode a polyA tail sequence, which may be important for nuclear export, translation and stability of mRNA transcribed from the vector. The 5' UTR may contain a translational enhancer sequence. The translational enhancer sequence may be the SP163 translational enhancer sequence.

The vector may comprise a multiple cloning site (MCS). A multiple cloning site may also be referred to as a polylinker. The MCS contains a plurality of restriction sites. The multiple cloning site may be as shown in FIG. 17. It may comprise the sequence set out in SEQ ID NO: 16.

In one aspect, the invention provides a pPEF vector comprising a *Gaussia* signal peptide. Nucleic acid expression vectors according to the present invention comprise nucleic acid encoding a signal peptide. A signal peptide is a short nucleic acid sequence present in the N-terminus of newly synthesised proteins. The signal peptide may be present in the N-terminus of proteins that are to be secreted. The signal peptide may direct the protein to the plasma membrane.

Preferably, the nucleic acid expression vectors of the present invention comprise nucleic acid encoding the signal peptide of *Gaussia* luciferase, referred to herein as *Gaussia* signal peptide, or GLUC. *Gaussia* luciferase signal peptide may have a sequence MGVKVLFALICIAVAEA (SEQ ID NO:1).

In another aspect, the vectors comprise nucleic acid encoding the signal peptide of PDX-Furin inhibitor. The signal peptide of PDX-Furin inhibitor may have the sequence MPSSVSWGILLLAGLCCLVPVSLA (SEQ ID NO:2).

Selectable Marker

In some aspects, nucleic acid vectors disclosed herein comprise nucleic acid encoding a selectable marker. A selectable marker is a gene introduced into a cell that confers a trait suitable for artificial selection. Selectable markers include antibiotic resistance genes. In some aspects, the nucleic acid vectors disclosed herein include nucleic acid encoding genes that infer resistance to puromycin, ampicillin, Zeocin® antibiotic, kanamycin, blasticidin, geneticin (G418), neomcyin, hygromycin, chloramphenicol or tetracycline.

Tags

In some aspects, the vector also includes nucleic acid encoding a tag. Tags may be useful for isolating the protein of interest, or may facilitate expression of the protein of interest. Suitable tags include GST (Glutathione-S-Transferase)-tag, HA-tag, Myc-tag, His-tag, V5-tag, Flag-tag, CBP (chitin binding protein)-tag, MBP (maltose binding protein)-tag, GFP-tag and its modifications, RFP-tag and its modifications, YFP-tag and its modifications, Lumio-tag, Nus-tag, Streptavidin-tag, T7-tag, S-tag, thioredoxin-tag and Softag. In certain aspects, the vector comprises a SUMO tag.

SUMO

SUMOstar is a technique developed by LifeSensors (www.lifesensors.com). SUMO-tag expression systems can maximize the yield of soluble, functional proteins in E. coli, yeast, insect and mammalian cells. SUMO functions as both a chaperonin and as an initiator of protein folding to dramatically improve the solubility and level of expression of your protein of interest. SUMO may be particularly useful in the expression of small proteins. For example, expression of nucleic acid encoding Noggin. SUMO may be incorporated into the vector. Alternatively, SUMO may be fused in frame to the nucleic acid of interest which is inserted into the vector.

Cells

The nucleic acid vectors disclosed herein are useful for the expression of peptides in cells. Any cell suitable for the expression of polypeptides may be used for producing peptides according to the invention. The cell may be a prokaryote or eukaryote. Preferably the cell is a eukaryotic cell such as a yeast cell, a plant cell, insect cell or, most preferably, a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Preferably the methods and plasmids of the invention relate to expression in mammalian cells. Any mammalian cell may be used. Suitable mammalian cells include established cell lines, including Human embryonic kidney cells (HEK293, particularly HEK293T cells, but also HEK293-EBNA1 cells and HEK293/TR cells), Chinese Hamster Ovary (CHO), CHO cell derivatives such as CHO-K1, CHOpro-3, and FreeStyle CHO—S cells, DUKX-X11, DG44, COS cells (monkey kidney cells), including COS-1 and COS-7 cells, Vero cells (African monkey kidney cells), HeLa cells (cervical adenocarcinoma cells), NSO cells (murine melanoma), Jurkat cells (immortalized human T lymphocytes), BHK cells (baby hamster kidney) and MCF cells (Michigan Cancer Foundation) such as MCF-7 cells, PER.C6, and L cell mouse fibroblasts such as those deposited at ATCC CRL 2648. In some cases, the cells are a human cell line.

Protein Expression

The methods and vectors of the present invention are suitable for the expression of any protein. They are particularly suited to proteins which have proved difficult to express in conventional protein expression vectors and systems. Nucleic acid encoding the protein of interest (referred to herein as the nucleic acid of interest, nucleic acid encoding the gene of interest) is introduced into the vector, and the vector is transfected into a cell. The protein is then produced by the cell.

Proteins particularly suited to the methods and plasmids of the present invention include antibodies, cytokines and growth factors, large proteins, secreted proteins, membrane proteins, kinases and receptors, and metalloproteinases.

The plasmids of the present invention are particularly useful for the expression of antibodies in mammalian cells.

Large proteins which may be expressed using the plasmids of the invention include proteins larger than THSD7A (Thrombospondin Type 1 Domain containing 7A; GenBank: NM_015204.2 GI:259013332) and PLA2R (Pongo abelii phospholipase A2 receptor 1; GenBank: NM_001132708.1 GI:197098169). The protein may be at least 1000 amino acids, at least 1200, at least 1400, at least 1600, at least 1800, at least 2000, or at least 2200 amino acids in length.

In other aspects, the protein is expressed as a fusion protein with a tag or other peptide sequence. In such cases, the fusion protein may be at least 1000 amino acids, at least 1200, at least 1400, at least 1600, at least 1800, at least 2000, or at least 2200 amino acids in length. Expression as a fusion protein may be particularly suitable where the protein to be expressed is a small protein or peptide. For example, the peptide may be 10 to 500 amino acids, 50 to 500, 100 to 400, 100 to 300, or 150 to 250 amino acids in length. The small protein may be expressed as a fusion protein with a tag which increases the size of the protein to be expressed. The tag may be removable from the expressed protein. Suitable tags include SUMO or Fc tags.

Secreted proteins which may be expressed using the plasmids of the invention include sVAP1 (synaptosomal associated protein; GenBank: NM_053052.3 GI: 224465201) and CD73 (GenBank: BC065937.1 GI: 42406318), and BMP4 (GenBank P12644; GI 115073). Cytokines and growth factors that may be expressed using the plasmids of the invention include Noggin (GenBank: U31202.1 GI: 1117816) and IFNb-1a (Interferon beta 1a; DrugBank: DB00060 (BIOD00093, BTD00093). Metalloproteinases that may be expressed using the plasmids of the invention include MMP12 (matrix metallopeptidase 12; GenBank: NM_002426.4 GI: 261878521). Kinases and receptors that may be expressed using the plasmids of the invention include RET (GenBank: KR709953.1 GI:823670247). An example of a membrane protein is Heparanase (GenBank Q9Y251.2 GI 296434532).

In some cases, the vector may be used to express a toxic protein. For expression of toxic proteins, it is advisable to use an inducible promoter. Use of an inducible promoter means that expression of the protein may be intermittent, rather than constitutive. By using intermittent expression of the toxic protein, negative effects on the growth and proliferation of host cells by the toxic protein may be minimised or avoided. Inducible promoters are those which initiate gene transcription in response to a stimulus, such as the presence of an inducing agent such as doxycycline.

An alternative strategy for expression of toxic proteins is to use riboswitches. A riboswitch is a regulator segment of a messenger RNA (mRNA) molecule that is able to bind a small molecule, resulting in a change in production of protein encoded by the mRNA. Thus, addition of the small molecule to the cell may stimulate production of the toxic protein from the mRNA, whereas the absence of the small molecule may allow the cells to grow and proliferate.

Methods of producing a peptide of interest may involve culture or fermentation of a cell modified to express the peptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted proteins. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express peptide of interest, that peptide is preferably isolated. Any suitable method for separating proteins from cell culture known in the art may be used. In order to isolate a protein of interest from a culture, it may be necessary to first separate the cultured cells from media containing the protein of interest. If the protein of interest is secreted from the cells, the cells may be separated from the culture media that contains the secreted protein by centrifugation. If the protein of interest collects within the cell, for example in the vacuole of the cell, it will be necessary to disrupt the cells prior to centrifugation, for example using sonication, rapid freeze-thaw or osmotic lysis. Centrifugation will produce a pellet containing the cultured cells, or cell debris of the cultured cells, and a supernatant containing culture medium, cell lysate and the protein of interest.

It may then be desirable to isolate the protein of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography, affinity chromatography, gel filtration, hydrophobic interactions, and reverse phase chromatography. These may be used as an alternative to precipitation, or may be performed subsequently to precipitation.

Once the protein of interest has been isolated from culture it may be necessary to concentrate the protein. A number of methods for concentrating a protein of interest are known in the art, such as ultrafiltration, lyophilisation or centrifugal concentration.

Sequence Identity

In certain aspects the invention concerns compounds which are nucleic acids comprising a sequence having a sequence identity of at least 70% with a given sequence. Alternatively, this identity may be any of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity.

Percentage (%) sequence identity is defined as the percentage of nucleic acid residues in a candidate sequence that are identical with residues in the given listed sequence (referred to by the SEQ ID No.) after aligning the sequences and introducing gaps if necessary, to achieve the maximum sequence identity, and not considering any conservative substitutions as part of the sequence identity. Sequence identity is preferably calculated over the entire length of the respective sequences.

Where the aligned sequences are of different length, sequence identity of the shorter comparison sequence may be determined over the entire length of the longer given sequence or, where the comparison sequence is longer than the given sequence, sequence identity of the comparison sequence may be determined over the entire length of the shorter given sequence.

For example, where a given sequence comprises 100 nucleic acids and the candidate sequence comprises 10 nucleic acids, the candidate sequence can only have a maximum identity of 10% to the entire length of the given sequence. This is further illustrated in the following example:

(A)
Given seq: XXXXXXXXXXXXXXX (15 nucleic acids)
Comparison seq: XXXXXYYYYYYY (12 nucleic acids)

The given sequence may, for example, be that encoding the plasmid as a whole, or an element within the plasmid, such as a sequence encoding a promoter. % sequence identity=the number of identically matching nucleic acid residues after alignment divided by the total number of nucleic acid residues in the longer given sequence, i.e. (5 divided by 15)×100=33.3%

Where the comparison sequence is longer than the given sequence, sequence identity may be determined over the entire length of the given sequence. For example:

(B) Given seq: XXXXXXXXXX (10 nucleic acids)
Comparison seq: XXXXXYYYYYYYZZYZZZZZZ (20 nucleic acids)

Again, the given sequence may, for example, be that encoding the plasmid as a whole, or an element within the plasmid, such as a sequence encoding a promoter. % sequence identity=number of identical nucleic acids after alignment divided by total number of nucleic acids in the given sequence, i.e. (5 divided by 10)×100=50%.

Alignment for purposes of determining percent nucleic acid sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used.

Identity of amino acid sequences may be determined in a similar manner involving aligning the sequences and introducing gaps if necessary, to achieve the maximum sequence identity, and calculating sequence identity over the entire length of the respective sequences. Where the aligned sequences are of different length, sequence identity may be determined as described above and illustrated in examples (A) and (B).

Kits

Also disclosed herein are kits. Kits may comprise a nucleic acid expression vector as disclosed herein and one or more reagents. Kits may include reagents suitable for cloning a nucleic acid of interest into the vector, and/or reagents for transfecting a host cell with the vector. The kit may include a host cell. Kits may also comprise instructions for use.

Methods

Disclosed herein are methods of making and using the nucleic acid expression vectors disclosed herein.

In one aspect, the disclosure provides a method of making an expression vector, the method comprising modifying a pPEF series vector to include a *Gaussia* signal peptide. The methods may involve reducing the size of the vector. The method may include removing non-essential sequences of the vector. The method may involve removing the f1 origin of replication. The method may involve removing the EM7 promoter. The method may involve introducing a transcriptional enhancer, such as an SP163 transcriptional enhancer. The method may also involve removing elements that are not essential for transfection, such as the selectable marker. For example, the method may involve the removal of an antibiotic resistance gene. The method may involve removing the selectable marker and the promoter that controls the expression of the selectable marker.

In another aspect, methods of transforming a cell are provided. The methods may involve introducing a nucleic acid expression vector as disclosed herein. The methods may involve introducing the expression vector into a host cell, and then subjecting the host cell to selection, such as antibiotic selection.

In some aspects, methods involve the production of a protein of interest. Such methods involve transforming a cell with a nucleic acid expression vector disclosed herein that contains nucleic acid encoding the protein of interest. The method may involve selecting transformed cells, such as by antibiotic selection or nucleic acid analysis. In some case, the method involves inducing transient expression of the nucleic acid of interest. The method may involve separating the protein of interest from the cells.

The method may involve lysing the cells to extract the protein of interest. In preferred aspects, the protein of interest is secreted from the cells. Such methods may involve isolating the protein of interest from the medium in which cells are cultured. Methods of isolating and extracting proteins are known in the art. Any suitable method for protein isolation or extraction may be used with the vectors and host cells disclosed herein, and may depend on the protein to be isolated or extracted.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

EXAMPLES

Example 1: Vector Optimisation

Our Protein Expression Facility (PEF) was established to produce milligrams of various proteins, which usually would not be available commercially, with the least costs for the researchers using our services. Back in 2010, when the mammalian expression platform was introduced in the Facility in addition to microbial and insect ones, it was chosen to use HEK293 EBNA1:pCEP stable episomal expression as one of the best described in the literature. It was shown to outperform stable expression based on pcDNA™3.1 vector when used with HEK293 cells and its derivatives (Durocher et al, 2002). However, in practice this system was not delivering consistently sufficient amounts of protein when used for different types and subclasses. Additionally, the newly created cell lines could lose their expression after a single freeze-thaw event. Since the employment of commercially available suspension grown strains and specially formulated media, although guaranteed to increase the recombinant yield, was not affordable, it was decided to focus our R&D on vector optimisation.

Vector design can significantly affect transcription and processing of the transcript, export of mRNA from the nucleus, targeting of mRNA, its stability and translation. This can be achieved through manipulations with promoters, 5 and 3' end UTRs and various DNA elements which enhance transcription such as Matrix Attachment Regions (MARs) and Ubiquitous Chromatin Opening Elements (UCOEs) to name some. One of the feasible to us approaches would be to concentrate our efforts on signal peptide optimisation as one of the most promising tools to increase recombinant yield. Literature search at the time highlighted the signal peptide of a marine copepod, *Gaussia princeps*, as a very promising one. The original work of Tannous and co-workers in 2005 showed that *Gaussia* luciferase (GLuc) is very efficiently secreted in mammalian cells. Several reports published later demonstrated that GLuc signal peptide consistently and significantly, up to 100 fold, outperformed various mammalian secretory signal peptides as well as the ones from other marine organisms (Knappskog et al, 2007; Stern et al, 2007; Wen et al, 2011). When compared to its mammalian counterparts, GLuc was shown to impact on protein production at post-transcriptional level, possibly through enhancement of mRNA-protein (mRNP) formation and transport to translocons. Tested together with the well-known mammalian signal peptide routinely used in the Facility, BM40 (Swaroop et al., 1988), it was thought to give us a good idea whether we are already utilizing the best approach for the production of soluble recombinant proteins or there is still some scope for an increase which we could benefit from when dealing with difficult-to-express targets.

Inspiration for introducing another variable, a vector different to pCEP-Pu, came from our previous experiments. In 2010, when trying to increase the production of a soluble Phospholipase A2 Receptor (PLA2R1) presented in the Examples section, we attempted the generation of double stable lines. The original episomal pCEP-Pu:PLA2R1 line yielded very low amounts of protein, approximately 100 microgram per litre on average. Since even this low yield would be lost upon freezing, new stable lines had to be created regularly to meet the demand. In addition to the full-length soluble PLA2R1, there were truncated forms which together exceeded the amount of the full-length protein. We speculated that Furin would be one of the reasons for the truncation. It is a common proprotein convertase which cleaves proteins destined for secretion. By blocking Furin we hoped to see the increase in the yield of the full-length PLA2R1 at the expense of diminishing truncated forms. We procured a construct containing alpha-1 PDX (Jean et al., 1998), a furin inhibitor, which came from Prof. Kidd's lab in the USA (Columbia University).

The a1-PDX coding sequence was subcloned into the following mammalian expression vectors:
 a) pCEP-Pu (pCEP-Pu/AC7 (Kohfeldt et al, 2007), based on pCEP4 (Invitrogen)—the most popular vector for episomal expression);
 b) pcDNA™4/HisMax (Invitrogen) vector, an advanced version of pcDNA™3.1, which is a popular vector for stable expression;
 c) pRTS-1 (Bornkamm et al., 2005), a kind gift of Prof. Dirk Eick, German Research Centre for Environmental Health (Munich).
 pCEP-Pu vector was chosen for transient transfection of the pCEP-Pu:PLA2R1 stable cell line. pcDNA™4/HisMax vector contained a Zeocin® antibiotic resistance gene, whereas pRTS-1 had a hygromycin resistance gene. Both allowed creation of double stable cell lines since the basal pCEP-Pu:PLA2R1 line had been selected via puromycin resistance.

Figure 1:
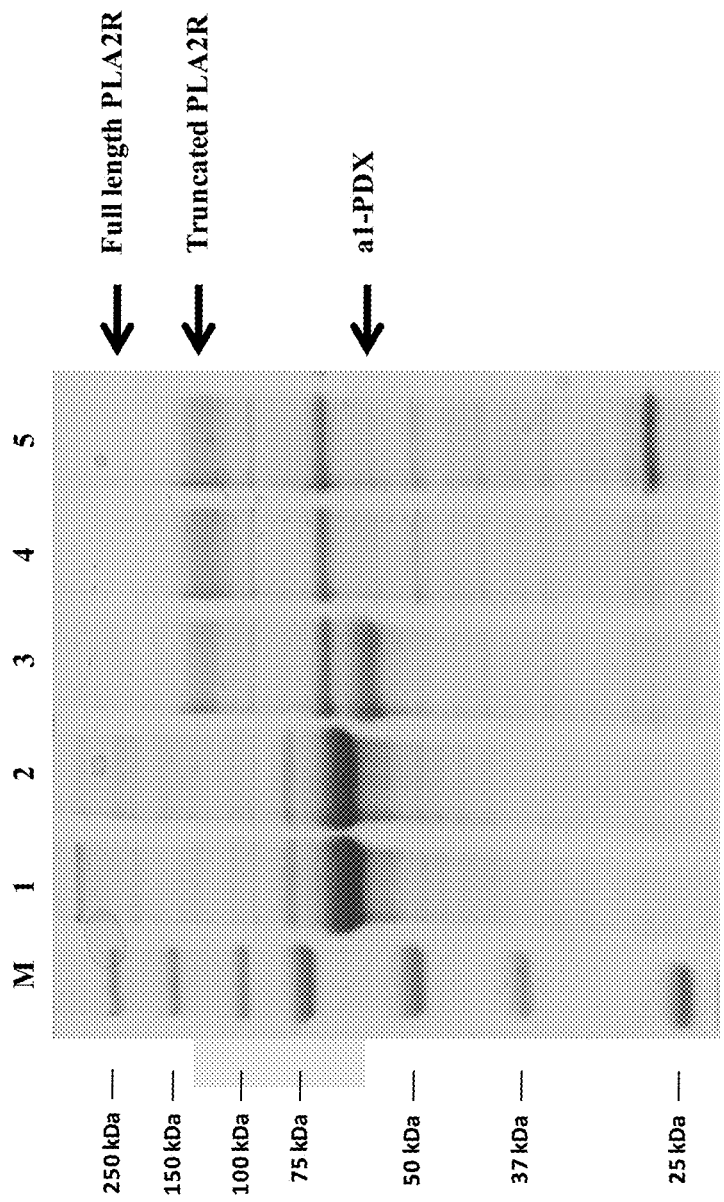
FIG. 1. Differential Expression of a1-PDX in pcDNA™4/HisMax vector, pCEP-Pu and RTS-1. Conditioned serum-free concentrated medium from: Lane 1: non-transfected HEK293EBNA1; Lane 2: HEK293EBNA1 stably expressing pCEP-Pu:PLA2R; Lane 3: HEK293EBNA1 stably expressing pCEP-Pu:PLA2R and pcDNA™4/HisMax:a1 vector; Lane 4: HEK293EBNA1 stably expressing pCEP-Pu:PLA2R and transiently expressing pCEP-Pu:a1 PDX; Lane 5: HEK293EBNA1 stably expressing pCEP-Pu:PLA2R and pRTS-1:a1 PDX induced with 0.5 µg/ml doxycylcine.

FIG. 1 shows the results of a1-PDX expression in double stable lines. While the effort did not increase the yield of the full-length PLA2R1 but, on the contrary, enhanced the production of the truncated PLA2R1 form, it did highlight pcDNA™4/HisMax vector as the most efficient for the expression of a1-PDX protein.

Figure 2A:
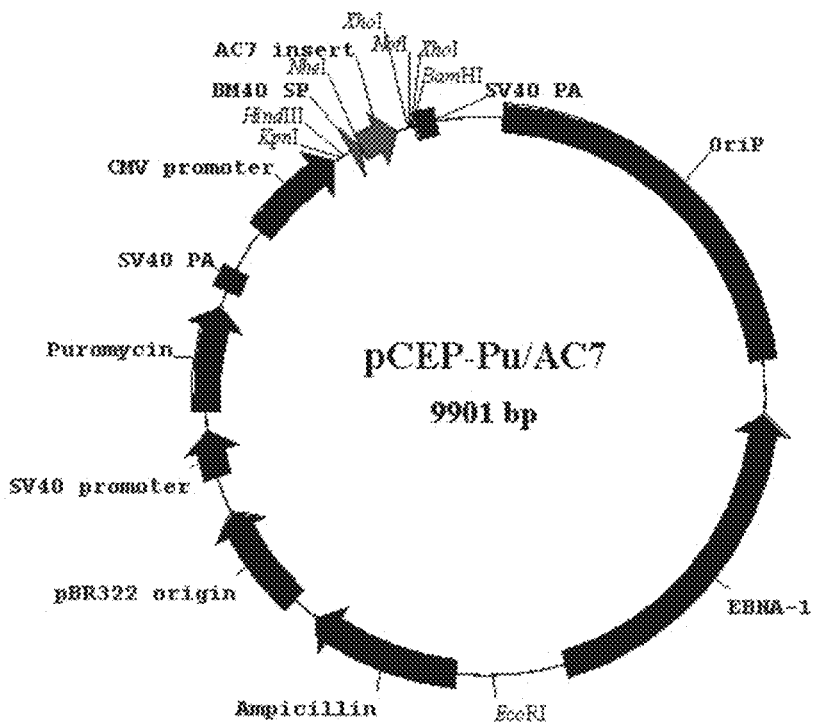
FIG. 2. Improving the yield and secretion of recombinant proteins through vector modifications. A: pCEP-Pu:AC7 (Kohfeldt et al 1997) based on pCEP4 (Invitrogen)—the most popular vector for episomal expression; B: pcDNA™4/HisMax (Invitrogen) vector, an advanced version of pcDNA™3.1 vector from the same manufacturer—the most popular vector for stable expression. Transcription enhancer—SP163 from pcDNA™4/HisMax vector (Invitrogen).
Figure 2B:
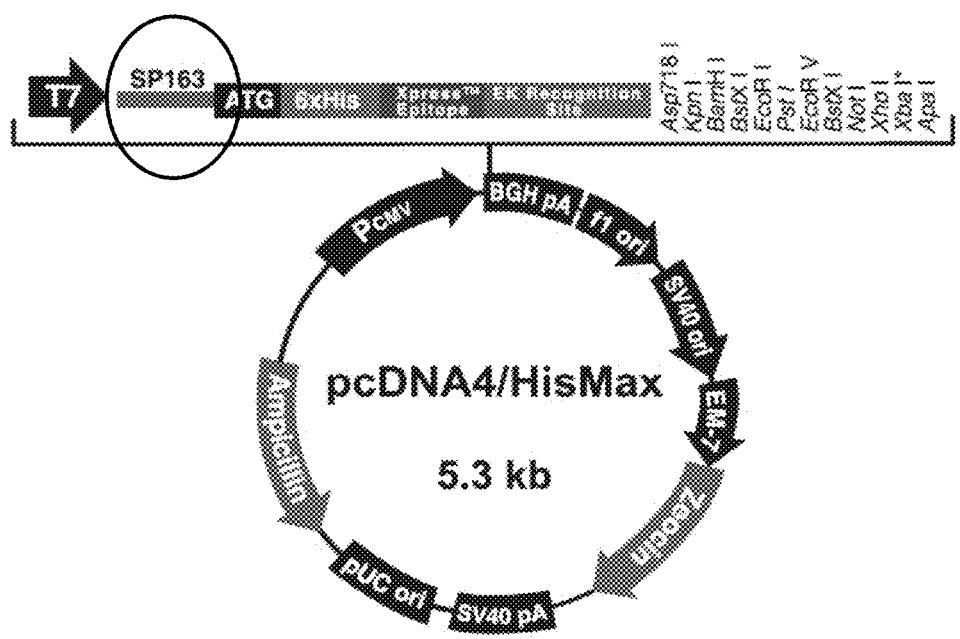

Thus, it was decided to concentrate our further R&D effort on two vectors, pCEP-Pu:AC7 and pcDNA™4/HisMax, two Signal Peptides (SP), BM40 (MRAWIFFLLCLAGRALA) (SEQ ID NO:3) and Gluc (MGVKVLFALICIAVAEA) (SEQ ID NO:1) and their combination with the SP163 Transcriptional enhancer which present in pcDNA™4/HisMax vector as shown in FIG. 2:

We chose a secreted form of Vascular Adhesion Protein-1 (sVAP-1), as the model protein for our expression studies which is described in the Examples section. It has been the best protein in our portfolio in terms of expression stability and high yield producing up to 60 mg/L (Heuts et al., 2011). The cloning strategy was as follows: We used the existing pCEP-Pu:sVAP-1 vector as the basis (described in the cited above paper and in the Examples section). The construct was digested with KpnI and NheI to drop the BM40 signal peptide and one of the 3 synthetic fragments presented in FIG. 3 was inserted.

Then we used the original pCEP-Pu:sVAP-1 (with the BM40 signal peptide) and the newly created pCEP-sVAP-1 constructs with fragments 1, 2 and 3 to excise a part of the Pcmv promoter and the ligated fragments with sVAP-1 after NdeI/BamHI digestion. Those larger fragments were ligated into NdeI/BamHI digested pcDNA™4/HisMax C vector.

The resulting pcDNA™4 based constructs should be named as follows: pPEF1 for pcDNA™4-SP163-BM40; pPEF2 for pcDNA™4-SP163-GLuc; pPEF3 for pcDNA™4-BM40 and pPEF4 for pcDNA™4-GLuc.

Figure 4:
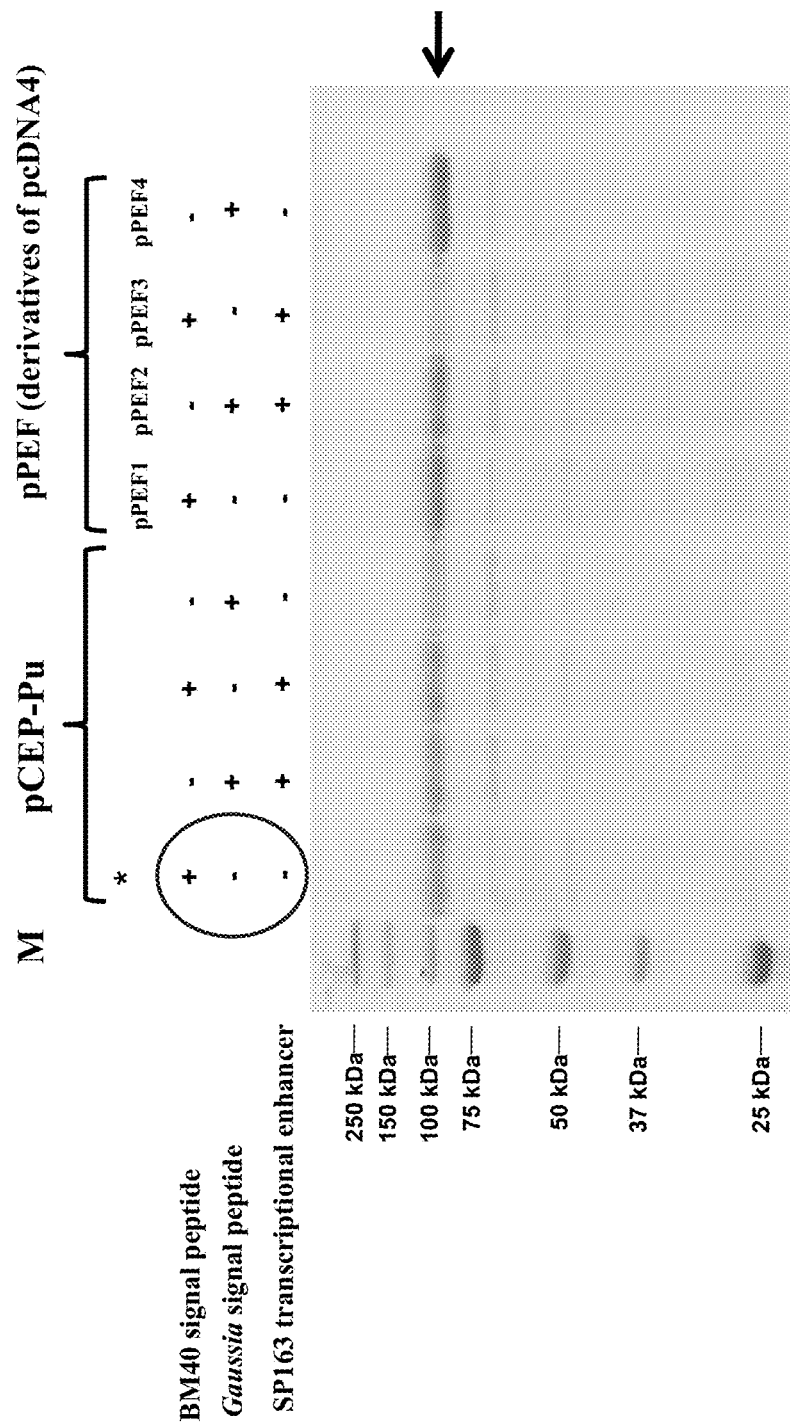
FIG. 4. Differential expression of sVAP-1 in the modified vectors. Yield in pCEP-Pu—up to 60 mg/L (Heuts et al, 2011); Yield in pPEF4—100 mg/L (predicted); Yield reported in literature—0.93 mg/L (Ohman et al, 2006). *indicates a combination which has been routinely tested in the laboratory and was used here as a control.

The expression constructs, pCEP—Pu based and pcDNA™4 derived, were transfected into HEK293 EBNA1 cells with Lipofectamine™ transfection reagent (Invitrogen/Life Technologies) following the manufacturer's instructions. A selective reagent (puromycin for pCEP-Pu derived constructs and Zeocin® antibiotic for pPEF1-4) was added 48 hours post-transfection. Pools of stable colonies were established and expanded after 3-4 weeks of culturing in case of pPEF vectors and 4-5 weeks for pCEP expression plasmids. Once the stable cells reached 100% confluency in a T25 culture flask, the complete medium was replaced with serum-free one (SFM) and cultured for 7 days. The SFM was then harvested and analysed for the presence of a secreted protein either by Coomassie staining or Western blotting (anti-His). FIG. 4 demonstrates the differential expression of sVAP-1 in various constructs with the pPEF suite showing an increase compared to the pCEP vectors.

Since the pPEF vectors, especially the ones incorporating GLuc, revealed a promising trend for enhancing protein production, it was chosen to test it further with PLA2R1 as the most difficult target in terms of low yield and reproduction (see the Examples section for the original cloning of pCEP-Pu:PLA2R1 and purification details). To generate pPEF1-4:PLA2R1, the corresponding constructs of pPEF:sVAP-1 were digested with NheI/NotI to drop the sVAP-1 coding sequence and replace it with the PLA2R1 excised with the NheI/NotI from the original pCEP-Pu:PLA2R1 (Kanigicherla et al., 2013). To create the pCEP-Pu suite of constructs, additional cloning steps had to be introduced in view of very limiting MCS of this vector backbone. The pCEP-Pu:AC7 vector was digested with KpnI and NheI to incorporate the synthetic fragments given in FIG. 3, also KpnI/NheI treated. The resulting pCEP-Pu derived vectors were NheI/NotI digested to omit the AC7 insert and to be ligated with PLA2R1 coding sequence instead.

Stable cell lines were created as described above for sVAP-1. It is noteworthy, that as previously, the selection process and the establishment of stable cells for pPEF constructs were a week or two quicker than for the pCEP suite. FIG. 5 summarizes the expression pattern for PLA2R1 in the pPEF and pCEP contexts. PLA2R1 was more highly expressed in the smaller, pPEF, context. Moreover, the highest yield was obtained from the smallest vector tested that contained the *Gaussia* signal peptide.

The same trend which had been observed for the sVAP-1 has been demonstrated for PLA2R1 as well. Although pPEF4 proves to produce the highest yield, in the case of PLA2R1 the pPEF2 version appears most suitable for a production of full-length protein which is thought to be heavily glycosylated. pPEF vectors therefore allow stable protein expression with high yield in mammalian cells.

Example 2: Optimisation of the Selective Marker

Once we established that GLuc in the context of pcDNA™4 derived vectors surpasses our usual combination of BM40 signal peptide with pCEP backbone, further attempts were made to better the expression of pPEF2 and pPEF4. In our view these vectors could be made leaner by removing unnecessary regulatory parts such as F1 origin and EM-7 promoter. This would result in smaller vectors thereby increasing transfection efficiency and improving protein yield yet further. The higher initial pool of transfected cells would increase the odds of the construct incorporated into transcriptional hot spots and producing "high expressor" stable cells.

We also wanted to try a different promoter driving the expression of the selective antibiotics' resistance instead of SV40. It was thought to serve two purposes. First, replacing SV40 promoter/origin of replication would make HEK293/T cell line amenable for stable expression. Most of the commercially available plasmids for mammalian expression contain SV40ori which causes genomic instability in cell lines expressing SV40 large T-antigen such as COS7 and HEK293/T (Hunter and Gurney, 1994). This is why HEK293/T cell line is utilised mostly for transient expression making use of its main advantage: a very easy adaptation for growth in suspension which is important for scaling up recombinant protein production. If we could succeed in modifying our vectors and make them suitable for this cell line, then we could achieve a further increase in yield: at the expense of quicker harvests and less labour involved when compared to culturing adherent cells such as HEK293 EBNA1. Second goal could be finding just the right degree of the expression of the resistance gene. Attenuation of selection marker is an important mechanism to create high stringency conditions. It helps bypass a very time-, resource- and labour-consuming process of clonal selection. It is possible now for big biopharmaceutical companies to have a completely automated selection process which is still costly. It is even more tedious for small settings such as individual labs. Transfected cells have to be diluted to obtain individual clones originating from single cells in 24- to 96-well plate formats. Each clone has to be amplified for simultaneous maintenance and screening. Once the screen has revealed the highest expression, the positive clone is chosen for amplification and expansion. However, the attenuated expression of the selective marker can do the perfect job in this regard. It is assumed that a weak promoter can provide just enough expression to confer antibiotic resistance when incorporated into actively transcribed euchromatin, on the provision that the main gene of interest remains intact upon insertion. Thus, only the best (and fewer) expressing cells should survive the selection.

When choosing candidates for the second promoter, we were looking for the ones which would be stronger than or comparable to the SV40. Two constitutive promoters, human elongation factor 1a promoter (EF1A) and chicken b-Actin promoter coupled with CMV early enhancer (CAGG), were reported to occupy intermediate strength position between CMV and SV40 when tested in HEK293/T cells (Qin et al., 2010). We ruled out the CAGG due to its large size, over 1.7 kb, and focused on the EF1A. Commercial vectors mostly contain the larger version of the EF1A promoter, spanning approximately 1.2 kb and include intron 2. Based on the original work of Uetsuki and co-authors (1989), we chose a part of the promoter which starts 73 bp upstream of the commercial EF1A promoter, continues into exon 1, skips the intron 2 and ends at the ATG start codon of exon 2. The total length is 330 bp and represents approximately a quarter of the standard EF1A promoter. We reasoned that the chosen fragment of the full length promoter, or minimal EF1A, should be comparable in strength to the SV40 one, since it contained at least 2 binding sites for Sp1 transcription factor. FIG. 6 represents Clustal multiple alignment of EF1A versions.

With the above considerations in mind, two synthetic constructs were designed: Synthetic fragment I with the minimal EF1A (1206 bp) (see FIG. 6B) and Synthetic fragment II with SV40 promoter (1214 bp) (see FIG. 6C).

Both fragments are flanked by NheI and PmlII restriction sites at 5' and 3' ends respectively. They incorporate MCS, BGH polyA, EF1A minimal (Fragment I) or SV40 promoter (Fragment II) and Zeocin® antibiotic resistance gene.

To create pPEF5.1 vector, pPEF4 was digested with NheI/PmlII and fused with the similarly digested Fragment I. When Fragment II was digested with NheI/PmlII and cloned into the prepared pPEF4 vector backbone, it resulted in pPEF5.2 vector. When either fragment was subcloned into the NheI/PmlII digested pPEF2 containing SP163 Transcriptional enhancer, then the Max versions of the above mentioned new vectors were produced: either pPEF5.1/Max or pPEF5.2/Max.

To assess whether these more customised vectors are comparable to their predecessors, pPEF2 and pPEF4, in terms of expression levels, we used the same model genes of interest as previously: sVAP and PLA2R1. Additionally, we decided to test the strength of our minimal EF1A promoter. sVAP and PLA2R1 coding sequences were subcloned into pPEF5.1/2 and pPEF5.1/2/Max respectively. HEK293 EBNA1 cell line was transfected with pPEF5.1:sVAP, pPEF5.2:sVAP, pPEF5.1/Max:PLA2R1 and pPEF5.2/Max: PLA2R1. HEK293/T cell line was transfected with pPEF5.1: sVAP and pPEF5.1/Max:PLA2R1.

Interestingly, all stable cell lines over-expressing EF1A minimal promoter took 1-2 weeks quicker to establish than their counterparts harbouring SV40 on/promoter. Also, the initial number of colonies which survived antibiotic selection was significantly higher. FIG. 7 shows the comparison of expression levels between the stable lines and the vectors.

Two important conclusions can be drawn from the experiments: Firstly, that the EF1A minimal promoter is more active than the SV40 creating less stringent conditions for the selection of the best clones; the SV40 provides the right degree of attenuated expression and therefore should be used for stable line selection unless further work on minimizing EF1A is attempted; Secondly that pPEF5.2 and pPEF5.2/ Max provide comparable if not higher levels of expression than their prototypes, pPEF2 and pPEF4. They should be used for standard protein expression.

Example 3: Human Vascular Adhesion Protein-1 (VAP-1)

This example demonstrates a robustness of our expression vectors providing a further potential in terms of expression levels for proteins with already high yields.

VAP1 is an endothelial copper-dependent amine oxidase involved in the recruitment and extravasation of leukocytes at sites of inflammation. VAP-1 is an important therapeutic target for several pathological conditions.

The intronless gene that encodes the soluble truncated, form of VAP-1 (sVAP-1; accession No NP 001264660.1; GI:480306390; residues 29-763) was codon-optimized for expression in human cells and synthesized by Qiagen. The gene was synthesized so that it is flanked at the 5'-end by a NheI restriction site and a BamHI restriction site at the 3'-end, thereby enabling directional subcloning into pCEP-Pu:AC7. The vector contains BM-40 signal peptide followed by NheI which allow extracellular expression of sVAP-1. The construct, as well as all the constructs provided in the Examples section, was DNA sequence verified.

HEK293 EBNA1 cells were transfected with 2 μg of plasmids using the transfection reagent Lipofectamine™ (Invitrogen) according to the manufacturer's instructions. The established HEK293 cells were transferred from the original 6-well plate to a 25 ml culture flask 24 hours post transfection. Antibiotic was added 48 hours post transfection. Stable colonies were pooled together after antibiotic selection for expansion. To harvest media, the cells were seeded into T225 flasks. After reaching cell confluence, the medium was replaced with fresh serum-free medium. Cells were cultured for 7 days followed by harvesting of conditioned medium and replacement with fresh medium. The collected medium, typically 500-550 ml, was centrifuged to precipitate cells and frozen at −20° C. until further use.

For protein purification, $CuSO_4$ was added to the medium to a final concentration of 0.1 mM, and the medium was incubated at 4° C. for at least 6 h (or on ice overnight). The medium containing sVAP-1 was concentrated to 50 ml using an Amicon stirred ultrafiltration cell fitted with a 30-kDa cut-off filter and subsequently concentrated further to 5 ml using a Vivaspin 20 centrifugal concentrator (Sartorius-Stedim). sVAP-1 was purified by size exclusion chromatography using a HiLoad 26/60 Superdex 200 preparative grade column, pre-equilibrated with 20 mM potassium $P_i$ buffer, pH 7.6, and 150 mM NaCl at 4° C. The same buffer was used throughout the purification procedure, and sVAP-1-containing fractions were pooled, concentrated, and stored at −80° C. until further use.

Example 4: Human Phospholipase A2 Receptor 1 (PLA2R1)

This example reveals a huge capacity of the pPEF system, especially pPEF5.2/Max version, for difficult/large proteins increasing expression levels 200-fold compared to the standard episomal approach.

PLA2R1 is a major target antigen in idiopathic membranous nephropathy, an organ-specific autoimmune disease. It was also reported to promote the accumulation of reactive oxygen species which induce cell death and senescence implying its role in cancer.

A mammalian codon optimised clone of human PLA2R1 (accession No NP 031392.3; GI: GI:55953104), covering amino acids 20-1397 which lacks the N-terminal signal peptide and C-terminal transmembrane domain, was synthesized (Genscript®) and included a short C-terminal linker and 10×His affinity tag. The complete insert was recovered from the supplied pUC57 by digestion with NheI and NotI enzymes and ligated into either pCEP-Pu/AC7 or any of the pPEF vectors cut with the same enzymes. HEK293 based stable cell lines were generated as described for sVAP1. PLA2R1 containing media were harvested as above. Immobilised metal affinity purification included one additional step for pCEP-based stable cell lines prior to loading the media onto AKTAxpress system (GE Healthcare). In view of very low expression level and hence the protein content, the media had to be concentrated approximately 50-fold using a Vivaflow Crossflow 200 (Sartorius Stedim Biotech) or LV Centramate Tangential Flow Filtration System (Pall Corporation). 20 mM Imidazole was added to the media and wash buffer (50 mM NaP, 0.3 M NaCl pH8.0) to increase stringency conditions. The media then was loaded on a 5 ml HisTrap excel column (GE Healthcare) and eluted in an increasing gradient of 500 mM imidazole. The flow-through was re-applied onto the column for the second run due to the fact that some protein was still present in it.

The eluted 2 ml fractions were analysed on a Coomassie stained SDS PAGE and the best fractions were pooled for concentrating and desalting. The desalted protein in the final buffer (PBS or 10 mM Tris, 150 mM NaCl, pH 7.4, 10% Glycerol) was snap frozen in liquid nitrogen and stored at −80° C. until further use.

Example 5: Expression of HPSE2

This example shows the supremacy of the pPEF vectors compared to the best commercial expression vectors for stable transfection.

Heparanase 2 (HPSE2) is an endoglycosidase that degrades heparin sulfate proteoglycans located on the extracellular matrix (ECM) and cell surface. The protein is involved in remodelling of ECM including angiogenesis and tumor progression. Loss-of-function mutations are strongly linked to urofacial syndrome.

At the time commercial HPSE2 produced in mammalian cells was not available, despite growing interest in fundamental research. Our previous attempts to over-express the protein in the bacterial or insect cells were not very successful in terms of yield and stability. Therefore we attempted to validate our pPEF vector system on this protein.

A complete coding sequence for HPSE2, accession No: AF282887.1; GI:10801198, was amplified by PCR approach to generate 2 DNA products: 1) the one encoding for a full length protein FL (aa 1-592), b) Δ41 fragment encoding for aa 42-592. Both DNA encoded for 10×His affinity tag at the C-termini. The FL contained its predicted native signal peptide according to SignalP 4.1 software, whereas Δ41 lacked it. The PCR products had introduced NheI and EcoRI flanking sites at 5' and 3' ends respectively to allow for a directional cloning into expression vectors. The full-length coding sequence (FL) was cloned into pcDNA™3.1+(Invitrogen), one of the most standard mammalian expression vectors, which is very similar in terms of vector backbone structure to our pPEF vectors. Both the FL- and Δ41-DNA coding sequences were cloned into NheI/EcoRI digested pPEF4.

The pcDNA™3.1:HPSE2_FL construct was transfected into HEK293 parental cell line since the vector contained a neomycin resistance gene which could not be used in HEK293 EBNA1 cells. The pPEF4:HPSE2_FL and pPEF4: HPSE_Δ41 were transfected into HEK293 EBNA1 cells according to the standard protocol described above.

Serum Free Medium was harvested after 7 days of culturing 100% confluent cells. Since little was known about the degree of secretion from the cells, they were harvested too for cell lysate analysis. FIG. 7 presents a Western blot by a standard Western protocol using specific anti-HPSE2_58 primary sera raised in rabbit.

Example 6: Recovery of Noggin

This example demonstrates the fact that the pPEF approach can be adapted for the expression of difficult/small targets through the addition of various tags. It is capable of delivering properly processed/folded enzymes the high activity of which is not affected by the presence of the tag. pPEF5.2 appears to perform better than pPEF5.2Max version for over-expression of small to medium sized proteins.

Noggin is an inhibitor of bone morphogenic proteins (BMPs). BMPs play important roles during various stages of development, especially during the establishment of dorsal structures and the development of nervous system. Noggin, together with other co-signalling extracellular factors, exerts correct spatial control of cell fate specification. Apart from its importance for the fundamental research, Noggin is an expensive reagent which is widely used for various cell culture applications. For example, it is used as a supplement for embryonic stem cells to maintain pluripotency or induce cell budding in some specialised cell cultures.

DNA coding for human Noggin accession No NM 005450.4; GI:189339247 (aa 28-232) lacking its predicted SP and introducing 10×His tag at the C-terminus was codon optimised by GenScript® USA Inc. and cloned into pPEF4 using NheI/EcoRI restriction sites. Newly created stable cell lines did not reveal detectable expression of Noggin by Coomassie staining or Western blotting.

More expression constructs were designed with another version of codon optimised coding sequence by DNA2.0 (USA). This time, two Noggin DNA sequences were made: one coding for the full length FL protein, aa 1-232, thereby incorporating the native SP, and a SUMO-Noggin fusion. The fusion protein (see FIG. 9C) comprised a 10×His tag, the N-terminal SUMOstar secretory tag (LifeSensors), and the mature form of Noggin, aa 28-232 (underlined).

The FL DNA was incorporated into pcDNA™4/HisMax vector using KpnI and EcoRV double digest. The fusion DNA was cloned into pPEF5.2 and pPEF5.2Max via NheI and NotI restriction sites.

Stable cell lines were created as described above and analysed for the expression of either FL Noggin or Sumo-Noggin fusion. No detectable expression level of FL Noggin were found in the stable lines transfected with pcDNA™4/HisMax:Noggin vector. FIG. 9 presents Coomassie staining and Western blotting of SDS PAGE of Sumo-Noggin fusions in pPEF5.2 and pPEF5.2/Max. As one can see, there is a higher expression level of the fusion protein in pPEF5.2 vector than in its Max version.

For scale-up production, 1L of Sumo-Noggin-containing serum-free media were harvested and loaded (cell-free) onto a 5 ml HisTrap Excel column for Affinity Chromatography purification using AKTAxpress (GE Healthcare) as described above.

The purified Sumo-Noggin fusion batch was divided into two halves: first half was left intact as a fusion, the second one was intended for Sumo-tag removal. The tag removal required some optimisation, since the manufacturer's recommended incubation temperature, up to 30° C., did not produce a fully cleaved Noggin. Instead, the following optimised conditions were established: 1U of SUMOstar protease (LifeSensors, Tebu-Bio) per 90 μg of the substrate for 1.5 hours at 40° C. FIG. 10 demonstrates the integrity of Noggin protein after the tag digest at such a relatively high temperature. This noteworthy stability testifies to a very efficient tight folding of the recombinant molecule despite the large tag.

To recover the cleaved Noggin, the fully digested fusion protein was incubated with Ni— NTA Agarose resin (Qiagen) at 4° C. to bind the cleaved Sumo-tag and SUMOstar protease (both are His-tagged). The unbound Noggin was collected and quantified (lane 5 on FIG. 9). The identity of Noggin was confirmed by Mass Spectroscopy analysis.

In activity assays in organoid cultures both proteins were found to be more enzymatically active than their commercial analogue, recombinant murine Noggin (PeproTech, Cat No 250-38).

Example 7: Expression of RET (Contains a Transmembrane Domain)

This example exhibits the suitability of pPEF for the expression of membrane proteins which are notorious for their toxic effect on the cell when over-expressed. This opens up an opportunity to use the vectors not only for recombinant protein production but also for drugs screen.

Rearranged during transfection (RET) is a proto-oncogene. It is a receptor which encodes for the signalling component of the glial cell line-derived neutrotrophic factor-family ligands receptor. This receptor tyrosine kinase is essential for spermatogenesis, development of the sensory, sympathetic, parasympathetic, and enteric nervous systems and the kidneys, as well as for maintenance of adult midbrain dopaminergic neurons. A number of loss-of-function mutations have been identified throughout the RET gene that lead to Hirschsprung disease, a congenital disorder characterized by a loss of enteric neurons in the distal portions of the colon and small intestine. Conversely, mutations that result in constitutively active receptors have been linked to tumors of various neuroendocrine tissues, including the thyroid, parathyroid, and adrenal glands. Some forms of RET have been used for high-throughput drug screens at the Cancer Research UK Manchester Institute, formerly the Paterson Institute for Cancer Research. Some short RET domains/regions are available in recombinant form commercially due to a huge interest in cancer research, but not long forms. It was chosen for our validation studies as a good example of membrane-associated receptor. Membrane bound proteins are thought to share the same metabolic pathway with the secreted proteins. On the other hand, over-expression of anchored proteins tends to have toxic effect due to cellular metabolic overburdening.

Human RET cDNA gene clone (cat: HG 11997-G) was ordered from Stratech Scientific Ltd. A RET51 cDNA form coding for aa 30-1114 (lacking its predicted signal peptide) and the C-terminal 10×His tag was amplified by PCR and cloned into pPEF5.1Max using NheI/NotI restriction sites.

RET51 stably expressing cells were harvested, lysed and analysed for RET expression by Western blotting technique as shown on FIG. 11.

Example 8: Matrix Metalloproteinase 12 (MMP-12)

This example shows the pPEF vectors as the robust tool to over-express difficult/toxic targets through inducible promoter modifications. It also demonstrates comparable performance in different HEK293-derived cell lines.

MMP12 is also known as macrophage elastase. It is a member of the matrix metalloproteinases. MMPs are a family of structurally related, zinc-containing enzymes that degrade the ECM and connective tissue proteins. The proteolytic effects of MMPs play an important role in vascular remodeling, cellular migration and the processing of ECM proteins and adhesion molecules, hence their huge implications for cancer and arthritis research. No wonder that this group of enzymes has been a pharmaceutical target for nearly 30 years, yet none of the developed drugs has successfully passed clinical trials. One of the main reasons for the failure—the complexity of MMPs regulation at various levels and their implication in a multitude of pathways. For example, in addition to MMP-12 diverse roles in elastolysis during uterine remodelling, tissue remodeling in inflammatory respiratory diseases such as chronic obstructive pulmonary diseases (COPD), elastin degradation in atherosclerotic lesions as well as lung cancer, esophageal squamous cell carcinoma, and skin cancer, it has been recently reported as a transcriptional factor conferring antiviral immunity (Marchant et al., 20014).

MMP-12 (accession No NP 002417.2) is synthesized as a 56 kD precursor molecule consisting of a propeptide (aa 17-60), catalytic (aa 106-263) and hemopexin (aa 277-470) domains connected via a short linker. One of the astounding properties of this enzyme is that it catalyses its own cleavage (auto-catalysis): once an active form is produced by yet an unknown mechanism, MMP-12 undergoes a cascade of cleaving events producing intermediate short-lived forms until the separate catalytic and hemopexin domains produced. Available commercial forms of recombinant MMP-12 are mostly produced in *E. coli* lacking specific activity. The only available enzymatically active recombinant MMP-12 is supplied as a 10 µg latent precursor which needs to be activated in vitro (R&D Systems, Cat No 917-MP-010).

Our initial efforts to stably over-express active form, Δ105 MMP-12 (aa 106-470) in pPEF4 and pPEF5.2Max failed. Intriguingly, repeated transfections produced the same scenario: initial small colonies, which always look a promising sign for an emerging cell line, would disappear after few days of culturing. We hypothesised that the increasing levels of active MMP-12 secreted into the media should degrade ECM thereby detaching stably expressing cells and eroding establishing colonies. The positive cells would be removed with old media. This is why a stable cell line could never be established. To test our hypothesis we performed transient transfections which confirmed our reasoning: Western analysis revealed the presence of MMP-12 72 hours post transfections. To adopt new approaches, we modified our expression vectors for inducible expression (approach 1), while also trying to over-express MMP-12 precursor (aa 17-470) in the standard pPEF5.2 with the use of specific inhibitors (approach 2).

For the first approach, a doxycycline inducible expression, we adopted the principle described for T-REx™ system developed by Life Technologies (tools.lifetechnologies.com). Firstly, HEK293 parental and HEK293 EBNA1 cell lines which would stably express tetracycline repressor (TetR) had to be generated. It was done by transfecting pcDNA™6/TR vector (Life Technologies) into these lines. Stable lines were selected by their resistance to blasticidin. Secondly, to introduce two tetracycline operator 2 (TetO$_2$) sites into the Pcmv promoter of our expression vectors, we digested pcDNA™5/FRT/TO vector (Life Technologies) with NdeI/KpnI. When we swapped the excised DNA fragment with the one from similarly digested pPEF5.2 and pPEF5.2/Max, we obtained the doxycycline (a more stable variant of tetracycline) inducible versions, pPEF5.2/TO and pPEF5.2/Max/TO respectively.

DNA sequence coding for the active form of MMP-12 (aa 106-470) was cloned into doxycycline inducible versions of pPEF, pPEF5.2/TO and pPEF5.2Max/TO, through NheI/NotI digest. Both constructs were transfected into HEK293 parental and HEK293 EBNA1 cell lines. When analysed for the expression levels, all 4 construct:cell line combinations demonstrated comparable levels of Δ105 MMP-12 expression when induced with doxycycline (FIG. 12).

The second approach, the over-expression of MMP-12 precursor in pPEF5.2Max with inhibitor's treatment (Z-Pro-Leu-Gly-NHOH broad range MMP inhibitor from Enzo Life Sciences), was also successful as demonstrated by FIG. 13. The propeptide form could be produced and "preserved" by blocking its further processing and auto-catalysis.

Example 9: Purification of Ricin Domain of PLA2R1

This example demonstrates high efficiency of pPEF to deliver small proteins via bicistronic modifications.

Initially we planned to over-express 2 domains of PLA2R1: Ricin and C-type lectin domain 3 (C3). Our previous experience showed that the mammalian HEK293-based expression system is not suitable for the production of small proteins which are below 40 kDa threshold. This might explain the failed initial attempts to over-express Noggin. This is why in the case of Ricin domain of PLA2R1 we looked for alternatives. One way to overcome the problem would be the attachment of a bulky tag such as Sumo. However, the disadvantage of this method is the need in additional steps aimed at tag removal and the recovery of a tag-less protein. It is costly, as well as time- and labour-consuming, delivering the protein of interest in the amounts which are a fraction of the initial yield. Therefore we decided to try a 2A approach instead (Luke, 2012) which would allow a simultaneous expression of two proteins driven by the same promoter. The principle is based on the insertion of the 2A-like viral sequences used to mediate protein cleavage from a single open reading frame through a ribosomal skip mechanism. We used a version of 2A sequence derived from porcine teschovirus-1 (P2A) as one of the most efficient and robust (Kim et al., 2011), delivering co-expressed proteins in the stoichiometry 1:1. The designed sequence is presented in FIG. 14. While the bicistronic P2A motif should allow for a simultaneous expression of the two domains (both with the C-terminal 10×His tags), the introduced Furin cleavage site should ensure the cleavage of the P2A motif from the Ricin domain by the endogenous Furin upon its secretion. It was expected that the C3 domain would be secreted too, following the signal peptide of the Ricin domain.

The DNA sequence encoding for the fragment was cloned into pPEF5.2 expression vector and a stable cell line was generated as described above.

Coomassie staining and Western blotting of the Ricin-C3 P2A conditioned media revealed the presence of positive band of approximately 25 kDa (FIG. 15, lane 2). Since the observed band could account for either histidine-tagged protein's expected size, it was unclear whether Ricin and C3 domains are expressed simultaneously.

To ascertain the presence of both recombinant proteins, small scale manual batch purification was performed. 16 ml conditioned media supplemented with 20 mM Imidazole, was incubated with pre-washed Ni-NTA agarose (QIAGEN) for 1 hour at room temperature. The single washing step was performed in 50 mM NaP, 0.3 M NaCl pH 8.0, 50 mM Imidazole. The bound protein was eluted in the same buffer containing 500 mM Imidazole.

After Coomassie analysis of all the purification steps (FIG. 15), the eluted protein was buffer exchanged into 10 mM Bis Tris, 150 mM NaCl, pH 7.4 10% Glycerol and snap frozen. The eluted band was analysed by Mass Spectrometry which detected the presence of Ricin domain only. Apparently, the addition of a signal peptide is an important prerequisite for the efficient secretion of the second protein when using the 2A approach.

Example 10: Strategy to Remove Lumio and 10×His Tag from MCS of pPEF5.2 to Produce pPEF5

In order to further reduce the size of the size of the vector, we removed the Lumio and 10×His tag sequences from the MCS. Primers were designed as shown in FIG. 29. pPEF5.2 plasmid was amplified via a PCR approach using the above primers. The resulting PCR product was digested with HpaI and AfeI and blunt ligated to produce a pPEF5 plasmid.

Example 11: Strategy to Replace Zeocin® Antibiotic Resistance Gene in pPEF5 with Puromycin to Produce pPEF5PuroR Synthetic PuroR DNA sequence with internal HindIII and PmlII restriction sites was commissioned from GenScript® (see FIG. 30). pPEF5 was digested with HindIII and PmlII to remove the DNA fragment coding for Zeocin® antibiotic resistance and replace it with HindIII/PmlII digested synthetic DNA coding for Puromycin resistance. The resulting vector was named pPEF5PuroR (shown in FIGS. 31A, B, C).

Example 12: Human Secreted Thrombospondin Type-1 Domain-Containing Protein 7A (THSD7A)—aa 48-1606

The protein is found almost exclusively in endothelial cells from placenta and umbilical cord. The encoded protein appears to interact with alpha (V) beta (3) integrin and paxillin to inhibit endothelial cell migration and tube formation. This protein may be involved in cytoskeletal organization. Variations in this gene may be associated with low bone mineral density in osteoporosis.

A synthetic DNA fragment coding for codon optimised soluble form of THSD7A with 10×His tag at the C-terminus was ordered from GenScript®. The DNA was subcloned into NheI/BamHI digested pPEF5PuroR. HEK293 EBNA1 cells were transfected with 2 µg of THSD7A constructs using Lipofectamine 2000 transfection reagent (Life Technologies) according to the manufacturer's instructions. Stable cell lines were established after 6 weeks of selection. A Western blotting analysis of the complete conditioned media demonstrated THSD7A expression is shown in FIG. 32.

Example 13: Human Secreted Amyloid Precursor Protein (APP) α (Aa 18-612) and β (Aa 18-596) Forms APP is a single-pass transmembrane protein expressed at high levels in the brain and metabolized in a rapid and highly complex fashion by a series of sequential proteases. Research suggests that physiologic generation of the neurotoxic Aβ peptide from sequential APP proteolysis is the crucial step in the development of Alzheimer's Disease (AD) which is the leading cause of dementia worldwide, is characterized by the accumulation of the β-amyloid peptide (Aβ) within the brain.

Corresponding DNA fragments coding for a and p forms of APP were PCR amplified from the APP mRNA transcript (GenBank accession No: NM 201414.2). The PCR products had introduced flanking NheI and NotI restriction sites. Both encoding DNAs were subcloned into pPEF5PuroR.

Transfection and creation of APPα and APP β stable cell lines were carried out according to the established protocol described above. Media from both stable cell lines were harvested for manual protein purification (batch method) as described for the Example No 9 in our Specifications document. Aliquots of the purified protein were analysed by Coomassie staining for protein integrity and purity. See FIG. 33A.

Figure 33C:
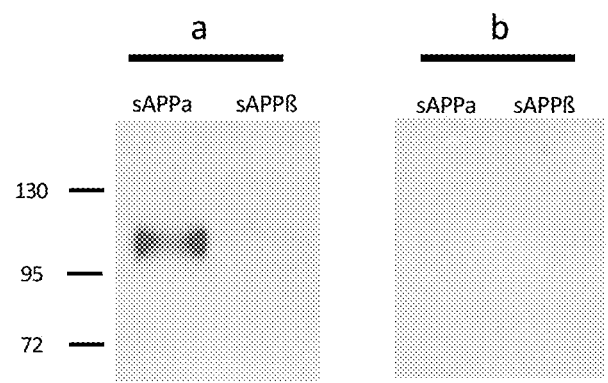

Further analysis with isoform-specific neoepitope antibodies (antibodies which recognise a specific C-terminal amino acid) (See FIG. 33B) and comparison of the purified proteins with their commercial analogues demonstrated their superior qualities (see FIG. 33C).

Example 14: Trastuzumab (TZM)

Trastuzumab represents a distinct class or recombinant proteins, monoclonal recombinant antibodies or mAbs. The recombinant IgG1 kappa, humanized monoclonal antibody that selectively binds with high affinity in a cell-based assay to the extracellular domain of the human epidermal growth factor receptor protein, is an extremely popular therapeutic. It is used to treat breast cancer.

The DNA sequences of Heavy and Light chains of TZM were obtained from DrugBank (Accession Number DB00072).

The synthetic DNA sequence coding for codon optimised Heavy and Light chains of Trastuzumab connected via a P2A sequence (as described for the Example 9 in the original Specifications document) and with NheI and BamHI flanking sites was ordered from GenScript®.

The DNA was digested with NheI/BamHI and subcloned into pPEF5PuroR.

HEK293 EBNA1 cells were transfected according to the standard protocol. TZM expressing stable cell line was established after 4 weeks of selection. Coomassie staining of conditioned SFM showed high expression levels of Trastuzumab is shown in FIG. 34.

Example 15: Validation of the Expression System in CHO-K1 Cells. A

The Expression of Trastuzumab (TZM) in CHO-K1 Cells.

The above TZM expression construct was transfected into CHO-K1 cell line, using the same protocol as for HEK293 EBNA1. Stable CHO-K1 cell lines were established after 4 weeks of antibiotic selection. Coomassie staining of the conditioned SFM media revealed a perceptible TZM expression, although lower than in HEK293 EBNA1 cells (see FIG. 35).

B: The Expression of Human Secreted Amyloid Precursor Protein Beta Form (APPs) in CHO-K1 Cells.

APPβ expression construct was transfected into CHO-K1 cells and established stable cell lines were analysed for APPβ expression levels. Comparative Coomassie staining revealed a higher expression level of the protein in CHO-K1 cells than in the stable HEK293 EBNA1 (see FIG. 36).

Example 16: Establishment of a Minimal EF1A Promoter

In Example 2 we developed a short version of EF1A promoter. However, despite representing only a quarter of length of the traditionally used EF1A promoter, it still demonstrated elevated activity when compared with the SV40 one. This higher strength of expression is not desirable when governing a selectable marker since it reduces the stringency of selection. Further attempts to attenuate promoter activity are reduce its size have been undertaken with the strategy described below. The constructs are shown schematically in FIG. 37A and their sequences provided in FIG. 37B.

Primers were designed to delete regions from the 5' end of the original minimal EF1A promoter in pPEF5.1 vector (all the primers introduced a StuI restriction site). Sequences are given in FIG. 37B.

pPEF5.1 vector was used as a template to create shorter versions of EF1A promoter via a PCR approach using the above primers. The generated PCR products were digested with StuI and self-ligated to produce pPEF5.11, pPEF5.12 and pPEF5.13 respectively. All three vectors were digested with NheI and NotI to accommodate the same PLA2R gene as described in the original Specification document. pPEF5.11:PLA2R, pPEF5.12:PLA2R and pPEF5.13:PLA2R constructs were transfected into HEK293T cell line as described previously. Stable cell lines harbouring pPEF5.11:PLA2R and pPEF5.12:PLA2R were established much quicker than the one over-expressing pPEF5.13:PLA2R. The latter cell line was formed from very few cells which survived antibiotic selection. Coomassie staining analysis of the conditioned media from all 3 stable cell lines demonstrated a comparable expression level of PLA2R for pPEF5.11 and pPEF5.12 and no detectable expression for pPEF5.13 (see FIG. 38).

It appears that the third version of the minimal EF1A promoter, EF1A3, is non-functional. The other two versions, EF1A1 and EF1A2, showed a similar expression level in HEK293T cells. It is recommended to test their strength in HEK293 EBNA1 line. It is possible, that although EF1A2 version has a greater potential for increased selection stringency, it could not be achieved in HEK293T due to some intrinsic metabolic bottlenecks. EBNA1 cell line has always proved to be the best cell line in terms of high expression levels when the same construct was expressed in HEK293 parental, HEK293 EBNA1 and HEK293T derivatives. Therefore, it can be assumed, that once placed in the genomic and metabolic context of this host cell line, EF1A2 minimal promoter can execute a better selection, hence a stronger drive for high-expressing stable clones, when compared to EF1A1.

REFERENCES

Durocher, Y., Perret, S. and A. Kamen. High-Level And High-Throughput Recombinant Protein Production By Transient Transfection Of Suspension-Growing Human 293-EBNA1 Cells. *Nucleic Acid Research*, Vol. 30, No 2, pp 1-9, 2002.

Tannous, B. A., Kim, D-E., Fernandez, J. L., Weissleder, R. and X. O. Breakefield. Codon-Optimised *Gaussia* Luciferase cDNA For Mammalian Gene Expression In Culture And In Vivo. *Molecular Therapy*, Vol. 11, No 3, pp 435-443, 2005.

Knappskog, S., Ravneberg, H., Gjerdrum, C., Tröβe, C., Stern, B. and I. F. Pryme. The Level Of Synthesis And Secretion Of *Gaussia princeps* Luciferase In Transfected CHO Cells Is Heavily Dependent On The Choice Of Signal Peptide. *Journal of Biotechnology*, No 128, pp 705-715, 2007.

Stern. B., Olsen, L. C., Tröβe, C., Ravneberg, H. and I. F. Pryme. Improving Mammalian Cell Factories: The Selection Of Signal Peptide Has a Major Impact On Recombinant Protein Synthesis And Secretion In Mammalian Cells. *Trends In Cell And Molecular Biology*, No 2, pp 1-17, 2007.

Wen, B., Deng, Y., Guan, J., Yan, W., Wang, Y., Tan, W. and J. Gao. Signal Peptide Replacements Enhance Expression And Secretion Of Hepatatis C Virus Envelope Glycoproteins. *Acta Biochimica Et Biophysica Sinica*, Vol. 43, No 2, pp 96-102, 2011.

Swaroop, A., Hogan, B. L. M. and U. Franke. Molecular Analysis Of The cDNA For Human SPARC/Osteonectin/ BM-40: Sequence, Expression, And Localisation Of The Gene To Chromosome 5q31-q33. *Genomics*, No 2, pp 37-47, 1988.

Jean, F., Stella, K., Thomas, L., Liu, G., Xiang, Y., Reason, A. J. and G. Thomas. α1-Antitrypsin Portland, A Bioengineered Serpin Highly Selective For Furin: Application As An Antipathogenic Agent. *Proceedings Of The National Academy Of Sciences* USA, Vol. 95, pp 7293-7298, 1998.

Bornkamm, G. W., Berens, C., Kuklik-Roos, C., Bechet, J-M., Laux, G., Bachl, J., Korndoerfer, M., Schlee, M., Hölzel, M., Malamoussi, A., Chapman, R. D., Nimmerjahn, F., Mautner, J., Hillen, W., Bujard, H. and J. Feuillard. Stringent Doxycycline-Dependent Control Of Gene Activities Using An Episomal One-Vector System. *Nucleic Acid Research*, Vol. 33, No 16, e137, pp 1-11, 2005.

Kohfeldt, E., Maurer, P., Vannahme, C. and R. Timpl. Properties Of The Extracellular Calcium Binding Module Of The Proteoglycan Testican. *FEBS Letters*, Vol. 414, No 3, pp 557-561, 1997.

Heuts, D. P. H. M., Gummadova, J. O., Pang, J., Rigby, S. E. J. and N. S. Scrutton. Reaction Of Vascular Adhesion Protein-1 (VAP-1) With Primary Amines: Mechanistic Insights From Isotope Effects And Quantitative Structure-Activity Relationships. *The Journal Of Biological Chemistry*, Vol. 286, No 34, pp 29584-29593, 2011.

Kanigicherla, D., Gummadova, J., McKenzie, E. A., Roberts, S. A., Harris, S., Nikam, M., Poulton, K., McWilliam, L., Short, C. D., Venning, M. and P. E. Brenchley. Anti-PLA2R1 Antibodies Measured By ELISA Predict Long-Term Outcome In A Prevalent Population Of Patients With Idiopathic Membranous Nephropathy. *Kidney International*, No 5, pp 940-948, 2013.

Hunter, D. J. and E. G. Gurney. The Genomic Instability Associated With Integrated Simian Virus 40 DNA Is Dependent On The Origin Of Replication And Early Control Region. *Journal Of Virology*, Vol. 68, No 2, pp 787-796, 1994.

Qin, J. Y., Zhang, L., Clift, K. L., Hulur, I., Xiang, A. P., Ren, B-Z. and B. T. Lahn. Systematic Comparison Of Constitutive Promoters And The Doxycycline-Inducible Promoter. *PLoS ONE*, Vol. 5, No 5, e10611, 2010.

Uetsuki, T., Naito, A., Nagata, S. and Y. Kaziro. Isolation And Characterization Of The Human Chromosomal Gene For Polypeptide Chain Elongation Factor-1α. *The Journal Of Biological Chemistry*, Vol. 264, No 10, pp 5791-5798, 1989.

Öhman, J., Jakobsson, E., Kallström, U., Elmblad, A., Ansari, A., Kalderen, C., Robertson, E., Danielsson, E., Gustavsson, A-L., Varadi, A., Ekblom, J., Holmgren, E., Doverskog, M., Abrahmsen, L. and J. Nilsson. Production Of a Truncated Soluble Human Semicarbazide-Sensitive Amine Oxidase Mediated By a GST-Fusion Protein Secreted From HEK293 Cells. *Protein Expression And Purification*, No 46, pp 321-331, 2006.

Petersen, N., Brunak, S., von Heijine, G. and H. Nielsen. SignalP 4.0: Discriminating Signal Peptides From Transmembrane Regions. *Nature Methods*, No 8, pp 785-786, 2011.

Myers, M. and L. M. Mulligan. The RET Receptor Is Linked To Stress Response Pathways. *Cancer Research*, No 64, pp 4453-4463, 2004.

Marchant, D. J., Bellac, C. L., Moraes, T. J., Wadsworth, S. J., Dufour, A., Butler, G. S., Bilawchuk, L. M., Hendry, R. G., Robertson, A. G., Cheung, C. T., Ng, J., Ang, L., Luo, Z., Heilbron, K., Norris, M. J., Duan, W., Bucyk, T., Karpov, A., Devel, L., Georgiadis, D., Hegele, R. G., Luo, H., Granville, D. J., Dive, V., McManus, B. M and Christopher M. Overall. a New Transcriptional Role For Matrix Metalloproteinase-12 In Antiviral Immunity. *Nature Medicine, Vol.* 20, No 5, pp 493-502, 2014.

G. A. Luke. Translating 2A Research Into Practice. *Innovations in Biotechnology,* 2012. InTech, Available from: www.intechopen.com Kim, J. H., Lee, S-R., Li, L-H., Park, H-J., Park, J-H., Lee, K. Y., Kim, M.-K., Shin, B. A. and S-Y. Choi. High Cleavage Efficiency Of A 2A Peptide Derived From Porcine Teschovirus-1 In Human Cell Lines, Zebrafish And Mice. *Plos ONE,* Vol. 6, No 4, e18556, pp 1-8, 2011.

The invention claimed is:

1. A nucleic acid expression vector for expressing a peptide of interest in a mammalian cell, the vector comprising a vector backbone;

the vector backbone comprising:
- a first promoter for bacterial cells and a first selectable marker downstream of the first promoter;
- a second promoter for eukaryotic cells and a second selectable marker downstream of the second promoter, wherein the second promoter is different from the first promoter and the second selectable marker is different from the first selectable marker;
- nucleic acid encoding signal peptide from *Gaussia* luciferase;
- a multiple cloning site, for inserting a nucleic acid encoding the peptide of interest in-frame with the signal peptide;
- a third promoter for expressing the nucleic acid encoding the peptide of interest; and
- a 3' UTR sequence comprising a polyadenylation sequence;

wherein the vector backbone consists of 4600 or fewer nucleic acid base pairs.

2. The nucleic acid expression vector according to claim 1, wherein the second promoter is weaker than an EF1A promoter.

3. The nucleic acid expression vector according to claim 1 wherein the nucleic acid encoding signal peptide from *Gaussia* luciferase (GLUC) encodes a peptide having at least 90% sequence identity to SEQ ID NO: 1.

4. The nucleic acid expression vector according to claim 1 further comprising the nucleic acid encoding the peptide of interest.

5. The nucleic acid expression vector according to claim 4 wherein the peptide of interest is a mammalian protein.

6. The nucleic acid expression vector according to claim 1 wherein the third promoter is a promoter for constitutive expression.

7. The nucleic acid expression vector according to claim 6 wherein the third promoter is a CMV promoter.

8. The nucleic acid expression vector according to claim 1 wherein the third promoter is a promoter for inducible expression.

9. The nucleic acid expression vector according to claim 8 wherein the third promoter is a doxycycline inducible promoter.

10. A host cell comprising the nucleic acid expression vector of claim 1.

11. The host cell according to claim 10, wherein the host cell is a mammalian cell.

12. The host cell according to claim 11, wherein the mammalian cell is selected from a HEK293 cell, a CHO cell, a COS cell, a HeLa cell, a Vero cell, a NSO cell, a Jurkat cell, a BHK cell, an MCF cell, or an L cell mouse fibroblast.

13. A kit for gene expression comprising a vector according to claim 1, a mammalian cell, and a reagent.

14. A method for expressing a gene of interest, the method comprising:
  inserting nucleic acid encoding the gene of interest into a nucleic acid expression vector according to claim 1;
  transfecting the nucleic acid expression vector comprising the gene of interest into a mammalian cell; and
  culturing the transfected cell.

15. The method according to claim 14 further comprising the step of purifying the protein encoded by the gene of interest.

16. A nucleic acid expression vector for expressing a peptide of interest in a mammalian cell, the vector comprising a vector backbone; the vector backbone comprising:
  a first promoter for bacterial cells and a first selectable marker downstream of the first promoter;
  a second promoter for eukaryotic cells and a second selectable marker downstream of the second promoter, wherein the second promoter is different from the first promoter and the second selectable marker is different from the first selectable marker;
  nucleic acid encoding signal peptide from *Gaussia* luciferase;
  a multiple cloning site, for inserting a nucleic acid encoding the peptide of interest in-frame with the signal peptide;
  a third promoter for expressing the nucleic acid encoding the peptide of interest;
  a translational enhancer; and
  a 3' UTR sequence comprising a polyadenylation sequence;
wherein the vector backbone consists of 4800 or fewer nucleic acid base pairs.

17. The nucleic acid expression vector according to claim 16 wherein the translational enhancer is SP163.

18. A nucleic acid expression vector for expressing a peptide of interest in a mammalian cell, the vector comprising a vector backbone; the vector backbone comprising:
  a first promoter for bacterial cells and a first selectable marker downstream of the first promoter;
  a second promoter for eukaryotic cells and a second selectable marker downstream of the second promoter, wherein the second promoter is different from the first promoter and the second selectable marker is different from the first selectable marker;
  nucleic acid encoding signal peptide from *Gaussia* luciferase;
  a multiple cloning site, for inserting a nucleic acid encoding the peptide of interest in-frame with the signal peptide;
  a third promoter for expressing the nucleic acid encoding the peptide of interest;
  nucleic acid encoding a SUMO-tag; and
  a 3' UTR sequence comprising a polyadenylation sequence;
wherein the vector backbone consists of 4900 or fewer nucleic acid base pairs.

19. A nucleic acid expression vector comprising a vector backbone, the vector backbone comprising:
  a first promoter for bacterial cells and a first selectable marker downstream of the first promoter;
  a second promoter for eukaryotic cells and a second selectable marker downstream of the second promoter, wherein the second promoter is different from the first promoter and the second selectable marker is different from the first selectable marker;
  a CMV promoter for expressing nucleic acid encoding a peptide of interest;
  nucleic acid encoding *Gaussia* luciferase signal peptide downstream of the CMV promoter;
  a multiple cloning site downstream of the nucleic acid encoding *Gaussia* luciferase signal peptide, for inserting the nucleic acid encoding the peptide of interest in-frame with the *Gaussia* luciferase signal peptide; and
  a polyadenylation sequence downstream of both the multiple cloning site and the second selectable marker;
  wherein the second promoter is an SV40 promoter or a promoter that has weaker expression induction than an SV40 promoter; and
  wherein the vector backbone consists of fewer than 4600 nucleic acid base pairs.

20. A method of making a nucleic acid expression vector, the method comprising introducing a nucleic acid that encodes *Gaussia* signal peptide into a plasmid that comprises:
  a first promoter for bacterial cells and a first selectable marker downstream of the first promoter;
  a second promoter for eukaryotic cells and a second selectable marker downstream of the second promoter, wherein the second promoter is different from the first promoter and the second selectable marker is different from the first selectable marker;
  a multiple cloning site, for inserting nucleic acid encoding a peptide of interest in-frame with the signal peptide;
  a third promoter for expressing the nucleic acid encoding the peptide of interest; and
  a 3' UTR sequence comprising a polyadenylation sequence;

wherein the resulting nucleic acid expression vector comprises a vector backbone consisting of 4600 or fewer nucleic acid base pairs.

21. A nucleic acid expression vector having 100% sequence identity to SEQ ID NO: 40.

* * * * *

SEQUENCE LISTING

```
<160> NUMBER OF SEQ ID NOS: 48

<210> SEQ ID NO 1
<211> LENGTH: 17
<212> TYPE: PRT
<213> ORGANISM: Artificial Sequence
<220> FEATURE:
<223> OTHER INFORMATION: Gaussia luciferase signal peptide

<400> SEQUENCE: 1

Met Gly Val Lys Val Leu Phe Ala Leu Ile Cys Ile Ala Val Ala Glu
1               5                   10                  15

Ala

<210> SEQ ID NO 2
<211> LENGTH: 24
<212> TYPE: PRT
<213> ORGANISM: Artificial Sequence
<220> FEATURE:
<223> OTHER INFORMATION: PDX-Furin inhibitor signal peptide

<400> SEQUENCE: 2

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 3
<211> LENGTH: 17
<212> TYPE: PRT
<213> ORGANISM: Artificial Sequence
<220> FEATURE:
<223> OTHER INFORMATION: BM40 signal peptide

<400> SEQUENCE: 3

Met Arg Ala Trp Ile Phe Phe Leu Leu Cys Leu Ala Gly Arg Ala Leu
1               5                   10                  15

Ala

<210> SEQ ID NO 4
<211> LENGTH: 298
<212> TYPE: DNA
<213> ORGANISM: Artificial Sequence
<220> FEATURE:
<223> OTHER INFORMATION: DNA fragment 1

<400> SEQUENCE: 4
gctgggtacc gaaattaata cgactcacta tagggagacc caagctggct tgcgtttaaa      60
cttaagctta gcgcagaggc ttggggcagc cgagcggcag ccaggccccg gcccgggcct    120
cggttccaga agggagagga gcccgccaag gcgcgcaaga gagcgggctg cctcgcagtc    180
cgagccggag agggagcgcg agccgcgccg gccccggacg gcctccgaaa ccatgagggc    240
ctggatcttc tttctccttt gcctggccgg gagggctctg gcagccccgc tagccgag    298
```

<210> SEQ ID NO 5
<211> LENGTH: 301
<212> TYPE: DNA
<213> ORGANISM: Artificial Sequence
<220> FEATURE:
<223> OTHER INFORMATION: DNA fragment 2

<400> SEQUENCE: 5

```
gctgggtacc gaaattaata cgactcacta tagggagacc caagctggct tgcgtttaaa      60
cttaagctta gcgcagaggc ttggggcagc cgagcggcag ccaggccccg gcccgggcct     120
cggttccaga agggagagga gcccgccaag gcgcgcaaga gagcgggctg cctcgcagtc     180
cgagccggag agggagcgcg agccgcgccg gccccggacg gcctccgaaa ccatgggagt     240
caaagttctg tttgccctga tctgcatcgc tgtggccgag ccaagcccca cgctagccga     300
g                                                                    301
```

<210> SEQ ID NO 6
<211> LENGTH: 116
<212> TYPE: DNA
<213> ORGANISM: Artificial Sequence
<220> FEATURE:
<223> OTHER INFORMATION: DNA fragment 3

<400> SEQUENCE: 6

```
gctgggtacc gaaattaata cgactcacta tagggggaacc agccaccatg ggagtcaaag     60
ttctgtttgc cctgatctgc atcgctgtgg ccgaggccaa gcccacgcta gccgag         116
```

<210> SEQ ID NO 7
<211> LENGTH: 428
<212> TYPE: DNA
<213> ORGANISM: Artificial Sequence
<220> FEATURE:
<223> OTHER INFORMATION: F1ori sequence

<400> SEQUENCE: 7

```
gcgccctgta gcggcgcatt aagcgcggcg ggtgtggtgg ttacgcgcag cgtgaccgct      60
acacttgcca gcgccctagc gcccgctcct ttcgctttct tcccttcctt tctcgccacg     120
ttcgccggct ttccccgtca gctctaaat cgggggctcc ctttagggtt ccgatttagt      180
gctttacggc acctcgaccc caaaaaactt gattagggtg atggttcacg tagtgggcca     240
tcgccctgat agacggtttt tcgccctttg acgttggagt ccacgttctt taatagtgga     300
ctcttgttcc aaactggaac aacactcaac cctatctcgg tctattcttt tgatttataa     360
gggattttgc cgatttcggc ctattggtta aaaaatgagc tgatttaaca aaaatttaac     420
gcgaatta                                                              428
```

<210> SEQ ID NO 8
<211> LENGTH: 74
<212> TYPE: DNA
<213> ORGANISM: Artificial Sequence
<220> FEATURE:
<223> OTHER INFORMATION: EM7 sequence

<400> SEQUENCE: 8

```
cagcacgtgt tgacaattaa tcatcggcat agtatatcgg catagtataa tacgacaagg      60
tgaggaacta aatc                                                       74
```

<210> SEQ ID NO 9
<211> LENGTH: 1290

<212> TYPE: DNA
<213> ORGANISM: Artificial Sequence
<220> FEATURE:
<223> OTHER INFORMATION: EF1a Genomic

<400> SEQUENCE: 9

```
aacccagaga tcgctgcgtt cccgcccct cacccgcccg ctctcgtcat cactgaggtg      60
gagaagagca tgcgtgaggc tccggtgccc gtcagtgggc agagcgcaca tcgcccacag    120
tccccgagaa gttgggggga ggggtcggca attgaaccgg tgcctagaga aggtggcgcg    180
gggtaaactg ggaaagtgat gtcgtgtact ggctccgcct ttttcccgag ggtgggggag    240
aaccgtatat aagtgcagta gtcgccgtga acgttctttt tcgcaacggg tttgccgcca    300
gaacacaggt aagtgccgtg tgtggttccc gcgggcctgg cctctttacg ggttatggcc    360
cttgcgtgcc ttgaattact tccacgcccc tggctgcagt acgtgattct tgatcccgag    420
cttcggggttg gaagtgggtg ggagagttcg aggccttgcg cttaaggagc cccttcgcct    480
cgtgcttgag ttgaggcctg gcctgggcgc tgggccgcc gcgtgcgaat ctggtggcac    540
cttcgcgcct gtctcgctgc tttcgataag tctctagcca tttaaaattt tgatgacct    600
gctgcgacgc tttttttctg gcaagatagt cttgtaaatg cgggccaaga tctgcacact    660
ggtatttcgg ttttggggc cgcgggcggc gacggggccc gtgcgtccca gcgcacatgt    720
tcggcgaggc ggggcctgcg agcgcggcca ccgagaatcg gacggggta gtctcaagct    780
ggccggcctg ctctggtgcc tggcctcgcg ccgccgtgta tcgccccgcc ctgggcggca    840
aggctggccc ggtcggcacc agttgcgtga gcggaaagat ggccgcttcc cggccctgct    900
gcagggagct caaaatggag gacgcggcgc tcgggagagc gggcgggtga gtcacccaca    960
caaaggaaaa gggccttttcc gtcctcagcc gtcgcttcat gtgactccac ggagtaccgg   1020
gcgccgtcca ggcacctcga ttagttctcg agcttttgga gtacgtcgtc tttaggttgg   1080
ggggaggggt tttatgcgat ggagtttccc cacactgagt gggtggagac tgaagttagg   1140
ccagcttggc acttgatgta attctccttg gaatttgccc tttttgagtt tggatcttgg   1200
ttcattctca agcctcagac agtggttcaa agtttttttc ttccatttca ggtgtcgtga   1260
aaactacccc taaaagccaa aatgggaaag                                    1290
```

<210> SEQ ID NO 10
<211> LENGTH: 342
<212> TYPE: DNA
<213> ORGANISM: Artificial Sequence
<220> FEATURE:
<223> OTHER INFORMATION: EF1A pPEF

<400> SEQUENCE: 10

```
aacccagaga tcgctgcgtt cccgcccct cacccgcccg ctctcgtcat cactgaggtg      60
gagaagagca tgcgtgaggc tccggtgccc gtcagtgggc agagcgcaca tcgcccacag    120
tccccgagaa gttgggggga ggggtcggca attgaaccgg tgcctagaga aggtggcgcg    180
gggtaaactg ggaaagtgat gtcgtgtact ggctccgcct ttttcccgag ggtgggggag    240
aaccgtatat aagtgcagta gtcgccgtga acgttctttt tcgcaacggg tttgccgcca    300
gaacacaggt gtcgtgaaaa ctaccccta aagccaaaat gg                        342
```

<210> SEQ ID NO 11
<211> LENGTH: 1217
<212> TYPE: DNA
<213> ORGANISM: Artificial Sequence
<220> FEATURE:

<223> OTHER INFORMATION: EF1A commercial

<400> SEQUENCE: 11

| | |
|---|---:|
| agatctcgtg aggctccggt gcccgtcagt gggcagagcg cacatcgccc acagtccccg | 60 |
| agaagttggg gggaggggtc ggcaattgaa ccggtgccta gagaaggtgg cgcggggtaa | 120 |
| actgggaaag tgatgtcgtg tactggctcc gcctttttcc cgagggtggg ggagaaccgt | 180 |
| atataagtgc actagtcgcc gtgaacgttc ttttcgcaa cgggtttgcc gccagaacac | 240 |
| aggtaagtgc cgtgtgtggt tcccgcgggc ctggcctctt tacgggttat ggcccttgcg | 300 |
| tgccttgaat tacttccacc tggctgcagt acgtgattct tgatcccgag cttcgggttg | 360 |
| gaagtgggtg ggagagttcg tggccttgcg cttaaggagc cccttcgcct cgtgcttgag | 420 |
| ttgtggcctg gctgggcgc tggggccgcc gcgtgcgaat ctggtggcac cttcgcgcct | 480 |
| gtctcgctgc tttcgataag tctctagcca tttaaaattt tgatgacct gctgcgacgc | 540 |
| ttttttctg gcaagatagt cttgtaaatg cgggccaaga tcagcacact ggtatttcgg | 600 |
| tttttgggc cgcgggcggc gacggggccc gtgcgtccca gcgcacatgt tcggcgaggc | 660 |
| ggggcctgcg agcgcggcca ccgagaatcg gacgggggta gtctcaagct gcccggcctg | 720 |
| ctctggtgcc tggcctcgcg ccgccgtgta tcgccccgcc ctgggcggca aggctggccc | 780 |
| ggtcggcacc agttgcgtga gcggaaagat ggccgcttcc cggccctgct gcagggagca | 840 |
| caaaatggag gacgcggcgc tcgggagagc gggcgggtga gtcacccaca caaaggaaaa | 900 |
| gggcctttcc gtcctcagcc gtcgcttcat gtgactccac ggagtaccgg gcgccgtcca | 960 |
| ggcacctcga ttagttctcc agcttttgga gtacgtcgtc tttaggttgg ggggagggggt | 1020 |
| tttatgcgat ggagtttccc cacactgagt gggtggagac tgaagttagg ccagcttggc | 1080 |
| acttgatgta attctccttg gaatttgccc ttttgagtt tggatcttgg ttcattctca | 1140 |
| agcctcagac agtggttcaa agttttttc ttccatttca ggtgtcgtga aaactacccc | 1200 |
| taaaagccaa aagatct | 1217 |

<210> SEQ ID NO 12
<211> LENGTH: 1206
<212> TYPE: DNA
<213> ORGANISM: Artificial Sequence
<220> FEATURE:
<223> OTHER INFORMATION: Fragment I with minimal EF1A

<400> SEQUENCE: 12

| | |
|---|---:|
| gctagccgag gttaactgtt gtcctggctg ttgcggttcc ggacaccatc atcaccacca | 60 |
| tcaccatcac cattgaggat ccagtgtggt ggaattctgc agatatccag cacagtggcg | 120 |
| gccgctcgag tctagagggc ccgtttaaac ccgctgatca gcctcgactg tgccttctag | 180 |
| ttgccagcca tctgttgttt gcccctcccc cgtgccttcc ttgaccctgg aaggtgccac | 240 |
| tcccactgtc ctttcctaat aaaatgagga aattgcatcg cattgtctga gtaggtgtca | 300 |
| ttctattctg gggggtgggg tggggcagga cagcaagggg gaggattggg aagacaatag | 360 |
| caggcatgct ggggatgcgg tgggctctat ggcttctgag gcggaaagaa ccagctgggg | 420 |
| ctctaggggg tatccccacg cgccctgtag cggcgcatta agcgcggcgg gtgtggtggt | 480 |
| tacgcaaccc agagatcgct cgcttccgc cccctcaccc gcccgctctc gtcatcactg | 540 |
| aggtggagaa gagcatgcgt gaggctccgg tgcccgtcag tgggcagagc gcacatcgcc | 600 |
| cacagtcccc gagaagttgg ggggaggggt cggcaattga accggtgcct agagaaggtg | 660 |
| gcgcggggta aactgggaaa gtgatgtcgt gtactggctc cgcctttttc ccgagggtgg | 720 |

```
gggagaaccg tatataagtg cagtagtcgc cgtgaacgtt ctttttcgca acgggtttgc    780
cgccagaaca caggtgtcgt gaaaactacc cctaaaagct tcaaaatggc caagttgacc    840
agtgccgttc cggtgctcac cgcgcgcgac gtcgccggag cggtcgagtt ctggaccgac    900
cggctcgggt tctcccggga cttcgtggag acgacttcg ccggtgtggt ccgggacgac    960
gtgaccctgt tcatcagcgc ggtccaggac caggtggtgc cggacaacac cctggcctgg    1020
gtgtgggtgc gcggcctgga cgagctgtac gccgagtggt cggaggtcgt gtccacgaac    1080
ttccgggacg cctccgggcc ggccatgacc gagatcggcg agcagccgtg ggggcgggag    1140
ttcgccctgc gcgaccccgg ccggcaactgc gtgcacttcg tggccgagga gcaggactga    1200
cacgtg                                                               1206
```

<210> SEQ ID NO 13
<211> LENGTH: 1214
<212> TYPE: DNA
<213> ORGANISM: Artificial Sequence
<220> FEATURE:
<223> OTHER INFORMATION: Fragment II with SV40 promoter

<400> SEQUENCE: 13

```
gctagccgag gttaactgtt gtcctggctg ttgcggttcc ggacaccatc atcaccacca     60
tcaccatcac cattgaggat ccagtgtggt ggaattctgc agatatccag cacagtggcg    120
gccgctcgag tctagagggc ccgtttaaac ccgctgatca gcctcgactg tgccttctag    180
ttgccagcca tctgttgttt gcccctcccc cgtgccttcc ttgacccctgg aaggtgccac    240 tcccactgtc ctttcctaat aaaatgagga aattgcatcg cattgtctga gtaggtgtca    300
ttctattctg gggggtgggg tggggcagga cagcaagggg gaggattggg aagacaatag    360
caggcatgct ggggatgcgg tgggctctat ggcttctgag gcggaaagaa ccagctgggg    420
ctctaggggg tatccccacg cgccctgtag cggcgcatta agcgcggcgg gtgtggtggt    480
tacgcctgtg aatgtgtgt cagttagggt gtggaaagtc cccaggctcc ccagcaggca    540
gaagtatgca aagcatgcat ctcaattagt cagcaaccag gtgtggaaag tccccaggct    600
ccccagcagg cagaagtatg caaagcatgc atctcaatta gtcagcaacc atagtcccgc    660
ccctaactcc gcccatcccg ccctaactc cgcccagttc cgcccattct ccgccccatg    720
gctgactaat ttttttatt tatgcagagg ccgaggccgc ctctgcctct gagctattcc    780
agaagtagtg aggaggcttt tttggaggcc taggcttttg caaaaagctt aaaatggcca    840
agttgaccag tgccgttccg gtgctcaccg cgcgcgacgt cgccgagcg gtcgagttct    900 ggaccgaccg gctcgggttc tcccgggact tcgtggagga cgacttcgcc ggtgtggtcc    960
gggacgacgt gaccctgttc atcagcgcgg tccaggacca ggtggtgccg gacaacaccc    1020
tggcctgggt gtgggtgcgc ggcctggacg agctgtacgc cgagtggtcg gaggtcgtgt    1080
ccacgaactt ccgggacgcc tccggccgg ccatgaccga gatcggcgag cagccgtggg    1140
ggcgggagtt cgccctgcgc gaccgccg gcaactgcgt gcacttcgtg gccgaggagc    1200
aggactgaca cgtg                                                      1214
```

<210> SEQ ID NO 14
<211> LENGTH: 315
<212> TYPE: PRT
<213> ORGANISM: Artificial Sequence
<220> FEATURE:
<223> OTHER INFORMATION: N-terminal SUUMOstar secretory tag

<400> SEQUENCE: 14

```
His His His His His His His His Gly Ser Leu Gln Asp Ser
1               5                   10                  15

Glu Val Asn Gln Glu Ala Lys Pro Glu Val Lys Pro Glu Val Lys Pro
            20                  25                  30

Glu Thr His Ile Asn Leu Lys Val Ser Asp Gly Ser Ser Glu Ile Phe
        35                  40                  45

Phe Lys Ile Lys Lys Thr Thr Pro Leu Arg Arg Leu Met Glu Ala Phe
50                  55                  60

Ala Lys Arg Gln Gly Lys Glu Met Asp Ser Leu Thr Phe Leu Tyr Asp
65                  70                  75                  80

Gly Ile Glu Ile Gln Ala Asp Gln Thr Pro Glu Asp Leu Asp Met Glu
                85                  90                  95

Asp Asn Asp Ile Ile Glu Ala His Arg Glu Gln Ile Gly Gly Gln His
            100                 105                 110

Tyr Leu His Ile Arg Pro Ala Pro Ser Asp Asn Leu Pro Leu Val Asp
        115                 120                 125

Leu Ile Glu His Pro Asp Pro Ile Phe Asp Pro Lys Glu Lys Asp Leu
130                 135                 140

Asn Glu Thr Leu Leu Arg Ser Leu Leu Gly Gly His Tyr Asp Pro Gly
145                 150                 155                 160

Phe Met Ala Thr Ser Pro Pro Glu Asp Arg Pro Gly Gly Gly Gly
                165                 170                 175

Pro Ala Gly Gly Ala Glu Asp Leu Ala Glu Leu Asp Gln Leu Leu Arg
            180                 185                 190

Gln Arg Pro Ser Gly Ala Met Pro Ser Glu Ile Lys Gly Leu Glu Phe
        195                 200                 205

Ser Glu Gly Leu Ala Gln Gly Lys Lys Gln Arg Leu Ser Lys Lys Leu
210                 215                 220

Arg Arg Lys Leu Gln Met Trp Leu Trp Ser Gln Thr Phe Cys Pro Val
225                 230                 235                 240

Leu Tyr Ala Trp Asn Asp Leu Gly Ser Arg Phe Trp Pro Arg Tyr Val
                245                 250                 255

Lys Val Gly Ser Cys Phe Ser Lys Arg Ser Cys Ser Val Pro Glu Gly
            260                 265                 270

Met Val Cys Lys Pro Ser Lys Ser Val His Leu Thr Val Leu Arg Trp
        275                 280                 285

Arg Cys Gln Arg Arg Gly Gly Gln Arg Cys Trp Ile Pro Ile Gln
290                 295                 300

Tyr Pro Ile Ile Ser Glu Cys Lys Cys Ser Cys
305                 310                 315
```

<210> SEQ ID NO 15
<211> LENGTH: 352
<212> TYPE: PRT
<213> ORGANISM: Artificial Sequence
<220> FEATURE:
<223> OTHER INFORMATION: Ricin-C3 P2A of PLA2R1

<400> SEQUENCE: 15

```
Leu Ala Glu Gly Val Ala Ala Leu Thr Pro Glu Arg Leu Leu Glu
1               5                   10                  15

Trp Gln Asp Lys Gly Ile Phe Val Ile Gln Ser Glu Ser Leu Lys Lys
            20                  25                  30

Cys Ile Gln Ala Gly Lys Ser Val Leu Thr Leu Glu Asn Cys Lys Gln
```

```
            35                  40                  45
Ala Asn Lys His Met Leu Trp Lys Trp Val Ser Asn His Gly Leu Phe
 50                  55                  60

Asn Ile Gly Gly Ser Gly Cys Leu Gly Leu Asn Phe Ser Ala Pro Glu
 65                  70                  75                  80

Gln Pro Leu Ser Leu Tyr Glu Cys Asp Ser Thr Leu Val Ser Leu Arg
                 85                  90                  95

Trp Arg Cys Asn Arg Lys Met Ile Thr Gly Pro Leu Gln Tyr Ser Val
                100                 105                 110

Gln Val Ala His Asp Asn Thr Val Val Ala Ser Arg Lys Tyr Ile His
            115                 120                 125

Lys Trp Ile Ser Tyr Gly Ser Gly Gly Asp Ile Cys Glu Tyr Leu
130                 135                 140

His Lys Asp Leu His Thr Ile Lys Gly Asn Thr Gly Ser Gly His His
145                 150                 155                 160

His His His His His His His Arg Arg Lys Arg Gly Ser Gly Ala
                165                 170                 175

Thr Asn Phe Ser Leu Leu Lys Gln Ala Gly Asp Val Glu Glu Asn Pro
            180                 185                 190

Gly Pro Gln Glu Gly Trp Glu Arg His Gly Gly Phe Cys Tyr Lys Ile
        195                 200                 205

Asp Thr Val Leu Arg Ser Phe Asp Gln Ala Ser Ser Gly Tyr Tyr Cys
210                 215                 220

Pro Pro Ala Leu Val Thr Ile Thr Asn Arg Phe Glu Gln Ala Phe Ile
225                 230                 235                 240

Thr Ser Leu Ile Ser Ser Val Val Lys Met Lys Asp Ser Tyr Phe Trp
                245                 250                 255

Ile Ala Leu Gln Asp Gln Asn Asp Thr Gly Glu Tyr Thr Trp Lys Pro
            260                 265                 270

Val Gly Gln Lys Pro Glu Pro Val Gln Tyr Thr His Trp Asn Thr His
        275                 280                 285

Gln Pro Arg Tyr Ser Gly Gly Cys Val Ala Met Arg Gly Arg His Pro
290                 295                 300

Leu Gly Arg Trp Glu Val Lys His Cys Arg His Phe Lys Ala Met Ser
305                 310                 315                 320

Leu Cys Lys Gln Pro Val Glu Asn Gln Glu Lys Ala Glu Tyr Glu Glu
                325                 330                 335

Arg Trp Pro Gly Ser Gly His His His His His His His His
            340                 345                 350

<210> SEQ ID NO 16
<211> LENGTH: 346
<212> TYPE: DNA
<213> ORGANISM: Artificial Sequence
<220> FEATURE:
<223> OTHER INFORMATION: pPEF5.2

<400> SEQUENCE: 16
atataagcag agctcgttta gtgaaccgtc agatctctag aagctgggta ccgaaattaa      60
tacgactcac tatagggaa ccagccacca tgggagtcaa agttctgttt gccctgatct     120
gcatcgctgt ggccgaggcc aagcccacgc tagccgaggt tgctttgagg atccagtgtg     180
gtggaattct gcagatatcc agcacagtgg cggccgctcg agtctagagg gcccgtttaa     240
acccgctgat cagcctcgac tgtgccttct agttgccagc catctgttgt ttgcccctcc     300
```

```
cccgtgcctt ccttgaccct ggaaggtgcc actcccactg tcctttt            346
```

<210> SEQ ID NO 17
<211> LENGTH: 4561
<212> TYPE: DNA
<213> ORGANISM: Artificial Sequence
<220> FEATURE:
<223> OTHER INFORMATION: pPEF5.2

<400> SEQUENCE: 17

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtccgccc cctattgacg tcaatgacgg taaatggccc gcctggcatt    540
atgcccagta catgacctta cgggactttc ctacttggca gtacatctac gtattagtca    600
tcgctattac catggtgatg cggttttggc agtacaccaa tgggcgtgga tagcggtttg    660
actcacgggg atttccaagt ctccacccca ttgacgtcaa tgggagtttg ttttggcacc    720
aaaatcaacg ggactttcca aatgtcgta ataaccccgc cccgttgacg caaatgggcg    780
gtaggcgtgt acggtgggag gtctatataa gcagagctcg tttagtgaac cgtcagatct    840
ctagaagctg ggtaccgaaa ttaatacgac tcactatagg gaaccagcc accatgggag    900
tcaaagttct gtttgccctg atctgcatcg ctgtggccga ggccaagccc acgctagccg    960
aggttgcttt gaggatccag tgtggtggaa ttctgcagat atccagcaca gtggcggccg   1020
ctcgagtcta gagggcccgt ttaaacccgc tgatcagcct cgactgtgcc ttctagttgc   1080
cagccatctg ttgtttgccc ctcccccgtg ccttccttga ccctggaagg tgccactccc   1140
actgtccttt cctaataaaa tgaggaaatt gcatcgcatt gtctgagtag gtgtcattct   1200
attctggggg gtggggtggg gcaggacagc aaggggagg attgggaaga caatagcagg   1260
catgctgggg atgcggtggg ctctatggct tctgaggcgg aaagaaccag ctggggctct   1320
agggggtatc cccacgcgcc ctgtagcggc gcattaagcg cggcgggtgt ggtggttacg   1380
cctgtggaat gtgtgtcagt tagggtgtgg aaagtcccca ggctcccag caggcagaag   1440
tatgcaaagc atgcatctca attagtcagc aaccaggtgt ggaaagtccc caggctcccc   1500
agcaggcaga agtatgcaaa gcatgcatct caattagtca gcaaccatag tcccgcccct   1560
aactccgccc atcccgcccc taactccgcc cagttccgcc cattctccgc cccatggctg   1620
actaatttt tttatttatg cagaggccga ggccgcctct gcctctgagc tattccagaa   1680
gtagtgagga ggctttttg gaggcctagg cttttgcaaa aagcttaaaa tggccaagtt   1740
gaccagtgcc gttccggtgc tcaccgcgcg cgacgtcgcc ggagcggtcg agttctggac   1800
cgaccggctc gggttctccc gggacttcgt ggaggacgac ttcgccggtg tggtccggga   1860
cgacgtgacc ctgttcatca gcgcggtcca ggaccaggtg gtgccggaca acaccctggc   1920
ctgggtgtgg gtgcgcggcc tggacgagct gtacgccgag tggtcggagg tcgtgtccac   1980
gaacttccgg gacgcctccg gccggccat gaccgagatc ggcgagcagc cgtggggggcg   2040
```

```
ggagttcgcc ctgcgcgacc cggccggcaa ctgcgtgcac ttcgtggccg aggagcagga    2100
ctgacacgtg ctacgagatt tcgattccac cgccgccttc tatgaaaggt tgggcttcgg    2160
aatcgttttc cgggacgccg gctggatgat cctccagcgc ggggatctca tgctggagtt    2220
cttcgcccac cccaacttgt ttattgcagc ttataatggt tacaaataaa gcaatagcat    2280
cacaaatttc acaaataaag catttttttc actgcattct agttgtggtt tgtccaaact    2340
catcaatgta tcttatcatg tctgtatacc gtcgacctct agctagagct tggcgtaatc    2400
atggtcatag ctgtttcctg tgtgaaattg ttatccgctc acaattccac acaacatacg    2460
agccggaagc ataaagtgta aagcctgggg tgcctaatga gtgagctaac tcacattaat    2520
tgcgttgcgc tcactgcccg ctttccagtc gggaaacctg tcgtgccagc tgcattaatg    2580
aatcggccaa cgcgcgggga gaggcggttt gcgtattggg cgctcttccg cttcctcgct    2640
cactgactcg ctgcgctcgg tcgttcggct gcggcgagcg gtatcagctc actcaaaggc    2700
ggtaatacgg ttatccacag aatcagggga taacgcagga agaacatgt gagcaaaagg    2760 ccagcaaaag gccaggaacc gtaaaaaggc cgcgttgctg gcgttttttcc ataggctccg    2820 cccccctgac gagcatcaca aaaatcgacg ctcaagtcag aggtggcgaa acccgacagg    2880
actataaaga taccaggcgt ttccccctgg aagctccctc gtgcgctctc ctgttccgac    2940
cctgccgctt accggatacc tgtccgcctt tctcccttcg ggaagcgtgg cgctttctca    3000
atgctcacgc tgtaggtatc tcagttcggt gtaggtcgtt cgctccaagc tgggctgtgt    3060
gcacgaaccc cccgttcagc ccgaccgctg cgccttatcc ggtaactatc gtcttgagtc    3120
caacccggta agacacgact tatcgccact ggcagcagcc actggtaaca ggattagcag    3180
agcgaggtat gtaggcggtg ctacagagtt cttgaagtgg tggcctaact acggctacac    3240
tagaaggaca gtatttggta tctgcgctct gctgaagcca gttaccttcg gaaaaagagt    3300
tggtagctct tgatccggca aacaaaccac cgctggtagc ggtggttttt tgtttgcaa    3360 gcagcagatt acgcgcagaa aaaaaggatc tcaagaagat cctttgatct tttctacggg    3420
gtctgacgct cagtggaacg aaaactcacg ttaagggatt ttggtcatga gattatcaaa    3480
aaggatcttc acctagatcc ttttaaatta aaaatgaagt tttaaatcaa tctaaagtat    3540
atatgagtaa acttggtctg acagttacca atgcttaatc agtgaggcac ctatctcagc    3600
gatctgtcta tttcgttcat ccatagttgc ctgactcccc gtcgtgtaga taactacgat    3660
acgggagggc ttaccatctg gccccagtgc tgcaatgata ccgcgagacc cacgctcacc    3720
ggctccagat ttatcagcaa taaaccagcc agccggaagg gccgagcgca gaagtggtcc    3780
tgcaacttta tccgcctcca tccagtctat taattgttgc cgggaagcta gagtaagtag    3840
ttcgccagtt aatagtttgc gcaacgttgt tgccattgct acaggcatcg tggtgtcacg    3900
ctcgtcgttt ggtatggctt cattcagctc cggttcccaa cgatcaaggc gagttacatg    3960
atcccccatg ttgtgcaaaa aagcggttag ctccttcggt cctccgatcg ttgtcagaag    4020
taagttggcc gcagtgttat cactcatggt tatggcagca ctgcataatt ctcttactgt    4080
catgccatcc gtaagatgct tttctgtgac tggtgagtac tcaaccaagt cattctgaga    4140
atagtgtatg cggcgaccga gttgctcttg cccggcgtca atacgggata ataccgcgcc    4200
acatagcaga actttaaaag tgctcatcat tggaaaacgt tcttcggggc gaaaactctc    4260
aaggatctta ccgctgttga gatccagttc gatgtaaccc actcgtgcac ccaactgatc    4320
ttcagcatct tttactttca ccagcgtttc tgggtgagca aaaacaggaa ggcaaaatgc    4380
```

```
cgcaaaaaag ggaataaggg cgacacggaa atgttgaata ctcatactct tccttttca     4440 atattattga agcatttatc agggttattg tctcatgagc ggatacatat ttgaatgtat    4500
ttagaaaaat aaacaaatag gggttccgcg cacatttccc cgaaaagtgc cacctgacgt    4560
c                                                                    4561

<210> SEQ ID NO 18
<211> LENGTH: 4746
<212> TYPE: DNA
<213> ORGANISM: Artificial Sequence
<220> FEATURE:
<223> OTHER INFORMATION: pPEF5.2 max

<400> SEQUENCE: 18
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtccgccc cctattgacg tcaatgacgg taaatggccc gcctggcatt     540
atgcccagta catgacctta cgggactttc ctacttggca gtacatctac gtattagtca     600
tcgctattac catggtgatg cggttttggc agtacaccaa tgggcgtgga tagcggtttg     660
actcacgggg atttccaagt ctccacccca ttgacgtcaa tgggagtttg ttttggcacc     720
aaaatcaacg ggactttcca aaatgtcgta ataaccccgc cccgttgacg caaatgggcg     780
gtaggcgtgt acggtgggag gtctatataa gcagagctcg tttagtgaac cgtcagatct     840
ctagaagctg ggtaccgaaa ttaatacgac tcactatagg gagacccaag ctggcttgcg     900
tttaaactta agcttagcgc agaggcttgg ggcagccgag cggcagccag gccccggccc     960
gggcctcggt tccagaaggg agaggagccc gccaaggcgc gcaagagagc gggctgcctc    1020
gcagtccgag ccggagaggg agcgcgagcc gcgccggccc cggacggcct ccgaaaccat    1080
gggagtcaaa gttctgtttg ccctgatctg catcgctgtg gccgaggcca gcccacgct    1140 agccgaggtt gctttgagga tccagtgtgg tggaattctg cagatatcca gcacagtggc    1200
ggccgctcga gtctagaggg cccgtttaaa cccgctgatc agcctcgact gtgccttcta    1260
gttgccagcc atctgttgtt tgcccctccc ccgtgccttc cttgaccctg gaaggtgcca    1320
ctcccactgt cctttcctaa taaaatgagg aaattgcatc gcattgtctg agtaggtgtc    1380
attctattct ggggggtggg gtggggcagg acagcaaggg ggaggattgg gaagacaata    1440
gcaggcatgc tggggatgcg gtgggctcta tggcttctga gcggaaaga accagctggg    1500 gctctagggg gtatccccac gcgccctgta gcggcgcatt aagcgcggcg ggtgtggtgg    1560
ttacgcctgt ggaatgtgtg tcagttaggg tgtggaaagt ccccaggctc ccagcaggc    1620 agaagtatgc aaagcatgca tctcaattag tcagcaacca ggtgtggaaa gtccccaggc    1680
tccccagcag gcagaagtat gcaaagcatg catctcaatt agtcagcaac catagtcccg    1740
cccctaactc cgcccatccc gcccctaact ccgcccagtt ccgcccattc tccgccccat    1800
ggctgactaa ttttttttat ttatgcagag gccgaggccg cctctgcctc tgagctattc    1860
```

-continued

```
cagaagtagt gaggaggctt ttttggaggc ctaggctttt gcaaaaagct taaaatggcc      1920
aagttgacca gtgccgttcc ggtgctcacc gcgcgcgacg tcgccggagc ggtcgagttc      1980
tggaccgacc ggctcgggtt ctcccggcac ttcgtggagg acgacttcgc cggtgtggtc      2040
cgggacgacg tgaccctgtt catcagcgcg gtccaggacc aggtggtgcc ggacaacacc      2100
ctggcctggg tgtgggtgcg cggcctggac gagctgtacg ccgagtggtc ggaggtcgtg      2160
tccacgaact tccgggacgc ctccgggccg gccatgaccg agatcggcga gcagccgtgg      2220
gggcgggagt tcgccctgcg cgacccggcc ggcaactgcg tgcacttcgt ggccgaggag      2280
caggactgac acgtgctacg agatttcgat tccaccgccg ccttctatga aaggttgggc      2340
ttcggaatcg ttttccggga cgccggctgg atgatcctcc agcgcgggga tctcatgctg      2400
gagttcttcg cccacccccaa cttgtttatt gcagcttata atggttacaa ataaagcaat      2460
agcatcacaa atttcacaaa taaagcattt ttttcactgc attctagttg tggtttgtcc      2520
aaactcatca atgtatctta tcatgtctgt ataccgtcga cctctagcta gagcttggcg      2580
taatcatggt catagctgtt tcctgtgtga aattgttatc cgctcacaat tccacacaac      2640
atacgagccg gaagcataaa gtgtaaagcc tggggtgcct aatgagtgag ctaactcaca      2700
ttaattgcgt tgcgctcact gcccgctttc cagtcgggaa acctgtcgtg ccagctgcat      2760
taatgaatcg gccaacgcgc ggggagaggc ggtttgcgta ttgggcgctc ttccgcttcc      2820
tcgctcactg actcgctgcg ctcggtcgtt cggctgcggc gagcggtatc agctcactca      2880
aaggcggtaa tacggttatc cacagaatca ggggataacg caggaaagaa catgtgagca      2940
aaaggccagc aaaaggccag gaaccgtaaa aaggccgcgt tgctggcgtt tttccatagg      3000
ctccgccccc ctgacgagca tcacaaaaat cgacgctcaa gtcagaggtg gcgaaacccg      3060
acaggactat aaagatacca ggcgtttccc cctggaagct ccctcgtgcg ctctcctgtt      3120
ccgaccctgc cgcttaccgg atacctgtcc gcctttctcc cttcgggaag cgtggcgctt      3180
tctcaatgct cacgctgtag gtatctcagt tcggtgtagg tcgttcgctc caagctgggc      3240
tgtgtgcacg aaccccccgt tcagcccgac cgctgcgcct tatccggtaa ctatcgtctt      3300
gagtccaacc cggtaagaca cgacttatcg ccactggcag cagccactgg taacaggatt      3360
agcagagcga ggtatgtagg cggtgctaca gagttcttga agtggtggcc taactacggc      3420
tacactagaa ggacagtatt tggtatctgc gctctgctga gccagttac cttcggaaaa      3480 agagttggta gctcttgatc cggcaaacaa accaccgctg gtagcggtgg tttttttgtt      3540
tgcaagcagc agattacgcg cagaaaaaaa ggatctcaag aagatccttt gatcttttct      3600
acggggtctg acgctcagtg gaacgaaaac tcacgttaag ggattttggt catgagatta      3660
tcaaaaagga tcttcaccta gatcctttta aattaaaaat gaagttttaa atcaatctaa      3720
agtatatatg agtaaacttg gtctgacagt taccaatgct taatcagtga ggcacctatc      3780
tcagcgatct gtctatttcg ttcatccata gttgcctgac tccccgtcgt gtagataact      3840
acgatacggg agggcttacc atctggcccc agtgctgcaa tgataccgcg agacccacgc      3900
tcaccggctc cagatttatc agcaataaac cagccagccg gaagggccga gcgcagaagt      3960
ggtcctgcaa ctttatccgc ctccatccag tctattaatt gttgccggga agctagagta      4020
agtagttcgc cagttaatag tttgcgcaac gttgttgcca ttgctacagg catcgtggtg      4080
tcacgctcgt cgtttggtat ggcttcattc agctccggtt cccaacgatc aaggcgagtt      4140
acatgatccc ccatgttgtg caaaaaagcg gttagctcct tcggtcctcc gatcgttgtc      4200
```

| | |
|---|---:|
| agaagtaagt tggccgcagt gttatcactc atggttatgg cagcactgca taattctctt | 4260 |
| actgtcatgc catccgtaag atgcttttct gtgactggtg agtactcaac caagtcattc | 4320 |
| tgagaatagt gtatgcggcg accgagttgc tcttgcccgg cgtcaatacg ggataatacc | 4380 |
| gcgccacata gcagaacttt aaaagtgctc atcattggaa acgttcttc ggggcgaaaa | 4440 |
| ctctcaagga tcttaccgct gttgagatcc agttcgatgt aacccactcg tgcacccaac | 4500 |
| tgatcttcag catcttttac tttcaccagc gtttctgggt gagcaaaaac aggaaggcaa | 4560 |
| aatgccgcaa aaaagggaat aagggcgaca cggaaatgtt gaatactcat actcttcctt | 4620 |
| tttcaatatt attgaagcat ttatcagggt tattgtctca tgagcggata catatttgaa | 4680 |
| tgtatttaga aaaataaaca ataggggtt ccgcgcacat ttccccgaaa agtgccacct | 4740 |
| gacgtc | 4746 |

<210> SEQ ID NO 19
<211> LENGTH: 5223
<212> TYPE: DNA
<213> ORGANISM: Artificial Sequence
<220> FEATURE:
<223> OTHER INFORMATION: pPEF1

<400> SEQUENCE: 19

| | |
|---|---:|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag cgttttgcg ctgcttcgcg atgtacgggc cagatatacg cgttgacatt | 240 |
| gattattgac tagttattaa tagtaatcaa ttacgggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtccgccc cctattgacg tcaatgacgg taaatggccc gcctggcatt | 540 |
| atgcccagta catgacctta cgggactttc ctacttggca gtacatctac gtattagtca | 600 |
| tcgctattac catggtgatg cggttttggc agtacaccaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta ataaccccgc cccgttgacg caaatgggcg | 780 |
| gtaggcgtgt acggtgggag gtctatataa gcagagctcg tttagtgaac cgtcagatct | 840 |
| ctagaagctg ggtaccgaaa ttaatacgac tcactatagg gagacccaag ctggcttgcg | 900 |
| tttaaactta agcttagcgc agaggcttgg ggcagccgag cggcagccag gcccggccc | 960 |
| gggcctcggt tccagaaggg agaggagccc gccaaggcgc gcaagagagc gggctgcctc | 1020 |
| gcagtccgag ccggagaggg agcgcgagcc gcgccggccc cggacggcct ccgaaaccat | 1080 |
| gagggcctgg atcttctttc tcctttgcct ggccgggagg gctctggcag ccccgctagc | 1140 |
| cgagggatcc agtgtggtgg aattctgcag atatccagca cagtggcggc cgctcgagtc | 1200 |
| tagagggccc gtttaaaccc gctgatcagc ctcgactgtg ccttctagtt gccagccatc | 1260 |
| tgttgtttgc ccctccccg tgccttcctt gaccctggaa ggtgccactc ccactgtcct | 1320 |
| ttcctaataa aatgaggaaa ttgcatcgca ttgtctgagt aggtgtcatt ctattctggg | 1380 |
| gggtggggtg gggcaggaca gcaaggggga ggattggaa gacaatagca ggcatgctgg | 1440 |
| ggatgcggtg ggctctatgg cttctgaggc ggaaagaacc agctggggct ctagggggta | 1500 |

```
tccccacgcg ccctgtagcg gcgcattaag cgcggcgggt gtggtggtta cgcgcagcgt    1560
gaccgctaca cttgccagcg ccctagcgcc cgctcctttc gctttcttcc cttcctttct    1620
cgccacgttc gccggctttc cccgtcaagc tctaaatcgg ggcatccctt tagggttccg    1680
atttagtgct ttacggcacc tcgacoccaa aaaacttgat tagggtgatg gttcacgtag    1740
tgggccatcg ccctgataga cggttttttcg ccctttgacg ttggagtcca cgttctttaa    1800
tagtggactc ttgttccaaa ctggaacaac actcaaccct atctcggtct attcttttga    1860
tttataaggg attttgggga tttcggccta ttggttaaaa aatgagctga tttaacaaaa    1920
atttaacgcg aattaattct gtggaatgtg tgtcagttag ggtgtggaaa gtccccaggc    1980
tccccaggca ggcagaagta tgcaaagcat gcatctcaat tagtcagcaa ccaggtgtgg    2040
aaagtcccca ggctccccag caggcagaag tatgcaaagc atgcatctca attagtcagc    2100
aaccatagtc ccgcccctaa ctccgcccat cccgcccctz actccgccca gttccgccca    2160
ttctccgccc catggctgac taattttttt tatttatgca gaggccgagg ccgcctctgc    2220
ctctgagcta ttccagaagt agtgaggagg ctttttttgga ggcctaggct tttgcaaaaa    2280
gctcccggga gcttgtatat ccattttcgg atctgatcag cacgtgttga caattaatca    2340
tcggcatagt atatcggcat agtataatac gacaaggtga ggaactaaac catggccaag    2400
ttgaccagtg ccgttccggt gctcaccgcg cgcgacgtcg ccggagcggt cgagttctgg    2460
accgaccggc tcgggttctc ccgggacttc gtggaggacg acttcgccgg tgtggtccgg    2520
gacgacgtga ccctgttcat cagcgcggtc caggaccagg tggtgccgga acaccctg    2580
gcctgggtgt gggtgcgcgg cctggacgag ctgtacgccg agtggtcgga ggtcgtgtcc    2640
acgaacttcc gggacgcctc cgggccggcc atgaccgaga tcggcgagca gccgtggggg    2700
cgggagttcg ccctgcgcga cccggccggc aactgcgtgc acttcgtggc cgaggagcag    2760
gactgacacg tgctacgaga tttcgattcc accgccgcct tctatgaaag gttgggcttc    2820
ggaatcgttt tccgggacgc cggctggatg atcctccagc gcggggatct catgctggag    2880
ttcttcgccc accccaactt gtttattgca gcttataatg gttacaaata aagcaatagc    2940
atcacaaatt tcacaaataa agcattttt tcactgcatt ctagttgtgg tttgtccaaa    3000
ctcatcaatg tatcttatca tgtctgtata ccgtcgacct ctagctagag cttggcgtaa    3060
tcatggtcat agctgtttcc tgtgtgaaat tgttatccgc tcacaattcc acacaacata    3120
cgagccggaa gcataaagtg taaagcctgg ggtgcctaat gagtgagcta actcacatta    3180
attgcgttgc gctcactgcc cgcttttcag tcgggaaacc tgtcgtgcca gctgcattaa    3240
tgaatcggcc aacgcgcggg gagaggcggt ttgcgtattg ggcgctcttc cgcttcctcg    3300
ctcactgact cgctgcgctc ggtcgttcgg ctgcggcgag cggtatcagc tcactcaaag    3360
gcggtaatac ggttatccac agaatcaggg gataacgcag gaaagaacat gtgagcaaaa    3420
ggccagcaaa aggccaggaa ccgtaaaaag gccgcgttgc tggcgttttt ccataggctc    3480
cgcccccctg acgagcatca caaaaatcga cgctcaagtc agaggtggcg aaacccgaca    3540
ggactataaa gataccaggc gtttccccct ggaagctccc tcgtgcgctc tcctgttccg    3600
accctgccgc ttaccggata cctgtccgcc tttctccctt cgggaagcgt ggcgctttct    3660
caatgctcac gctgtaggta tctcagttcg gtgtaggtcg ttcgctccaa gctgggctgt    3720
gtgcacgaac cccccgttca gcccgaccgc tgcgccttat ccggtaacta tcgtcttgag    3780
tccaacccgg taagacacga cttatcgcca ctggcagcag ccactggtaa caggattagc    3840
```

```
agagcgaggt atgtaggcgg tgctacagag ttcttgaagt ggtggcctaa ctacggctac    3900
actagaagga cagtatttgg tatctgcgct ctgctgaagc cagttacctt cggaaaaaga    3960
gttggtagct cttgatccgg caaacaaacc accgctggta gcggtggttt ttttgtttgc    4020
aagcagcaga ttacgcgcag aaaaaaagga tctcaagaag atcctttgat cttttctacg    4080
gggtctgacg ctcagtggaa cgaaaactca cgttaaggga ttttggtcat gagattatca    4140
aaaaggatct tcacctagat ccttttaaat taaaaatgaa gttttaaatc aatctaaagt    4200
atatatgagt aaacttggtc tgacagttac caatgcttaa tcagtgaggc acctatctca    4260
gcgatctgtc tatttcgttc atccatagtt gcctgactcc ccgtcgtgta gataactacg    4320
atacgggagg gcttaccatc tggccccagt gctgcaatga taccgcgaga cccacgctca    4380
ccggctccag atttatcagc aataaaccag ccagccggaa gggccgagcg cagaagtggt    4440
cctgcaactt tatccgcctc catccagtct attaattgtt gccgggaagc tagagtaagt    4500
agttcgccag ttaatagttt gcgcaacgtt gttgccattg ctacaggcat cgtggtgtca    4560
cgctcgtcgt ttggtatggc ttcattcagc tccggttccc aacgatcaag gcgagttaca    4620
tgatccccca tgttgtgcaa aaaagcggtt agctccttcg gtcctccgat cgttgtcaga    4680
agtaagttgg ccgcagtgtt atcactcatg gttatggcag cactgcataa ttctcttact    4740
gtcatgccat ccgtaagatg cttttctgtg actggtgagt actcaaccaa gtcattctga    4800
gaatagtgta tgcggcgacc gagttgctct tgcccggcgt caatacggga taataccgcg    4860
ccacatagca gaactttaaa agtgctcatc attggaaaac gttcttcggg gcgaaaactc    4920
tcaaggatct taccgctgtt gagatccagt tcgatgtaac ccactcgtgc acccaactga    4980
tcttcagcat cttttacttt caccagcgtt tctgggtgag caaaaacagg aaggcaaaat    5040
gccgcaaaaa agggaataag ggcgacacgg aaatgttgaa tactcatact cttcctttt    5100 caatattatt gaagcattta tcagggttat tgtctcatga gcggatacat atttgaatgt    5160
atttagaaaa ataaacaaat aggggttccg cgcacatttc cccgaaaagt gccacctgac    5220
gtc                                                                  5223

<210> SEQ ID NO 20
<211> LENGTH: 5226
<212> TYPE: DNA
<213> ORGANISM: Artificial Sequence
<220> FEATURE:
<223> OTHER INFORMATION: pPEF2

<400> SEQUENCE: 20
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtccgccc cctattgacg tcaatgacgg taaatggccc gcctggcatt     540
atgcccagta catgacctta cggactttc ctacttggca gtacatctac gtattagtca    600
tcgctattac catggtgatg cggttttggc agtacaccaa tgggcgtgga tagcggtttg    660
```

```
actcacgggg atttccaagt ctccacccca ttgacgtcaa tgggagtttg ttttggcacc      720
aaaatcaacg ggacttttcca aaatgtcgta ataacccgc cccgttgacg caaatgggcg      780
gtaggcgtgt acggtgggag gtctatataa gcagagctcg tttagtgaac cgtcagatct      840
ctagaagctg gtaccgaaa ttaatacgac tcactatagg gagacccaag ctggcttgcg      900
tttaaactta agcttagcgc agaggcttgg ggcagccgag cggcagccag gccccggccc      960
gggcctcggt tccagaaggg agaggagccc gccaaggcgc gcaagagagc gggctgcctc     1020
gcagtccgag ccggagaggg agcgcgagcc gcgccggccc cggacggcct ccgaaaccat     1080
gggagtcaaa gttctgtttg ccctgatctg catcgctgtg gccgaggcca agcccacgct     1140
agccgaggga tccagtgtgg tggaattctg cagatatcca gcacagtggc ggccgctcga     1200
gtctagaggg cccgtttaaa cccgctgatc agcctcgact gtgccttcta gttgccagcc     1260
atctgttgtt tgcccctccc ccgtgccttc cttgaccctg gaaggtgcca ctcccactgt     1320
cctttcctaa taaaatgagg aaattgcatc gcattgtctg agtaggtgtc attctattct     1380
ggggggtggg gtggggcagg acagcaaggg ggaggattgg gaagacaata gcaggcatgc     1440
tggggatgcg gtgggctcta tggcttctga ggcggaaaga accagctggg gctctagggg     1500
gtatccccac gcgccctgta gcggcgcatt aagcgcggcg ggtgtggtgg ttacgcgcag     1560
cgtgaccgct acacttgcca gcgccctagc gcccgctcct ttcgctttct tcccttcctt     1620
tctcgccacg ttcgccggct ttccccgtca agctctaaat cggggcatcc ctttagggtt     1680
ccgatttagt gctttacggc acctcgaccc caaaaaactt gattagggtg atggttcacg     1740
tagtgggcca tcgccctgat agacggtttt tcgccctttg acgttggagt ccacgttctt     1800
taatagtgga ctcttgttcc aaactggaac aacactcaac cctatctcgg tctattcttt     1860
tgatttataa gggattttgg ggatttcggc ctattggtta aaaaatgagc tgatttaaca     1920
aaaatttaac gcgaattaat tctgtggaat gtgtgtcagt tagggtgtgg aaagtccccca    1980 ggctccccag gcaggcagaa gtatgcaaag catgcatctc aattagtcag caaccaggtg    2040
tggaaagtcc ccaggctccc cagcaggcag aagtatgcaa agcatgcatc tcaattagtc    2100
agcaaccata gtcccgcccc taactccgcc catcccgccc ctaactccgc ccagttccgc    2160
ccattctccg ccccatggct gactaatttt ttttatttat gcagaggccg aggccgcctc    2220
tgcctctgag ctattccaga agtagtgagg aggcttttt ggaggcctag gcttttgcaa     2280
aaagctcccg ggagcttgta tatccatttt cggatctgat cagcacgtgt tgacaattaa    2340
tcatcggcat agtatatcgg catagtataa tacgacaagg tgaggaacta aaccatggcc    2400
aagttgacca gtgccgttcc ggtgctcacc gcgcgcgacg tcgccggagc ggtcgagttc    2460
tggaccgacc ggctcgggtt ctcccgggac ttcgtggagg acgacttcgc cggtgtggtc    2520
cgggacgacg tgaccctgtt catcagcgcg gtccaggacc aggtggtgcc ggacaacacc    2580
ctggcctggg tgtgggtgcg cggcctggac gagctgtacg ccgagtggtc ggaggtcgtg    2640
tccacgaact tccgggacgc ctccgggccg gccatgaccg agatcggcga gcagccgtgg    2700
gggcgggagt cgccctgcg cgacccggcc ggcaactgcg tgcacttcgt ggccgaggag    2760
caggactgac acgtgctacg agatttcgat tccaccgccg ccttctatga aaggttgggc    2820
ttcggaatcg ttttccggga cgccggctgg atgatcctcc agcgcgggga tctcatgctg    2880
gagttcttcg cccacccca cttgtttatt gcagcttata atggttacaa ataaagcaat    2940
agcatcacaa atttcacaaa taaagcattt ttttcactgc attctagttg tggtttgtcc    3000
```

```
aaactcatca atgtatctta tcatgtctgt ataccgtcga cctctagcta gagcttggcg    3060
taatcatggt catagctgtt tcctgtgtga aattgttatc cgctcacaat tccacacaac    3120
atacgagccg gaagcataaa gtgtaaagcc tggggtgcct aatgagtgag ctaactcaca    3180
ttaattgcgt tgcgctcact gcccgctttc cagtcgggaa acctgtcgtg ccagctgcat    3240
taatgaatcg gccaacgcgc ggggagaggc ggtttgcgta ttgggcgctc ttccgcttcc    3300
tcgctcactg actcgctgcg ctcggtcgtt cggctgcggc gagcggtatc agctcactca    3360
aaggcggtaa tacggttatc cacagaatca ggggataacg caggaaagaa catgtgagca    3420
aaaggccagc aaaaggccag gaaccgtaaa aaggccgcgt tgctggcgtt tttccatagg    3480
ctccgccccc ctgacgagca tcacaaaaat cgacgctcaa gtcagaggtg gcgaaacccg    3540
acaggactat aaagatacca ggcgtttccc cctggaagct ccctcgtgcg ctctcctgtt    3600
ccgaccctgc cgcttaccgg atacctgtcc gcctttctcc cttcgggaag cgtggcgctt    3660
tctcaatgct cacgctgtag gtatctcagt tcggtgtagg tcgttcgctc caagctgggc    3720
tgtgtgcacg aaccccccgt tcagcccgac cgctgcgcct tatccggtaa ctatcgtctt    3780
gagtccaacc cggtaagaca cgacttatcg ccactggcag cagccactgg taacaggatt    3840
agcagagcga ggtatgtagg cggtgctaca gagttcttga agtggtggcc taactacggc    3900
tacactagaa ggacagtatt tggtatctgc gctctgctga agccagttac cttcggaaaa    3960
agagttggta gctcttgatc cggcaaacaa accaccgctg gtagcggtgg tttttttgtt    4020
tgcaagcagc agattacgcg cagaaaaaaa ggatctcaag aagatccttt gatcttttct    4080
acggggtctg acgctcagtg gaacgaaaac tcacgttaag ggattttggt catgagatta    4140
tcaaaaagga tcttcaccta gatcctttta aattaaaaat gaagttttaa atcaatctaa    4200
agtatatatg agtaaacttg gtctgacagt taccaatgct taatcagtga ggcacctatc    4260
tcagcgatct gtctatttcg ttcatccata gttgcctgac tccccgtcgt gtagataact    4320
acgatacggg agggcttacc atctggcccc agtgctgcaa tgataccgcg agacccacgc    4380
tcaccggctc cagatttatc agcaataaac cagccagccg aagggccga gcgcagaagt    4440 ggtcctgcaa ctttatccgc ctccatccag tctattaatt gttgccggga agctagagta    4500
agtagttcgc cagttaatag tttgcgcaac gttgttgcca ttgctacagg catcgtggtg    4560
tcacgctcgt cgtttggtat ggcttcattc agctccggtt cccaacgatc aaggcgagtt    4620
acatgatccc ccatgttgtg caaaaaagcg gttagctcct tcggtcctcc gatcgttgtc    4680
agaagtaagt tggccgcagt gttatcactc atggttatgg cagcactgca taattctctt    4740
actgtcatgc catccgtaag atgcttttct gtgactggtg agtactcaac caagtcattc    4800
tgagaatagt gtatgcggcg accgagttgc tcttgcccgg cgtcaatacg ggataatacc    4860
gcgccacata gcagaacttt aaaagtgctc atcattggaa aacgttcttc ggggcgaaaa    4920
ctctcaagga tcttaccgct gttgagatcc agttcgatgt aacccactcg tgcacccaac    4980
tgatcttcag catcttttac tttcaccagc gtttctgggt gagcaaaaac aggaaggcaa    5040
aatgccgcaa aaagggaat aagggcgaca cggaaatgtt gaatactcat actcttcctt    5100
tttcaatatt attgaagcat ttatcagggt tattgtctca tgagcggata catatttgaa    5160
tgtatttaga aaaataaaca aataggggtt ccgcgcacat ttccccgaaa agtgccacct    5220
gacgtc                                                              5226
```

<210> SEQ ID NO 21
<211> LENGTH: 5068

<212> TYPE: DNA
<213> ORGANISM: Artificial Sequence
<220> FEATURE:
<223> OTHER INFORMATION: pPEF3

<400> SEQUENCE: 21

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtccgccc cctattgacg tcaatgacgg taaatggccc gcctggcatt     540
atgcccagta catgacctta cgggactttc ctacttggca gtacatctac gtattagtca     600
tcgctattac catggtgatg cggttttggc agtacaccaa tgggcgtgga tagcggtttg     660
actcacgggg atttccaagt ctccacccca ttgacgtcaa tgggagtttg ttttggcacc     720
aaaatcaacg ggactttcca aaatgtcgta ataaccccgc cccgttgacg caaatgggcg     780
gtaggcgtgt acggtgggag gtctatataa gcagagctcg tttagtgaac cgtcagatct     840
ctagaagctg ggtaccttaa ggcgccagct gatcaagctt ctgcctgccg cctgcctgcc     900
tgccactgag ggttcccagc accatgaggg cctggatctt ctttctcctt tgcctggccg     960
ggagggctct ggcagccccg ctagccgagg atccagtgt ggtggaattc tgcagatatc    1020
cagcacagtg gcggccgctc gagtctagag ggcccgttta aacccgctga tcagcctcga    1080
ctgtgccttc tagttgccag ccatctgttg tttgcccctc cccgtgcctt ccttgaccc     1140
tggaaggtgc cactcccact gtccttttcct aataaaatga ggaaattgca tcgcattgtc    1200
tgagtaggtg tcattctatt ctggggggtg ggtggggca ggacagcaag ggggaggatt     1260
gggaagacaa tagcaggcat gctggggatg cggtgggctc tatggcttct gaggcggaaa    1320
gaaccagctg gggctctagg gggtatcccc acgcgccctg tagcggcgca ttaagcgcgg    1380
cgggtgtggt ggttacgcgc agcgtgaccg ctacacttgc cagcgcccta gcgcccgctc    1440
ctttcgcttt cttcccttcc tttctcgcca cgttcgccgg ctttccccgt caagctctaa    1500
atcggggcat ccctttaggg ttccgattta gtgctttacg gcacctcgac cccaaaaaac    1560
ttgattaggg tgatggttca cgtagtgggc catcgccctg atagacggtt tttcgccctt    1620
tgacgttgga gtccacgttc tttaatagtg gactcttgtt ccaaactgga acaacactca    1680
accctatctc ggtctattct tttgatttat aagggatttt ggggatttcg gcctattggt    1740
taaaaaatga gctgatttaa caaaaattta acgcgaatta attctgtgga atgtgtgtca    1800
gttagggtgt ggaaagtccc caggctcccc aggcaggcag aagtatgcaa agcatgcatc    1860
tcaattagtc agcaaccagg tgtggaaagt ccccaggctc cccagcaggc agaagtatgc    1920
aaagcatgca tctcaattag tcagcaacca tagtcccgcc cctaactccg cccatcccgc    1980
ccctaactcc gcccagttcc gcccattctc cgccccatgg ctgactaatt ttttttattt    2040
atgcagaggc cgaggccgcc tctgcctctg agctattcca gaagtagtga ggaggctttt    2100
ttggaggcct aggcttttgc aaaaagctcc cgggagcttg tatatccatt ttcggatctg    2160
```

```
atcagcacgt gttgacaatt aatcatcggc atagtatatc ggcatagtat aatacgacaa    2220
ggtgaggaac taaaccatgg ccaagttgac cagtgccgtt ccggtgctca ccgcgcgcga    2280
cgtcgccgga gcggtcgagt tctggaccga ccggctcggg ttctcccggg acttcgtgga    2340
ggacgacttc gccggtgtgg tccgggacga cgtgaccctg ttcatcagcg cggtccagga    2400
ccaggtggtg ccggacaaca ccctggcctg ggtgtgggtg cgcggcctgg acgagctgta    2460
cgccgagtgg tcgaggtcg tgtccacgaa cttccgggac gcctccggc cggccatgac     2520
cgagatcggc gagcagccgt gggggcggga gttcgccctg cgcgacccgg ccggcaactg    2580
cgtgcacttc gtggccgagg agcaggactg acacgtgcta cgagatttcg attccaccgc    2640
cgccttctat gaaaggttgg gcttcggaat cgttttccgg gacgccggct ggatgatcct    2700
ccagcgcggg gatctcatgc tggagttctt cgcccacccc aacttgttta ttgcagctta    2760
taatggttac aaataaagca atagcatcac aaatttcaca aataaagcat ttttttcact    2820
gcattctagt tgtggtttgt ccaaactcat caatgtatct tatcatgtct gtataccgtc    2880
gacctctagc tagagcttgg cgtaatcatg gtcatagctg tttcctgtgt gaaattgtta    2940
tccgctcaca attccacaca acatacgagc cggaagcata aagtgtaaag cctggggtgc    3000
ctaatgagtg agctaactca cattaattgc gttgcgctca ctgcccgctt ccagtcggg    3060
aaacctgtcg tgccagctgc attaatgaat cggccaacgc gcggggagag cggtttgcg    3120
tattgggcgc tcttccgctt cctcgctcac tgactcgctg cgctcggtcg ttcggctgcg    3180
gcgagcggta tcagctcact caaaggcggt aatacggtta ccacagaat caggggataa     3240
cgcaggaaag aacatgtgag caaaaggcca gcaaaaggcc aggaaccgta aaaaggccgc    3300
gttgctggcg ttttttccata ggctccgccc cctgacgag catcacaaaa atcgacgctc    3360
aagtcagagg tggcgaaacc cgacaggact ataaagatac caggcgtttc ccctggaag    3420
ctccctcgtg cgctctcctg ttccgaccct gccgcttacc ggatacctgt ccgcctttct    3480
cccttcggga agcgtggcgc tttctcaatg ctcacgctgt aggtatctca gttcggtgta    3540
ggtcgttcgc tccaagctgg gctgtgtgca cgaaccccc gttcagcccg accgctgcgc     3600
cttatccggt aactatcgtc ttgagtccaa cccggtaaga cacgacttat cgccactggc    3660
agcagccact ggtaacagga ttagcagagc gaggtatgta ggcggtgcta cagagttctt    3720
gaagtggtgg cctaactacg gctacactag aaggacagta tttggtatct gcgctctgct    3780
gaagccagtt accttcggaa aaagagttgg tagctcttga tccggcaaac aaaccaccgc    3840
tggtagcggt ggtttttttg tttgcaagca gcagattacg cgcagaaaaa aaggatctca    3900
agaagatcct ttgatctttt ctacggggtc tgacgctcag tggaacgaaa actcacgtta    3960
agggattttg gtcatgagat tatcaaaaag gatcttcacc tagatccttt taaattaaaa    4020
atgaagtttt aaatcaatct aaagtatata tgagtaaact tggtctgaca gttaccaatg    4080
cttaatcagt gaggcaccta tctcagcgat ctgtctattt cgttcatcca tagttgcctg    4140
actccccgtc gtgtagataa ctacgatacg ggagggctta ccatctggcc ccagtgctgc    4200
aatgataccg cgagacccac gctcaccggc tccagattta tcagcaataa accagccagc    4260
cggaagggcc gagcgcagaa gtggtcctgc aactttatcc gcctccatcc agtctattaa    4320
ttgttgccgg gaagctagag taagtagttc gccagttaat agtttgcgca acgttgttgc    4380
cattgctaca ggcatcgtgg tgtcacgctc gtcgtttggt atggcttcat tcagctccgg    4440
ttcccaacga tcaaggcgag ttacatgatc ccccatgttg tgcaaaaaag cggttagctc    4500
cttcggtcct ccgatcgttg tcagaagtaa gttggccgca gtgttatcac tcatggttat    4560
```

| | |
|---|---|
| ggcagcactg cataattctc ttactgtcat gccatccgta agatgctttt ctgtgactgg | 4620 |
| tgagtactca accaagtcat tctgagaata gtgtatgcgg cgaccgagtt gctcttgccc | 4680 |
| ggcgtcaata cgggataata ccgcgccaca tagcagaact ttaaaagtgc tcatcattgg | 4740 |
| aaaacgttct tcggggcgaa aactctcaag gatcttaccg ctgttgagat ccagttcgat | 4800 |
| gtaacccact cgtgcaccca actgatcttc agcatctttt actttcacca gcgtttctgg | 4860 |
| gtgagcaaaa acaggaaggc aaaatgccgc aaaaaaggga ataagggcga cacggaaatg | 4920 |
| ttgaatactc atactcttcc tttttcaata ttattgaagc atttatcagg gttattgtct | 4980 |
| catgagcgga tacatatttg aatgtattta gaaaaataaa caaatagggg ttccgcgcac | 5040 |
| atttccccga aaagtgccac ctgacgtc | 5068 |

<210> SEQ ID NO 22
<211> LENGTH: 5041
<212> TYPE: DNA
<213> ORGANISM: Artificial Sequence
<220> FEATURE:
<223> OTHER INFORMATION: pPEF4

<400> SEQUENCE: 22

| | |
|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtccgccc cctattgacg tcaatgacgg taaatggccc gcctggcatt | 540 |
| atgcccagta catgacctta cgggactttc ctacttggca gtacatctac gtattagtca | 600 |
| tcgctattac catggtgatg cggttttggc agtacaccaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta ataaccccgc cccgttgacg caaatgggcg | 780 |
| gtaggcgtgt acggtgggag gtctatataa gcagagctcg tttagtgaac cgtcagatct | 840 |
| ctagaagctg ggtaccgaaa ttaatacgac tcactatagg gaaccagcc accatgggag | 900 |
| tcaaagttct gtttgccctg atctgcatcg ctgtggccga ggccaagccc acgctagccg | 960 |
| agggatccag tgtggtggaa ttctgcagat atccagcaca gtggcggccg ctcgagtcta | 1020 |
| gagggcccgt ttaaacccgc tgatcagcct cgactgtgcc ttctagttgc cagccatctg | 1080 |
| ttgtttgccc ctcccccgtg ccttccttga ccctggaagg tgccactccc actgtccttt | 1140 |
| cctaataaaa tgaggaaatt gcatcgcatt gtctgagtag gtgtcattct attctggggg | 1200 |
| gtggggtggg gcaggacagc aaggggagg attgggaaga caatagcagg catgctgggg | 1260 |
| atgcggtggg ctctatggct tctgaggcgg aaagaaccag ctggggctct agggggtatc | 1320 |
| cccacgcgcc ctgtagcggc gcattaagcg cggcgggtgt ggtggttacg cgcagcgtga | 1380 |
| ccgctacact tgccagcgcc ctagcgcccg ctcctttcgc tttcttccct tcctttctcg | 1440 |
| ccacgttcgc cggctttccc cgtcaagctc taaatcgggg catcccttta gggttccgat | 1500 |

```
ttagtgcttt acggcacctc gaccccaaaa aacttgatta gggtgatggt tcacgtagtg    1560
ggccatcgcc ctgatagacg ttttttcgcc ctttgacgtt ggagtccacg ttctttaata    1620
gtggactctt gttccaaact ggaacaacac tcaaccctat ctcggtctat tcttttgatt    1680
tataagggat tttggggatt tcggcctatt ggttaaaaaa tgagctgatt taacaaaaat    1740
ttaacgcgaa ttaattctgt ggaatgtgtg tcagttaggg tgtggaaagt ccccaggctc    1800
cccaggcagg cagaagtatg caaagcatgc atctcaatta gtcagcaacc aggtgtggaa    1860
agtccccagg ctccccagca ggcagaagta tgcaaagcat gcatctcaat tagtcagcaa    1920
ccatagtccc gcccctaact ccgcccatcc cgccccctaac tccgcccagt ccgcccatt     1980 ctccgcccca tggctgacta attttttta tttatgcaga ggccgaggcc gcctctgcct     2040
ctgagctatt ccagaagtag tgaggaggct ttttggagg cctaggcttt tgcaaaaagc      2100
tcccgggagc ttgtatatcc attttcggat ctgatcagca cgtgttgaca attaatcatc    2160
ggcatagtat atcggcatag tataatacga caaggtgagg aactaaacca tggccaagtt    2220
gaccagtgcc gttccggtgc tcaccgcgcg cgacgtcgcc ggagcggtcg agttctggac    2280
cgaccggctc gggttctccc gggacttcgt ggaggacgac ttcgccggtg tggtccggga    2340
cgacgtgacc ctgttcatca gcgcggtcca ggaccaggtg gtgccggaca caccctggc     2400 ctgggtgtgg gtgcgcggcc tggacgagct gtacgccgag tggtcggagg tcgtgtccac    2460
gaacttccgg gacgcctccg gccggccat gaccgagatc ggcgagcagc cgtggggcg      2520 ggagttcgcc ctgcgcgacc cggccggcaa ctgcgtgcac ttcgtggccg aggagcagga    2580
ctgacacgtg ctacgagatt tcgattccac cgccgccttc tatgaaaggt tgggcttcgg    2640
aatcgttttc cgggacgccg gctggatgat cctccagcgc ggggatctca tgctggagtt    2700
cttcgcccac cccaacttgt ttattgcagc ttataatggt tacaaataaa gcaatagcat    2760
cacaaatttc acaaataaag catttttttc actgcattct agttgtggtt tgtccaaact    2820
catcaatgta tcttatcatg tctgtatacc gtcgacctct agctagagct tggcgtaatc    2880
atggtcatag ctgtttcctg tgtgaaattg ttatccgctc acaattccac acaacatacg    2940
agccggaagc ataaagtgta aagcctgggg tgcctaatga gtgagctaac tcacattaat    3000
tgcgttgcgc tcactgcccg ctttccagtc gggaaacctg tcgtgccagc tgcattaatg    3060
aatcggccaa cgcgcgggga gaggcggttt gcgtattggg cgctcttccg cttcctcgct    3120
cactgactcg ctgcgctcgg tcgttcggct gcggcgagcg gtatcagctc actcaaaggc    3180
ggtaatacgg ttatccacag aatcagggga taacgcagga agaacatgt gagcaaaagg     3240 ccagcaaaag gccaggaacc gtaaaaaggc cgcgttgctg gcgttttttcc ataggctccg    3300 ccccctgac gagcatcaca aaatcgacg ctcaagtcag aggtggcgaa acccgacagg      3360
actataaaga taccaggcgt ttccccctgg aagctccctc gtgcgctctc ctgttccgac    3420
cctgccgctt accggatacc tgtccgcctt tctcccttcg ggaagcgtgg cgctttctca    3480
atgctcacgc tgtaggtatc tcagttcggt gtaggtcgtt cgctccaagc tgggctgtgt    3540
gcacgaaccc ccgttcagc ccgaccgctg cgccttatcc ggtaactatc gtcttgagtc     3600
caacccggta agacacgact tatcgccact ggcagcagcc actggtaaca ggattagcag    3660
agcgaggtat gtaggcggtg ctacagagtt cttgaagtgg tggcctaact acggctacac    3720
tagaaggaca gtatttggta tctgcgctct gctgaagcca gttaccttcg gaaaaagagt    3780
tggtagctct tgatccggca aacaaaccac cgctggtagc ggtggttttt ttgtttgcaa    3840
gcagcagatt acgcgcagaa aaaaaggatc tcaagaagat cctttgatct tttctacggg    3900
```

-continued

```
gtctgacgct cagtggaacg aaaactcacg ttaagggatt ttggtcatga gattatcaaa    3960
aaggatcttc acctagatcc ttttaaatta aaaatgaagt tttaaatcaa tctaaagtat    4020
atatgagtaa acttggtctg acagttacca atgcttaatc agtgaggcac ctatctcagc    4080
gatctgtcta tttcgttcat ccatagttgc ctgactcccc gtcgtgtaga taactacgat    4140
acgggagggc ttaccatctg gccccagtgc tgcaatgata ccgcgagacc cacgctcacc    4200
ggctccagat ttatcagcaa taaaccagcc agccggaagg gccgagcgca gaagtggtcc    4260
tgcaacttta tccgcctcca tccagtctat taattgttgc cgggaagcta gagtaagtag    4320
ttcgccagtt aatagtttgc gcaacgttgt tgccattgct acaggcatcg tggtgtcacg    4380
ctcgtcgttt ggtatggctt cattcagctc cggttcccaa cgatcaaggc gagttacatg    4440
atcccccatg ttgtgcaaaa aagcggttag ctccttcggt cctccgatcg ttgtcagaag    4500
taagttggcc gcagtgttat cactcatggt tatggcagca ctgcataatt ctcttactgt    4560
catgccatcc gtaagatgct tttctgtgac tggtgagtac tcaaccaagt cattctgaga    4620
atagtgtatg cggcgaccga gttgctcttg cccggcgtca atacgggata ataccgcgcc    4680
acatagcaga actttaaaag tgctcatcat tggaaaacgt tcttcgggc gaaaactctc     4740 aaggatctta ccgctgttga tccagttc gatgtaaccc actcgtgcac ccaactgatc     4800
ttcagcatct tttactttca ccagcgtttc tgggtgagca aaaacaggaa ggcaaaatgc    4860
cgcaaaaaag ggaataaggg cgacacggaa atgttgaata ctcatactct ccttttttca    4920
atattattga agcatttatc agggttattg tctcatgagc ggatacatat ttgaatgtat    4980
ttagaaaaat aaacaaatag gggttccgcg cacatttccc cgaaaagtgc cacctgacgt    5040
c                                                                   5041
```

<210> SEQ ID NO 23
<211> LENGTH: 4553
<212> TYPE: DNA
<213> ORGANISM: Artificial Sequence
<220> FEATURE:
<223> OTHER INFORMATION: pPEF5.1

<400> SEQUENCE: 23

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtccgccc cctattgacg tcaatgacgg taaatggccc gcctggcatt     540
atgcccagta catgacctta cgggactttc ctacttggca gtacatctac gtattagtca    600
tcgctattac catggtgatg cggttttggc agtacaccaa tgggcgtgga tagcggtttg    660
actcacgggg atttccaagt ctccacccca ttgacgtcaa tgggagtttg ttttggcacc    720
aaaatcaacg ggactttcca aaatgtcgta ataaccccgc cccgttgacg caaatgggcg    780
gtaggcgtgt acggtgggag gtctatataa gcagagctcg tttagtgaac cgtcagatct    840
```

```
ctagaagctg ggtaccgaaa ttaatacgac tcactatagg ggaaccagcc accatgggag    900
tcaaagttct gtttgccctg atctgcatcg ctgtggccga ggccaagccc acgctagccg    960
aggttgcttt gaggatccag tgtggtggaa ttctgcagat atccagcaca gtggcggccg   1020
ctcgagtcta gagggcccgt ttaaacccgc tgatcagcct cgactgtgcc ttctagttgc   1080
cagccatctg ttgtttgccc ctcccccgtg ccttccttga ccctggaagg tgccactccc   1140
actgtccttt cctaataaaa tgaggaaatt gcatcgcatt gtctgagtag gtgtcattct   1200
attctggggg gtggggtggg gcaggacagc aaggggagg attgggaaga caatagcagg   1260
catgctgggg atgcggtggg ctctatggct tctgaggcgg aaagaaccag ctggggctct   1320
aggggggtatc cccacgcgcc ctgtagcggc gcattaagcg cggcgggtgt ggtggttacg   1380
caacccagag atcgctgcgt tcccgccccc tcacccgccc gctctcgtca tcactgaggt   1440
ggagaagagc atgcgtgagg ctccggtgcc cgtcagtggg cagagcgcac atcgcccaca   1500
gtccccgaga agttgggggg aggggtcggc aattgaaccg gtgcctagag aaggtggcgc   1560
ggggtaaact gggaaagtga tgtcgtgtac tggctccgcc ttttcccga gggtggggga   1620
gaaccgtata taagtgcagt agtcgccgtg aacgttcttt ttcgcaacgg gtttgccgcc   1680
agaacacagg tgtcgtgaaa actacccta aaagcttcaa aatggccaag ttgaccagtg   1740
ccgttccggt gctcaccgcg cgcgacgtcg ccggagcggt cgagttctgg accgaccggc   1800
tcgggttctc ccgggacttc gtggaggacg acttcgccgg tgtggtccgg gacgacgtga   1860
ccctgttcat cagcgcggtc caggaccagg tggtgccgga caacaccctg gcctgggtgt   1920
gggtgcgcgg cctggacgag ctgtacgccg agtggtcgga ggtcgtgtcc acgaacttcc   1980
gggacgcctc cgggccggcc atgaccgaga tcggcgagca gccgtggggg cgggagttcg   2040
ccctgcgcga cccggccggc aactgcgtgc acttcgtggc cgaggagcag gactgacacg   2100
tgctacgaga tttcgattcc accgccgcct tctatgaaag gttgggcttc ggaatcgttt   2160
tccgggacgc cggctggatg atcctccagc gcggggatct catgctggag ttcttcgccc   2220
accccaactt gtttattgca gcttataatg gttacaaata aagcaatagc atcacaaatt   2280
tcacaaataa agcatttttt tcactgcatt ctagttgtgg tttgtccaaa ctcatcaatg   2340
tatcttatca tgtctgtata ccgtcgacct ctagctagag cttggcgtaa tcatggtcat   2400
agctgttttcc tgtgtgaaat tgttatccgc tcacaattcc acacaacata cgagccggaa   2460
gcataaagtg taaagcctgg ggtgcctaat gagtgagcta actcacatta attgcgttgc   2520
gctcactgcc cgctttccag tcgggaaacc tgtcgtgcca gctgcattaa tgaatcggcc   2580
aacgcgcggg gagaggcggt ttgcgtattg ggcgctcttc cgcttcctcg ctcactgact   2640
cgctgcgctc ggtcgttcgg ctgcggcgag cggtatcagc tcactcaaag gcggtaatac   2700
ggttatccac agaatcaggg gataacgcag gaaagaacat gtgagcaaaa ggccagcaaa   2760
aggccaggaa ccgtaaaaag gccgcgttgc tggcgttttt ccataggctc cgcccccctg   2820
acgagcatca caaaaatcga cgctcaagtc agaggtggcg aaacccgaca ggactataaa   2880
gataccaggc gtttccccct ggaagctccc tcgtgcgctc tcctgttccg accctgccgc   2940
ttaccggata cctgtccgcc tttctccctt cgggaagcgt ggcgctttct caatgctcac   3000
gctgtaggta tctcagttcg gtgtaggtcg ttcgctccaa gctgggctgt gtgcacgaac   3060
cccccgttca gcccgaccgc tgcgccttat ccggtaacta tcgtcttgag tccaacccgg   3120
taagacacga cttatcgcca ctggcagcag ccactggtaa caggattagc agagcgaggt   3180
atgtaggcgg tgctacagag ttcttgaagt ggtggcctaa ctacggctac actagaagga   3240
```

```
cagtatttgg tatctgcgct ctgctgaagc cagttacctt cggaaaaaga gttggtagct    3300
cttgatccgg caaacaaacc accgctggta gcggtggttt ttttgtttgc aagcagcaga    3360
ttacgcgcag aaaaaaagga tctcaagaag atcctttgat cttttctacg gggtctgacg    3420
ctcagtggaa cgaaaactca cgttaaggga ttttggtcat gagattatca aaaggatct    3480 tcacctagat ccttttaaat taaaaatgaa gttttaaatc aatctaaagt atatatgagt    3540
aaacttggtc tgacagttac caatgcttaa tcagtgaggc acctatctca gcgatctgtc    3600
tatttcgttc atccatagtt gcctgactcc ccgtcgtgta gataactacg atacgggagg    3660
gcttaccatc tggccccagt gctgcaatga taccgcgaga cccacgctca ccggctccag    3720
atttatcagc aataaaccag ccagccggaa gggccgagcg cagaagtggt cctgcaactt    3780
tatccgcctc catccagtct attaattgtt gccgggaagc tagagtaagt agttcgccag    3840
ttaatagttt gcgcaacgtt gttgccattg ctacaggcat cgtggtgtca cgctcgtcgt    3900
ttggtatggc ttcattcagc tccggttccc aacgatcaag gcgagttaca tgatccccca    3960
tgttgtgcaa aaaagcggtt agctccttcg gtcctccgat cgttgtcaga agtaagttgg    4020
ccgcagtgtt atcactcatg gttatggcag cactgcataa ttctcttact gtcatgccat    4080
ccgtaagatg cttttctgtg actggtgagt actcaaccaa gtcattctga atagtgta    4140 tgcggcgacc gagttgctct tgcccggcgt caatacggga taataccgcg ccacatagca    4200
gaactttaaa agtgctcatc attggaaaac gttcttcggg gcgaaaactc tcaaggatct    4260
taccgctgtt gagatccagt tcgatgtaac ccactcgtgc acccaactga tcttcagcat    4320
cttttacttt caccagcgtt tctgggtgag caaaaacagg aaggcaaaat gccgcaaaaa    4380
agggaataag ggcgacacgg aaatgttgaa tactcatact cttcctttt caatattatt    4440 gaagcattta tcagggttat tgtctcatga gcggatacat atttgaatgt atttagaaaa    4500
ataaacaaat aggggttccg cgcacatttc cccgaaaagt gccacctgac gtc           4553
```

<210> SEQ ID NO 24
<211> LENGTH: 4738
<212> TYPE: DNA
<213> ORGANISM: Artificial Sequence
<220> FEATURE:
<223> OTHER INFORMATION: pPEF5.1max

<400> SEQUENCE: 24

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtccgccc cctattgacg tcaatgacgg taaatggccc gcctggcatt    540
atgcccagta catgacctta cgggactttc ctacttggca gtacatctac gtattagtca    600
tcgctattac catggtgatg cggttttggc agtacaccaa tgggcgtgga tagcggtttg    660
actcacgggg atttccaagt ctccacccca ttgacgtcaa tgggagtttg ttttggcacc    720
```

```
aaaatcaacg ggactttcca aaatgtcgta ataaccccgc cccgttgacg caaatgggcg    780
gtaggcgtgt acggtgggag gtctatataa gcagagctcg tttagtgaac cgtcagatct    840
ctagaagctg ggtaccgaaa ttaatacgac tcactatagg gagacccaag ctggcttgcg    900
tttaaactta agcttagcgc agaggcttgg ggcagccgag cggcagccag gccccggccc    960
gggcctcggt tccagaaggg agaggagccc gccaaggcgc gcaagagagc gggctgcctc   1020
gcagtccgag ccgagagggg agcgcgagcc gcgccggccc cggacggcct ccgaaaccat   1080
gggagtcaaa gttctgtttg ccctgatctg catcgctgtg gccgaggcca agcccacgct   1140
agccgaggtt gctttgagga tccagtgtgg tggaattctg cagatatcca gcacagtggc   1200
ggccgctcga gtctagaggg cccgtttaaa cccgctgatc agcctcgact gtgccttcta   1260
gttgccagcc atctgttgtt tgcccctccc ccgtgccttc cttgaccctg gaaggtgcca   1320
ctcccactgt cctttcctaa taaaatgagg aaattgcatc gcattgtctg agtaggtgtc   1380
attctattct ggggggtggg gtggggcagg acagcaaggg ggaggattgg gaagacaata   1440
gcaggcatgc tggggatgcg gtgggctcta tggcttctga ggcggaaaga accagctggg   1500
gctctagggg gtatccccac gcgccctgta gcggcgcatt aagcgcggcg ggtgtggtgg   1560
ttacgcaacc cagagatcgc tgcgttcccg ccccctcacc cgcccgctct cgtcatcact   1620
gaggtggaga agagcatgcg tgaggctccg gtgcccgtca gtgggcagag cgcacatcgc   1680
ccacagtccc cgagaagttg ggggggaggg tcggcaattg aaccggtgcc tagagaaggt   1740
ggcgcggggt aaactgggaa agtgatgtcg tgtactggct ccgcctttt cccgagggtg   1800 ggggagaacc gtatataagt gcagtagtcg ccgtgaacgt tctttttcgc aacgggtttg   1860
ccgccagaac acaggtgtcg tgaaaactac ccctaaaagc ttcaaaatgg ccaagttgac   1920
cagtgccgtt ccggtgctca ccgcgcgcga cgtcgccgga gcggtcgagt ctggaccga   1980 ccggctcggg ttctcccggg acttcgtgga ggacgacttc gccggtgtgg tccgggacga   2040
cgtgaccctg ttcatcagcg cggtccagga ccaggtggtg ccggacaaca ccctggcctg   2100
ggtgtgggtg cgcggcctgg acgagctgta cgccgagtgg tcggaggtcg tgtccacgaa   2160
cttccgggac gcctccgggc cggccatgac cgagatcggc gagcagccgt ggggcggga   2220 gttcgccctg cgcgacccgg ccggcaactg cgtgcacttc gtggccgagg agcaggactg   2280
acacgtgcta cgagatttcg attccaccgc cgccttctat gaaaggttgg gcttcggaat   2340
cgttttccgg gacgccggct ggatgatcct ccagcgcggg gatctcatgc tggagttctt   2400
cgcccacccc aacttgttta ttgcagctta taatggttac aaataaagca atagcatcac   2460
aaatttcaca aataaagcat ttttttcact gcattctagt tgtggtttgt ccaaactcat   2520
caatgtatct tatcatgtct gtataccgtc gacctctagc tagagcttgg cgtaatcatg   2580
gtcatagctg tttcctgtgt gaaattgtta tccgctcaca attccacaca acatacgagc   2640
cggaagcata aagtgtaaag cctggggtgc ctaatgagtg agctaactca cattaattgc   2700
gttgcgctca ctgcccgctt tccagtcggg aaacctgtcg tgccagctgc attaatgaat   2760
cggccaacgc gcgggagag gcggtttgcg tattgggcgc tcttccgctt cctcgctcac   2820
tgactcgctg cgctcggtcg ttcggctgcg gcgagcggta tcagctcact caaaggcggt   2880
aatacggtta tccacagaat caggggataa cgcaggaaag aacatgtgag caaaaggcca   2940
gcaaaaggcc aggaaccgta aaaaggccgc gttgctggcg ttttccata ggctccgccc   3000 ccctgacgag catcacaaaa atcgacgctc aagtcagagg tggcgaaacc cgacaggact   3060
ataaagatac caggcgtttc ccctggaag ctccctcgtg cgctctcctg ttccgaccct   3120
```

| | | | |
|---|---|---|---|
| gccgcttacc | ggatacctgt | ccgcctttct | cccttcggga agcgtggcgc tttctcaatg | 3180 |
| ctcacgctgt | aggtatctca | gttcggtgta | ggtcgttcgc tccaagctgg gctgtgtgca | 3240 |
| cgaacccccc | gttcagcccg | accgctgcgc | cttatccggt aactatcgtc ttgagtccaa | 3300 |
| cccggtaaga | cacgacttat | cgccactggc | agcagccact ggtaacagga ttagcagagc | 3360 |
| gaggtatgta | ggcggtgcta | cagagttctt | gaagtggtgg cctaactacg gctacactag | 3420 |
| aaggacagta | tttggtatct | gcgctctgct | gaagccagtt accttcggaa aaagagttgg | 3480 |
| tagctcttga | tccggcaaac | aaaccaccgc | tggtagcggt ggtttttttg tttgcaagca | 3540 |
| gcagattacg | cgcagaaaaa | aaggatctca | agaagatcct ttgatctttt ctacggggtc | 3600 |
| tgacgctcag | tggaacgaaa | actcacgtta | agggattttg gtcatgagat tatcaaaaag | 3660 |
| gatcttcacc | tagatccttt | taaattaaaa | atgaagtttt aaatcaatct aaagtatata | 3720 |
| tgagtaaact | tggtctgaca | gttaccaatg | cttaatcagt gaggcaccta tctcagcgat | 3780 |
| ctgtctattt | cgttcatcca | tagttgcctg | actccccgtc gtgtagataa ctacgatacg | 3840 |
| ggagggctta | ccatctggcc | ccagtgctgc | aatgataccg cgagacccac gctcaccggc | 3900 |
| tccagattta | tcagcaataa | accagccagc | cggaagggcc gagcgcagaa gtggtcctgc | 3960 |
| aactttatcc | gcctccatcc | agtctattaa | ttgttgccgg gaagctagag taagtagttc | 4020 |
| gccagttaat | agtttgcgca | acgttgttgc | cattgctaca ggcatcgtgg tgtcacgctc | 4080 |
| gtcgtttggt | atggcttcat | tcagctccgg | ttcccaacga tcaaggcgag ttacatgatc | 4140 |
| ccccatgttg | tgcaaaaaag | cggttagctc | cttcggtcct ccgatcgttg tcagaagtaa | 4200 |
| gttggccgca | gtgttatcac | tcatggttat | ggcagcactg cataattctc ttactgtcat | 4260 |
| gccatccgta | agatgctttt | ctgtgactgg | tgagtactca accaagtcat tctgagaata | 4320 |
| gtgtatgcgg | cgaccgagtt | gctcttgccc | ggcgtcaata cgggataata ccgcgccaca | 4380 |
| tagcagaact | ttaaaagtgc | tcatcattgg | aaaacgttct cggggcgaaa actctcaag | 4440 |
| gatcttaccg | ctgttgagat | ccagttcgat | gtaacccact cgtgcaccca actgatcttc | 4500 |
| agcatctttt | actttcacca | gcgtttctgg | gtgagcaaaa acaggaaggc aaaatgccgc | 4560 |
| aaaaaggga | ataagggcga | cacgaaaatg | ttgaatactc atactcttcc tttttcaata | 4620 |
| ttattgaagc | atttatcagg | gttattgtct | catgagcgga tacatatttg aatgtattta | 4680 |
| gaaaaataaa | caaataggg | ttccgcgcac | atttccccga aaagtgccac ctgacgtc | 4738 |

<210> SEQ ID NO 25
<211> LENGTH: 9901
<212> TYPE: DNA
<213> ORGANISM: Artificial Sequence
<220> FEATURE:
<223> OTHER INFORMATION: pCEP-Pu/AC7

<400> SEQUENCE: 25

| | | | |
|---|---|---|---|
| gccccgccgc | cggacgaact | aaacctgact | acggcatctc tgccccttct tcgctggtac | 60 |
| gaggagcgct | tttgttttgt | attcggggca | gtgcatgtaa tcccttcagt tggttggtac | 120 |
| aacttgccaa | ctgggccctg | ttccacatgt | gacacggggg gggaccaaac acaaaggggt | 180 |
| tctctgactg | tagttgacat | ccttataaat | ggatgtgcac atttgccaac actgagtggc | 240 |
| tttcatcctg | gagcagactt | tgcatgctgt | ggactgcaac acaacattgc ctttatgtgt | 300 |
| aactcttggc | tgaagctctt | acaccaatgc | tgggggacat gtacctccca ggggcccagg | 360 |
| aagactacgg | gaggctacac | caacgtcaat | cagagggggcc tgtgtagcta ccgataagcg | 420 |

```
gaccctcaag agggcattag caatagtgtt tataaggccc ccttgttaac cctaaacggg    480
tagcatatgc ttcccgggta gtagtatata ctatccagac taaccctaat tcaatagcat    540
atgttaccca acgggaagca tatgctatcg aattagggtt agtaaaaggg tcctaaggaa    600
cagcgatatc tcccacccca tgagctgtca cggttttatt tacatgggt  caggattcca    660 cgagggtagt gaaccatttt agtcacaagg gcagtggctg aagatcaagg agcgggcagt    720
gaactctcct gaatcttcgc ctgcttcttc attctccttc gtttagctaa tagaataact    780
gctgagttgt gaacagtaag gtgtatgtga ggtgctcgaa acaaggtttt caggtgacgc    840
ccccagaata aaatttggac gggggttca  gtggtggcat tgtgctatga caccaatata    900
accctcacaa accccttggg caataaatac tagtgtagga atgaaacatt ctgaatatct    960
ttaacaatag aaatccatgg ggtggggaca agccgtaaag actggatgtc catctcacac   1020
gaatttatgg ctatgggcaa cacataatcc tagtgcaata tgatactggg gttattaaga   1080
tgtgtcccag gcagggacca agacaggtga accatgttgt tacactctat ttgtaacaag   1140
gggaaagaga gtggacgccg acagcagcgg actccactgg ttgtctctaa caccccgaa    1200 aattaaacgg ggctccacgc caatgggcc  cataaacaaa gacaagtggc cactcttttt   1260
tttgaaattg tggagtgggg gcacgcgtca gcccccacac gccgccctgc ggttttggac   1320
tgtaaaataa gggtgtaata acttggctga ttgtaacccc gctaaccact gcggtcaaac   1380
cacttgccca caaaaccact aatggcaccc cggggaatac ctgcataagt aggtgggcgg   1440
gccaagatag gggcgcgatt gctgcgatct ggaggacaaa ttacacacac ttgcgcctga   1500
gcgccaagca caggggttgtt ggtcctcata ttcacgaggt cgctgagagc acggtgggct   1560
aatgttgcca tgggtagcat atactaccca aatatctgga tagcatatgc tatcctaatc   1620
tatatctggg tagcataggc tatcctaatc tatatctggg tagcatatgc tatcctaatc   1680
tatatctggg tagtatatgc tatcctaatt tatatctggg tagcataggc tatcctaatc   1740
tatatctggg tagcatatgc tatcctaatc tatatctggg tagtatatgc tatcctaatc   1800
tgtatccggg tagcatatgc tatcctaata gagattaggg tagtatatgc tatcctaatt   1860
tatatctggg tagcatatac tacccaaata tctggatagc atatgctatc ctaatctata   1920
tctgggtagc atatgctatc ctaatctata tctgggtagc ataggctatc ctaatctata   1980
tctgggtagc atatgctatc ctaatctata tctgggtagt atatgctatc ctaattata   2040 tctgggtagc ataggctatc ctaatctata tctgggtagc atatgctatc ctaatctata   2100
tctgggtagt atatgctatc ctaatctgta tccgggtagc atatgctatc ctcatgcata   2160
tacagtcagc atatgatacc cagtagtaga gtgggagtgc tatcctttgc atatgccgcc   2220
acctcccaag ggggcgtgaa ttttcgctgc ttgtccttt  cctgcatgct ggttgctccc   2280
attcttaggt gaatttaagg aggccaggct aaagccgtcg catgtctgat tgctcaccag   2340
gtaaatgtcg ctaatgtttt ccaacgcgag aaggtgttga gcgcggagct gagtgacgtg   2400
acaacatggg tatgcccaat tgccccatgt tgggaggacg aaaatggtga caagacagat   2460
ggccagaaat acaccaacag cacgcatgat gtctactggg gatttattct ttagtgcggg   2520
ggaatacacg gcttttaata cgattgaggg cgtctcctaa caagttacat cactcctgcc   2580
cttcctcacc ctcatctcca tcacctcctt catctccgtc atctccgtca tcaccctccg   2640
cggcagcccc ttccaccata ggtggaaacc agggaggcaa atctactcca tcgtcaaagc   2700
tgcacacagt caccctgata ttgcaggtag gagcgggctt tgtcataaca aggtccttaa   2760
tcgcatcctt caaaacctca gcaaatatat gagtttgtaa aaagaccatg aaataacaga   2820
```

```
caatggactc ccttagcggg ccaggttgtg ggccgggtcc aggggccatt ccaaagggga    2880
gacgactcaa tggtgtaaga cgacattgtg gaatagcaag ggcagttcct cgccttaggt    2940
tgtaaaggga ggtcttacta cctccatata cgaacacacc ggcgacccaa gttccttcgt    3000
cggtagtcct ttctacgtga ctcctagcca ggagagctct taaaccttct gcaatgttct    3060
caaatttcgg gttggaacct ccttgaccac gatgctttcc aaaccaccct ccttttttgc    3120
gcctgcctcc atcaccctga ccccggggtc cagtgcttgg gccttctcct gggtcatctg    3180
cggggccctg ctctatcgct cccgggggca cgtcaggctc accatctggg ccaccttctt    3240
ggtggtattc aaaataatcg gcttccccta cagggtggaa aaatggcctt ctacctggag    3300
ggggcctgcg cggtggagac ccggatgatg atgactgact actgggactc ctgggcctct    3360
tttctccacg tccacgacct ctctttcacg acttcccccc ctggctcttt    3420
cacgtcctct accccggcgg cctccactac ctcctcgacc ccggcctcca ctacctcctc    3480
gaccccggcc tccactgcct cctcgacccc ggcctccacc tctgctcct gcccctcctg    3540 ctcctgcccc tcctcctgct cctgcccctc ctgcccctcc tgctcctgcc cctcctgccc    3600
ctcctgctcc tgcccctcct gcccctcctg ctcctgcccc tcctgcccct cctcctgctc    3660
ctgcccctcc tgcccctcct cctgctcctg cccctcctgc cctcctgct cctgcccctc    3720 ctgcccctcc tgctcctgcc cctcctgccc ctcctgctcc tgcccctcct gctcctgccc    3780
ctcctgctcc tgcccctcct gctcctgccc ctcctgcccc tcctgcccct cctcctgctc    3840
ctgcccctcc tgctcctgcc cctcctgccc ctcctgcccc tcctgctcct gcccctcctc    3900
ctgctcctgc ccctcctgcc cctcctgccc ctcctcctgc cctgcccct cctgcccctc    3960 ctcctgctcc tgcccctcct cctgctcctg cccctcctgc cctcctgcc cctcctcctg    4020 ctcctgcccc tcctgcccct cctcctgctc ctgcccctcc tcctgctcct gccccctcctg    4080 cccctcctgc cctcctcct gctcctgccc ctcctgcccc ctgcccct cctgcccctc    4140 ctgcccctcc tgcccctcct cctgctcctg cccctcctcc tgctcctgcc cctcctgctc    4200
ctgcccctcc cgctcctgct cctgctcctg ttccaccgtg ggtcccttt cagccaatgc    4260 aacttggacg ttttggggt ctccggacac catctctatg tcttggccct gatcctgagc    4320 cgccggggc tcctggtctt ccgcctcctc gtcctcgtcc tcttcccgt cctcgtccat    4380 ggttatcacc ccctcttctt tgaggtccac tgccgccgga gccttctggt ccagatgtgt    4440
ctcccttctc tcctaggcca tttccaggtc ctgtacctgg cccctcgtca gacatgattc    4500
acactaaaag agatcaatag acatctttat tagacgacgc tcagtgaata cagggagtgc    4560
agactcctgc cccctccaac agcccccccca ccctcatccc cttcatggtc gctgtcagac    4620
agatccaggt ctgaaaattc cccatcctcc gaaccatcct cgtcctcatc accaattact    4680
cgcagcccgg aaaactcccg ctgaacatcc tcaagatttg cgtcctgagc ctcaagccag    4740
gcctcaaatt cctcgtcccc cttttttgctg gacggtaggg atggggattc tcgggacccc    4800
tcctcttcct cttcaaggtc accagacaga gatgctactg gggcaacgga agaaaagctg    4860
ggtgcggcct gtgaggatca gcttatcgat gataagctgt caaacatgag aattcttgaa    4920
gacgaaaggg cctcgtgata cgcctatttt tataggttaa tgtcatgata ataatggttt    4980
cttagacgtc aggtggcact tttcgggaa atgtgcgcgg aaccctatt tgtttatttt    5040 tctaaataca ttcaaatatg tatccgctca tgagacaata accctgataa atgcttcaat    5100
aatattgaaa aaggaagagt atgagtattc aacatttccg tgtcgccctt attccctttt    5160
```

```
ttgcggcatt ttgccttcct gttttttgctc acccagaaac gctggtgaaa gtaaaagatg    5220
ctgaagatca gttgggtgca cgagtgggtt acatcgaact ggatctcaac agcggtaaga    5280
tccttgagag ttttcgcccc gaagaacgtt ttccaatgat gagcactttt aaagttctgc    5340
tatgtggcgc ggtattatcc cgtgttgacg ccgggcaaga gcaactcggt cgccgcatac    5400
actattctca gaatgacttg gttgagtact caccagtcac agaaaagcat cttacggatg    5460
gcatgacagt aagagaatta tgcagtgctg ccataaccat gagtgataac actgcggcca    5520
acttacttct gacaacgatc ggaggaccga aggagctaac cgcttttttg cacaacatgg    5580
gggatcatgt aactcgcctt gatcgttggg aaccggagct gaatgaagcc ataccaaacg    5640
acgagcgtga caccacgatg cctgcagcaa tggcaacaac gttgcgcaaa ctattaactg    5700
gcgaactact tactctagct tcccggcaac aattaataga ctggatggag gcggataaag    5760
ttgcaggacc acttctgcgc tcggcccttc cggctggctg gtttattgct gataaatctg    5820
gagccggtga gcgtgggtct cgcggtatca ttgcagcact ggggccagat ggtaagccct    5880
cccgtatcgt agttatctac acgacgggga gtcaggcaac tatggatgaa cgaaatagac    5940
agatcgctga gataggtgcc tcactgatta agcattggta actgtcagac caagtttact    6000
catatatact ttagattgat ttaaaacttc attttttaatt taaaaggatc taggtgaaga    6060
tcctttttga taatctcatg accaaaatcc cttaacgtga gttttcgttc cactgagcgt    6120
cagacccccg agaaaagatc aaaggatctt cttgagatcc ttttttttctg cgcgtaatct    6180
gctgcttgca acaaaaaaa ccaccgctac cagcggtggt ttgtttgccg gatcaagagc    6240
taccaactct ttttccgaag gtaactggct tcagcagagc gcagatacca atactgtcc    6300
ttctagtgta gccgtagtta ggccaccact tcaagaactc tgtagcaccg cctacatacc    6360
tcgctctgct aatcctgtta ccagtggctg ctgccagtgg cgataagtcg tgtcttaccg    6420
ggttggactc aagacgatag ttaccggata aggcgcagcg gtcgggctga acgggggtt    6480
cgtgcacaca gcccagcttg gagcgaacga cctacaccga actgagatac ctacagcgtg    6540
agctatgaga aagcgccacg cttcccgaag ggagaaaggc ggacaggtat ccggtaagcg    6600
gcagggtcgg aacaggagag cgcacgaggg agcttccagg gggaaacgcc tggtatcttt    6660
atagtcctgt cgggtttcgc cacctctgac ttgagcgtcg attttttgtga tgctcgtcag    6720
gggggcggag cctatggaaa aacgccagca acgcggcctt tttacggttc ctggccttt    6780
gctgcgccgc gtgcggctgc tggagatggc ggacgcgatg gatatgttct gccaagggtt    6840
ggtttgcgca ttcacagttc tccgcaagaa ttgattggct ccaattcttg gagtggtgaa    6900
tccgttagcg aggccatcca gcctcgcgtc gaactagatg atccgctgtg gaatgtgtgt    6960
cagttagggt gtgaaagtc cccaggctcc ccagcaggca gaagtatgca aagcatgcat    7020
ctcaattagt cagcaaccag gtgtggaaag tccccaggct ccccagcagg cagaagtatg    7080
caaagcatgc atctcaatta gtcagcaacc atagtcccgc ccctaactcc gcccatcccg    7140
cccctaactc cgcccagttc cgcccattct ccgccccatg gctgactaat ttttttttatt    7200
tatgcagagg ccgaggccgc ctcggcctct gagctattcc agaagtagtg aggaggcttt    7260
tttggagggt gaccgccacg accggtgccg ccaccatccc ctgacccacg ccctgaccc    7320
ctcacaagga gacgaccttc catgaccgag tacaagccca cggtgcgcct cgccacccgc    7380
gacgacgtcc ccgggccgt acgcaccctc gccgccgcgt cgccgactac ccccgccacg    7440
cgccacaccg tcgaccccga ccgccacatc gaacgcgtca ccgagctgca agaactcttc    7500
ctcacgcgcg tcgggctcga catcggcaag gtgtgggtcg cggacgacgg cgccgcggtg    7560
```

```
gcggtctgga ccacgccgga gagcgtcgaa gcggggcgg tgttcgccga gatcggcccg    7620
cgcatggccg agttgagcgg ttcccggctg gccgcgcagc aacagatgga aggcctcctg    7680
gcgccgcacc ggcccaagga gcccgcgtgg ttcctggcca ccgtcggcgt ctcgcccgac    7740
caccagggca agggtctggg cagcgccgtc gtgctcccg gagtggaggc ggccgagcgc    7800
gccggggtgc ccgccttcct ggagacctcc gcgccccgca acctccccct ctacgagcgg    7860
ctcggcttca ccgtcaccgc cgacgtcgag tgcccgaagg accgcgcgac ctggtgcatg    7920
acccgcaagc ccggtgcctg acgcccgccc cacgacccgc agcgcccgac cgaaaggagc    7980
gcacgacccg gtccgacggc ggcccacggg tcccagggg gtcgacctcg aaacttgttt    8040
attgcagctt ataatggtta caaataaagc aatagcatca caaatttcac aaataaagca    8100 ttttttcac tgcattctag ttgtggtttg tccaaactca tcaatgtatc ttatcatgtc    8160
tggatcgatc cgaacccctt cctcgaccaa ttctcatgtt tgacagctta tcatcgcaga    8220
tccgggcaac gttgttgcat tgctgcaggc gcagaactgg taggtatgga agatctatac    8280
attgaatcaa tattggcaat tagccatatt agtcattggt tatatagcat aaatcaatat    8340
tggctattgg ccattgcata cgttgtatct atatcataat atgtacattt atattggctc    8400
atgtccaata tgaccgccat gttgacattg attattgact agttattaat agtaatcaat    8460 tacgggtca ttagttcata gcccatatat ggagttccgc gttacataac ttacggtaaa    8520
tggcccgcct ggctgaccgc ccaacgaccc ccgcccattg acgtcaataa tgacgtatgt    8580
tcccatagta acgccaatag ggactttcca ttgacgtcaa tgggtggagt atttacggta    8640
aactgcccac ttggcagtac atcaagtgta tcatatgcca agtccgcccc ctattgacgt    8700
caatgacggt aaatggcccg cctggcatta tgcccagtac atgaccttac ggactttcc    8760 tacttggcag tacatctacg tattagtcat cgctattacc atggtgatgc ggttttggca    8820
gtacaccaat gggcgtggat agcggtttga ctcacgggga tttccaagtc tccaccccat    8880
tgacgtcaat gggagtttgt tttggcacca aaatcaacgg gactttccaa aatgtcgtaa    8940
taaccccgcc ccgttgacgc aaatgggcgg taggcgtgta cggtgggagg tctatataag    9000
cagagctcgt ttagtgaacc gtcagatctc tagaagctgg gtaccttaag gcgccagctg    9060
atcaagcttc tgcctgccgc ctgcctgcct gccactgagg gttcccagca ccatgagggc    9120
ctggatcttc tttctccttt gcctggccgg gagggctctg gcagcccgc tagctctcac    9180 tgaaacagat atatgcaagt tgccgaaaga cgaaggaact tgcagggatt tcatattaaa    9240
atggtactat gatccaaaca ccaaaagctg tgcaagattc tggtatggag gttgtggtgg    9300
aaacgaaaac aaatttggat cacagaaaga atgtgaaaag gtttgcgctc ctgtgctcgc    9360
caaacccgga gtcatcagtg tgatgggaac ctaagcgtgg gtggccaaca tcatataccT    9420
cttgaagaag aaggagtcag ccatcgccaa cttgtctcga ggtccgcggc cgctcgaggc    9480
cggcaaggcc ggatccagac atgataagat acattgatga gtttggacaa accacaacta    9540
gaatgcagtg aaaaaaatgc tttatttgtg aaatttgtga tgctattgct ttatttgtaa    9600
ccattataag ctgcaataaa caagttaaca acaacaattg cattcatttt atgtttcagg    9660 ttcagggga ggtggggagg ttttttaaag caagtaaaac ctctacaaat gtggtatggc    9720
tgattatgat ccggctgcct cgcgcgtttc ggtgatgacg gtgaaaacct ctgacacatg    9780
cagctcccgg agacggtcac agcttgtctg taagcggatg ccgggagcag acaagcccgt    9840
cagggcgcgt cagcgggtgt tggcgggtgt cggggcgcag ccatgaccgg tcgactctag    9900
```

| a | 9901 |

<210> SEQ ID NO 26
<211> LENGTH: 163
<212> TYPE: DNA
<213> ORGANISM: Artificial Sequence
<220> FEATURE:
<223> OTHER INFORMATION: QBI SP163 translational enhancer

<400> SEQUENCE: 26

| agcgcagagg cttggggcag ccgagcggca gccaggcccc ggcccgggcc tcggttccag | 60 |
| aagggagagg agcccgccaa ggcgcgcaag agagcgggct gcctcgcagt ccgagccgga | 120 |
| gagggagcgc gagccgcgcc ggccccggac ggcctccgaa acc | 163 |

<210> SEQ ID NO 27
<211> LENGTH: 73
<212> TYPE: DNA
<213> ORGANISM: Artificial Sequence
<220> FEATURE:
<223> OTHER INFORMATION: Polylinker/MCS

<400> SEQUENCE: 27

| acgctagccg aggttaactg ttgtcctggc tgttgcggtt ccggacacca tcatcaccac | 60 |
| catcaccatc acc | 73 |

<210> SEQ ID NO 28
<211> LENGTH: 77
<212> TYPE: DNA
<213> ORGANISM: Artificial Sequence
<220> FEATURE:
<223> OTHER INFORMATION: Polylinker/MCS

<400> SEQUENCE: 28

| attgaggatc cagtgtggtg gaattctgca gatatccagc acagtggcgg ccgctcgagt | 60 |
| ctagagggcc cgtttaa | 77 |

<210> SEQ ID NO 29
<211> LENGTH: 73
<212> TYPE: DNA
<213> ORGANISM: Artificial Sequence
<220> FEATURE:
<223> OTHER INFORMATION: Polylinker/MCS

<400> SEQUENCE: 29

| acgctagccg aggttgcttt gaggatccag tgtggtggaa ttctgcagat atccagcaca | 60 |
| gtggcggccg ctc | 73 |

<210> SEQ ID NO 30
<211> LENGTH: 21
<212> TYPE: DNA
<213> ORGANISM: Artificial Sequence
<220> FEATURE:
<223> OTHER INFORMATION: 31

<400> SEQUENCE: 30

| gagtctagag ggcccgttta a | 21 |

<210> SEQ ID NO 31
<211> LENGTH: 344
<212> TYPE: DNA
<213> ORGANISM: Artificial Sequence
<220> FEATURE:
<223> OTHER INFORMATION: SV40 promoter

<400> SEQUENCE: 31

```
ctgtggaatg tgtgtcagtt agggtgtgga aagtccccag gctccccagc aggcagaagt    60
atgcaaagca tgcatctcaa ttagtcagca accaggtgtg gaaagtcccc aggctcccca   120
gcaggcagaa gtatgcaaag catgcatctc aattagtcag caaccatagt cccgccccta   180
actccgccca tcccgcccct aactccgccc agttccgccc attctccgcc ccatggctga   240
ctaattttt ttatttatgc agaggccgag gccgcctctg cctctgagct attccagaag   300
tagtgaggag gcttttttgg aggcctaggc ttttgcaaaa agct                    344
```

<210> SEQ ID NO 32
<211> LENGTH: 577
<212> TYPE: DNA
<213> ORGANISM: Artificial Sequence
<220> FEATURE:
<223> OTHER INFORMATION: CMV immediate early promoter

<400> SEQUENCE: 32

```
acattgatta ttgactagtt attaatagta atcaattacg gggtcattag ttcatagccc    60
atatatggag ttccgcgtta cataacttac ggtaaatggc ccgcctggct gaccgcccaa   120
cgacccccgc ccattgacgt caataatgac gtatgttccc atagtaacgc caatagggac   180
tttccattga cgtcaatggg tggactattt acggtaaact gcccacttgg cagtacatca   240
agtgtatcat atgccaagtc cgccccctat tgacgtcaat gacggtaaat ggcccgcctg   300
gcattatgcc cagtacatga ccttacggga ctttcctact tggcagtaca tctacgtatt   360
agtcatcgct attaccatgg tgatgcggtt ttggcagtac accaatgggc gtggatagcg   420
gtttgactca cggggatttc caagtctcca ccccattgac gtcaatggga gtttgttttg   480
gcaccaaaat caacgggact ttccaaaatg tcgtaataac cccgccccgt tgacgcaaat   540
gggcggtagg cgtgtacggt gggaggtcta tataagc                            577
```

<210> SEQ ID NO 33
<211> LENGTH: 342
<212> TYPE: DNA
<213> ORGANISM: Artificial Sequence
<220> FEATURE:
<223> OTHER INFORMATION: EF1 alpha promoter minimal

<400> SEQUENCE: 33

```
aacccagaga tcgctgcgtt cccgcccct cacccgcccg ctctcgtcat cactgaggtg    60
gagaagagca tgcgtgaggc tccggtgccc gtcagtgggc agagcgcaca tcgcccacag   120
tccccgagaa gttggggga ggggtcggca attgaaccgg tgcctagaga aggtggcgcg   180
gggtaaactg ggaaagtgat gtcgtgtact ggctccgcct ttttcccgag ggtggggag   240
aaccgtatat aagtgcagta gtcgccgtga acgttctttt tcgcaacggg tttgccgcca   300
gaacacaggt gtcgtgaaaa ctaccccta aagccaaaat gg                      342
```

<210> SEQ ID NO 34
<211> LENGTH: 1285
<212> TYPE: DNA
<213> ORGANISM: Artificial Sequence
<220> FEATURE:
<223> OTHER INFORMATION: EF1 alpha promoter genomic

<400> SEQUENCE: 34

```
aacccagaga tcgctgcgtt cccgcccct cacccgcccg ctctcgtcat cactgaggtg    60
```

| | | | |
|---|---|---|---|
| gagaagagca | tgcgtgaggc | tccggtgccc gtcagtgggc | agagcgcaca tcgcccacag | 120 |
| tccccgagaa | gttggggga | ggggtcggca attgaaccgg | tgcctagaga aggtggcgcg | 180 |
| ggtaaactg | ggaaagtgat | gtcgtgtact ggctccgcct | ttttcccgag ggtgggggag | 240 |
| aaccgtatat | aagtgcagta | gtcgccgtga acgttctttt | tcgcaacggg tttgccgcca | 300 |
| gaacacaggt | aagtgccgtg | tgtggttccc gcgggcctgg | cctctttacg ggttatggcc | 360 |
| cttgcgtgcc | ttgaattact | tccacgcccc tggctgcagt | acgtgattct tgatcccgag | 420 |
| cttcggttg | gaagtgggtg | ggagagttcg aggccttgcg | cttaaggagc cccttcgcct | 480 |
| cgtgcttgag | ttgaggcctg | gcctgggcgc tggggccgcc | gcgtgcgaat ctggtggcac | 540 |
| cttcgcgcct | gtctcgctgc | tttcgataag tctctagcca | tttaaaattt ttgatgacct | 600 |
| gctgcgacgc | tttttttctg | gcaagatagt cttgtaaatg | cgggccaaga tctgcacact | 660 |
| ggtatttcgg | tttttgggc | cgcgggcggc gacggggccc | gtgcgtccca gcgcacatgt | 720 |
| tcggcgaggc | ggggcctgcg | agcgcggcca ccgagaatcg | gacggggta gtctcaagct | 780 |
| ggccggcctg | ctctggtgcc | tggcctcgcg ccgccgtgta | tcgccccgcc ctgggcggca | 840 |
| aggctggccc | ggtcggcacc | agttgcgtga gcggaaagat | ggccgcttcc cggccctgct | 900 |
| gcagggagct | caaaatggag | gacgcggcgc tcggagagc | gggcgggtga gtcacccaca | 960 |
| caaaggaaaa | gggccttcc | gtcctcagcc gtcgcttcat | gtgactccac ggagtaccgg | 1020 |
| gcgccgtcca | ggcacctcga | ttagttctcg agcttttga | gtacgtcgtc tttaggttgg | 1080 |
| ggggagggt | tttatgcgat | ggagtttccc cacactgagt | gggtggagac tgaagttagg | 1140 |
| ccagcttggc | acttgatgta | attctccttg gaatttgccc | tttttgagtt tggatcttgg | 1200 |
| ttcattctca | agcctcagac | agtggttcaa agttttttc | ttccatttca ggtgtcgtga | 1260 |
| aaactacccc | taaaagccaa | aatgg | | 1285 |

<210> SEQ ID NO 35
<211> LENGTH: 1217
<212> TYPE: DNA
<213> ORGANISM: Artificial Sequence
<220> FEATURE:
<223> OTHER INFORMATION: EF1 alpha promoter commercial

<400> SEQUENCE: 35

| | | | |
|---|---|---|---|
| agatctcgtg | aggctccggt | gcccgtcagt gggcagagcg | cacatcgccc acagtccccg | 60 |
| agaagttggg | gggaggggtc | ggcaattgaa ccggtgccta | gagaaggtgg cgcggggtaa | 120 |
| actgggaaag | tgatgtcgtg | tactggctcc gccttttcc | cgagggtggg ggagaaccgt | 180 |
| atataagtgc | actagtcgcc | gtgaacgttc ttttcgcaa | cgggtttgcc gccagaacac | 240 |
| aggtaagtgc | cgtgtgtggt | tcccgcgggc ctggcctctt | tacgggttat ggcccttgcg | 300 |
| tgccttgaat | tacttccacc | tggctgcagt acgtgattct | tgatcccgag cttcggttg | 360 |
| gaagtgggtg | ggagagttcg | tggccttgcg cttaaggagc | cccttcgcct cgtgcttgag | 420 |
| ttgtggcctg | gcctgggcgc | tggggccgcc gcgtgcgaat | ctggtggcac cttcgcgcct | 480 |
| gtctcgctgc | tttcgataag | tctctagcca tttaaaattt | ttgatgacct gctgcgacgc | 540 |
| tttttttctg | gcaagatagt | cttgtaaatg cgggccaaga | tcagcacact ggtatttcgg | 600 |
| ttttgggc | cgcgggcggc | gacggggccc gtgcgtccca | gcgcacatgt tcggcgaggc | 660 |
| ggggcctgcg | agcgcggcca | ccgagaatcg gacggggta | gtctcaagct gcccggcctg | 720 |
| ctctggtgcc | tggcctcgcg | ccgccgtgta tcgccccgcc | ctgggcggca aggctggccc | 780 |
| ggtcggcacc | agttgcgtga | gcggaaagat ggccgcttcc | cggccctgct gcagggagca | 840 |

```
caaaatggag gacgcggcgc tcgggagagc gggcgggtga gtcacccaca caaaggaaaa    900
gggcctttcc gtcctcagcc gtcgcttcat gtgactccac ggagtaccgg gcgccgtcca    960
ggcacctcga ttagttctcc agcttttgga gtacgtcgtc tttaggttgg ggggagggggt  1020 tttatgcgat ggagtttccc cacactgagt gggtggagac tgaagttagg ccagcttggc   1080
acttgatgta attctccttg gaatttgccc tttttgagtt tggatcttgg ttcattctca   1140
agcctcagac agtggttcaa agtttttttc ttccatttca ggtgtcgtga aaactacccc   1200
taaaagccaa aagatct                                                  1217

<210> SEQ ID NO 36
<211> LENGTH: 122
<212> TYPE: DNA
<213> ORGANISM: Artificial Sequence
<220> FEATURE:
<223> OTHER INFORMATION: Deletion fragment of MCS primer

<400> SEQUENCE: 36
cgctgtggcc gaggccaagc ccacgctagc cgaggttaac tgttgtcctg gctgttgcgg     60
ttccggacac catcatcacc accatcacca tcaccattga ggatccagtg tggtggaatt    120
ct                                                                   122

<210> SEQ ID NO 37
<211> LENGTH: 21
<212> TYPE: DNA
<213> ORGANISM: Artificial Sequence
<220> FEATURE:
<223> OTHER INFORMATION: pPEF5.2 reverse primer

<400> SEQUENCE: 37
caacagccag gacaacagtt a                                               21

<210> SEQ ID NO 38
<211> LENGTH: 30
<212> TYPE: DNA
<213> ORGANISM: Artificial Sequence
<220> FEATURE:
<223> OTHER INFORMATION: pPEF5.2 Forward primer introducing AfeI

<400> SEQUENCE: 38
ggtgagcgct tgaggatcc agtgtggtgg                                       30

<210> SEQ ID NO 39
<211> LENGTH: 901
<212> TYPE: DNA
<213> ORGANISM: Artificial Sequence
<220> FEATURE:
<223> OTHER INFORMATION: Synthetic PuroR DNA

<400> SEQUENCE: 39
caaagcatgc atctcaatta gtcagcaacc aggtgtggaa agtccccagg ctccccagca     60
ggcagaagta tgcaaagcat gcatctcaat tagtcagcaa ccatagtccc gcccctaact    120
ccgcccatcc cgcccctaac tccgcccagt tccgcccatt ctccgcccca tggctgacta    180
atttttttta tttatgcaga ggccgaggcc gcctctgcct ctgagctatt ccagaagtag    240
tgaggaggct ttttggaggc ctaggctttt gcaaaaagc ttgaggaact aaaccatgac     300
cgagtacaag cccacggtgc gcctcgccac ccgcgacgac gtcccagggc cgtacgcac     360 cctcgccgcc gcgttcgccg actaccccgc cacgcgccac accgtcgatc cggaccgcca    420
```

```
catcgagcgg gtcaccgagc tgcaagaact cttcctcacg cgcgtcgggc tcgacatcgg    480
caaggtgtgg gtcgcggacg acggcgccgc ggtggcggtc tggaccacgc cggagagcgt    540
cgaagcgggg gcggtgttcg ccgagatcgg cccgcgcatg gccgagttga gcggttcccg    600
gctggccgcg cagcaacaga tggaaggcct cctggcgccg caccggccca aggagcccgc    660
gtggttcctg gccaccgtcg gcgtctcgcc cgaccaccag ggcaagggtc tgggcagcgc    720
cgtcgtgctc cccggagtgg aggcggccga gcgcgccggg gtgcccgcct tcctggagac    780
atccgcgccc cgcaacctcc ccttctacga gcggctcggc ttcaccgtca ccgccgacgt    840
cgaggtgccc gaaggaccgc gcacctggtg catgacccgc aagcccggtg cctgacacgt    900
g                                                                   901
```

<210> SEQ ID NO 40
<211> LENGTH: 4802
<212> TYPE: DNA
<213> ORGANISM: Artificial Sequence
<220> FEATURE:
<223> OTHER INFORMATION: pPEF5PuroR

<400> SEQUENCE: 40

```
gacggatcgg gagatctccc gatccctat ggtcgactct cagtacaatc tgctctgatg    60
ccgcatagtt aagccagtat ctgctccctg cttgtgtgtt ggaggtcgct gagtagtgcg    120
cgagcaaaat ttaagctaca acaaggcaag cttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtccgccc cctattgacg tcaatgacgg taaatggccc gcctggcatt    540
atgcccagta catgacctta cgggactttc ctacttggca gtacatctac gtattagtca    600
tcgctattac catggtgatg cggttttggc agtacaccaa tgggcgtgga tagcggtttg    660
actcacgggg atttccaagt ctccacccca ttgacgtcaa tgggagtttg ttttggcacc    720
aaaatcaacg ggactttcca aaatgtcgta ataaccccgc cccgttgacg caaatgggcg    780
gtaggcgtgt acggtgggag gtctatataa gcagagctcg tttagtgaac cgtcagatct    840
ctagaagctg ggtaccgaaa ttaatacgac tcactatagg ggaaccagcc accatgggag    900
tcaaagttct gtttgccctg atctgcatcg ctgtggccga ggccaagccc acgctagccg    960
aggttgcttt gaggatccag tgtggtgaa ttctgcagat atccagcaca gtggcggccg    1020
ctcgagtcta gagggcccgt ttaaacccgc tgatcagcct cgactgtgcc ttctagttgc    1080
cagccatctg ttgtttgccc ctccccgtg ccttccttga cctggaaggt tgccactccc    1140
actgtccttt cctaataaaa tgaggaaatt gcatcgcatt gtctgagtag gtgtcattct    1200
attctggggg gtggggtggg gcaggacagc aaggggagg attgggaaga caatagcagg    1260
catgctgggg atgcggtggg ctctatggct tctgaggcgg aaagaaccag ctggggctct    1320 aggggggtatc cccacgcgcc ctgtagcggc gcattaagcg cggcgggtgt ggtggttacg    1380
cctgtggaat gtgtgtcagt tagggtgtgg aaagtcccca ggctcccag caggcagaag    1440 tatgcaaagc atgcatctca attagtcagc aaccaggtgt ggaaagtccc caggctcccc    1500
agcaggcaga agtatgcaaa gcatgcatct caattagtca gcaaccatag tcccgcccct    1560
```

```
aactccgccc atcccgcccc taactccgcc cagttccgcc cattctccgc cccatggctg    1620
actaattttt tttatttatg cagaggccga ggccgcctct gcctctgagc tattccagaa    1680
gtagtgagga ggcttttttg gaggcctagg cttttgcaaa aagcttgagg aactaaacca    1740
tgaccgagta caagcccacg gtgcgcctcg ccacccgcga cgacgtcccc agggccgtac    1800
gcaccctcgc cgccgcgttc gccgactacc ccgccacgcg ccacaccgtc gatccggacc    1860
gccacatcga gcgggtcacc gagctgcaag aactcttcct cacgcgcgtc gggctcgaca    1920
tcggcaaggt gtgggtcgcg gacgacggcg ccgcggtggc ggtctggacc acgccggaga    1980
gcgtcgaagc gggggcggtg ttcgccgaga tcggcccgcg catggccgag ttgagcggtt    2040
cccggctggc cgcgcagcaa cagatggaag gcctcctggc gccgcaccgg cccaaggagc    2100
ccgcgtggtt cctggccacc gtcggcgtct cgcccgacca ccagggcaag ggtctgggca    2160
gcgccgtcgt gctccccgga gtggaggcgg ccgagcgcgc cggggtgccc gccttcctgg    2220
agacatccgc gccccgcaac ctccccttct acgagcggct cggcttcacc gtcaccgccg    2280
acgtcgaggt gcccgaagga ccgcgcacct ggtgcatgac ccgcaagccc ggtgcctgac    2340
acgtgaaagt gctacgagat ttcgattcca ccgccgcctt ctatgaaagg ttgggcttcg    2400
gaatcgtttt ccgggacgcc ggctggatga tcctccagcg cggggatctc atgctggagt    2460
tcttcgccca ccccaacttg tttattgcag cttataatgg ttacaaataa agcaatagca    2520
tcacaaattt cacaaataaa gcattttttt cactgcattc tagttgtggt ttgtccaaac    2580
tcatcaatgt atcttatcat gtctgtatac cgtcgacctc tagctagagc ttggcgtaat    2640
catggtcata gctgtttcct gtgtgaaatt gttatccgct cacaattcca cacaacatac    2700
gagccggaag cataaagtgt aaagcctggg gtgcctaatg agtgagctaa ctcacattaa    2760
ttgcgttgcg ctcactgccc gctttccagt cgggaaacct gtcgtgccag ctgcattaat    2820
gaatcggcca acgcgcgggg agaggcggtt tgcgtattgg gcgctcttcc gcttcctcgc    2880
tcactgactc gctgcgctcg gtcgttcggc tgcggcgagc ggtatcagct cactcaaagg    2940
cggtaatacg gttatccaca gaatcagggg ataacgcagg aaagaacatg tgagcaaaag    3000
gccagcaaaa ggccaggaac cgtaaaaagg ccgcgttgct ggcgtttttc cataggctcc    3060
gcccccctga cgagcatcac aaaaatcgac gctcaagtca gaggtggcga aacccgacag    3120
gactataaag ataccaggcg tttccccctg gaagctccct cgtgcgctct cctgttccga    3180
ccctgccgct taccggatac ctgtccgcct ttctcccttc gggaagcgtg gcgctttctc    3240
aatgctcacg ctgtaggtat ctcagttcgg tgtaggtcgt tcgctccaag ctgggctgtg    3300
tgcacgaacc ccccgttcag cccgaccgct gcgccttatc cggtaactat cgtcttgagt    3360
ccaacccggt aagacacgac ttatcgccac tggcagcagc cactggtaac aggattagca    3420
gagcgaggta tgtaggcggt gctacagagt tcttgaagtg gtggcctaac tacggctaca    3480
ctagaaggac agtatttggt atctgcgctc tgctgaagcc agttaccttc ggaaaaagag    3540
ttggtagctc ttgatccggc aaacaaacca ccgctggtag cggtggtttt tttgtttgca    3600
agcagcagat tacgcgcaga aaaaaaggat ctcaagaaga tcctttgatc ttttctacgg    3660
ggtctgacgc tcagtggaac gaaaactcac gttaaggat tttggtcatg agattatcaa    3720
aaaggatctt cacctagatc cttttaaatt aaaaatgaag ttttaaatca atctaaagta    3780
tatatgagta aacttggtct gacagttacc aatgcttaat cagtgaggca cctatctcag    3840
cgatctgtct atttcgttca tccatagttg cctgactccc cgtcgtgtag ataactacga    3900
```

| | |
|---|---|
| tacgggaggg cttaccatct ggccccagtg ctgcaatgat accgcgagac ccacgctcac | 3960 |
| cggctccaga tttatcagca ataaaccagc cagccggaag ggccgagcgc agaagtggtc | 4020 |
| ctgcaacttt atccgcctcc atccagtcta ttaattgttg ccgggaagct agagtaagta | 4080 |
| gttcgccagt taatagtttg cgcaacgttg ttgccattgc tacaggcatc gtggtgtcac | 4140 |
| gctcgtcgtt tggtatggct tcattcagct ccggttccca acgatcaagg cgagttacat | 4200 |
| gatcccccat gttgtgcaaa aaagcggtta gctccttcgg tcctccgatc gttgtcagaa | 4260 |
| gtaagttggc cgcagtgtta tcactcatgg ttatggcagc actgcataat tctcttactg | 4320 |
| tcatgccatc cgtaagatgc ttttctgtga ctggtgagta ctcaaccaag tcattctgag | 4380 |
| aatagtgtat gcggcgaccg agttgctctt gcccggcgtc aatacgggat aataccgcgc | 4440 |
| cacatagcag aactttaaaa gtgctcatca ttggaaaacg ttcttcgggg cgaaaactct | 4500 |
| caaggatctt accgctgttg agatccagtt cgatgtaacc cactcgtgca cccaactgat | 4560 |
| cttcagcatc ttttactttc accagcgttt ctgggtgagc aaaaacagga aggcaaaatg | 4620 |
| ccgcaaaaaa gggaataagg gcgacacgga aatgttgaat actcatactc ttcctttttc | 4680 |
| aatattattg aagcatttat cagggttatt gtctcatgag cggatacata tttgaatgta | 4740 |
| tttagaaaaa taaacaaata ggggttccgc gcacatttcc ccgaaaagtg ccacctgacg | 4800 |
| tc | 4802 |

<210> SEQ ID NO 41
<211> LENGTH: 290
<212> TYPE: DNA
<213> ORGANISM: Artificial Sequence
<220> FEATURE:
<223> OTHER INFORMATION: Minimal EF1A1

<400> SEQUENCE: 41

| | |
|---|---|
| cctcacccgc ccgctctcgt catcactgag gtggagaaga gcatgcgtga ggctccggtg | 60 |
| cccgtcagtg ggcagagcgc acatcgccca cagtccccga gaagttgggg ggaggggtcg | 120 |
| gcaattgaac cggtgcctag agaaggtggc gcggggtaaa ctgggaaagt gatgtcgtgt | 180 |
| actggctccg cctttttccc gagggtgggg gagaaccgta tataagtgca gtagtcgccg | 240 |
| tgaacgttct ttttcgcaac gggtttgccg ccagaacaca ggtgtcgtga | 290 |

<210> SEQ ID NO 42
<211> LENGTH: 156
<212> TYPE: DNA
<213> ORGANISM: Artificial Sequence
<220> FEATURE:
<223> OTHER INFORMATION: Minimal EF1A2

<400> SEQUENCE: 42

| | |
|---|---|
| gcctagagaa ggtggcgcgg ggtaaactgg gaaagtgatg tcgtgtactg gctccgcctt | 60 |
| tttcccgagg gtgggggaga accgtatata agtgcagtag tcgccgtgaa cgttcttttt | 120 |
| cgcaacgggt ttgccgccag aacacaggtg tcgtga | 156 |

<210> SEQ ID NO 43
<211> LENGTH: 157
<212> TYPE: DNA
<213> ORGANISM: Artificial Sequence
<220> FEATURE:
<223> OTHER INFORMATION: Minimal EF1A3

<400> SEQUENCE: 43

| | |
|---|---|
| aacccagaga tcgctgcgtt cccgccccct cacccgcccg ctctcgtcat cactgagcct | 60 |

```
ttttcccgag ggtgggggag aaccgtatat aagtgcagta gtcgccgtga acgttcttt    120 tcgcaacggg tttgccgcca gaacacaggt gtcgtga                            157

<210> SEQ ID NO 44
<211> LENGTH: 26
<212> TYPE: DNA
<213> ORGANISM: Artificial Sequence
<220> FEATURE:
<223> OTHER INFORMATION: Forward primer EF_Forward1

<400> SEQUENCE: 44
tttaggcctc acccgcccgc tctcgt                                         26

<210> SEQ ID NO 45
<211> LENGTH: 22
<212> TYPE: DNA
<213> ORGANISM: Artificial Sequence
<220> FEATURE:
<223> OTHER INFORMATION: Forward primer EF_Forward2

<400> SEQUENCE: 45
tttaggccta gagaaggtgg cg                                             22

<210> SEQ ID NO 46
<211> LENGTH: 30
<212> TYPE: DNA
<213> ORGANISM: Artificial Sequence
<220> FEATURE:
<223> OTHER INFORMATION: Reverse primer EF_Reverse1&2

<400> SEQUENCE: 46
tttaggcctg cgtaaccacc acacccgccg                                     30

<210> SEQ ID NO 47
<211> LENGTH: 24
<212> TYPE: DNA
<213> ORGANISM: Artificial Sequence
<220> FEATURE:
<223> OTHER INFORMATION: Forward primer EF_Forward3

<400> SEQUENCE: 47
tttaggcctt tttcccgagg gtgg                                           24

<210> SEQ ID NO 48
<211> LENGTH: 27
<212> TYPE: DNA
<213> ORGANISM: Artificial Sequence
<220> FEATURE:
<223> OTHER INFORMATION: Reverse primer EF_Reverse3

<400> SEQUENCE: 48
tttaggcctc agtgatgacg agagcgg                                        27
```